US008609681B2

(12) United States Patent
Schudok et al.

(10) Patent No.: US 8,609,681 B2
(45) Date of Patent: Dec. 17, 2013

(54) SPIROCYCLIC NITRILES AS PROTEASE INHIBITORS

(75) Inventors: Manfred Schudok, Frankfurt am Main (DE); Michael Wagner, Frankfurt am Main (DE); Armin Bauer, Frankfurt am Main (DE); Anna Kohlmann, Frankfurt am Main (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/248,366

(22) Filed: Sep. 29, 2011

(65) Prior Publication Data

US 2012/0015933 A1 Jan. 19, 2012

Related U.S. Application Data

(60) Division of application No. 12/277,880, filed on Nov. 25, 2008, now Pat. No. 8,039,480, which is a continuation of application No. PCT/EP2007/004550, filed on May 23, 2007.

(30) Foreign Application Priority Data

Jun. 1, 2006 (DE) .......................... 10 2006 025 630

(51) Int. Cl.
*A61K 31/44* (2006.01)
*C07D 221/02* (2006.01)
(52) U.S. Cl.
USPC ........................................... 514/278; 546/16
(58) Field of Classification Search
None
See application file for complete search history.

(56) References Cited

U.S. PATENT DOCUMENTS 6,720,319 B2   4/2004   Liu et al.
7,067,507 B2 *  6/2006   Pulley et al. .................. 514/183

FOREIGN PATENT DOCUMENTS

| EP | 0621267 | 10/1994 |
|---|---|---|
| WO | WO 99/24460 | 5/1999 |
| WO | WO 00/55125 | 9/2000 |
| WO | WO 2004/052921 | 6/2004 |
| WO | WO 2005021584 | * 3/2005 |
| WO | WO 2005/040142 | 5/2005 |

OTHER PUBLICATIONS

Yamashita. Current Pharmaceutical Design, 2000, 6, 1-24.*
"Diabetes mellitus, type 1", http://www.nlm.nih.gov/cgi/mesh/2009/MB_cgi?mode=&term=Diabetes+Mellitus,+Type+1&field=entry, accessed May 26, 2009.*
"Diabetes mellitus, type 2", http://www.nlm.nih.gov/cgi/mesh/2009/MB_cgi?mode=&term=Diabetes+Mellitus,+Type+2&field=entry, accessed May 26, 2009.*
Bromme, D., et al., Human Cathepsin O2, A Matrix Protein-Degrading Cysteine Protease Expressed in Osteoclasts, The Journal of Biological Chemistry, vol. 271, No. 4, (1996), pp. 2126-2132.
Grabowska, U. B., et al., Recent Developments in Cathepsin K Inhibitor Design, Curr. Opin. Drug Disc. Dev., vol. 8, No. 5, pp. 619-630, (2005).
Hou, W.-S., et al., Cathespin K is a Critical Protease in Synovial Fibroblast-Mediated Collagen Degradation, American Journal of Pathology, vol. 159, No. 6, (2001), pp. 2167-2177.
Kim, W., et al., Recent Developments of Cathepsin Inhibitors and Their Selectivity, Expert Opin. Ther. Patents, vol. 13, No. 3, pp. 419-432, (2002).
Mehrotra, M. M., et al., Discovery of Novel 2,8-Diazaspiro[4.5]Decanes as Orally active Glycoprotein IIb-IIIa Antagonists, J. Med. Chem., (2004), vol. 47, pp. 2037-2061.
Thurmond, R. L., et al., Cathepsin S Inhibitors as Novel Immunomodulators, Curr. Opin. Invest. Drugs, vol. 6, No. 5, pp. 473-482, (2005).
Yasuda, Y., et al., The Role of Cathepsins in Osteoporosis and Arthritis: Rationale for the Design of New Therapeutics, Advanced Drug Delivery Reviews, vol. 57, (2005), pp. 973-993.
Baici et al., Cathepsin B in Osteoarthritis: Uncontrolled Proteolysis in the Wrong Place, Seminars in Arthritis and Rheumatism (2005) 34(6) Suppl. 2 pp. 24-28.
Abbenante et al., Protease inhibitors in the Clinic, Medicinal Chemistry (2005) 1 pp. 71-104.
Najer et al. Guanidines douees d'activite antihypertensive, 4e memoire: N-beta-guanidinoethyl azaspiro alcanes, Bull. Soc. Chim. France (Memoires Presentes a la Societe Chimique (1964) pp. 2572-2581.
Wu, W.-L., et al., Design and Synthesis of Orally Efficacious Benzimidazoles as Melanin-Concentrating Hormone Receptor 1 Antagonists, Bioorganic & Medicinal Chemistry Letters, vol. 16, (2006), pp. 3674-2678.
International Search Report for WO2007/137738 dated Dec. 6, 2007.

* cited by examiner

*Primary Examiner* — Noble Jarrell
(74) *Attorney, Agent, or Firm* — Kelly L. Bender

(57) ABSTRACT

The invention relates to substituted carbo- and heterocyclic spiro compounds of the formula Ia which inhibit thiol proteases, to processes for their preparation and to the use thereof as medicaments.

15 Claims, No Drawings

SPIROCYCLIC NITRILES AS PROTEASE INHIBITORS

This application is a divisional of U.S. application Ser. No. 12/277,880, filed Nov. 25, 2008, now U.S. Pat. No. 8,039,480, which is a continuation of International Application No. PCT/EP2007/004550, filed May 23, 2007, which are incorporated herein by reference in their entirety; and claims the benefit of priority of German Patent Application No. 102006025630.1, filed Jun. 1, 2006.

The invention relates to substituted carbo- and heterocyclic spiro compounds of the formula Ia which inhibit thiol proteases, to processes for their preparation and to the use thereof as medicaments.

Proteolytic enzymes, known as proteases and peptidases, are very important enzymes which make up about 2% of the genes in the human organism, pathogenic microorganisms and also other life forms. Their particular significance is that they influence many physiological processes by playing an important role in the activation, synthesis or degradation of other proteins. This inevitably gives rise to a crucial regulatory function starting at conception, birth, growth, maturation, aging, diseases up to death.

The balance of the different processes is of crucial significance for the life and survival of the organism. When there is an imbalance of protease-catalyzed processes as a result of endogenous or exogenous factors such as genetic predisposition or environmental factors, massive disruption can occur in the normal development process, acute to serious chronic health disorders up to and including life-threatening diseases.

Equally, proteases are essential and responsible in replication and transmission processes of viral, bacterial and other parasitic organisms which are responsible, for instance, for infection disorders, and equally essential, of course, for all further physiological and pathophysiological processes in the plant and animal kingdom.

Caused by this general great significance for our health, a multitude of protease inhibitors have already been developed, which are on the market or in all stages of development: not only as medicaments, but also as diagnostics, vaccines or food supplements.

A distinction is drawn between 5 classes of proteolytic enzymes, divided according to the catalytically active radicals relevant for the enzymatic hydrolysis: aspartyl proteases, serine proteases, cysteine proteases, metalloproteases and threonine protreases. Inhibitors of all of these classes are the subject of comprehensive studies in a wide field for the control of various types of disorders. Several very effective protease inhibitors are on the market, for example ACE inhibitors, HIV-1 protease inhibitors, and also thrombin and elastase inhibitors, followed by a large number of inhibitors in clinical phases. A summary can be found, for instance, in Medicinal Chemistry, 2005, Vol. 1, No. 1, p. 71-104.

Cysteine (thiol) proteases are divided into three main classes: Papain-like, ICE-like (caspases) and Picornaviral proteases. From the point of view of the mechanism, the hydrolysis of the amide bond proceeds in a similar way to that in the case of the class of the serine proteases, via an attack of the thiolate anion at the carbonyl carbon and formation of a tetrahedral transition state. The most prominent representatives of the papain superfamily, as the largest and most significant group of the thiol proteases, are the cathepsins which have a natural wide distribution in various tissues and to which an important function is attributed both in normal physiological and pathological processes. Particular emphasis should be given to intracellular protein degradation and remodeling processes. Accordingly, significance is ascribed to cysteine cathepsins in the following general disorder types: musculoskeletal disorders, particularly bone degradation disorders, inflammatory disorders, particularly arthritides, atherosclerotic disorders, emphysemas, dystrophies, cancers, disorders of the periodontal apparatus, infectious disorders (viral, parasitic and bacterial infections), neurodegenerative disorders, disorders of the immune system, ischemias, leukodystrophies, glomerulonephritis. According to the nature of the proteases, the pathogenic properties are exerted especially by three high-level mechanisms: the degradation of (connective) tissue, which initiates many types of symptoms and also further processes, the generation of pathogenic or bioactive proteins and peptides which themselves exert their action directly or in signal cascades, and antigen processing, for example the presentation of antigenic peptides at the cell surface, which then finally initiates an immune response.

Known representatives of the cysteine cathepsins are particularly Cathepsin B, H, K, L, F, V, W, X, O, C and S (A. J. Barrett; N. D. Rawlings; J. F. Woessner; ed.; Handbook of Proteolytic Enzymes, 2nd. ed., 2004; Publisher: Elsevier, London).

Cathepsin F was found for the first time in macrophages and is involved in antigen processing. Caused by the occurrence in stimulated lung macrophages, an important function in inflammatory respiratory pathway disorders has been postulated.

Cathepsin L is involved in normal lysosomal proteolysis, but also in various disease events such as melanoma metastatis.

Cathepsin S plays a key role in many processes which are of significance in the context of antigen presentation and are thus present to an enhanced degree in antigen-presenting cells. In this regard, inhibitors of cathepsin S are possibly active agents in the prevention, inhibition or treatment of immune or autoimmune disorders. Moreover, cathepsin S is also secreted by several antigen-presenting cells and thus plays a role in extracellular matrix interactions which likewise have crucial significance in many pathological processes. Emphasis is given here to various (auto)immune and inflammatory disorders; particularly Alzheimer's disease, Huntington's disease, juvenile diabetes, multiple sclerosis, pemphigus vulgaris, Graves' disease, Myasthenia gravis, systemic Lupus erythematosus, IBD, rheumatoid arthritis and Hashimoto's thyroiditis, MS, ALS, allerigic disorders such as asthma, allogenic immune responses such as rejection reactions in organ transplants or tissue grafts. Moreover, cathepsin S is connected with COPD (such as emphysema), bronchiolitis, excessive respiratory pathway elastolysis in asthma and bronchitis, pneumonitis, but also with cardiovascular disorders such as plaque ruptures and atheromers, and also endometriosis and chronic neuropathic pain. Cathepsin S is also connected with fibrillary disorders, and inhibitors can thus possibly be used for the treatment of systemic amyloidosis.

Increased levels of cathepsin B and corresponding distributions are found in various tumors—a role in tumor invasion and metastatis is thus ascribed to cathepsin B. Enhanced cathepsin B activity is likewise found in rheumatoid arthritis, osteoarthritis, acute pancreatitis, inflammatory respiratory pathway disorders, *Pneumocystis carinii* and bone and joint disorders. A significant increase in synovial cathepsin B levels has been detected in osteoarthritis models. A review of cytokine-independent overexpression and relevance for osteoarthritis can be found in A. Baici et al., Seminars in Arthritis and Rheumatism, 34, 6, Suppl. 2, 24-28 (2005).

Cathepsin K expression is particularly marked (but not exclusively) in osteoclasts (for example D. Brömme et al., J.

Biol. Chem. 271, 2126-32 (1996)) and represents about 98% of the total cysteine protease activity there, mainly localized intracellularly within the lysosome. An autosomal recessive disruption of cathepsin K expression (absence through mutation), pycnodysostosis, is characterized by an osteopetrotic phenotype, with reduced bone resorption, ossification disorders and massive growth disorders. It has likewise been possible to show with cathepsin K antisense nucleotides and knockout mice that cathepsin K is responsible for osteoclast-mediated bone degradation. It is therefore assumed that inhibition of cathepsin K leads to reduced bone resorption and should thus constitute a possible therapy for all disorders which are characterized by elevated bone degradation, i.e. particularly for the treatment of osteoporosis. Caused by a significantly increased activity in the slightly acidic range between pH 4 and 8, enzymatic degradation of the collagen network in bone proceeds accompanied by acidolytic destruction of the mineral matrix. Here, particularly human collagen type I is affected as a main constituent of the protease in bone; this has been proven to be a very good substrate for cathepsin K. Therefore, other disorders which are accompanied by increased catabolic activity at the collagen level are also connected with cathepsins and particularly with cathepsin K. Foremost among these is osteoarthritis, characterized by an imbalance of cartilage matrix buildup and degradation, caused by catabolically active enzymes, for example metalloproteinases, among others. It is therefore obvious and has now also been proved that an inhibition of cathepsin K might likewise have favorable effects here on the disease process (synovial fibroblast-mediated collagen degradation by cathepsin K is described in W.-S. Hou et al., Am. J. Pathol. 159, 2167-2177 (2001)). The significance of cathepsins K and S in musculoskeletal disorders such as osteoporosis and osteoarthritis is described in detail by D. Brömme et al., Advanced Drug Delivery Reviews 57, 973-993 (2005).

Caused by the above-described detailed findings concerning cysteine cathepsins in various disease processes, they are considered to be very promising points of attack in drug development, such that an intensive search has commenced for specific, group-specific or even unspecific inhibitors.

Inhibitors of cysteine proteases have been known for sometime, for example cystatines as endogenous polypeptide inhibitors. Low molecular weight inhibitors were isolated from *aspergillus* for the first time in 1981. These are potent irreversible inhibitors with low toxicity, but also inadequate specificity, since not only cathepsins B, K, L, S and H but also calpaines are widely inhibited. Since then, a multitude of inhibitors with different specificities or mechanisms has been found—therefore, both irreversibly covalently binding and reversibly covalently binding or reversibly noncovalently binding inhibitors have been found or synthesized. More recent developments have been described in detail (W. Kim, K. Kang, Expert Opin. Ther. Patents 13, 3, 419-32 (2002); U. B. Grabowska, Curr. Opin. Drug Disc Dev. 8, 5, 619-30 (2005); R. L. Thurmond et al., Curr. Opin. Invest. Drugs 6, 5, 473-482 (2005)).

Reversibly covalently binding inhibitors are of particular interest. From this group, particularly the class of the nitriles has been identified as very promising. These are described in detail, for example in the applications WO99/24460, WO2000/55125, WO2004/052921 and also in WO2005/040142.

In the effort to find effective compounds for treating disorders caused directly or indirectly by cysteine cathepsins, it has now been found that the inventive spiro compounds, spirocyclic nitriles, are strong inhibitors of the cysteine cathepsins, particularly of cathepsin K and/or S, while other cysteine proteases such as calpain are inhibited much more weakly, if at all. Moreover, the inventive compounds have improved bioavailability, which has also been shown already in vitro in corresponding Caco permeability tests.

The invention therefore relates to a compound of the formula I

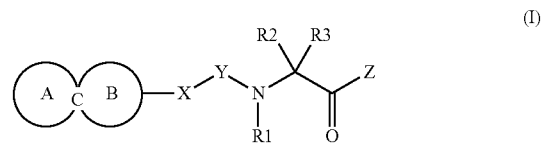

and/or all stereoisomeric forms of the compound of the formula I and/or mixtures of these forms in any ratio, and/or a physiologically tolerated salt of the compound of the formula I, and/or solvates or hydrates of the compound of the formula I, and/or prodrugs of the compound of the formula I, where the

radical is a spiro compound,
in which the sub-rings

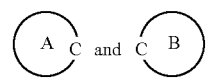

are in each case the same or different and are each independently a) a saturated or partly saturated —($C_3$-$C_{11}$)-cycloalkyl, in which cycloalkyl is unbridged, bridged or fused and is unsubstituted or independently, according to the ring size, mono-, di-, tri, tetra- or pentasubstituted by R4, or b) a saturated or partly saturated, three- to eleven-membered heterocycle which, according to the ring size, may contain one, two, three or four identical or different heteroatoms from the group of oxygen, nitrogen or sulfur, and in which the heterocycle is unbridged, bridged or fused and is unsubstituted or independently, according to the ring size, mono-, di-, tri-, tetra- or pentasubstituted by R4, where R4 is —$NO_2$, —CN, =O, =S, —OH, —$CF_3$, —$SF_5$, —($C_0$-$C_3$)-alkylene-S—R10, —Si—$(CH_3)_3$, —O—$CF_3$, —($C_0$-$C_3$)-alkylene-C(O)—N(R21)-R22, —($C_0$-$C_3$)-alkylene-C(O)—R10, —($C_0$-$C_3$)-alkylene-C(O)—O—R10, —($C_0$-$C_3$)-alkylene-S(O)—R10, —S—$CF_3$, —($C_0$-$C_3$)-alkylene-S(O)$_2$—R10, —($C_0$-$C_5$)-alkylene-S(O)$_2$—N(R21)-R22, —($C_0$-$C_3$)-alkylene-O—R10, —($C_0$-$C_3$)-alkylene-N(R21)-R22, —($C_0$-$C_3$)-alkylene-N(R10)-S(O)$_2$—R10, —($C_0$-$C_5$)-alkylene-($C_1$-$C_3$)-fluoroalkyl, —($C_0$-$C_5$)-alkylene-($C_3$-$C_8$)-cycloalkyl-R23, —($C_0$-$C_5$)-alkylene-N(R10)-C(O)—R21, —($C_0$-$C_5$)-alkylene-N(R10)-C(O)—N(R10)-R21, —($C_0$-$C_5$)-alkylene-O—C(O)—R21, —($C_0$-$C_5$)-alkylene-O—C(O)—O—R21, —($C_0$-$C_5$)-alkylene-NH—C(O)—O—R21, —($C_0$-$C_5$)-alkylene-O—C(O)—N(R10)-R21, —($C_0$-$C_4$)-alkyl, where alkyl is unsubstituted or mono-, di- or trisubstituted independently by R9, —($C_0$-$C_4$)-alkylene-aryl, where aryl is selected from the group of phenyl, indanyl, indenyl, naphthyl, 1,2,3,4-tetrahydronaphthyl, biphenylyl, 2-biphenylyl, 3-biphenylyl, 4-biphenylyl, anthryl or fluoroenyl, where aryl is unsubstituted or mono-, di- or trisubstituted independently by R8, or —(C₀-C₄)-alkylene-Het, where Het is selected from the group of acridinyl, azepinyl, azetidinyl, aziridinyl, benzimidazolinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, deca-hydroquinolinyl, dibenzofuranyl, dibenzothiophenyl, dihydrofuran[2,3-b]-tetrahydrofuranyl, dihydrofuranyl, dioxolyl, dioxanyl, 2H, 6H-1,5,2-dithiazinyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolidinyl, 2-isothiazolinyl, isothiazolyl, isoxazolyl, isoxazolidinyl, 2-isoxazolinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, oxothiolanyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pryidooxazolyl, pyridoimidazolyl, pyridothiazolyl, pyridothiophenyl, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyridinyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienoimidazolyl, thienooxazolyl, thienopyridine, thienothiazolyl, thiomorpholinyl, thiophenyl, triazinyl, 1,2,3-triazolyl, 1,2,4-triazolyl, 1,2,5-triazolyl, 1,3,4-triazolyl and xanthenyl, and this Het radical is unsubstituted or independently mono-, di- or trisubstituted by R8, or two adjacent R4, together with the ring atoms to which they are bonded, form a four- to eight-membered heterocycle or phenyl which, together with the sub-ring to which the heterocycle or the phenyl is fused, forms a bicyclic system, R8 is halogen, carbamimidoyl, —NO₂, =O, —CF₃, —SF₅, —C(O)—O—R10, —CN, —C(O)—NH₂, —OH, —NH₂, —O—CF₃, —S—CF₃, —C(O)—N(R10)-R20, —N(R10)-R20, —(C₁-C₈)-alkyl, where alkyl is unsubstituted or mono-, di- or trisubstituted independently by fluorine, chlorine, bromine, iodine, —NH₂, —OH, methoxy radical, —SO₂—CH₃, SO₂—NH₂ or —SO₂—CF₃ or is mono- to decasubstituted by fluorine, —O—(C₁-C₈)-alkyl, where alkyl is unsubstituted or mono-, di- or trisubstituted independently by fluorine, chlorine, bromine, iodine, NH₂, —OH, methoxy radical, —SO₂—CH₃ or —SO₂—CF₃ or is mono- to decasubstituted by fluorine, —S—(C₁-C₈)-alkyl, where alkyl is unsubstituted or mono-, di- or trisubstituted independently by fluorine, chlorine, bromine, iodine, NH₂, —OH, methoxy radical, —SO₂—CH₃ or —SO₂—CF₃ or is mono- to decasubstituted by fluorine, —(C₀-C₄)-alkylene-(C₃-C₈)-cycloalkyl or —O—(C₀-C₄)-alkylene-(C₃-C₈)-cycloalkyl, R9 is a halogen, —NO₂, —CN, =O, =S, —OH, —CF₃, —SF₅, —C(O)—O—R10, —N(R21)-R22, —C(O)—N (R21)-R22, —(C₀-C₃)-alkylene-O—R10, —(C₀-C₃)-alkylene-S—R10, —S—R10, —Si—(CH₃)₃, —N(R10)-S (O)ᵤ—R10, where u is the integer 1 or 2, —SOᵣ—R10, where r is the integer 1 or 2, —S(O)ᵥ—N(R10)-R20, where v is the integer 1 or 2, —C(O)—R10, —(C₁-C₈)-alkyl, —O—R19, —(C₁-C₈)-alkoxy, phenyl, phenyloxy-, —(C₁-C₃)-fluoroalkyl, —NH—C(O)—NH—R21, —O—C(O)—R10, —(C₀-C₄)-alkyl-C(O)—O—C(R19, R11)-O—C(O)—R12, —O—CF₃, —(C₀-C₄)-alkyl-C(O)—O—C(R19, R11)-O—C(O)—O—R12, —O—C(O)—N—R10, —N(R21)-C(O)—R22, —NH—C(O)—O—R10, —S—CF₃, Het, where Het is unsubstituted or mono-, di- or trisubstituted independently by R8, or is a radical from the following list

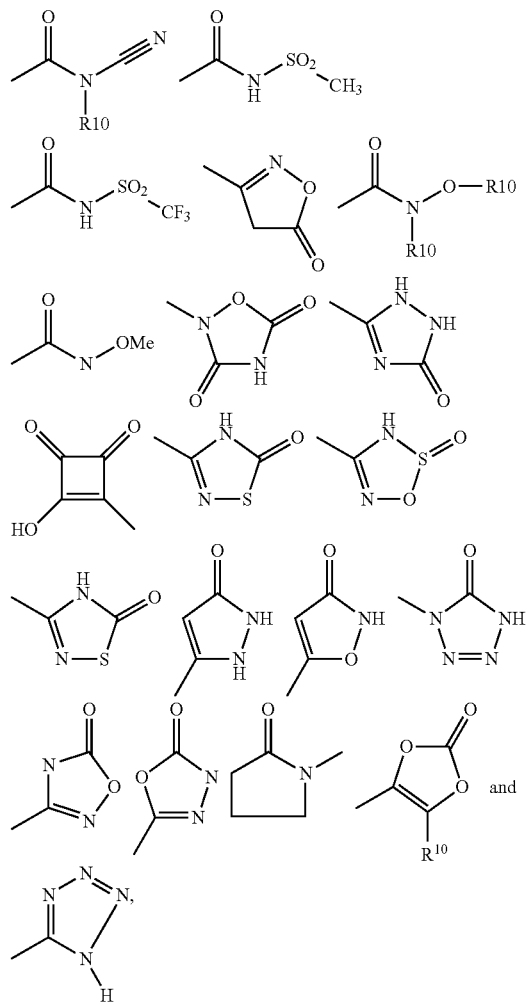

where Me is methyl

R10 and R20 are the same or different and are each independently a hydrogen atom, —(C₁-C₆)-alkyl, —(C₀-C₄)-alkyl-O—(C₀-C₄)-alkyl, —(C₁-C₃)-fluoroalkyl, —(C₀-C₅)-alkyl-(C₃-C₈)-cycloalkyl, —(C₀-C₂)-alkylene-aryl, where aryl is as defined above and is unsubstituted or mono-, di- or trisubstituted independently by —(C₁-C₆)-alkyl, —O—(C₁-C₆)-alkyl, halogen or —(C₃-C₈)-cycloalkyl, or —(C₀-C₂)-alkylene-Het, where Het is as defined above and is unsubstituted or mono-, di- or trisubstituted independently by —(C₁-C₆)-alkyl, —O—(C₁-C₆)-alkyl, halogen or —(C₃-C₈)-cycloalkyl, R19 and R11 are the same or different and are each independently a hydrogen atom or —(C₁-C₆)-alkyl, or R19 and R11, together with the carbon atom to which they are bonded, form a three- to six-membered cycloalkyl ring which is unsubstituted or mono-, di- or trisubstituted independently by R10, R12 is —(C$_1$-C$_6$)-alkyl, —(C$_1$-C$_6$)-alkyl-OH, —(C$_1$-C$_6$)-alkyl-O—(C$_1$-C$_6$)-alkyl, —(C$_3$-C$_8$)-cycloalkyl, —(C$_1$-C$_6$)-alkyl-O—(C$_1$-C$_8$)-alkyl-(C$_3$-C$_8$)-cycloalkyl, —(C$_1$-C$_6$)-alkyl-(C$_3$-C$_8$)-cycloalkyl where the cycloalkyl radical is unsubstituted or mono-, di- or trisubstituted independently by —OH, —O—(C$_1$-C$_4$)-alkyl or R10, R21 and R22 are the same or different and are each independently a hydrogen atom, —(C$_1$-C$_6$)-alkyl where alkyl is unsubstituted or mono-, di- or trisubstituted independently by R8, —(C$_0$-C$_6$)-alkylene-(C$_3$-C$_8$)-cycloalkyl, —SO$_t$—R10 where t is the integer 1 or 2, —(C$_1$-C$_3$)-fluoroalkyl, —O—R12, —S—R12, —(C$_0$-C$_6$)-alkylene-aryl where aryl is as defined above and alkylene and aryl are each unsubstituted or mono-, di- or trisubstituted independently by R8 or —(C$_0$-C$_6$)-alkylene-Het where Het is as defined above and alkylene and Het are each unsubstituted or mono-, di- or trisubstituted independently by R8, R21 and R22, together with the nitrogen atom to which they are bonded, form a four- to eight-membered monocyclic heterocyclic ring which, as well as the nitrogen atom, may additionally contain, according to the ring size, one or two identical or different heteroatoms from the group of oxygen, nitrogen and sulfur, and in which the heterocyclic ring is unsubstituted or mono-, di- or trisubstituted independently by R8, R23 is a hydrogen atom, —OH or —O—(C$_1$-C$_4$)-alkyl, X is a covalent bond, —N(R7)-, —O—, —S— or —(C(R13)(R14))$_n$- where n is the integer 1, 2 or 3, R7 is a hydrogen atom, —(C$_0$-C$_4$)-alkylene-(C$_3$-C$_6$)-cycloalkyl or —(C$_1$-C$_6$)-alkyl, R13 and R14 are the same or different and are each independently a hydrogen atom, —(C$_0$-C$_4$)-alkylene-(C$_3$-C$_6$)-cycloalkyl, —(C$_1$-C$_3$)-fluoroalkyl or —(C$_1$-C$_4$)-alkyl, R13 and R14, together with the carbon atom to which they are bonded, form a three- to six-membered cycloalkyl ring which is unsubstituted or mono-, di- or trisubstituted independently by R10, Y is a covalent bond, —C(O)—, —S(O)—, —S(O$_2$)—, —C(NR1)-, —C(S)—, —C(=N—CN)—, —C(=CHNO$_2$)— or —CH(CF$_3$)—, R1 is a hydrogen atom, —(C$_1$-C$_4$)-alkyl or —(C$_0$-C$_4$)-alkylene-(C$_3$-C$_6$)-cycloalkyl, R2 and R3 are the same or different and are each independently a hydrogen atom,
—(C$_1$-C$_{10}$)-alkyl, —(C$_0$-C$_4$)-alkylene-(C$_3$-C$_8$)-cycloalkyl, —(C$_1$-C$_6$)-fluoroalkyl, —(C$_0$-C$_4$)-alkylene-aryl, where aryl is unsubstituted or mono-, di- or trisubstituted independently by R8, —(C$_0$-C$_4$)-alkylene-Het where Het is unsubstituted or mono-, di- or trisubstituted independently by R8, —(C$_1$-C$_4$)-alkylene-R15-R16 or —(C$_0$-C$_4$)-alkylene-C(R27)(R28)(R29), R27 is a hydrogen atom, halogen, —(C$_1$-C$_9$)-alkyl, —(C$_1$-C$_3$)-fluoroalkyl, —(C$_0$-C$_4$)-alkylene-(C$_3$-C$_6$)-cycloalkyl, —(C$_0$-C$_4$)-alkylene-aryl, where aryl is unsubstituted or mono-, di- or trisubstituted independently by R8, —(C$_0$-C$_4$)-alkylene-Het where Het is unsubstituted or mono-, di- or trisubstituted independently by R8, or —(C$_0$-C$_4$)-alkylene-R15-R16, R28 and R29 are the same or different and are each independently a hydrogen atom, —(C$_1$-C$_4$)-alkyl or halogen, R15 is —N(R17)-, —O—, —S—, —S(O)—, —S(O$_2$)—, —C(O)—, —C(O)—O—, —O—C(O)—, —O—C(O)—O—, —N(R17)-C(O)—, —C(O)—N(R17)—, —S(O$_2$)—N(R17)-, —S(O)—N(R17)-, —N(R17)-S(O$_2$)—, —N(R17)-C(O)—O—, —O—C(O)—N(R17)-, —N(R17)-C(O)—N(R18)-, —N(R17)-C(N(R17))-N(R18)-, —N(R17)-C(N(R17))- or —N(R17)-S(O$_2$)—N(R18)-, where R17 and R18 are the same or different and are each independently a hydrogen atom or —(C$_1$-C$_6$)-alkyl, R16 is a hydrogen atom, —(C$_1$-C$_6$)-alkyl, —(C$_0$-C$_4$)-alkylene-(C$_3$-C$_6$)-cycloalkyl, —(C$_1$-C$_3$)-fluoroalkyl, —(C$_0$-C$_4$)-alkylene-aryl, where aryl is unsubstituted or mono-, di- or trisubstituted independently by R8, —(C$_0$-C$_4$)-alkylene-Het where Het is unsubstituted or mono-, di- or trisubstituted independently by R8, R2 and R3, together with the carbon atom to which they are bonded, form a three- to six-membered cycloalkyl ring which is unsubstituted or mono-, di- or trisubstituted independently by R8, or R2 and R3, together with the carbon atom to which they are bonded, form a three- to six-membered heterocycloalkyl radical which is unsubstituted or mono-, di- or trisubstituted independently by R10, and Z is the —N(R26)-(C(R24)(R25))$_m$—CN radical where
R26 is a hydrogen atom, —(C$_1$-C$_4$)-alkyl or —(C$_0$-C$_4$)-alkylene-(C$_3$-C$_6$)-cycloalkyl, R24 and R25 are the same or different and are each independently a hydrogen atom, —(C$_1$-C$_6$)-alkyl, —(C$_0$-C$_4$)-alkylene-(C$_3$-C$_6$)-cycloalkyl, —(C$_1$-C$_3$)-fluoroalkyl, —(C$_1$-C$_4$)-alkylene-R15-R16, —(C$_0$-C$_4$)-alkylene-aryl, where aryl is unsubstituted or mono-, di- or trisubstituted independently by R8, —(C$_0$-C$_4$)-alkylene-Het where Het is unsubstituted or mono-, di- or trisubstituted independently by R8, and m is the integer 1, 2 or 3, R24 and R25, together with the carbon atom to which they are bonded, form a three- to six-membered cycloalkyl ring which is unsubstituted or mono-, di- or trisubstituted independently by R10 or fluorine, or R24 and R25, together with the carbon atom to which they are bonded, form a three- to six-membered heterocycloalkyl radical which is unsubstituted or mono-, di- or trisubstituted independently by R10 or fluorine.

2) The invention further provides the compound of the formula I where
the sub-ring

has been selected from the following group

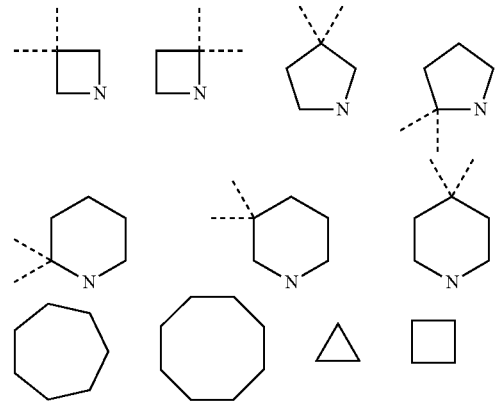

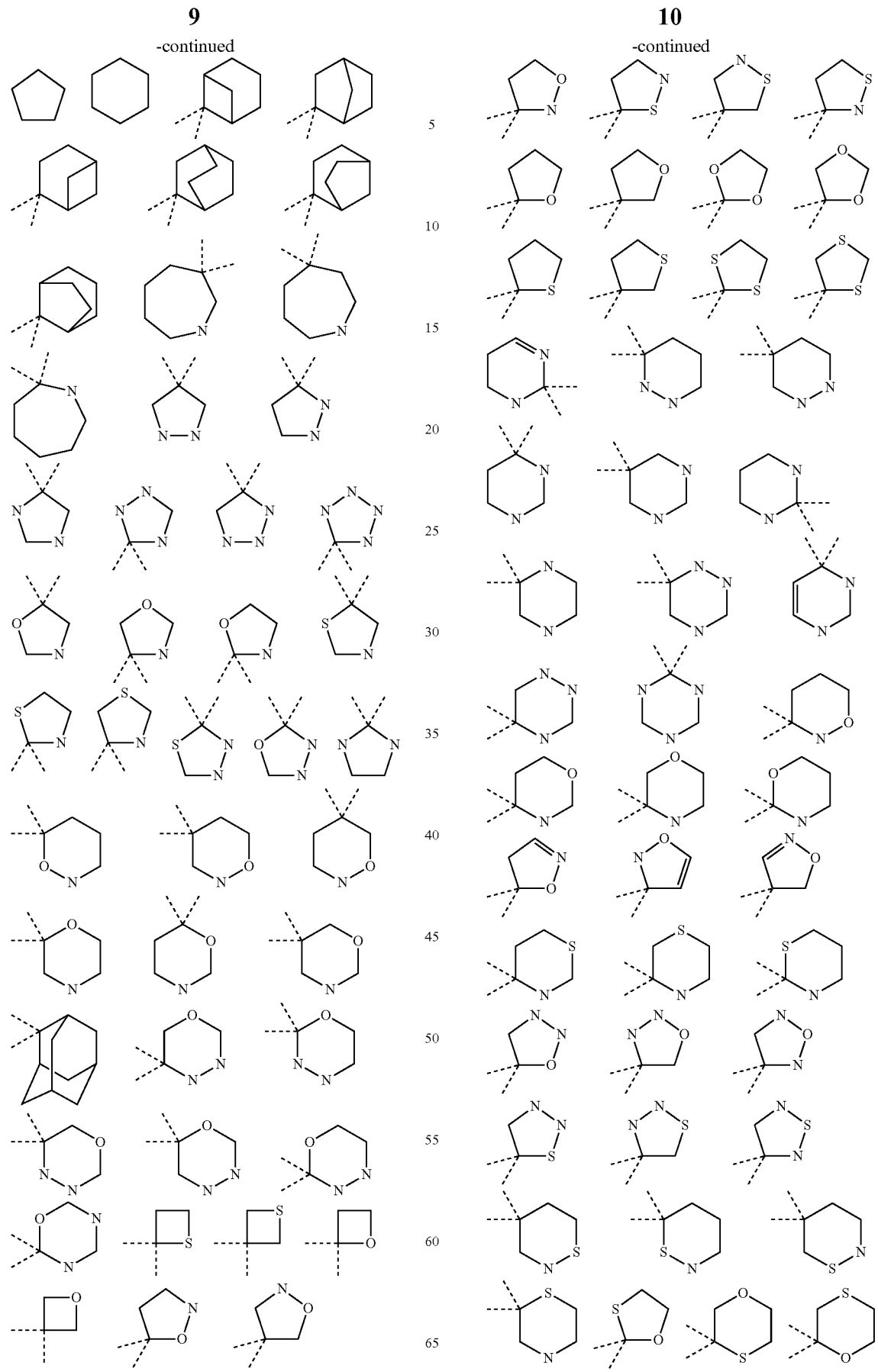

-continued
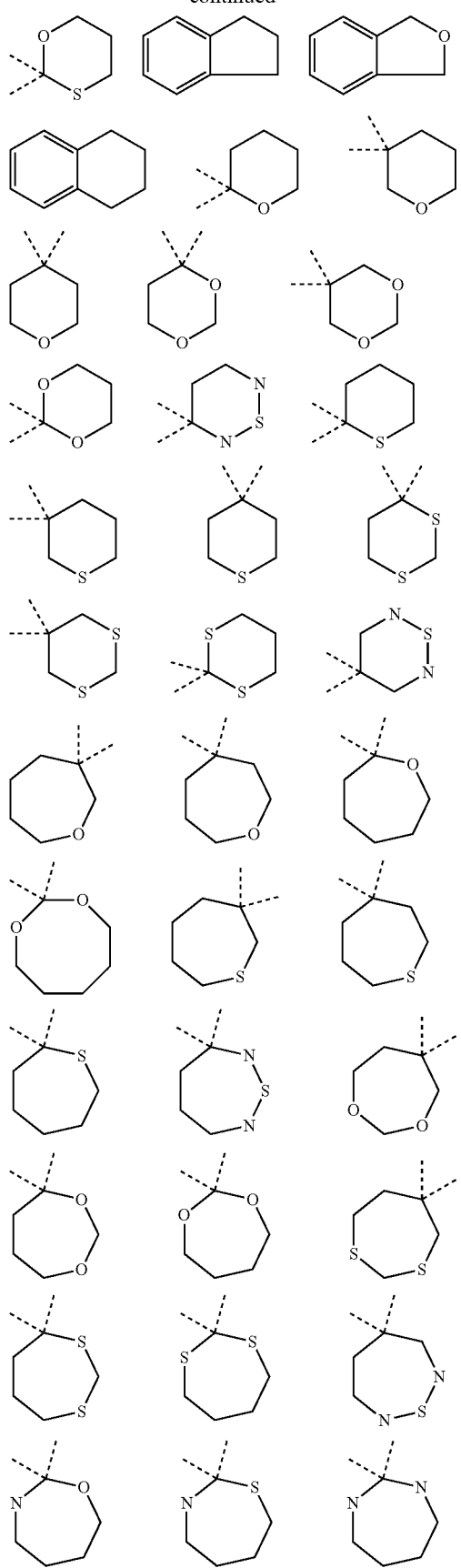
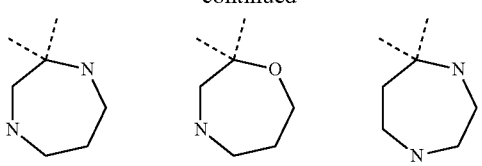
-continued
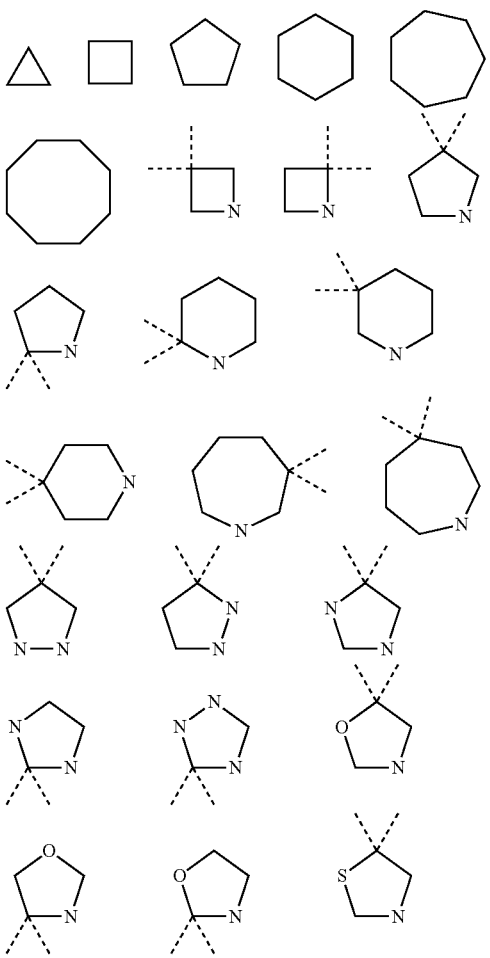
where the dotted lines indicate the particular point of attachment to the second sub-ring, single bonds in the structures listed may be replaced partly by double bonds, or further ring systems may be fused on, and
in which the sub-ring
has been selected from the following group

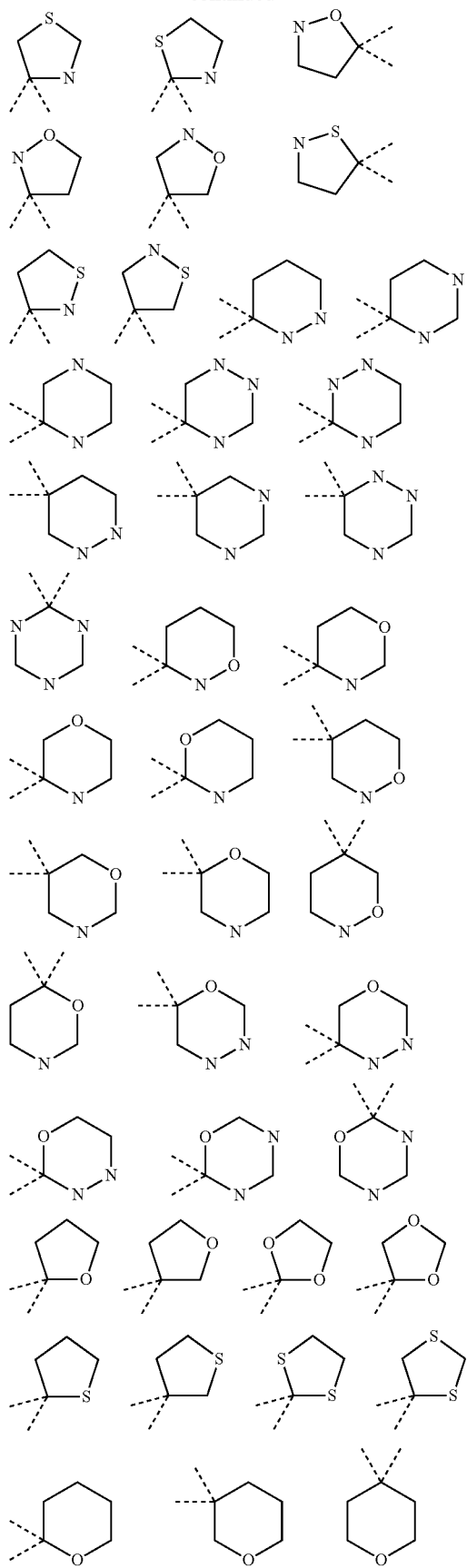

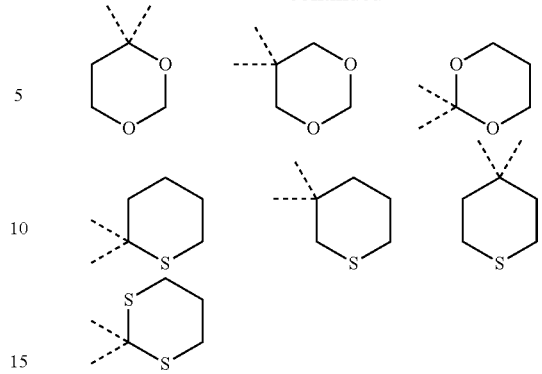

where the dotted lines indicate the particular point of attachment to the second sub-ring, single bonds in the structures listed may be replaced partly by double bonds, and the two sub-rings A and B are unsubstituted or independently mono- to tetrasubstituted by R4, and the X, Y, R1, R2, R3, R4 and Z radicals are each as defined above.

3) The invention further provides the compound of the formula I where
the sub-rings

have in each case been selected from cyclopropane cyclobutane, cyclopentane, cyclohexane, cycloheptane, cyclooctane, bicyclo[4.2.0]octane, octahydroindene, decalin, decahydrobenzocycloheptene, dodecahydroheptalene, bicyclo[3.1.1]heptane, bicyclo[2.2.1]heptane, bicyclo[3.3.0]octane, bicyclo[2.2.2]octane, spiro[2.5]octane, spiro[3.4]octane, azepane, azepine, azetidine, aziridine, azirine, azocane, benzimidazoline, 2,3-dihydrobenzo[b]thiophene, 1,3-dihydrobenzo[c]thiophene, 2,3-dihydrobenzofuran, 2,3-dihydrobenzooxazole, 2,3-dihydrobenzothiazole, 1,3-dihydroisobenzofuran, 4,5-dihydroisothiazole, 2,3-dihydroisoxazole, 2,5-dihydroisoxazole, 4,5-dihydroisoxazole, 5,6-dihydro-4H-[1,2]oxazine, benzo[1,3]dioxole, 1,4-diazepane, 1,2-diazepine, 1,3-diazepine, 1,4-diazepine, diaziridine, diazirine, 1,4-diazocane, dioxane, 1,3-dioxane, dioxazine, [1,3]dioxepane, 1,4-diozocane, dioxole, dioxolane, 1,3-di-oxolane, 1,3-di-oxolene, [1,3]dithiane, [1,3]dithiolane, hexahydropyridazine, hexahydropyrimidine, imidazoline, imidazolidine, indane, indoline, isoindoline, isothiazolidine, isothiazoline, isoxazoline, isoxazolidine, 2-isoxazoline, morpholine, [1,3,4]oxadiazinane, [1,3,5]oxadiazinane, [1,2,3]oxadiazolidine, [1,3,4]oxadiazolidine, 1,2-oxathiepane, 1,2-oxathiolane, [1,3]oxathiolane, 1,4-oxazepane, 1,2-oxazine, 1,3-oxazine, 1,4-oxazine, oxazinane, 1,3-oxazinane, oxazocane, oxaziridine, oxazolidine, oxepane, oxetane, oxirane, oxocane, piperazine, piperidine, pyran, pyrazoline, pyrazolidine, pyrrolidine, pyrrolidinone, pyrroline, tetrahydroquinoline, tetrahydrofuran, tetrahydroisoquinoline, 1,2,3,4-tetrahydronaphthalene, tetrahydropyran, tetrahydropyridine, 1,2,3,4-tetrahydro-pyrimidine, 1,2,5,6-tetrahydropyrimidine, tetrahydrothiophene, tetrazine, thiadiazine, [1,2,6]thiadiazinane, [1,3,4]thiadiazolidine, 1,2-thiazine, 1,3-thiazine, 1,4-thiazine, [1,2]thiazinane, [1,3]thiazinane, thiazolidine, thiazoline, thiepane, thietane, thiomorpholine, thiopyran, 1,2,3-triazine, 1,2,4-triazine, 1,3,5-triazine, [1,2,4]triazinane or [1,2,4]triazolidine, and in which the two sub-rings are each unsubstituted or independently, according to the ring size, mono-, di-, tri-, tetra- or pentasubstituted by R4, where R4 is —NO$_2$, —CN, =O, =S, —OH, —CF$_3$, —SF$_5$, —(C$_0$-C$_3$)-alkylene-S—R10, —Si—(CH$_3$)$_3$, —O—CF$_3$, —(C$_0$-C$_3$)-alkylene-C(O)—N(R21)-R22, —(C$_0$-C$_3$)-alkylene-C(O)—R10, —(C$_0$-C$_3$)-alkylene-C(O)—O—R10, —(C$_0$-C$_3$)-alkylene-S(O)—R10, —S—CF$_3$, —(C$_0$-C$_3$)-alkylene-S(O)$_2$—R10, —(C$_0$-C$_5$)-alkylene-S(O)$_2$—N(R21)-R22, —(C$_0$-C$_3$)-alkylene-O—R10, —(C$_0$-C$_3$)-alkylene-N(R21)-R22, —(C$_0$-C$_3$)-alkylene-N(R10)-S(O)$_2$—R10, —(C$_0$-C$_5$)-alkylene-(C$_1$-C$_3$)-fluoroalkyl, —(C$_0$-C$_5$)-alkylene-(C$_3$-C$_8$)-cycloalkyl-R23, —(C$_0$-C$_5$)-alkylene-N(R10)-C(O)—R21, —(C$_0$-C$_5$)-alkylene-N(R10)-C(O)—N(R10)-R21, —(C$_0$-C$_5$)-alkylene-NH—C(O)—O—R21, —(C$_0$-C$_5$)-alkylene-O—C(O)—N(R10)-R21, —(C$_0$-C$_4$)-alkyl, where alkyl is unsubstituted or mono-, di- or trisubstituted independently by R9, —(C$_0$-C$_4$)-alkylene-aryl, where aryl is selected from the group of phenyl, indanyl, indenyl, naphthyl, biphenylyl, 2-biphenylyl, 3-biphenylyl, 4-biphenylyl, anthryl or fluoroenyl, where aryl is unsubstituted or mono-, di- or trisubstituted independently by R8, or —(C$_0$-C$_4$)-alkylene-Het, where Het is selected from the group of acridinyl, azepinyl, azetidinyl, aziridinyl, benzimidazolinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, deca-hydroquinolinyl, dibenzofuranyl, dibenzothiophenyl, dihydrofuran[2,3-b]-tetrahydrofuranyl, dihydrofuranyl, dioxolyl, dioxanyl, 2H, 6H-1,5,2-dithiazinyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolidinyl, 2-isothiazolinyl, isothiazolyl, isoxazolyl, isoxazolidinyl, 2-isoxazolinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, oxothiolanyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pryidooxazolyl, pyridoimidazolyl, pyridothiazolyl, pyridothiophenyl, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyridinyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienoimidazolyl, thienooxazolyl, thienopyridine, thienothiazolyl, thiomorpholinyl, thiophenyl, triazinyl, 1,2,3-triazolyl, 1,2,4-triazolyl, 1,2,5-triazolyl, 1,3,4-triazolyl and xanthenyl, and this Het radical is unsubstituted or independently mono-, di- or trisubstituted by R8, R8 is halogen, carbamimidoyl, —NO$_2$, =O, —CF$_3$, —SF$_5$, —C(O)—O—R10, —CN, —C(O)—NH$_2$, —OH, —NH$_2$, —O—CF$_3$, —C(O)—N(R10)-R20, —N(R10)-R20, —(C$_3$-C$_8$)-cycloalkyl, —O—(C$_1$-C$_8$)-alkyl, —O—(C$_0$-C$_4$)-alkylene-(C$_3$-C$_6$)-cycloalkyl, (C$_1$-C$_8$)-alkyl, —(C$_0$-C$_4$)-alkylene-(C$_3$-C$_8$)-cycloalkyl, where the alkyl radicals mentioned are each unsubstituted or mono-, di- or trisubstituted independently by halogen, NH$_2$, —OH, —O—CH$_3$, —SO$_2$—CH$_3$ or —SO$_2$—CF$_3$, R9 is halogen, —NO$_2$, —CN, =O, —OH, —CF$_3$, —C(O)—O—R10, —N(R21)-R22, —C(O)—N(R21)-R22, —(C$_3$-C$_8$)-cycloalkyl, —(C$_0$-C$_3$)-alkylene-O—R10, —Si—(CH$_3$)$_3$, —N(R10)-S(O)$_u$—R10 where u is the integer 1 or 2, —S—R10, —SO$_r$—R10 where r is the integer 1 or 2, —S(O)$_v$—N(R10)-R20 where v is the integer 1 or 2, —C(O)—R10, —(C$_1$-C$_8$)-alkyl, —(C$_1$-C$_8$)-alkoxy, phenyl, phenyloxy-, —(C$_1$-C$_3$)-fluoroalkyl, —O—R19, —NH—C(O)—NH—R10, —(C$_0$-C$_4$)-alkyl-C(O)—O—C(R19, R11)-O—C(O)—R12, —NH—C(O)—NH—R21, —N(R21)-C(O)—R22, —(C$_0$-C$_4$)-alkyl-C(O)—O—C(R19, R11)-O—C(O)—O—R12, —NH—C(O)—O—R10, —O—CF$_3$, Het, where Het is as defined above and is unsubstituted or mono-, di- or trisubstituted independently by R8, or a radical from the following list

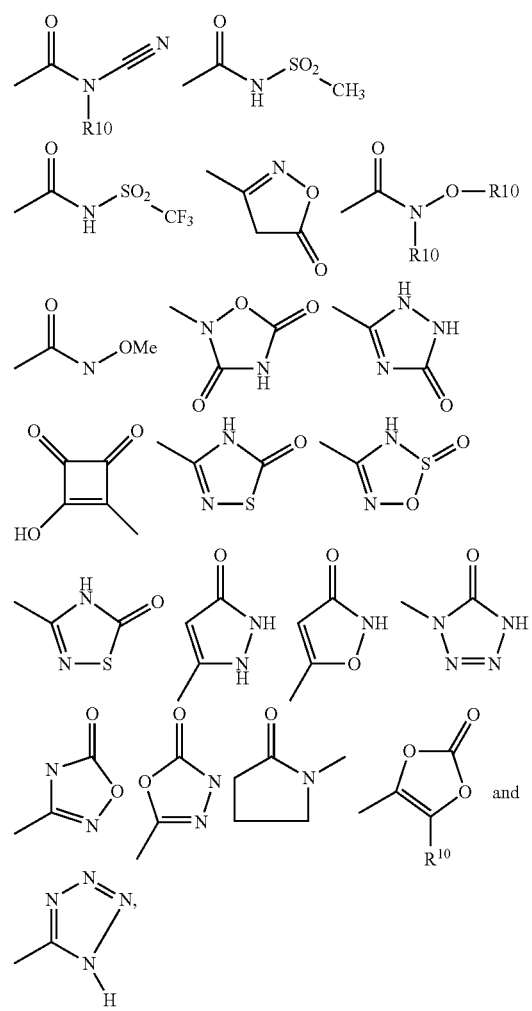

where Me is methyl,

R10 and R20 are the same or different and are each independently a hydrogen atom, —(C$_1$-C$_6$)-alkyl, —(C$_0$-C$_4$)-alkyl-OH, —(C$_1$-C$_3$)-fluoroalkyl, —(C$_0$-C$_4$)-alkyl-O—(C$_1$-C$_4$)-alkyl, —(C$_0$-C$_5$)-alkyl-(C$_3$-C$_8$)-cycloalkyl, —(C$_0$-C$_2$)-alkylene-aryl, where aryl is as defined above and is unsubstituted or mono-, di- or trisubstituted independently by —(C$_1$-C$_6$)-alkyl, —O—(C$_1$-C$_6$)-alkyl, halogen or —(C$_3$-C$_8$)-cycloalkyl, or —(C$_0$-C$_2$)-alkylene-Het where Het is as defined above and is unsubstituted or mono-, di- or trisubstituted independently by —(C$_1$-C$_6$)-alkyl, —O—(C$_1$-C$_6$)-alkyl, halogen or —(C$_3$-C$_8$)-cycloalkyl, R19 and R11 are the same or different and are each independently a hydrogen atom or —(C$_1$-C$_6$)-alkyl, or R19 and R11, together with the carbon atom to which they are bonded, form a three- to six-membered cycloalkyl ring which is unsubstituted or mono-, di- or trisubstituted independently by R10, R12 is —(C$_1$-C$_6$)-alkyl, —(C$_1$-C$_6$)-alkyl-OH, —(C$_1$-C$_6$)-alkyl-O—(C$_1$-C$_6$)-alkyl, —(C$_3$-C$_8$)-cycloalkyl, —(C$_1$-C$_6$)-alkyl-O—(C$_1$-C$_8$)-alkyl-(C$_3$-C$_8$)-cycloalkyl, —(C$_1$-C$_6$)-alkyl-(C$_3$-C$_8$)-cycloalkyl, where the cycloalkyl radical is unsubstituted or mono-, di- or trisubstituted independently by —OH, —O—(C$_1$-C$_4$)-alkyl or R10, R21 and R22 are the same or different and are each independently a hydrogen atom, —(C$_1$-C$_6$)-alkyl, where alkyl is unsubstituted or mono-, di- or trisubstituted independently by R8, —O—R12, —(C$_0$-C$_6$)-alkylene-(C$_3$-C$_8$)-cycloalkyl, —SO$_t$—R10, where t is the integer 1 or 2, —(C$_1$-C$_3$)-fluoroalkyl, —(C$_0$-C$_6$)-alkylene-aryl where aryl is as defined above and alkylene and aryl are unsubstituted or mono-, di- or trisubstituted independently by R8, or —(C$_0$-C$_6$)-alkylene-Het where Het is as defined above and alkylene and Het are unsubstituted or mono-, di- or trisubstituted independently by R8, R21 and R22, together with the nitrogen atom to which they are bonded, form a four- to eight-membered heterocyclic ring which, as well as the nitrogen atom, may additionally contain, according to the ring size, one or two identical or different heteroatoms from the group of oxygen, nitrogen or sulfur, and in which the heterocycle is unsubstituted or mono-, di- or trisubstituted independently by R8, R23 is a hydrogen atom, —OH or —O—(C$_1$-C$_4$)-alkyl, X is a covalent bond, —N(R7)- or —O—, where R7 is a hydrogen atom, —(C$_0$-C$_4$)-alkylene-(C$_3$-C$_6$)-cycloalkyl or —(C$_1$-C$_4$)-alkyl, Y is a covalent bond, —C(O)—, —C(S)—, —C(=N—CN)—, —C(=CHNO$_2$)— or —S(O$_2$)—, R1 is a hydrogen atom, R2 and R3 are the same or different and are each independently a hydrogen atom or —(C$_0$-C$_3$)-alkylene-C(R27)(R28)(R29), R27 is a hydrogen atom, halogen, —(C$_1$-C$_9$)-alkyl, —(C$_1$-C$_3$)-fluoroalkyl, —(C$_0$-C$_4$)-alkylene-(C$_3$-C$_6$)-cycloalkyl, —(C$_0$-C$_4$)-alkylene-aryl where aryl is as defined above and is unsubstituted or mono-, di- or trisubstituted independently by R8, —(C$_0$-C$_4$)-alkylene-Het where Het is as defined above and is unsubstituted or mono-, di- or trisubstituted independently by R8, or —(C$_0$-C$_4$)-alkylene-R15-R16, R28 and R29 are the same or different and are each independently a hydrogen atom, —(C$_1$-C$_4$)-alkyl or fluorine, R28 and R29, together with the carbon atom to which they are bonded, form a —(C$_3$-C$_6$)-cycloalkyl, R15 is —N(R17)-, —O—, —S—, —S(O)—, —S(O$_2$)—, —C(O)—, —C(O)—O—, —O—C(O)—, —N(R17)-C(O)—, —C(O)—N(R17)-, —S(O$_2$)—N(R17)-, —N(R17)-S(O$_2$)—, —N(R17)-C(O)—O—, —O—C(O)—N(R17)-, —N(R17)-C(O)—N(R18)- or —N(R17)-S(O$_2$)—N(R18)-, where R17 and R18 are the same or different and are each independently a hydrogen atom or —(C$_1$-C$_6$)-alkyl, R16 is a hydrogen atom, —(C$_1$-C$_6$)-alkyl, —(C$_0$-C$_4$)-alkylene-(C$_3$-C$_6$)-cycloalkyl, —(C$_1$-C$_3$)-fluoroalkyl, —(C$_0$-C$_4$)-alkylene-aryl where aryl is as defined above and is unsubstituted or mono-, di- or trisubstituted independently by R8, —(C$_0$-C$_4$)-alkylene-Het where Het is as defined above and is unsubstituted or mono-, di- or trisubstituted independently by R8, R2 and R3, together with the carbon atom to which they are bonded, form a three- to six-membered cycloalkyl ring which is unsubstituted or mono-, di- or trisubstituted independently by R8, or R2 and R3, together with the carbon atom to which they are bonded, form a three- to six-membered heterocycloalkyl radical which is unsubstituted or mono-, di- or trisubstituted independently by R10, and Z is the —N(R26)-C(R24)(R25)-CN radical, where R26 is a hydrogen atom, —(C$_1$-C$_4$)-alkyl or —(C$_0$-C$_4$)-alkylene-(C$_3$-C$_6$)-cycloalkyl, R24 and R25 are the same or different and are each independently a hydrogen atom, —(C$_1$-C$_6$)-alkyl, —(C$_0$-C$_4$)-alkylene-(C$_3$-C$_6$)-cycloalkyl, —(C$_1$-C$_3$)-fluoroalkyl, —(C$_0$-C$_4$)-alkylene-aryl where aryl is as defined above and is unsubstituted or mono-, di- or trisubstituted independently by R8, —(C$_0$-C$_4$)-alkylene-Het where Het is as defined above and is unsubstituted or mono-, di- or trisubstituted by R8, or —(C$_1$-C$_4$)-alkylene-R15-R16, or R24 and R25, together with the carbon atom to which they are bonded, form a three- to six-membered cycloalkyl ring which is unsubstituted or mono-, di- or trisubstituted independently by R10 or fluorine, R24 and R25, together with the carbon atom to which they are bonded, form a three- to six-membered heterocycloalkyl radical which is unsubstituted or mono-, di- or trisubstituted independently by R10 or fluorine.

4) The invention further provides the compound of the formula Ia

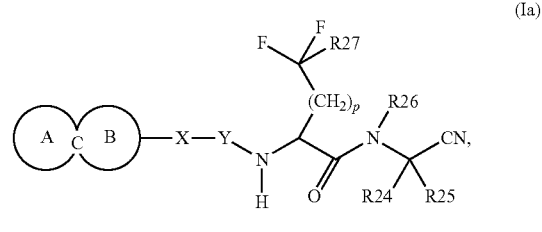

(Ia)

where the sub-rings

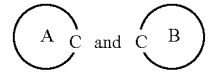

are each selected from the abovementioned groups, and in which the two sub-rings are each unsubstituted or independently, according to the ring size, mono-, di-, tri-, tetra- or pentasubstituted by R4, R4 is —NO$_2$, —CN, =O, =S, —OH, —CF$_3$, —SF$_5$, —(C$_0$-C$_3$)-alkylene-S—R10, —O—CF$_3$, —Si—(CH$_3$)$_3$, —O—CF$_3$, —(C$_0$-C$_5$)-alkylene-O—C(O)—R21, —(C$_0$-C$_5$)-alkylene-C(O)—O—R10, —(C$_0$-C$_3$)-alkylene-O—R10, —(C$_0$-C$_3$)-alkylene-N(R21)-R22, —(C$_0$-C$_3$)-alkylene-N(R10)—S(O$_2$)—R10, —(C$_0$-C$_5$)-alkylene-(C$_3$-C$_8$)-cycloalkyl-R23, —(C$_0$-C$_5$)-alkylene-(C$_1$-C$_3$)- fluoroalkyl, —($C_0$-$C_5$)-alkylene-N(R10)-C(O)—R21, —($C_0$-$C_3$)-alkylene-C(O)—N(R21)-R22, —($C_0$-$C_4$)-alkyl where alkyl is unsubstituted or mono-, di- or trisubstituted independently by R9, —($C_0$-$C_4$)-alkylene-aryl where aryl is selected from the group of phenyl, indanyl, indenyl, naphthyl, where aryl is unsubstituted or mono-, di- or trisubstituted independently by R8, or —($C_0$-$C_4$)-alkylene-Het where Het is selected from the group of azetidinyl, benzimidazolinyl, benzimidazolyl, benzofuranyl, benzothiophenyl, benzoxazolyl, benzthiazolyl, benzisoxazolyl, benzisothiazolyl, quinolinyl, dioxolyl, dioxanyl, furanyl, imidazolidinyl, imidazolinyl, imidazolyl, indolinyl, indolyl, 3H-indolyl, isoindolinyl, isoindolyl, isoquinolinyl, isothiazolidinyl, 2-isothiazolinyl, isothiazolyl, isoxazolyl, isoxazolidinyl, 2-isoxazolinyl, morpholinyl, octahydroisoquinolinyl, oxazolyl, oxazolidinyl, pyrimidinyl, piperazinyl, piperidinyl, pyranyl, pyrazinyl, pyrazolinyl, pyrazolyl, pyridazinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyridinyl, thiazolyl, thienyl, thienopyridinyl, thiomorpholinyl, thiophenyl, and this Het radical is unsubstituted or independently mono-, di- or trisubstituted by R8, R8 is halogen, carbamimidoyl, —$NO_2$, =O, —$CF_3$, —$SF_5$, —C(O)—O—R10, —CN, —C(O)—$NH_2$, —OH, —$NH_2$, —O—$CF_3$, —C(O)—N(R10)-R20, —N(R10)-R20, —($C_3$-$C_8$)-cycloalkyl, —O—($C_1$-$C_8$)-alkyl, —O—($C_0$-$C_4$)-alkylene-($C_3$-$C_6$)-cycloalkyl, —($C_1$-$C_8$)-alkyl, —($C_0$-$C_4$)-alkylene-($C_3$-$C_8$)-cycloalkyl, where the alkyl radicals mentioned are each unsubstituted or mono-, di- or trisubstituted independently by halogen, $NH_2$, —OH, —O—$CH_3$, —$SO_2$—$CH_3$ or —$SO_2$—$CF_3$, R9 is halogen, —$NO_2$, —CN, =O, —OH, —$CF_3$, —C(O)—O—R10, —C(O)—N(R21)-R22, —N(R21)-R22, —($C_3$-$C_8$)-cycloalkyl, —($C_0$-$C_3$)-alkylene-O—R10, —Si($CH_3$)$_3$, —N(R10)-S(O)$_u$—R10 where u is the integer 1 or 2, —S—R10, —$SO_r$—R10 where r is the integer 1 or 2, —S(O)$_v$—N(R10)-R20 where v is the integer 1 or 2, —C(O)—R10, —($C_1$-$C_8$)-alkyl, —($C_1$-$C_8$)-alkoxy, phenyl, phenyloxy-, —($C_1$-$C_3$)-fluoroalkyl, —O—R19, —NH—C(O)—NH—R10, —($C_0$-$C_4$)-alkyl-C(O)—O—C(R11,R19)-O—C(O)—R12, —NH—C(O)—NH—R21, —N(R21)-C(O)—R22, —($C_0$-$C_4$)-alkyl-C(O)—O—C(R11,R19)-O—C(O)—O—R12, —NH—C(O)—O—R10, —O—$CF_3$ or Het where Het is as defined above and is unsubstituted or mono-, di- or trisubstituted independently by R8, R10 and R20 are the same or different and are each independently a hydrogen atom, —($C_1$-$C_6$)-alkyl, —($C_0$-$C_4$)-alkyl-OH, —($C_1$-$C_3$)-fluoroalkyl, —($C_0$-$C_4$)-alkyl-O—($C_1$-$C_4$)-alkyl, —($C_0$-$C_5$)-alkyl-($C_3$-$C_8$)-cycloalkyl, —($C_0$-$C_2$)-alkylene-aryl where aryl is as defined above and is unsubstituted or mono-, di- or trisubstituted independently by —($C_1$-$C_6$)-alkyl, —O—($C_1$-$C_6$)-alkyl, halogen or —($C_3$-$C_8$)-cycloalkyl, or —($C_0$-$C_2$)-alkylene-Het where Het is as defined above and is unsubstituted or mono-, di- or trisubstituted independently by —($C_1$-$C_6$)-alkyl, —O—($C_1$-$C_6$)-alkyl, halogen or —($C_3$-$C_8$)-cycloalkyl, R11 and R19 are the same or different and are each independently a hydrogen atom or —($C_1$-$C_6$)-alkyl, R12 is —($C_1$-$C_6$)-alkyl, —($C_1$-$C_6$)-alkyl-OH, —($C_1$-$C_6$)-alkyl-O—($C_1$-$C_6$)-alkyl, —($C_3$-$C_8$)-cycloalkyl, —($C_1$-$C_6$)-alkyl-O—($C_1$-$C_8$)-alkyl-($C_3$-$C_8$)-cycloalkyl, —($C_1$-$C_6$)-alkyl-($C_3$-$C_8$)-cycloalkyl, where the cycloalkyl radical is unsubstituted or mono-, di- or trisubstituted independently by —OH, —O—($C_1$-$C_4$)-alkyl or R10, R21 and R22 are the same or different and are each independently a hydrogen atom, —($C_1$-$C_6$)-alkyl where alkyl is unsubstituted or mono-, di- or trisubstituted independently by R8, —($C_0$-$C_6$)-alkylene-($C_3$-$C_8$)-cycloalkyl, —$SO_t$—R10 where t is the integer 1 or 2, —($C_1$-$C_3$)-fluoroalkyl, —O—R12, —($C_0$-$C_6$)-alkylene-aryl where aryl is as defined above and alkylene and aryl are each unsubstituted or mono-, di- or trisubstituted independently by R8 or —($C_0$-$C_6$)-alkylene-Het where Het is as defined above and alkylene and Het are each unsubstituted or mono-, di- or trisubstituted independently by R8, R21 and R22, together with the nitrogen atom to which they are bonded, form a four- to eight-membered monocyclic heterocyclic ring which, as well as the nitrogen atom, additionally, according to the ring size, may contain one or two identical or different heteroatoms from the group of oxygen, nitrogen or sulfur and in which the heterocycle is unsubstituted or mono-, di- or trisubstituted independently by R8, R23 is a hydrogen atom, —OH or —O—($C_1$-$C_4$)-alkyl, X is a covalent bond, —N(R7)- or —O—, where R7 is a hydrogen atom, —($C_0$-$C_4$)-alkylene-($C_3$-$C_6$)-cycloalkyl or —($C_1$-$C_4$)-alkyl, Y is —C(O)—, —C(S)— or —S($O_2$)—, p is the integer 1 or 2, R27 is a hydrogen atom, —($C_1$-$C_6$)-alkyl, —($C_0$-$C_4$)-alkylene-($C_3$-$C_6$)-cycloalkyl, halogen, —($C_0$-$C_4$)-alkylene-Het where Het is as defined above and is unsubstituted or substituted by halogen, —($C_1$-$C_6$)-alkyl, —O—($C_1$-$C_3$)-fluoroalkyl or —O—($C_1$-$C_6$)-alkyl, or —($C_0$-$C_2$)-alkylene-phenyl where phenyl is unsubstituted or substituted by halogen, —($C_1$-$C_6$)-alkyl, —O—($C_1$-$C_3$)-fluoroalkyl or —O—($C_1$-$C_6$)-alkyl, R26 is a hydrogen atom, —($C_1$-$C_4$)-alkyl or —($C_0$-$C_4$)-alkylene-($C_3$-$C_6$)-cycloalkyl, R24 and R25 are the same or different and are each independently a hydrogen atom, —($C_1$-$C_6$)-alkyl, —($C_0$-$C_4$)-alkylene-($C_3$-$C_6$)-cycloalkyl, —($C_1$-$C_3$)-fluoroalkyl, —($C_0$-$C_4$)-alkylene-aryl where aryl is as defined above and is unsubstituted or mono-, di- or trisubstituted independently by R8, or —($C_0$-$C_4$)-alkylene-Het where Het is as defined above and is unsubstituted or mono-, di- or trisubstituted independently by R8, R24 and R25, together with the carbon atom to which they are bonded, form a three- to six-membered cycloalkyl ring which is unsubstituted or mono-, di- or trisubstituted independently by R10 or fluorine, R24 and R25, together with the carbon atom to which they are bonded, form a three- to six-membered heterocycloalkyl radical which is unsubstituted or mono-, di- or trisubstituted independently by R10 or fluorine.

5) The invention further provides the compound of the formula Ia where
the sub-rings

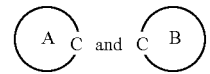

have each been selected from cyclopropane, cyclobutane, cyclopentane, cyclohexane, cycloheptane, cyclooctane, bicyclo[4.2.0]octane, octahydroindene, decalin, decahydrobenzocycloheptene, dodecahydroheptalene, bicyclo

[3.1.1]heptane, bicyclo[2.2.1]heptane, bicyclo[3.3.0]octane, bicyclo[2.2.2]octane, spiro[2.5]octane, spiro[3.4]octane, azepane, azepine, azetidine, aziridine, azirine, azocane, benzimidazoline, 2,3-dihydrobenzo[b]thiophene, 1,3-dihydrobenzo[c]thiophene, 2,3-dihydrobenzofuran, 2,3-dihydrobenzooxazole, 2,3-dihydrobenzothiazole, 1,3-dihydroisobenzofuran, 4,5-dihydroisothiazole, 2,3-dihydroisoxazole, 2,5-dihydroisoxazole, 4,5-dihydroisoxazole, 5,6-dihydro-4H-[1,2]oxazine, benzo[1,3]dioxole, 1,4-diazepane, 1,2-diazepine, 1,3-diazepine, 1,4-diazepine, diaziridine, diazirine, 1,4-diazocane, dioxane, 1,3-dioxane, dioxazine, [1,3]dioxepane, 1,4-diozocane, dioxole, dioxolane, 1,3-dioxolane, 1,3-dioxolene, [1,3]dithiane, [1,3]dithiolane, hexahydropyridazine, hexahydropyrimidine, imidazoline, imidazolidine, indane, indoline, isoindoline, isothiazolidine, isothiazoline, isoxazoline, isoxazolidine, 2-isoxazoline, morpholine, [1,3,4]oxadiazinane, [1,3,5]oxadiazinane, [1,2,3]oxadiazolidine, [1,3,4]oxadiazolidine, 1,2-oxathiepane, 1,2-oxathiolane, [1,3]oxathiolane, 1,4-oxazepane, 1,2-oxazine, 1,3-oxazine, 1,4-oxazine, oxazinane, 1,3-oxazinane, oxazocane, oxaziridine, oxazolidine, oxepane, oxetane, oxirane, oxocane, piperazine, piperidine, pyran, pyrazoline, pyrazolidine, pyrrolidine, pyrrolidinone, pyrroline, tetrahydroquinoline, tetrahydrofuran, tetrahydroisoquinoline, 1,2,3,4-tetrahydronaphthalene, tetrahydropyran, tetrahydropyridine, 1,2,3,4-tetrahydro-pyrimidine, 1,2,5,6-tetrahydropyrimidine, tetrahydrothiophene, tetrazine, thiadiazine, [1,2,6]thiadiazinane, [1,3,4]thiadiazolidine, 1,2-thiazine, 1,3-thiazine, 1,4-thiazine, [1,2]thiazinane, [1,3]thiazinane, thiazolidine, thiazoline, thiepane, thietane, thiomorpholine, thiopyran, 1,2,3-triazine, 1,2,4-triazine, 1,3,5-triazine, [1,2,4]triazinane or [1,2,4]triazolidine, and in which the two sub-rings are each unsubstituted or independently, according to the ring size, mono-, di-, tri-, tetra- or pentasubstituted by R4, and the X, Y, R27, p, R26, R24, R25 and R4 radicals are each as defined under 4).

6) The invention further provides the compound of the formula Ia where
the sub-rings

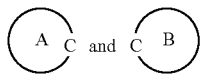

are each independently selected from the group of azetidine, cyclopropyl, cyclobutyl, cyclopentyl, cyclohexyl, 1,3-dihydroisobenzofuran, 2,3-dihydroisoxazole, 2,5-dihydroisoxazole, 4,5-dihydroisoxazole, 1,3-dioxane, dioxolane, 1,3-dioxolane, imidazolidine, indane, morpholine, 1,3-oxazinane, oxazolidine, piperazine, piperidine, pyrrolidine, tetrahydrofuran, and 1,2,3,4-tetrahydronaphthalene, and in which the two sub-rings are each unsubstituted or independently, according to the ring size, mono-, di- or trisubstituted by R4, R4 is =O, =S, —($C_0$-$C_3$)-alkylene-C(O)—O—R10, —($C_0$-$C_3$)-alkylene-N(R21)-R22, —($C_0$-$C_3$)-alkylene-NH—C(O)—R21, —($C_0$-$C_4$)-alkylene-($C_3$-$C_6$)-cycloalkyl-R23, —($C_0$-$C_3$)-alkylene-O—R10, —($C_0$-$C_4$)-alkylene-phenyl, where phenyl is unsubstituted or mono-, di- or trisubstituted independently by R8, or —($C_0$-$C_4$)-alkyl where alkyl is unsubstituted or mono-, di- or trisubstituted independently by R9, R8 is fluorine, chlorine, bromine, —O—($C_1$-$C_3$)-fluoroalkyl or —O—($C_1$-$C_4$)-alkyl, R9 is halogen, —$NO_2$, —CN, =O, —OH, —$CF_3$, —C(O)—O—R10, —C(O)—N(R21)-R22, —N(R21)-R22, —($C_3$-$C_8$)-cycloalkyl, —($C_0$-$C_3$)-alkylene-O—R10, —Si—$(CH_3)_3$, —N(R10)-S(O)$_u$—R10 where u is the integer 1 or 2, —S—R10, —$SO_r$—R10 where r is the integer 1 or 2, —S(O)$_v$—N(R10)-R20 where v is the integer 1 or 2, —C(O)—R10, —($C_1$-$C_8$)-alkyl, —($C_1$-$C_8$)-alkoxy, phenyl, phenyloxy-, —($C_1$-$C_3$)-fluoroalkyl, —O—R19, —NH—C(O)—NH—R10, —($C_0$-$C_4$)-alkyl-C(O)—O—C(R11,R19)-O—C(O)—R12, —NH—C(O)—NH—R21, —N(R21)-C(O)—R22, —($C_0$-$C_4$)-alkyl-C(O)—O—C(R11,R19)-O—C(O)—O—R12, —NH—C(O)—O—R10 or —O—$CF_3$, R10 and R20 are the same or different and are each independently a hydrogen atom or —($C_1$-$C_6$)-alkyl, R11 and R19 are the same or different and are each independently a hydrogen atom or —($C_1$-$C_6$)-alkyl, R12 is —($C_1$-$C_6$)-alkyl, —($C_1$-$C_6$)-alkyl-OH, —($C_1$-$C_6$)-alkyl-O—($C_1$-$C_6$)-alkyl, —($C_3$-$C_8$)-cycloalkyl, —($C_1$-$C_6$)-alkyl-O—($C_1$-$C_8$)-alkyl-($C_3$-$C_8$)-cycloalkyl, —($C_1$-$C_6$)-alkyl-($C_3$-$C_8$)-cycloalkyl, where the cycloalkyl radical is unsubstituted or mono-, di- or trisubstituted independently by —OH, —O—($C_1$-$C_4$)-alkyl or R10, R21 and R22 are the same or different and are each independently a hydrogen atom, —($C_1$-$C_6$)-alkyl, —($C_0$-$C_6$)-alkylene-($C_3$-$C_8$)-cycloalkyl, —O—R12, —$SO_t$—R10 where t is the integer 1 or 2, or —($C_1$-$C_3$)-fluoroalkyl, R23 is a hydrogen atom, —OH or —O—($C_1$-$C_4$)-alkyl, X is a covalent bond or —N(R7)- where R7 is a hydrogen atom or —($C_1$-$C_4$)-alkyl, Y is —C(O)— or —S($O_2$)—, p is the integer 1 or 2, R26 is a hydrogen atom, R27 is a hydrogen atom, —($C_1$-$C_6$)-alkyl, —($C_0$-$C_4$)-alkylene-($C_3$-$C_6$)-cycloalkyl, —($C_0$-$C_2$)-alkylene-phenyl where phenyl is unsubstituted or substituted by halogen, —($C_1$-$C_6$)-alkyl, —O—($C_1$-$C_3$)-fluoroalkyl or —O—($C_1$-$C_6$)-alkyl, or —($C_0$-$C_2$)-alkylene-pyridyl, R24 and R25 are the same or different and are each independently a hydrogen atom, —($C_1$-$C_4$)-alkyl or —($C_0$-$C_4$)-alkylene-($C_3$-$C_6$)-cycloalkyl, R24 and R25, together with the carbon atom to which they are bonded, form a cycloalkyl ring which is selected from the group of cyclopropyl, cyclobutyl, cyclopentyl and cyclohexyl, and is unsubstituted or mono-, di- or trisubstituted independently by R10 or fluorine, R24 and R25, together with the carbon atom to which they are bonded, form a three- to six-membered heterocycloalkyl radical selected from the group of aziridine, azetidine, diazetidine, diaziridine, hexohydropyridazine, hexohydropyrimidine, imidazolidine, morpholine, oxadiazinane, oxadiazolidine, oxathianane, oxathiolane, oxazetidine, oxazolidine, oxetane, oxirane, piperazine, piperidine, pyrazolidine, pyrrolidine, tetrahydrofuran, tetrahydropyran, tetrahydrothiophene, tetrahydrothiopyran, tetrazinane, thiadiazolidine, thiazetidine, thiaziridine, thiazolidine, thietane, thiirane, thiomorpholine, triazetidine, triazinane or triazolidine, which is unsubstituted or mono-, di- or trisubstituted independently by R10 or fluorine.

7) The invention further provides the compound of the formula Ia where
the sub-ring

is selected from the group of azetidine, cyclopropyl, cyclobutyl, cyclopentyl, cyclohexyl, 1,3-dihydroisobenzofuran, 1,3-dioxane, 1,3-dioxolane, imidazolidine, indane, morpholine, 1,3-oxazinane, piperazine, piperidine, pyrrolidine, tetrahydrofuran, and 1,2,3,4-tetrahydronaphthalene,
the sub-ring

is selected from the group of azetidine, cyclopropyl, cyclopentyl, cyclohexyl, morpholine, oxazolidine, piperidine and pyrrolidine, and in which the two sub-rings are unsubstituted or independently, according to the ring size, mono-, di- or tri-substituted by R4 where R4 is —O—($C_1$-$C_4$)-alkyl, =O, —($C_0$-$C_4$)-alkylene-($C_3$-$C_6$)-cycloalkyl, —($C_1$-$C_4$)-alkyl or —($C_0$-$C_4$)-alkylene-phenyl where phenyl is unsubstituted or substituted by F, Cl, Br or —O—($C_1$-$C_4$)-alkyl, X is a covalent bond or —NH—, Y is —C(O)— or —S($O_2$)—, p is the integer 1, R27 is a hydrogen atom, —($C_1$-$C_6$)-alkyl, 4-F-benzyl or benzyl, R26 is a hydrogen atom, R24 and R25 are the same or different and are each independently a hydrogen atom, methyl or ethyl, R24 and R25, together with the carbon atom to which they are bonded, form a cyclopropyl or cyclobutyl radical, or R24 and R25, together with the carbon atom to which they are bonded, form a piperidine ring which is unsubstituted or substituted by —($C_1$-$C_4$)-alkyl.

8) The invention further provides compounds of the formula I or Ia from the group of N—[(S)-1-(1-cyanocyclopropylcarbamoyl)-3,3-difluorobutyl]-3-azaspiro[5.5]undecane-3-carboxamide, N—[(S)-1-(1-cyanocyclopropylcarbamoyl)-3,3-difluorobutyl]-8-azaspiro[4.5]decane-8-carboxamide, N—[(S)-1-(1-cyanocyclopropylcarbamoyl)-3,3-difluorobutyl]-1,4-dioxa-8-azaspiro[4.5]decane-8-carboxamide, N—[(S)-1-(1-cyanocyclopropylcarbamoyl)-3,3-difluorobutyl]-2-azaspiro[5.5]undecane-2-carboxamide, N—[(S)-1-(1-cyanocyclopropylcarbamoyl)-3,3-difluorohexyl]-8-azaspiro[4.5]decane-8-carboxamide, N—[(S)-1-(1-cyanocyclopropylcarbamoyl)-3,3-difluorohexyl]-3-azaspiro[5.5]undecane-3-carboxamide, N—[(S)-1-(1-cyanocyclopropylcarbamoyl)-3,3-difluorobutyl]-2-(4-methoxyphenyl)-1-oxo-2,8-diazaspiro[4.5]decane-8-carboxamide, N—[(S)-1-(1-cyanocyclopropylcarbamoyl)-3,3-difluorobutyl]-4-oxo-1-phenyl-1,3,8-tri-azaspiro[4.5]decane-8-carboxamide, N—[(S)-1-(1-cyanocyclopropylcarbamoyl)-3,3-difluorobutyl]-1,5-dioxa-9-aza-spiro[5.5]undecane-9-carboxamide, N—[(S)-1-(1-cyanocyclopropylcarbamoyl)-3,3-difluorobutyl]-1-oxo-2,8-diazaspiro[4.5]decane-8-carboxamide, N—[(S)-1-(1-cyanocyclopropylcarbamoyl)-3,3-difluorobutyl]-2-methyl-1-oxo-2,8-diazaspiro[4.5]decane-8-carboxamide, N—[(S)-1-(1-cyanocyclopropylcarbamoyl)-3,3-difluorobutyl]-3,3-dimethyl-1-oxa-5,9-diazaspiro[5.5]undecane-9-carboxamide, N—[(S)-1-(1-cyanocyclopropylcarbamoyl)-3,3-difluoro-4-phenylbutyl]-8-azaspiro[4.5]decane-8-carboxamide, N—[(S)-1-(1-cyanocyclopropylcarbamoyl)-3,3-difluorobutyl]-2,4-dioxo-1,3,8-triazaspiro[4.5]decane-8-carboxamide, N—[(S)-1-(1-cyanocyclopropylcarbamoyl)-3,3-difluorobutyl]-2-azaspiro[4.4]nonane-2-carboxamide, N—[(S)-1-(1-cyanocyclopropylcarbamoyl)-3,3-difluorobutyl]-2-benzyl-1-oxo-2,8-diazaspiro[4.5]decane-8-carboxamide, N—[(S)-1-(1-cyanocyclopropylcarbamoyl)-3,3-difluorobutyl]-2-(4-fluoro phenyl)-1-oxo-2,8-diazaspiro[4.5]decane-8-carboxamide, N—[(S)-1-(1-cyanocyclopropylcarbamoyl)-3-methylbutyl]-1,4-dioxaspiro[4.5]decane-8-carboxamide, N—[(S)-1-(1-cyanocyclopropylcarbamoyl)-3,3-difluorobutyl]-3-phenyl-1,5-dioxa-9-azaspiro[5.5]undecane-9-carboxamide, N-[1-(1-cyanocyclopropylcarbamoyl)cyclohexyl]-8-azaspiro[4.5]decane-8-carboxamide, N—[S)-(1-cyanocyclopropylcarbamoyl)cyclohexylmethyl]-8-azaspiro[4.5]decane-8-carboxamide, N—[(S)-1-(1-cyanocyclopropylcarbamoyl)-3,3-difluorobutyl]-9-butyl-3,9-diazaspiro[5.5]undecane-3-carboxamide, N—[(S)-1-(1-cyanocyclopropylcarbamoyl)-3,3-difluorobutyl]-9-cyclopropyl-3,9-diazaspiro[5.5]undecane-3-carboxamide, N—[(S)-1-(1-cyanocyclopropylcarbamoyl)-3-methylbutyl] spiro[2.3]hexane-1-carboxamide, N—[(S)-1-(1-cyanocyclopropylcarbamoyl)-3,3-difluoro-4-phenylbutyl]-8-azaspiro[4.5]decane-8-carboxamide, N—[(S)-1-(1-cyanocyclopropylcarbamoyl)-3,3-difluorobutyl]spiro[2.3]hexane-1-carboxamide, N—[(S)-1-(1-cyanocyclopropylcarbamoyl)-3,3-difluorobutyl]-2,2-dimethyl-1-oxa-8-azaspiro[4.5]decane-8-carboxamide, N—[(S)-1-(1-cyanocyclopropylcarbamoyl)-3,3-difluorobutyl]-2-azaspiro[4.5]decane-2-carboxamide,

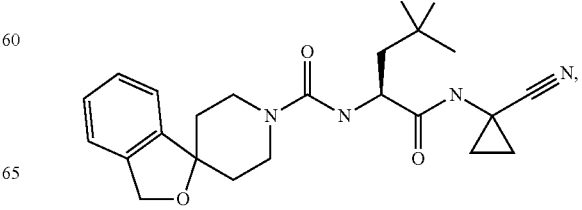

-continued

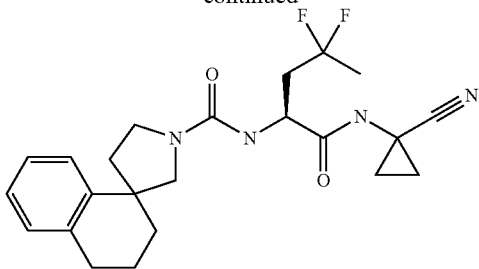

N—[(S)-1-(1-cyanocyclopropylcarbamoyl)-3,3-difluorobutyl]-1-oxa-4-azaspiro[4.5]decane-4-carboxamide,
N-(1-cyanocyclopropyl)-(S)-2-[3-(1,4-dioxaspiro[4.5]dec-8-yl)ureido]-4,4-difluoropentoxide,

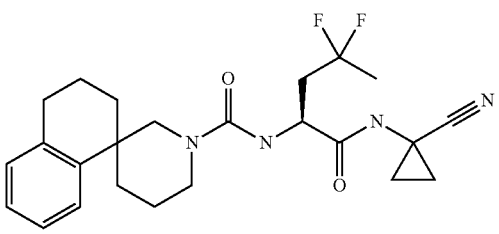 [SMILES: CC(F)(F)C[C@H](NC(=O)N1CCCC2(CCCc3ccccc32)C1)C(=O)NC1(C#N)CC1]

N—[(S)-1-(1-cyanocyclopropylcarbamoyl)3,3-difluorobutyl]-7-cyclopropyl-2,7-diazaspiro[3.5]nonane-2-carboxamide,
N—[(S)-1-(1-cyanocyclopropylcarbamoyl)-3,3-difluorobutyl]-2-cyclopropyl-2,7-diazaspiro[3.5]nonane-7-carboxamide,
N—[(S)-1-(1-cyanocyclopropylcarbamoyl)-3,3-difluorobutyl]-2-propyl-2,7-diazaspiro[3.5]nonane-7-carboxamide,
N-(1-cyanocyclopropyl)-(S)-2-(8-azaspiro[4.5]decane-8-sulfonylamino)-4,4-difluoropentoxide,
N—[(S)-1-(1-cyanocyclopropylcarbamoyl)-3,3-difluorobutyl]-4-cyclopropyl-1-oxa-4,9-diazaspiro[5.5]undecane-9-carboxamide,
N—[(S)-1-(1-cyanocyclopropylcarbamoyl)-3,3-difluorobutyl]-9-cyclopropyl-1-oxa-4,9-diazaspiro[5.5]undecane-4-carboxamide,
N—[(S)-1-(1-cyanocyclopropylcarbamoyl)-3,3-difluorobutyl]-2-cyclopropylmethyl-3-oxo-2,8-diazaspiro[4.5]decane-8-carboxamide,

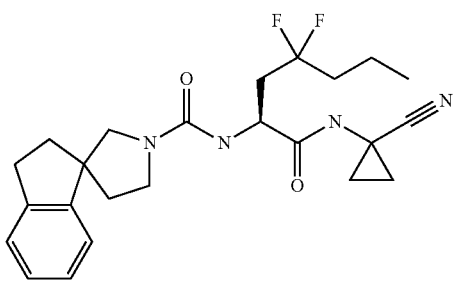 [SMILES: CCCC(F)(F)C[C@H](NC(=O)N1CCC2(CCc3ccccc32)C1)C(=O)NC1(C#N)CC1]

N—[(S)-1-(1-cyanocyclopropylcarbamoyl)-3,3-difluorohexyl]-2-(4-methoxyphenyl)-1-oxo-2,8-diazaspiro[4.5]decane-8-carboxamide,
N—[(S)-1-(1-cyanocyclopropylcarbamoyl)-3,3-difluorohexyl]-2-(4-methoxyphenyl)-2,8-diazaspiro[4.5]decane-8-carboxamide, N—[(S)-1-(1-cyanocyclopropylcarbamoyl)-3,3-difluorohexyl]-2-cyclopropyl-2,7-diazaspiro[3.5]nonane-7-carboxamide,
N—[(S)-1-(1-cyanocyclopropylcarbamoyl)-3,3-difluorohexyl]-2-cyclopropyl-2,8-diazaspiro[4.5]decane-8-carboxamide,
N—[(S)-1-(1-cyanocyclopropylcarbamoyl)-3,3-difluorohexyl]-9-cyclopropyl-3,9-diazaspiro[5.5]undecane-3-carboxamide,
N—[(S)-1-(1-cyanocyclopropylcarbamoyl)-3,3-difluorohexyl]-7-cyclopropyl-2,7-diazaspiro[3.5]nonane-2-carboxamide,
N—[(S)-1-(1-cyanocyclopropylcarbamoyl)-3,3-difluorohexyl]-7-propyl-2,7-diazaspiro[3.5]nonane-2-carboxamide,
N—[(S)-1-(1-cyanocyclopropylcarbamoyl)-3,3-difluoro-4-phenylbutyl]-9-cyclopropyl-3,9-diazaspiro[5.5]undecane-3-carboxamide,
N—[(S)-1-(1-cyanocyclopropylcarbamoyl)-3,3-difluoro-4-phenylbutyl]-2-cyclopropyl-2,7-diazaspiro[3.5]nonane-7-carboxamide,
N—[(S)-1-(1-cyanocyclopropylcarbamoyl)-3,3-difluoro-4-phenylbutyl]-2-propyl-2,7-diazaspiro[3.5]nonane-7-carboxamide,
N—[(S)-1-(1-cyanocyclopropylcarbamoyl)-3,3-difluoro-4-phenylbutyl]-7-cyclopropyl-2,7-diazaspiro[3.5]nonane-2-carboxamide,
N—[(S)-1-(1-cyanocyclopropylcarbamoyl)-3,3-difluorobutyl]-6-azaspiro[2.5]octane-6-carboxamide,
N—[(S)-1-(cyanomethylcarbamoyl)-3,3-difluorobutyl]-6-azaspiro[2.5]octane-6-carboxamide,
N—[(S)-1-(1-cyanocyclopropylcarbamoyl)-3,3-difluorohexyl]-6-azaspiro[2.5]octane-6-carboxamide,
N—[(S)-1-(4-cyano-1-methylpiperidin-4-ylcarbamoyl)-3,3-difluorobutyl]-6-azaspiro[2.5]octane-6-carboxamide,
N—[(S)-1-(4-cyano-1-methylpiperidin-4-ylcarbamoyl)-3,3-difluorohexyl]-6-azaspiro[2.5]octane-6-carboxamide,
N—[(S)-1-(1-cyanocyclopropylcarbamoyl)-3,3-difluoropentyl]- or N—[(S)-1-(1-cyanocyclopropylcarbamoyl)-3,3-difluoro-4-phenylbutyl]-6-azaspiro[2.5]octane-6-carboxamide.

The terms "$(C_1-C_3)$-alkyl", "$(C_1-C_4)$-alkyl" or "$(C_1-C_{10})$-alkyl" are understood to mean hydrocarbyl radicals whose carbon chain is straight or branched and contains from 1 to 3, from 1 to 4 or from 1 to 10 carbon atoms, for example methyl, ethyl, propyl, isopropyl, butyl, isobutyl, tert-butyl, pentyl, isopentyl, neopentyl, hexyl, 2,3-dimethylbutyl, neohexyl, heptyl, octanyl, nonanyl or decanyl.

The terms "—$(C_0-C_3)$-alkylene", "—$(C_0-C_4)$-alkylene" or "—$(C_0-C_5)$-alkylene" are understood to mean hydrocarbyl radicals whose carbon chain is straight or branched and contains from 1 to 3, from 1 to 4 or from 1 to 5 carbon atoms, for example methylene, ethylene, propylene, isopropylene, isobutylene, butylene, tert-butylene, isopentylene or neopentylene. "—$C_0$-Alkylene" is a covalent bond.

The term "$(C_1-C_8)$-alkoxy" is understood to mean radicals such as —O—$(C_1-C_8)$-alkyl where —$(C_1-C_8)$-alkyl is bonded by a carbon atom to an oxygen atom.

The radical "—C(O)-" is understood to mean a keto or aldehyde radical.

The "carbamimidoyl" radical is understood to mean a —C(NH$_2$)=NH radical.

The term "—$(C_3-C_8)$-cycloalkyl" is understood to mean radicals which derive from 3- to 8-membered monocycles such as the monocycles cyclopropane, cyclobutane, cyclopentane, cyclohexane, cycloheptane or cyclooctane.

The term "aryl" is understood to mean aromatic carbon radicals having from 6 to 14 carbon atoms in the ring. Aryl radicals are, for example, phenyl, indanyl, indenyl, naphthyl, 1,2,3,4-tetrahydronaphthyl, biphenylyl, 2-biphenylyl, 3-biphenylyl, 4-biphenylyl, anthryl or fluorenyl.

The term "a saturated or partly unsaturated —($C_3$-$C_{11}$)-cycloalkyl in which cycloalkyl is unbridged, bridged or fused" is understood to mean radicals, for example compounds which derive from 3- to 11-membered mono-, bicycles, bridged cycles or spirocycles: for example from the monocycles such as cyclopropane, cyclobutane, cyclopentane, cyclohexane, cycloheptane or cyclooctane, for example from the bicycles such as bicycloheptane, bicyclo[4.2.0]octane, octahydroindene, decalin, decahydro-benzocycloheptene or dodecahydroheptalene, for example from the bridged cycles such as bicyclo[3.1.1]heptane, bicyclo[2.2.1]heptane, bicyclo[3.3.0]octane or bicyclo[2.2.2]octane, or, for example, from the spirocycles such as spiro[2.5]octane and spiro[3.4]octane.

The term "a saturated or partly unsaturated three- to eleven-membered heterocycle which, according to the ring size, may contain one, two, three or four identical or different heteroatoms from the group of oxygen, nitrogen and sulfur, and in which the heterocycle is unbridged, bridged or fused" is understood to mean ring systems which have from three to eleven ring atoms and contain, as well as the carbon atoms, according to the ring size, one, two, three or four identical or different heteroatoms from the group of oxygen, nitrogen and sulfur. Examples of these ring systems are ring systems such as azepane, azepine, azetidine, aziridine, azirine, azocane, benzimidazoline, 2,3-dihydrobenzo[b]thiophene, 1,3-dihydrobenzo[c]thiophene, 2,3-dihydrobenzofuran, 2,3-dihydrobenzooxazole, 2,3-dihydrobenzothiazole, 1,3-dihydroisobenzofuran, 2,3-dihydroisoxazole, 2,5-dihydroisoxazole, 4,5-dihydroisoxazole, benzo[1,3]dioxole, 1,4-diazepane, 1,2-diazepine, 1,3-diazepine, 1,4-diazepine, diaziridine, diazirine, 1,4-diazocane, dioxane, 1,3-dioxane, dioxazin, 1,4-diozocane, dioxole, dioxolane, 1,3-dioxolane, 1,3-dioxolene, imidazoline, imidazolidine, indane, indoline, isoindoline, isothiazolidine, isothiazoline, isoxazoline, isoxazolidine, 2-isoxazoline, morpholine, 1,2-oxathiepane, 1,2-oxathiolane, 1,4-oxazepane, 1,2-oxazine, 1,3-oxazine, 1,4-oxazine, oxazinane, 1,3-oxazinane, oxazocane, oxaziridine, oxazolidine, oxetane, oxirane, oxocane, piperazine, piperidine, pyran, pyrazoline, pyrazolidine, pyrrolidine, pyrrolidinone, pyrroline, tetrahydroquinoline, tetrahydrofuran, tetrahydroisoquinoline, 1,2,3,4-tetrahydronaphthalene, tetrahydropyran, tetrahydropyridine, tetrazine, thiadiazine, 1,2-thiazine, 1,3-thiazine, 1,4-thiazine, thiazolidine, thiazoline, thietane, thiomorpholine, thiopyran, 1,2,3-triazine, 1,2,4-triazine or 1,3,5-triazine.

Spiro compounds are compounds of two or three rings in which, in each case, one ring atom belongs to two rings in common. Preference is given to spiro compounds which consist of two rings in which, in each case, one ring atom belongs to two ring atoms in common. This ring atom is either a carbon atom or a nitrogen atom, preferably a carbon atom. The spiro linkage of the two sub-rings may be via all conceivable positions. Preferred spiro compounds in all possible stereoisomeric forms are:

 

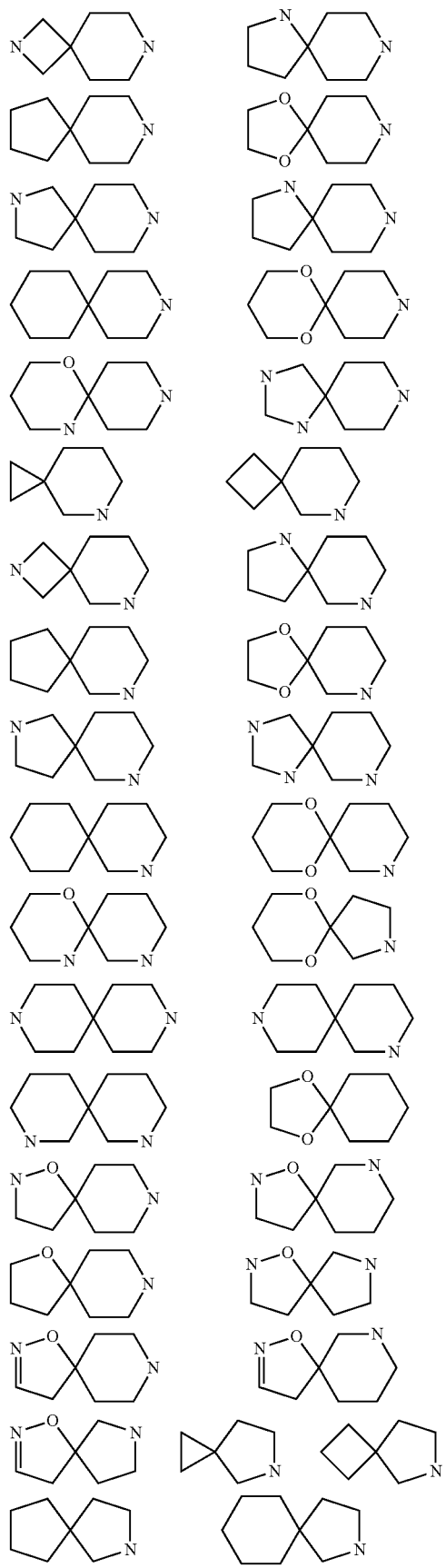

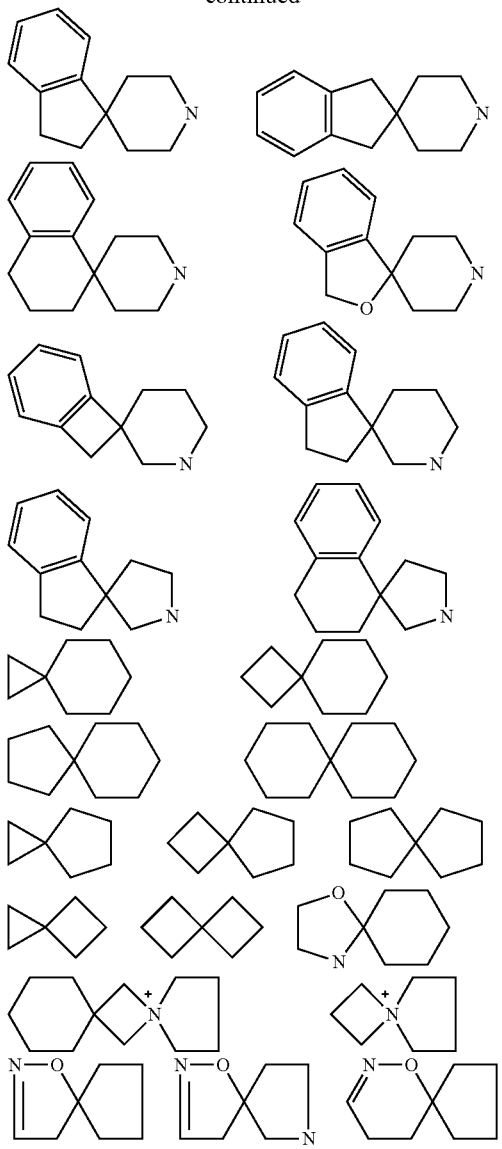

The term "halogen" is understood to mean fluorine, chlorine, bromine or iodine, preferably fluorine, chlorine or bromine, especially fluorine.

The term "Het ring" or "Het" is understood to mean ring systems which have 3 from 15 carbon atoms, are present in one, two or three ring systems bonded to one another and which, according to the ring size, contain one, two, three or four identical or different heteroatoms from the group of oxygen, nitrogen or sulfur. Examples of these ring systems are the acridinyl, azepanyl, azepinyl, azetidinyl, aziridinyl, benzimidazolinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, dibenzofuranyl, dibenzothiophenyl, dihydrofuran[2,3-b]-tetrahydrofuranyl, dihydrofuranyl, dioxolyl, dioxanyl, 2H, 6H-1,5,2-dithiazinyl, furanyl, furazanyl, homomorpholinyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolidinyl, 2-isothiazolinyl, isothiazolyl, isoxazolyl, isoxazolidinyl, 2-isoxazolinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, oxothiolanyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pyridooxazolyl, pyridoimidazolyl, pyridothiazolyl, pyridothiophenyl, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyridinyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienoimidazolyl, thienooxazolyl, thienopyridine, thienothiazolyl, thiomorpholinyl, thiophenyl, triazinyl, 1,2,3-triazolyl, 1,2,4-triazolyl, 1,2,5-triazolyl, 1,3,4-triazolyl and xanthenyl radicals.

The term "—($C_1$-$C_3$)-fluoroalkyl" is understood to mean a partially or completely fluorinated alkyl radical which derives, for example, from the following radicals: —$CF_3$, —$CHF_2$, —$CH_2F$, —CHF—$CF_3$, —CHF—$CHF_2$, —CHF—$CH_2F$, —$CH_2$—$CF_3$, —$CH_2$—$CHF_2$, —$CH_2$—$CH_2F$, —$CF_2$—$CF_3$, —$CF_2$—$CHF_2$, —$CF_2$—$CH_2F$, —$CH_2$—CHF—$CF_3$, —$CH_2$—CHF—$CHF_2$, —$CH_2$—CHF—$CH_2F$, —$CH_2$—$CH_2$—$CF_3$, —$CH_2$—$CH_2$—$CHF_2$, —$CH_2$—$CH_2$—$CH_2F$, —$CH_2$—$CF_2$—$CF_3$, —$CH_2$—$CF_2$—$CHF_2$, —$CH_2$—$CF_2$—$CH_2F$, —CHF—CHF—$CF_3$, —CHF—CHF—$CHF_2$, —CHF—CHF—$CH_2F$, —CHF—$CH_2$—$CF_3$, —CHF—$CH_2$—$CHF_2$, —CHF—$CH_2$—$CH_2F$, —CHF—$CF_2$—$CF_3$, —CHF—$CF_2$—$CHF_2$, —CHF—$CF_2$—$CH_2F$, —$CF_2$—CHF—$CF_3$, —$CF_2$—CHF—$CHF_2$, —$CF_2$—CHF—$CH_2F$, —$CF_2$—$CH_2$—$CF_3$, —$CF_2$—$CH_2$—$CHF_2$, —$CF_2$—$CH_2$—$CH_2F$, —$CF_2$—$CF_2$—$CF_3$, —$CF_2$—$CF_2$—$CHF_2$ or —$CF_2$—$CF_2$—$CH_2F$.

The terms "R2 and R3", "R19 and R11", "R13 and R14" or "R24 and R25, together with the carbon atom to which they are bonded, form a three- to six-membered cycloalkyl ring" are understood to mean cycloalkyl radicals such as cyclopropyl, cyclobutyl, cyclopentyl or cyclohexyl.

The terms "R2 and R3" or "R24 and R25, together with the carbon atom to which they are bonded, form a three- to six-membered heterocycle alkyl radical" are understood to mean radicals such as aziridine, azetidine, diazetidine, diaziridine, hexohydropyridazine, hexohydropyrimidine, imidazolidine, morpholine, oxadiazinane, oxadiazolidine, oxathianane, oxathiolane, oxazetidine, oxazolidine, oxetane, oxirane, piperazine, piperidine, pyrazolidine, pyrrolidine, tetrahydrofuran, tetrahydropyran, tetrahydrothiophene, tetrahydrothiopyran, tetrazinane, thiadiazolidine, thiazetidine, thiaziridine, thiazolidine, thietane, thiirane, thiomorpholine, triazetidine, triazinane or triazolidine.

The term "R21 and R22 together with the nitrogen atom to which they are bonded form a four- to eight-membered monocyclic heterocyclic ring which, as well as the nitrogen atom, may additionally, according to the ring size, also contain one or two identical or different heteroatoms from the group of oxygen, nitrogen and sulfur" is understood to mean radicals such as azepane, azepine, azetidine, dioxazole, dioxazine, 1,4-diazepane, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, morpholine, [1,4]oxazepane, oxazole, piperazine, piperidine, pyrazine, pyrazole, pyrazoline, pyrazolidine, pyridazine, pyridine, pyrimidine pyrrole, pyrrolidine, pyrrolidinone, pyrroline, tetrahydropyridine, tetrazine, tetrazole, thiazole, thiadiazole, thiazolidine, thiazoline, thiomorpholine, 1,2,3-triazine, 1,2,4-triazine, 1,3,5-triazine, 1,2,3-triazole or 1,2,4-triazole.

The term "two adjacent R4, together with the ring atoms to which they are bonded, form a four- to eight-membered heterocycle or phenyl which, together with the sub-ring to which the heterocycle or the phenyl is fused, forms a bicyclic system" is understood to mean compounds which consist of two connected ring systems in which one ring constitutes the sub-ring

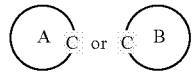

and the other ring forms a partly saturated or aromatic ring system which, according to the ring size, contains one, two or three identical or different heteroatoms from the group of oxygen, nitrogen and sulfur. Examples of these ring systems are radicals such as benzoimidazole, benzoisothiazole, benzoisoxazole, benzo[1,3]dioxole, benzofuranyl, benzothiazole, benzoisoxazole, benzothiofuran, benzothiophene, benzo[1,3]oxathiole, benzoxazole, benzothiazole, benzotriazolyl, quinazoline, quinazolone, quinoline, 4H-quinolizine, quinoxaline, chromane, chromene, cinnoline, 2,3-dihydrobenzo[1,4]dioxine, 2,3-dihydrobenzofuranyl, 1,3-dihydroisobenzofuran, 3,4-dihydro-2H-benzo[1,4]oxazine, 2,3-dihydrobenzooxazole, 2,3-dihydrobenzothiazole, 1,3-dihydrobenzo[c]thiophene, 2,3-dihydrobenzo[b]thiophene, indazole, indole, indoline, isobenzofuran, isoquinoline, isochromane, isoindazole, isoindole, isoindoline, 7-oxa-bicyclo[4.2.0]octa-1,3,5-triene, phthalazine, 2,3,4,5-tetrahydro-1H-benzo[b]azepine, 6,7,8,9-tetrahydro-5-oxa-9-aza-benzocycloheptene, 3,4,5,6-tetrahydro-2H-benzo[b][1,4]oxazozine, tetrahydroquinoline, 1,2,3,4-tetrahydroquinoxaline or tetrahydroisoquinoline.

The term "=O" is understood to mean an oxo radical as in carbonyl (—C(O)—) or sulfonyl or sulfoxide (S(O)₂ or S(O)).

The sub-structure

in the compound of the formula Ia is understood to mean a methylene radical in the case that p is 1 and an ethylene radical in the case that p is 2.

The inventive compounds can be prepared by well-known processes or by processes described here.

The invention further relates to a process for preparing the compounds of the formulae I and Ia and/or a stereoisomeric form of the compound of the formulae I and Ia and/or a physiologically compatible salt of the compound of the formulae I and Ia and/or a solvate or hydrate of the compound of the formulae I and Ia and/or an N-oxide of the compounds of the formula I, which comprises a) reacting a compound of the formula II

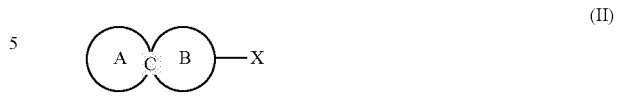

where A and B are each as defined in the compound of the formula I with a compound of the formula IIIa or IIIb or IIIc

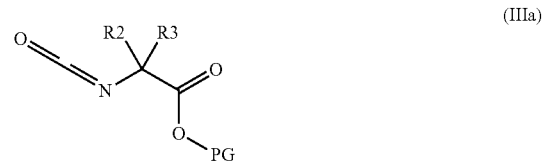

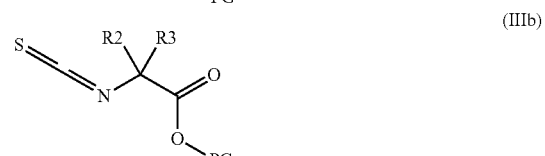

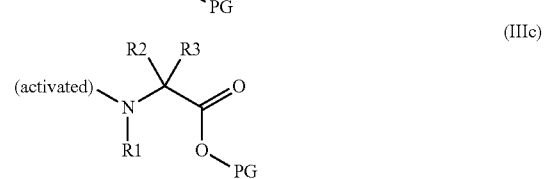

where X, R1, R2 and R3 are each as defined in the compound of the formula I, PG is an ester protecting group and "activated" means that the amine is present in an activated form, for example as a chlorocarbonyl compound, to give a compound of the formula IVa or IVb

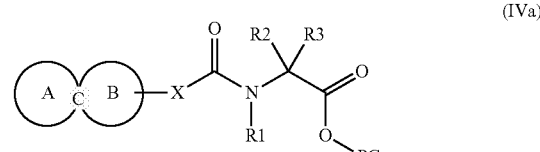

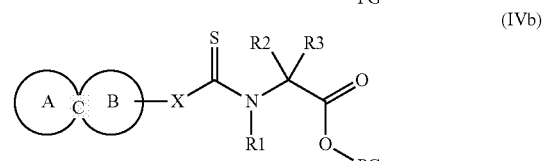

and reacting the resulting compounds of the formula IVa or IVb, after converting the ester to the carboxylic acid, with Z to give the compound of the formula I, or b) reacting a compound of the formula Va or Vb where A, B, X and Y are each as defined in the compound of the formula I

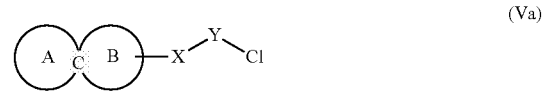

-continued

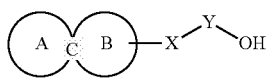
(Vb)

with a compound of the formula VI where R1, R2 and R3 are each as defined in the compound of the formula I and PG is an ester protecting group

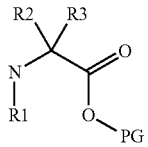
(VI)

to give a compound of the formula IVa or IVb, and reacting the resulting compound of the formula IVa or IVb, after converting the ester protecting group to the carboxylic acid, with Z to give the compound of the formula I, or c) reacting a compound of the formula VIIa or VIIb where A, B and X are each as defined in the compound of the formula I

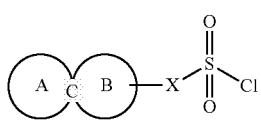
(VIIa)

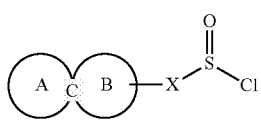
(VIIb)

with a compound of the formula VI

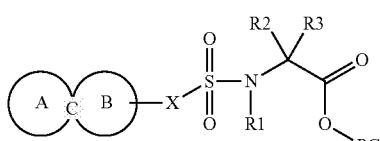
(VIIIa)

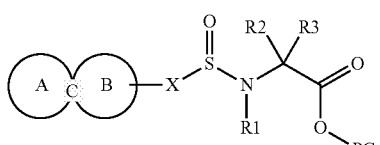
(VIIIb)

to give a compound of the formula VIIIa or VIIIb and reacting the resulting compound of the formula VIIIa or VIIIb, after converting the ester to the corresponding carboxylic acid, with Z to give the compound of the formulae I and Ia, or d) reacting a compound of the formula IX

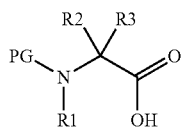
(IX)

with an amine Z where Z is as defined in the compound of the formula I to give a compound of the formula X

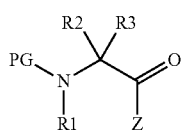
(X)

and then converting the compound X thus obtained in a protecting group elimination to give a compound of the formula XI

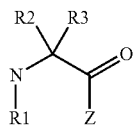
(XI)

and then reacting this compound XI with a compound Va or Vb, as detailed under b), to give the inventive compound of the formulae I and Ia, or e) separating a compound of the formulae I and Ia prepared by processes a), b), c) or d), or a suitable precursor of the formulae I and Ia which, owing to its chemical structure, occurs in enantiomeric or diastereomeric forms, into the pure enantiomers or diastereomers by salt formation with enantiomerically pure salts or bases, chromatography on chiral stationary phases or derivatization by means of chiral enantiomerically pure compounds such as amino acids, separating the diastereomers thus obtained, and eliminating the chiral auxiliary groups, or f) either isolating the compound of the formulae I and Ia prepared by processes a), b), c) or d) in free form or releasing it from physiologically incompatible salts or, in the case of the presence or acidic or basic groups, converting it to physiologically acceptable salts, or g) converting the compound of the formulae I and Ia prepared by processes a), b), c) or d), or a suitable precursor of the formulae I and Ia which, owing to its chemical structure, is capable of forming an N-oxide to an N-oxide or, in the case of the presence of an N-oxide, converting it to the free amine or the salt of an amine.

The synthesis of the inventive products can also proceed on the basis of three starting materials, any variation of the components which lead to the inventive structures being possible. For the sake of simplicity, the possible syntheses are described through these three components; however, this is not intended to constitute any restriction on the further means of synthesis.

For example, component A may be a spiro-amine:

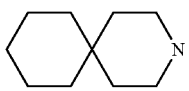 [SMILES: C1CCC2(CC1)CCNCC2]

For example, component B may be an amino acid derivative:

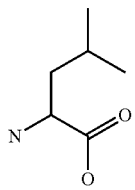

and for example, component C may be an amino nitrile:

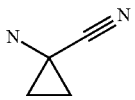

It is a preferred route to prepare, from these three starting materials by selection of suitable derivatives of these components, for example protected or modified precursors or precursors with defined stereochemistry, the inventive compounds through suitable coupling reactions, possibly after activation with reactive reagents such as known peptide coupling reagents or reagents which lead to activated urea precursors. Methods of peptide coupling are described, for instance, in Bodanszky (M. Bodanszky, Principles of Peptide Synthesis, 2nd ed, Springer, Berlin, 1993). Protecting groups, their introduction, detachment and stability are described, for example, in Greene (T. W. Greene, P. G. M. Wuts, Protective Groups in Organic Synthesis, 3rd ed, Wiley, New York, 1999). The preparation of ureas is described in detail, for example, in G. Sartori; R. Maggi, Acyclic and cyclic ureas. Science of Synthesis (2005), 18, 665-758. It is possible for many different suitable activation and coupling reagents which are known to those skilled in the art and some of which differ in their chemistry to be used. Merely by way of example, mention is made of carbodiimides, uronium salts or else chloroformic esters for carboxylic acid activation, and of phosgene, carbonyldiimidazole or else chloroformic esters for the preparation of activated urea precursors, and of chlorosulfonic acid or sulfur trioxide for the preparation of activated sulfonylurea precursors.

It is equally possible for the sequence of coupling to be varied, or else the individual component or the two-component unit (which has been obtained by coupling two adjacent individual components) on which the activation is undertaken, or for different protecting groups to be used, followed by the addition of the component which is still absent or of the components which are still absent. It is also possible to change the protecting groups, for example protecting group detachments on completion of coupling or at the end of the synthesis, to prepare the compound of the formulae I and Ia.

Moreover, the compound of the formulae I and Ia can be prepared via route 1a:

Route 1a

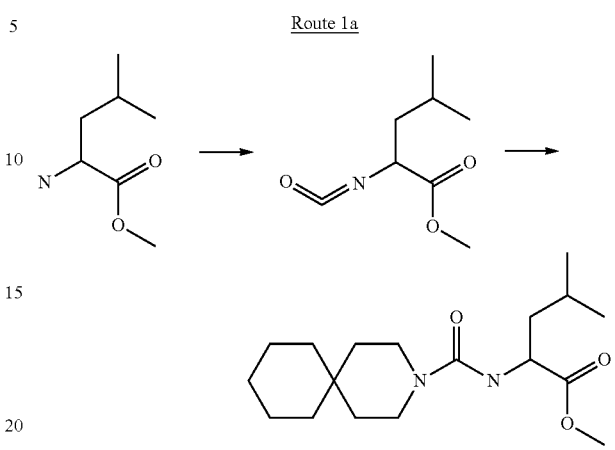

The component B—amino acid derivative—used is a suitable ester, for example a methyl ester, but many other ester protecting groups are also possible.

This derivative is activated on the nitrogen to give a urea precursor, for example by reaction with triphosgene, diphosgene or phosgene itself to give an isocyanate, so that a urea is formed by subsequent reaction with the spiro-amine A. However, many other types of activation are also possible; for example, reaction with carbonyldiimidazole affords the activated imidazolide, reaction with 4-nitrophenyl chloroformate affords the corresponding carbamate, and reaction with various similar activating carbonate reagents such as bis-succinimidyl carbonate or bis(4-nitrophenyl) carbonate affords corresponding derivatives. The analogous sulfur-containing derivatives (thiourea analogs) can be obtained correspondingly by the use of thiophosgene. However, it has to be taken into account that the strength of activation by the reagents listed is different, i.e. the subsequent reaction with the secondary spiro-amine can proceed at different speed or else afford very different yields or by-products.

Moreover, it might be necessary to achieve a preactivation by silylating the amine with, for example, trimethylsilyl chloride or bistrimethylsiliylacetamide or bistrifluoromethyltrimethylsilylacetamide in order that the actually activated urea precursor can form more easily. In addition, it might be advantageous in some cases to proceed from a free amino acid and to silylate it both on the nitrogen and on the carboxylic acid with one of the silylating reagents mentioned or else other suitable silylating reagents, and then to form the isocyanate.

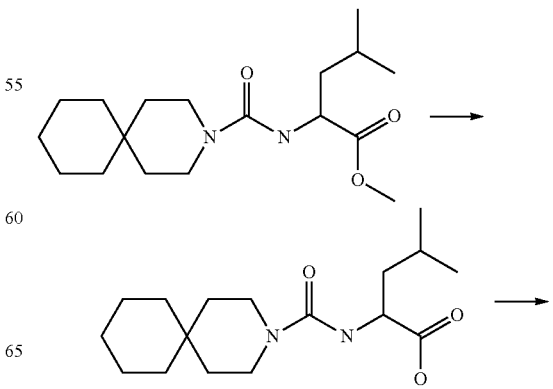

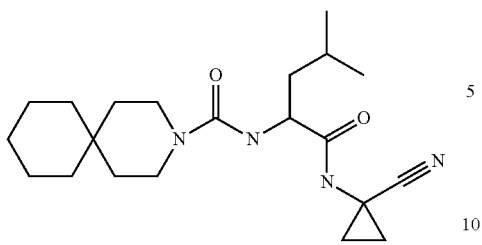

Next, the ester is cleaved under conditions which cause a minimum level of side reactions on the molecule, in the case of the methyl ester preferably under basic conditions, for example with NaOH or LiOH as a base, and it is advisable to avoid base excesses or long reaction times. In the case of a silyl protecting group, it may, though, also be sufficient to achieve ester cleavage by aqueous treatment, possibly with addition of a little mineral acid.

Before the amide bond can be formed with the 3rd component, the aminonitrile, the carboxylic acid is generally released from the salt with a mineral acid after the basic cleavage.

Subsequently, the peptide coupling can be effected by a multitude of methods known to those skilled in the art, as already mentioned above, if appropriate with addition of further auxiliary reagents for increasing the coupling efficiency or suppressing racemization.

Route 1b:

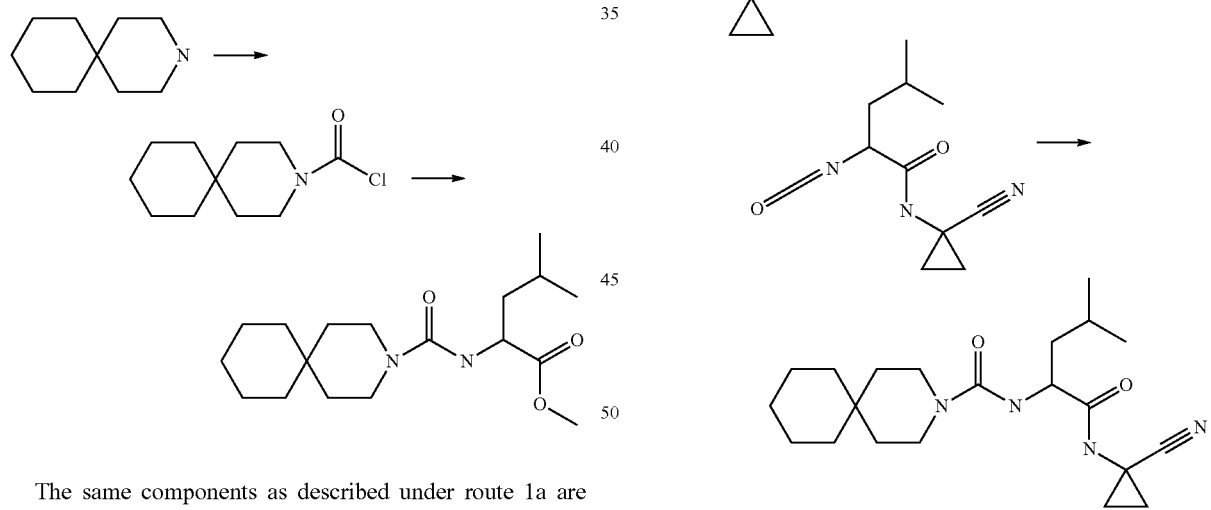

The same components as described under route 1a are used. In contrast to route 1a, however, the activation to give the urea precursor is not effected on component B, the amino acid derivative, but rather on component A, the spiro-amine. Since it is, however, a secondary amine, reactivities and yields are often changed compared to route 1a. For example, it is, though, possible to activate the spiro-amine as the chlorocarbonyl derivative by reaction with phosgene, triphosgene or diphosgene, and then to react the latter with the abovementioned amino acid ester. The abovementioned amino acid can also be used in the activated silylated form.

The further reaction, i.e. release of the carboxylic acid and coupling with the amine component C, is then effected as described under 1a.

Route 2a

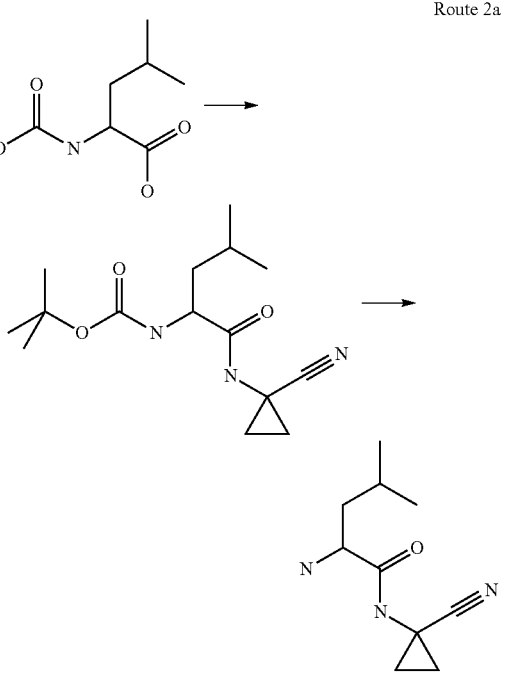

The starting material is a suitable N-terminally protected amino acid derivative B. This is first coupled with the aminonitrile C; in this reaction, the known methods of peptide bond formation can again be used. Subsequently, the N-terminal protecting group is eliminated and the elimination product is converted to the activated urea precursor as described under 1a. Under some circumstances, it is of particular significance here to use the protecting groups whose detachment conditions are compatible with the functionalities on the overall molecule B-C. This activated derivative, for example the isocyanate, is subsequently reacted with the spiro-amine to give the inventive compound I.

Route 2b

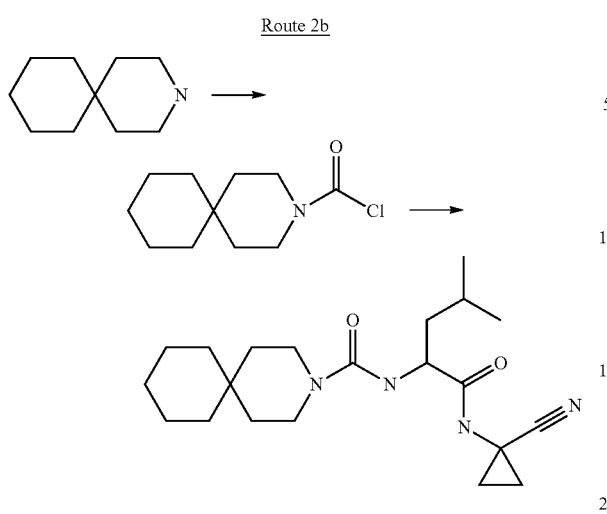

Alternatively, it is also possible here, analogously to the route described under 1b first to activate the spiro-amine A in order then to perform the reaction with component B-C to give the urea.

Chlorosulfonylamines or inventive sulfonylureas are prepared according to the following scheme:

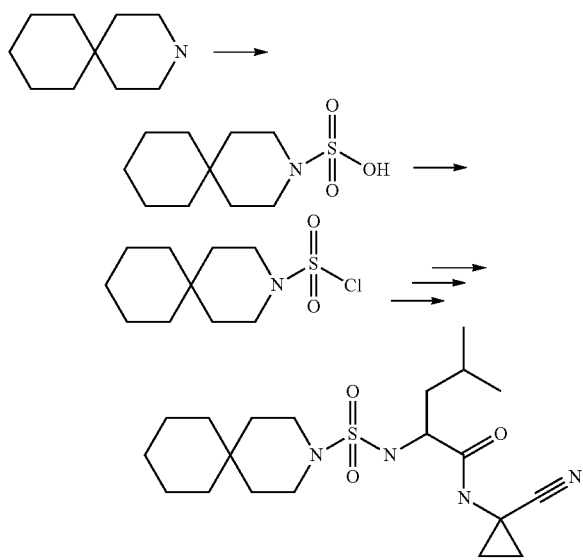

The synthesis of sulfonylureas is widely described. A frequently used method proceeds from an activation of the amines to give sulfonyl chlorides by reaction with preferably chlorosulfonic acid, and subsequent chlorination of the resulting sulfonic acid with, for example, phosphorus pentachloride or phosphorus oxychloride, followed by the reaction with the second amino component and a suitable base. Equally, it is also possible to use $SO_3$ in the first stage of the synthesis.

Moreover, it is also possible to achieve the desired conversion with sulfonyl chloride. Preference is given to undertaking the reaction on the secondary spiro-amine unit, followed by the reaction, for example, of the amino acid-amine, protected as the ester.

Subsequently, the ester is cleaved and reacted with the aminonitrile unit. Alternatively, it is also possible to react the activated spiro unit with the amino acid-amidonitrile, prepared from the N-terminally protected amino acid by coupling with the aminonitrile unit followed by the protecting group detachment.

Bisamides are prepared starting from amino acid units according to the following scheme:

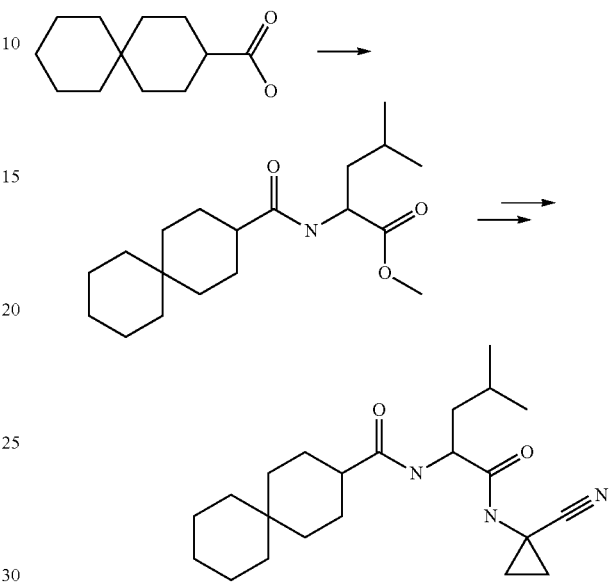

When the spiro unit is not present as a secondary amine but rather as a carboxylic acid, there is attachment to the amino acid via an amide bond. This can be effected in the synthesis either first, in which case an amino acid ester is used, followed as described above in the analogous case 1b by ester cleavage and amide coupling with the aminonitrile unit, or, when an amino acid-amidonitrile unit is used, as the second coupling stage in the synthesis, in each case accompanied by appropriate protecting group manipulations, as described above in case 2b.

Optically active carbon atoms in the inventive compounds of the formulae I and Ia may each independently be present in R or S configuration. The compounds of the formulae I and Ia may be present in the form of the pure enantiomers or pure diastereomers or in the form of mixtures in any proportions of the enantiomers and/or diastereomers, for example in the form of their racemates or enantiomeric diastereomer pairs. The present invention thus relates to pure enantiomers and mixtures of the enantiomers, and equally to pure diastereomers and mixtures of the diastereomers. The invention likewise encompasses mixtures of two or of more than two stereoisomers of the formulae I and Ia and likewise all possible mixing ratios of these stereoisomers in the mixtures. In the case that the compounds of the formulae I and Ia are present in the form of E or Z isomers, or cis or transisomers, or as a "spiran", the invention relates in each case both to the pure E and pure Z isomers, and to the pure cis or pure transisomers, and likewise, entirely analogously, to the corresponding spiroisomers, and also E/Z or cis/trans mixtures in any ratio. The invention likewise encompasses all tautomeric forms of the inventive compounds of the formulae I and Ia.

The compound of the formulae I and Ia is, when it occurs as a mixture of diastereomers or enantiomers or is obtained as mixtures thereof in the synthesis selected, separated into the pure stereoisomers, either by chromatography on a chiral or achiral support material, or, when the racemic compound of the formulae I and Ia is capable of salt formation, by fractional crystallization of the diastereomeric salts formed with an optically active base or acid as an auxiliary. Suitable chiral stationary phases for thin-layer or column chromatography separation of enantiomers are, for example, modified silica gel supports (so-called Pirkle phases) and high molecular weight carbohydrates such as triacetylcellulose. For analytical purposes, gas chromatography methods on chiral stationary phases can also be employed after appropriate derivatization known to those skilled in the art. For enantiomer separation of the racemic carboxylic acids, an optically active, generally commercially available base such as (−)-nicotine, (+)- and (−)-phenylethylamine, quinine bases, L-lysine or L- and D-arginine are used to form the differently soluble diastereomeric salts, the less soluble component is isolated as a solid, the more soluble diastereomer is separated from the mother liquor, and the pure enantiomers are obtained from the diastereomeric salts thus obtained. In a manner similar in principle, the racemic compounds of the formulae I and Ia which contain a basic group, for example an amino group, can be converted to the pure enantiomers with optically active acids, for example (+)-camphor-10-sulfonic acid, D- and L-tartaric acid, D- and L-lactic acid, and also (+)- and (−)-mandelic acid. It is also possible to convert chiral compounds which contain alcohol or amine functions to the corresponding esters or amides with correspondingly activated or optionally N-protected enantiomerically pure amino acids, or, conversely, to convert chiral carboxylic acids to the amides with carboxy-protected enantiomerically pure amino acids, or to the corresponding chiral esters with enantiomerically pure hydroxycarboxylic acids such as lactic acid. The chirality of the amino acid or alcohol radical introduced in enantiomerically pure form can then be utilized to separate the isomers by undertaking a separation of the diastereomers now present by crystallization or chromatography on suitable stationary phases, and then detaching the entrained chiral molecular moiety again by means of suitable methods.

Furthermore, the possibility arises for some of the inventive compounds to use diastereomerically or enantiomerically pure starting materials to prepare the skeleton structures. This also allows different or simplified processes for purifying the end products to be used. These starting materials have been prepared beforehand in enantiomerically or diastereomerically pure form by literature processes. To this end, for example, it is also possible to use enzymatic processes. It is possible either to use those enzymatic processes which proceed enantio- or diastereoselectively in one synthesis step, i.e. afford one compound selectively, or else in the sense of a kinetic enzymatic synthesis or cleavage in such a way that, for example, an enantiomer or diastereomer already present is converted highly preferentially in the enzymatic reaction, for example in the sense of a selective acylation or esterification or acyl cleavage or ester cleavage. Reactions used successfully are, for example, acylation reactions with lipases or acylase cleavages of N-acetyl compounds, or protease-mediated esterifications in organic solvents or ester cleavages, but many other possibilities are also conceivable.

When amino acid derivatives are used, they are frequently commercially available already in enantiomerically pure form. In the case of non-proteinogenic amino acids, they may, however, often also be prepared from enantiomerically or diastereomerically pure natural precursors, for example from proteinogenic amino acids or else other natural chiral starting materials of the chiral pool, or else these precursors are obtained in optically pure form by one of the separation methods mentioned or by use of different types of enzymatic processes and used correspondingly in the synthesis.

Acidic or basic products of the compound of the formulae I and Ia may be present in the form of their salts or in free form. Preference is given to pharmacologically acceptable salts, for example alkali metal or alkaline earth metal salts or hydrochlorides, hydrobromides, sulfates, hemisulfates, all possible phosphates and salts of the amino acids, natural bases or carboxylic acids. The present invention also includes all solvates of the compounds of the general formulae I and Ia, such as stoichiometric or nonstoichiometric hydrates or alcohol adducts.

The preparation of physiologically compatible salts from compounds of the formulae I and Ia capable of salt formation, including their stereoisomeric forms, is effected in a manner known per se. The acidic compounds of the formulae I and Ia form stable alkali metal, alkaline earth metal or optionally substituted ammonium salts with basic reagents such as hydroxides, carbonates, hydrogencarbonates, alkoxides and ammonia, or organic basis, for example methylamine, dimethylamine, ethylamine, trimethyl or triethylamine, ethanolamine, diethanolamine or triethanolamine, trometamol or else basic amino acids, for instance lysine, ornithine or arginine. When the compounds of the formulae I and Ia have basic groups, it is also possible to prepare stable acid addition salts with strong acid. For this purpose, useful acids are both inorganic and organic acids such as hydrochloric acid, hydrobromic acid, sulfuric acid, hemisulfuric acid, phosphoric acid, nitric acid, methanesulfonic acid, benzenesulfonic acid, p-toluenesulfonic acid, 4-bromobenzenesulfonic acid, cyclohexylamidosulfonic acid, trifluoromethylsulfonic acid, 2-hydroxyethanesulfonic acid, formic acid, acetic acid, oxalic acid, tartaric acid, succinic acid, glycerolphosphoric acid, lactic acid, malic acid, adipic acid, citric acid, fumaric acid, maleic acid, malonic acid, benzoic acid, sorbic acid, gluconic acid, glucuronic acid, palmitic acid, stearic acid or trifluoroacetic acid. Hydrates of the compounds of the formulae I and Ia can be prepared, for example, by (re)crystallization from an organic-aqueous solvent mixture, for example by using such organic solvents as dioxane, tetrahydrofuran, ethanol or methanol.

Conversely, it is also possible to prepare free acid or free base forms of the compounds of the formulae I and Ia from the corresponding salts. For example, a compound of the formulae I and Ia can be released from its acid salt form by treatment with suitable bases (such as ammonia solution, sodium hydroxide solution). In some special cases, treatment with oxiranes can also bring about a release; for example, hydrochlorides can be released by treatment with methyloxirane, particularly in the case of amino acid derivatives. Compounds of the formulae I and Ia which are present in the form of their base salt form can be converted to the free acid form by treatment with suitable acids (citric acid, hydrochloric acid or sulfuric acid).

Nitrogen compounds of the formulae I and Ia may also be present in the form of their N-oxides. These can be prepared by various processes which are known to those skilled in the art. For example, a nonoxidized form of a compound of the formulae I and Ia can be oxidized to the corresponding N-oxides by treatment with a suitable oxidizing agent (trifluoroperacetic acid, permaleic acid, perbenzoic acid, peracetic acid, meta-chloroperbenzoic acid) in suitable inert organic solvents. Alternatively, the N-oxides of the compounds of the formulae I and Ia can also be prepared by using starting materials or intermediates in the form of their N-oxides or preparing them as such.

Compounds of the formulae I and Ia in their nonoxidized form can also be prepared from the N-oxides of the compounds of the formulae I and Ia by treatment with reducing reagents (such as sulfur, sulfur dioxide, triphenylphosphine, various borohydrides, phosphorus trichloride or -bromide and the like) in suitable inert organic solvents.

Compounds of the formulae I and Ia which simultaneously bear a basic and an acidic group, for example an amino or guanidino group and a carboxyl group, may likewise be present in the form of their zwitterions (betaines), which are likewise included within the scope of the present invention.

The invention likewise encompasses all salts of the compounds of the formulae I and Ia which, owing to their low physiological tolerability, cannot be used directly in active pharmaceutical ingredients, but, for example, are used as intermediates on the route to the preparation of the inventive compounds, or else as starting materials for the synthesis of the physiologically tolerable salts. The invention further encompasses derivatives and modifications of the compounds of the formulae I and Ia, for example prodrugs, protected forms and other physiologically tolerable derivatives, and equally active or secondarily activable metabolites of the compounds of the formulae I and Ia. In particular, the invention encompasses prodrugs and protected forms of the compounds of the formulae I and Ia which can be converted to the compounds of the formulae I and Ia under physiological conditions. Suitable prodrugs of the compounds of the formulae I and Ia are in particular those chemically modified derivatives whose properties are modified in a desired manner, for example in relation to improved solubility, bioavailability, absorption, or prolonged exposure or duration of action. The possible prodrugs are known to those skilled in the art and widely described in the literature.

The invention also relates to medicaments characterized by an active content of at least one compound of the formulae I and Ia and/or of a physiologically compatible salt of the compound of the formulae I and Ia and/or a stereoisomeric or non-stereoisomeric form of the compound of the formulae I and Ia, together with a pharmaceutically suitable and physiologically compatible carrier, additive and/or other active ingredients and auxiliaries.

Owing to the pharmacological properties, the inventive compounds are suitable for the prophylaxis, secondary prevention and therapy of all of those disorders treatable by an inhibition of the cysteine proteases, particularly of the cathepsins. They are suitable both for acute treatment and for long-term therapy. Cathepsin inhibitors can be used in the case of abnormally elevated bone degradation, allergies, Alzheimer's disease, amyloidosis, ARDS, arterial thrombosis, asthma, atheromas, atherosclerosis, autoimmune disorders, bacterial infections, bronchiolitis, cerebral hemorrhage, cerebrovascular ischemea, Huntington's chorea, chronic inflammations, CIPD (chronic inflammatory demyelinizing polyradiculoneuropathy), Creutzfeldt-Jakob disease, Crohn's disease, diabetes (particularly the juvenile form), emphysema, encephalomyelitis, endometriosis, inflammatory respiratory disorders, inflammatory pancreatitis, epilepsy, disorders characterized by enhanced angiogenesis, excessive respiratory pathway elastolysis, tissue grafts, gingivitis, glomerulonephritis, glucocorticoid-induced osteoporosis, Graves' disease, Guillain-Barre syndrome, Hashimoto's thyroiditis, hepatitis, HIV infection, Huntington's disease, hypercalcemia, IBD, immune impairment, interstitial cystitis, bone fracture, bone loss, cancers, lupus erythematosus, malaria, metachromic leukodystrophy, metastasizing osteogenesis, metastatis, multiple sclerosis, multiple myeloma, muscular dystrophy, myasthenia gravis, neurodegenerative disorders, neuropathic pain, (particularly chronic neuropathic pain; but also diabetic neuropathy, post-therapeutic neuralgia, trigeminal neuralgia, painful diabetic polyneuropathy, post-stroke pain, post-amputation pain, myelopathic or radiculopathic pain, atypical facial pain and causalgia-like syndromes), organ rejection in transplants, osteoarthritis, osteogenesis imperfecta, osteoporosis, Paget's disease, pancreatitis, Parkinson's disease, pemphigus vulgaris, periodontitis, plaque rupture, *Pneumocystis carinii*, pneumonitis, psoriasis, restenosis, rheumatoid arthritis, scleroderma, systemic lupus erythematosus, trauma (brain, spinal cord), tumor cell invasion, viral infections, tooth loss, and preferably, but not exclusively, in the following types of cancer: breast cancer, intestinal cancer, ovarian cancer, cervical cancer, skin cancer, brain tumor, Kaposi's sarcoma, leukemia (B- and T-cell), lung cancer, lymph node cancer, pancreatic cancer, prostrate cancer and sarcomas.

Since many compounds of this invention are particularly inhibitors of the cysteine cathepsins B, K and S, it is possible with preference to treat disorders in which said cathepsins contribute to the pathology or/and symptoms. This relates particularly to: pain, especially neuropathic pain, osteoarthritis, osteoporosis and various cancer types. This likewise relates to various (auto)immune disorders, particularly of the rheumatoid type, which have likewise already been listed above, and disorders characterized by excessive elastolysis, particularly of the COPD type, and related disorders listed above, and also cardiovascular disorders characterized by vascular changes, such as atherosclerosis.

The inventive medicaments can be administered extravascularly, for example intramuscularly, subcutaneously, intraocularly, intraarticularly, intrasynovially, perorally, orally (buccally, perlingually, sublingually), rectally, vaginally, (trans)dermally, pulmonally (inhalatively) or nasally or intravascularly, for example intravenously, intraarterially, or intracardially, in each case as an injection or infusion. Preference is given to the oral administration form.

The invention also relates to a process for producing a medicament, which comprises bringing a compound of the formulae I and Ia into a suitable administration form with a pharmaceutically suitable and physiologically compatible carrier and optionally further suitable active ingredients, additives or auxiliaries.

Suitable solid or pharmaceutical formulation forms are, for example, granules, powders, coated tablets, tablets, (micro) capsules, suppositories, syrups, juices, suspensions, emulsions, drops or injectable solutions, and also preparations with protracted active ingredient release in whose production customary auxiliaries such as carriers, disintegrants, binders, coatings, swelling agents, glidants or lubricants, flavorings, sweeteners and solubilizers are used. Frequently used auxiliaries include magnesium carbonate, titanium dioxide, lactose, mannitol and other sugars, talc, milk protein, gelatine, starch, cellulose and derivatives thereof, animal and vegetable oils such as fish oil, sunflower oil, groundnut oil or sesame oil, polyethylene glycol and solvents such as sterile water and mono- or polyhydric alcohols such as glycerol.

Moreover, it is also possible, particularly in the production of suspensions, to use compounds with quite particular, specifically established surface properties. These include, for example, dry and wet grinding, micronization, spray drying, production of nanocrystals and similar processes, in which changing the surface properties allows, for example, improvement in solubilities or especially dissolution kinetics, which achieves, for example, improved uptake of the particular compound into the organism.

The pharmaceutical preparations are preferably produced and administered in dosage units, each unit containing a particular dose of the inventive compound of the formulae I and Ia as an active constituent. In the case of solid dosage units such as tablets, capsules, coated tablets or suppositories, this dose may be up to about 5000 mg, but preferably from about 50 to 1000 mg, and, in the case of injection solutions in ampule form, up to about 500 mg, but preferably from about 20 to 200 mg.

For the treatment of an adult patient of about 70 kg in weight, according to the activity of the compound of the formulae I and Ia, daily doses of from about 2 mg to 5000 mg of active ingredient, preferably from about 10 mg to 1000 mg, are indicated. Under some circumstances, however, higher or lower daily doses may also be appropriate. The daily dose can be administered either by a single dose in the form of a single dosage unit or else a plurality of smaller dosage units, or else by multiple administration of divided doses at particular intervals.

Inhibitors of the aforementioned type can be administered even as a monotherapy or in combination or together with other medicaments.

End products are generally determined by mass spectrometry methods (FAB-, ESI-MS) and $^1$H NMR (generally, unless stated otherwise, 500 MHz in DMSO-D6); in each case, the main peak or the two main peaks are specified. Temperatures are stated in degrees Celsius. Abbreviations used are either explained or correspond to the customary conventions.

Starting materials or synthesis intermediates are either obtainable commercially or are prepared as cited or described.

1-Oxa-8-azaspiro[4.5]decane, 2-oxa-8-azaspiro[4.5]decane, 2-oxa-7-azaspiro[4.5]decane, 1-oxa-7-azaspiro[4.5]decane, 2-oxa-7-azaspiro[3.5]nonane and also analogous or alkyl-substituted or -disubstituted derivatives are prepared as described in WO01/87838.

1,4-Dioxa-8-azaspiro[4.5]decane, 1-oxa-4,8-diazaspiro[4.5]decane, 1,5-dioxa-9-azaspiro[5.5]undecane, 1-oxa-5,9-diazaspiro[5.5]undecane or similar and substituted derivatives are prepared as in EP 0621267. The known method can likewise also be employed successfully by heating the keto precursor (for example the protected piperidone) with diols and a catalytic amount of p-toluenesulfonic acid on a water separator.

3-Azaspiro[5.5]undecane is also obtainable, for example, from 3-azaspiro[5.5]undecane-2,4-dione; the same applies for similar carbocyclic spiro compounds. The reduction can be effected with LiAlH$_4$.

2-Methyl-2,8-diazaspiro[4.5]decan-1-one, differently 2-substituted derivatives, analogous ureas and amines are described in J. Med. Chem. 47 (8), 2037-61 (2004), or can be obtained from the products described here by further reactions, for example reduction. Likewise described in this publication are substituted spiro-hydantoins and lactams with inverse amide formation (i.e. 2,8-diazaspiro[4.5]decan-3-one and derivatives), and also imides.

Many different spirocyclic indanes, indenes, tetralones and tetralins are commercially available.

The preparation of 6-azaspiro[2.5]octane and many further spiro compounds is described in Bull. Soc Chim. France 10, 2572-81 (1964).

ABBREVIATIONS USED

| | |
|---|---|
| bis(2-methoxyethyl)aminosulfur trifluoride | BAST |
| tert-butyl | tBu |
| 2,2'-bis(diphenylphosphino)-1,1'-binaphthyl | Binap |
| bis(oxo-3-oxazolidinyl)phosphoryl chloride | BOP-Cl |
| dibenzylideneacetone | dba |
| dichloromethane | DCM |
| dicyclohexylcarbodiimide | DCC |
| diethylphosphoryl cyanide | DEPC |
| diisopropylethylamine | DIPEA |
| 4-dimethylaminopyridine | DMAP |
| N,N-dimethylformamide | DMF |
| dimethyl sulfoxide | DMSO |
| 1,1'-bis(diphenylphosphino)ferrocene | DPPF |
| 1-(3-dimethylaminopropyl)-3-ethylcarbodiimide hydrochloride | EDCl |
| equivalents | eq. |
| saturated | sat. |
| O-(7-azabenzotriazol-1-yl)-N,N,N',N'-tetramethyluronium hexafluorophosphate | HATU |
| 7-aza-1-hydroxybenzotriazole | HOAt |
| lithium diisopropylamide | LDA |
| methanol | MeOH |
| methylmagnesium chloride solution | MeMgCl sol. |
| methyl tert-butyl ether | MTBE |
| N-bromosuccinimide | NBS |
| N-chlorosuccinimide | NCS |
| N-iodosuccinimide | NIS |
| N-ethylmorpholine | NEM |
| room temperature from 20° C. to 25° C. | RT |
| broad singlet | $s_b$ |
| tetrahydrofuran | THF |
| trifluoroacetic acid | TFA |
| O-((ethoxycarbonyl)cyanomethyleneamino)-N,N,N',N'-tetramethyluronium tetrafluoroborate | TOTU |

Unless specified otherwise herein, the following definitions will apply:

"Patient" means a warm blooded animal, such as for example rat, mice, dogs, cats, guinea pigs, and primates such as humans.

"Treat" or "treating" means to alleviate symptoms, eliminate the causation of the symptoms either on a temporary or permanent basis, or to prevent or slow the appearance of symptoms of the named disorder or condition.

"Therapeutically effective amount" means a quantity of the compound which is effective in treating the named disorder or condition.

"Pharmaceutically acceptable carrier" is a non-toxic solvent, dispersant, excipient, adjuvant or other material which is mixed with the active ingredient in order to permit the formation of a pharmaceutical composition, i.e., a dosage form capable of administration to the patient. One example of such a carrier is a pharmaceutically acceptable oil typically used for parenteral administration.

The citation of any reference herein should not be construed as an admission that such reference is available as "Prior Art" to the instant application.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

Various publications are cited herein, the disclosures of which are incorporated by reference in their entireties.

EXAMPLES

The examples which follow were prepared analogously to the general or specific methods specified above.

Example 1

Methyl (S)-2-benzyloxycarbonylamino-3-chlorocarbonylpropionate

Z-asp-OMe (175 g, 622 mmol) was dissolved in THF (1750 ml) and admixed with 2 ml of DMF. 86.9 g (684 mmol) of oxalyl chloride were dissolved in 200 ml of THF (slightly exothermic), cooled back to room temperature (RT) and added dropwise to the solution of the amino acid over 1 hour (h). After a further hour at RT, the solution was initially sparged with nitrogen for 10 min, concentrated on a rotary evaporator at a maximum of 30° C. and coevaporated repeatedly with toluene. The resulting dirty white solid was dried to constant weight under in-house vacuum (about 1.5 mbar) and reacted further without further purification. Yield: 186.6 g (quantitative).

Example 2

Methyl (S)-2-benzyloxycarbonylamino-4-oxopentanoate

Copper(I) bromide (60.9 g, 425 mmol, 1.2 equivalents (eq.)) was introduced into a 3 liter 4-neck flask (with dropping funnel, internal thermometer, argon inlet, rubber septa, in a cooling bath) and admixed with 250 ml of THF. A separate flask was initially charged at 10° C. with lithium bromide (75 g, 864 mmol, 2.4 eq.) and admixed with 470 ml of THF under argon. On completion of dissolution and recooling to RT, this solution was transferred to the suspension of the copper bromide. The resulting colorless to slightly greenish solution was cooled to −60° C., and methylmagnesium chloride (141 ml of a 3.0 M solution in THF, 423 mmol) was added within 15 min. A thick yellowish precipitate formed and the temperature rose to RT. After cooling again to −60° C., the solution from example 1 (prepared from 106 g of methyl (S)-2-benzyloxycarbonylamino-3-chlorocarbonylpropionate, 353 mmol, and 360 ml of THF) was added over about 30 min and the temperature was kept below −25° C. After the addition had ended, the mixture was stirred for another 1 h, and solid ammonium chloride (30 g) was added at −15° C. After a further 2 h, the mixture was filtered, the filtrate was diluted with 400 ml of heptane and 200 ml of saturated ammonium chloride solution were added. Once the mixture had been stirred at RT for 1 h, the organic phase was removed and washed repeatedly, and the aqueous phases were reextracted with ethyl acetate. The combined organic phases were dried over sodium sulfate, concentrated on a rotary evaporator under reduced pressure and chromatographed on 1 kg of silica gel with 1:3 to 1:1 ethyl acetate/heptane. After the products had been combined and dried under reduced pressure, 83 g (84% yield) of a white solid were obtained. $^1$H NMR (300 MHz, CDCl$_3$): 7.4 (m, 5H); 5.78 (m, 1H); 5.18 (s, 2H); 4.6 (s, 1H); 3.75 ("s", 3H); 3.3-2.9 (2 dd, 2H); 2.2 (s, 3H)

Example 3

Methyl (S)-2-benzyloxycarbonylamino-4-oxoheptanoate

The preparation was effected analogously to example 2, with the difference that N-propylmagnesium chloride (2 M in diethyl ether) was now used and a chromatographic purification was dispensed with. Instead, the resulting dark crude product was taken up in 1:1 DCM/heptane and filtered through Celite. After treatment with activated carbon and filtration, the desired product was obtained in 93% yield.
$^1$H NMR (300 MHz, CDCl$_3$): 7.4 (m, 5H); 5.78 (m, 1H); 5.17 (s, 2H); 4.6 (s, 1H); 3.73 ("s", 3H); 3.3-2.9 (2 dd, 2H); 2.4 (m, 2H); 1.6 (m, 2H, overlapping); 0.9 (m, 3H)

Example 4

Methyl (S)-2-benzyloxycarbonylamino-4,4-difluoropentaoate

BAST (Deoxofluor, 60 g, 271 mmol, 2.95 eq.) was initially charged in a 1 liter flask made of inert plastic and admixed with the ketone from example 2, dissolved/suspended in 40 ml of dichloromethane. After a reaction time of 1 day and again after 12 h, in each case 25 ml (113 mmol) of BAST were added and the mixture was stirred further at RT. After a further 12 h, dichloromethane was added and the resulting solution was rapidly added dropwise to an ice-cold saturated sodium hydrogencarbonate solution while keeping the temperature below 30° C. The organic phase was removed, the aqueous phase was extracted repeatedly with dichloromethane and the combined organic phases were washed with water, 1 N HCl and saturated in NaCl solution, dried over sodium solvate and concentrated under reduced pressure. The brown oil was then chromatographed on silica gel (3:1 heptane/MTBE to 2:1).

Product fractions were combined and concentrated by evaporation under reduced pressure.

Yield: 22.3 g, 56%. $^1$H NMR (300 MHz, CDCl$_3$): 7.4 (m, 5H); 5.45 (m, 1H); 5.18 (s, 2H); 4.6 (s, 1H); 3.78 ("s", 3H); 2.4 (m, 2H); 1.7 (m, 3H)

Example 5

Methyl (S)-2-benzyloxycarbonylamino-4,4-difluoroheptanoate

The preparation was effected analogously to example 4.
$^1$H NMR (300 MHz, CDCl$_3$): 7.4 (m, 5H); 5.46 (m, 1H); 5.17 (s, 2H); 4.6 (m, 1H); 3.77 ("s", 3H); 2.4 (m, 2H); 1.8 (m, 2H, overlapping); 1.5 (m, 2H); 0.95 (m, 3H)

All further reactions in the series of the 4,4-difluoroheptanoic acid derivatives to give the inventive end products were conducted entirely analogously to the corresponding pentanoic acid derivatives.

Example 6

Methyl (S)-2-amino-4,4-difluoropentanoate hydrobromide 10 g of the compound from example 4 were admixed at RT with 35 ml of 33% HBr in glacial acetic acid and stirred for 40 min. Subsequently, 400 ml of cold diethyl ether were added and the reaction mixture was stored at 4° C. for 3 h. The precipitated product was filtered off with suction through a glass frit, washed thoroughly with cold ether and freed of solvent residues under reduced pressure. It can be used directly in the next reaction. Yield: 6.67 g (82%)

$^1$H NMR: 8.5 (s$_b$, 3H); 4.3 (t, 1H); 3.76 (s, 3H); 2.53 (m, 2H); 1.7 (t, 3H).

Example 7

Methyl (S)-4,4-difluoro-2-isocyanatopentanoate

The compound from example 6 (6.76 g, 28.8 mmol) was initially charged and dissolved in 240 ml of dichloromethane and 9.46 ml (117 mmol, 4.05 eq) of pyridine, cooled down to 0° C. in an ice bath for 15 min and admixed with 19.86 ml of a 20% phosgene solution in toluene (37.54 mmol, 1.3 eq) within 20-30 seconds. The mixture was stirred at 0° C. for a further 2 h, then the reaction mixture was extracted with cold half-molar HCl and ice. The water phases were reextracted with dichloromethane, and the combined organic phases were washed with ice and saturated NaCl solution, then dried over MgSO$_4$ and filtered off from the desiccant. Concentration by evaporation under reduced pressure left 5.21 g of brown oil (corresponded to a yield of 94%), which was reacted further directly.

Example 8

(S)-2-[(3-Azaspiro[5.5]undecane-3-carbonyl)amino]-4,4-difluoropentanoic acid 252 mg (1.3 mmol) of the isocyanate from example 7 were dissolved at 0° C. in 5 ml of THF and admixed with 109 mg (3.25 mmol, 2.5 eq.) of sodium hydrogencarbonate and 209 mg (1.37 mmol, 1.05 eq.) of 3-azaspiro[5.5]undecane. The mixture was stirred overnight, precipitated salts were removed and the reaction mixture was treated directly with 2.5 ml of 1 M LiOH solution (2.5 mmol, 1.9 eq.). The reaction was monitored by HPLC-MS. When the mass peak of the reactant had disappeared completely, the mixture was acidified cautiously with dilute HCl and the product was isolated by extraction with ethyl acetate, drying of the organic phase over sodium sulfate and concentration under reduced pressure. Yield: 440 mg (quantitative). The crude product was used directly in the amide coupling which follows.

Example 9

N—[(S)-1-(1-cyanocyclopropylcarbamoyl)-3,3-difluorobutyl]-3-azaspiro[5.5]undecane-3-carboxamide The crude product from example 8, (S)-2-[(3-azaspiro[5.5] undecane-3-carbonyl)amino]-4,4-difluoropentanoic acid, was dissolved in 6 ml of 2:1 THF/DMF and admixed with 161.8 mg (1.365 mmol, 1.05 eq.) of 1-amino-1-cyclopropylnitrile hydrochloride and 176.9 mg (1.3 mmol, 1 eq.) of 1-hydroxy-7-azabenzotriazole, cooled to 0° C. and admixed with 250 mg (1.3 mmol, 1 eq.) of EDCl and with 0.496 ml (3.9 mmol, 3 eq.) of N-ethylmorpholine. Subsequently, the mixture was stirred at 0° C. to RT for 2 h, THF was distilled off under reduced pressure, ethyl acetate was added and the mixture was extracted by shaking with highly dilute HCl, sat. NaHCO$_3$ solution and sat. NaCl solution. After concentration of the organic phase, a preparative HPLC separation (Merck Hibar Purospher RP18, 250×25, Standard-Gradient of acetonitrile-water-TFA) was performed directly. Product fractions were combined and freeze-dried.

Yield: 222 mg, 43% of theory.

$^1$H NMR: 8.82 (s, 1H); 6.6 (s, 1H); 4.31 (m, 1H); 3.28 (about, 4H); 2.29 (m, 2H); 1.7-1.1 (m, about 20H); MS (ESI$^+$): 397.17

Example 10

8-azaspiro[4.5]decane-8-carbonyl chloride 1.57 ml of phosgene (20% solution in toluene, 2.96 mmol) were initially charged in 5 ml of dichloroethane and cooled to −20° C., then a mixture of 8-azaspiro-[4,5]decane (750 mg, 2.96 mmol) and triethylamine (1.28 ml, 9.2 mmol, 3.1 eq.) was added slowly. After 30 min, the mixture was allowed to come to RT; after 1 h, according to LC-MS, a little starting material was still present but also three new peaks. Subsequently, the mixture was added to 2 N aqueous HCl, the aqueous phase was extracted with dichloromethane, and the organic phase was washed with saturated NaHCO$_3$ solution and dried over sodium sulfate; subsequently, the mixture was concentrated by rotary evaporation under reduced pressure. Crude yield: 592 mg The material was reacted further directly without further purification. General method: see example 19.

Example 11

Benzyl (S)-4-carboxymethyl-5-oxooxazolidine-3-carboxylate

The compound is commercially available or can be prepared by literature methods by refluxing Z-Asp-OH with paraformaldehyde on a water separator in benzene.

Example 12

Benzyl (S)-4-chlorocarbonylmethyl-5-oxooxazolidine-3-carboxylate

The compound from example 11 was converted analogously to the manner described in example 1 to benzyl (S)-4-chlorocarbonylmethyl-5-oxooxazolidine-3-carboxylate. The product thus obtained was used without further purification in the subsequent reaction.

Example 13

Benzyl (S)-5-oxo-4-(2-oxopropyl)oxazolidine-3-carboxylate

CuBr (24.54 g, 168 mmol, 1.2 eq.) and LiBr (29.18 g, 336 mmol, 2.4 eq.) were initially charged in a baked-out flask under argon, then dissolved in 600 ml of absolute THF and stirred at RT for 20 min. This gave a clear yellow-orange solution. The mixture was then cooled to −78° C., and MeMgCl solution (55.46 ml, 168 mmol, 1.2 eq.) was added dropwise thereto. This led to a yellow suspension which was difficult to stir, so that a further 75 ml of THF were added dropwise; the mixture was subsequently stirred at −60° C. for 15 min. The carbonyl chloride from example 12 dissolved in about 150 ml of THF (41.67 g, 140 mmol) was initially stirred at −60° C. and then slowly added dropwise. The reaction mixture thus formed was stirred at this temperature for 1 h. The workup was effected by adding about 100 ml of saturated NH$_4$Cl solution; the mixture was stirred vigorously at −60° C. for 10 min, then 200 ml of heptane and 60 ml of water were added and the mixture was stirred at RT for a further 15 min. The phases were separated, and the aqueous phase was admixed with 50 ml of 1 M HCl (green solution) and extracted twice with about 100 ml of ethyl acetate. The combined organic phases were washed with 2 M HCl solution, saturated NaHCO$_3$ and saturated NaCl solution, dried over sodium sulfate and concentrated under reduced pressure. Subsequently, purification was effected by means of silica gel flash chromatography (5:1-2:1 heptane/ethyl acetate); production fractions were combined and freed of solvent residues under reduced pressure. Yield: 21.6 g, 56% of theory $^1$H NMR (250 MHz, 390 K, DMSO-d6): 7.35 (s, 5H); 5.43; 5.22 (2 d, 2H); 5.13 (d, 2H); 4.4 (dd, 1H); 3.26, 3.04 (each 2 dd, 2H); 2.07 (s, 3H).

Example 14

Benzyl (S)-4-(2,2-difluoropropyl)-5-oxooxazolidine-3-carboxylate 15.52 g of the compound from example 13 (56 mmol) were suspended in 5 ml of dichloromethane and admixed with stirring with 25 g (20.8 ml, 2.02 eq.) of BAST. For 14 days, the mixture was stirred under argon. Intermediate LC-MS spectra showed that the conversion was not yet complete after 3 and 9 days. For workup, the reaction solution was added dropwise to a cooled sodium hydrogencarbonate solution (vigorous gas evolution) and stirred further for about 30 min (no gas evolution), and the aqueous solution was then extracted by shaking twice with DCM. The aqueous phase was adjusted to pH 3 with dilute HCl solution and extracted by shaking with DCM twice more. The organic phases were combined and washed with saturated NaCl solution, dried over sodium sulfate and concentrated by evaporation under reduced pressure. The residue was chromatographed through silica gel with DCM/methanol (to 0-6% methanol), and product fractions were combined and freed of solvent residues under reduced pressure. Yield: 8 g, corresponds to 48% of theory.

Example 15

(S)-2-Benzyloxycarbonylamino-4,4-difluoropentanoic acid

The compound from example 14 (4.9 g, 16.37 mmol) was dissolved in 30 ml of acetone and cooled to 0° C., and then 1 N sodium hydroxide solution (32.74 ml, 32.74 mmol, 2 eq.) was added. For about 2.5 h, the reaction mixture was stirred at room temperature; reaction monitoring by LC-MS indicated complete conversion. This was followed by addition of 20 ml of 1 N HCl, distilling-off of acetone under reduced pressure and adjustment of the solution to pH 3 to 4. The mixture was extracted twice by shaking with ethyl acetate. The organic phase was washed with saturated NaCl solution, dried over sodium sulfate and concentrated by evaporation to dryness under reduced pressure. The crude product was chromatographed using silica gel with a DCM/methanol gradient (0-6% methanol).

Yield: 4.7 g (quantitative).

Example 16

(S)-2-tert-Butoxycarbonylamino-4,4-difluoropentanoic acid

The compound from example 15 (2.99 g, 10.44 mmol) was dissolved in 40 ml of methanol and 580 mg of 10% Pd/C were added. Hydrogenation was effected at 2 bar for 3 h. Only a vanishingly small Z elimination was detected. Another 300 mg of catalyst were added and hydrogenation was effected for a further 2 h-low conversion. The same amount of catalyst was added again and hydrogenation was effected overnight; only then was the conversion complete. The mixture was filtered off from the catalyst and concentrated by evaporation. The residue was partly dissolved in dioxane/water (40 ml), and sodium carbonate (700 mg, 0.6 eq), 10.4 ml of 1 N NaOH solution (10.4 mmol, 1 eq.) and 2.6 g of di-tert-butyl dicarbonate (11.94 mmol, 1.14 eq.) were added. After about 2 h, the conversion was complete. The solution was extracted with ether and the ether phase was discarded. Subsequently, the aqueous phase was acidified to pH 3 with 1 N HCl and extracted twice with ethyl acetate. The organic phase was washed with a saturated a NaCl solution, dried over sodium sulfate, filtered off from the desiccant and concentrated by evaporation under reduced pressure.

Yield: 950 mg, 36% of theory.
$^1$H NMR: 12.8 (s, 1H); 7.25 (d, 1H); 4.11 (t, 1H); 2.3 (m, br., 2H); 1.6 (t, 3H); 1.37 (s, 9H).

Example 17 tert-Butyl [(S)-1-(1-cyanocyclopropylcarbamoyl)-3,3-difluorobutyl]carbamate 1.35 g (5.33 mmol) of the product from example 16, 810 mg (6.83 mmol, 1.3 eq.) of 1-amino-1-cyclopropylnitrile hydrochloride and 943 mg (6.93 mmol, 1.3 eq.) of HOAt were dissolved or suspended in 18 ml of dichloromethane, cooled to 0° C. and then admixed with 1.33 g (6.93 mmol, 1.3 eq.) of EDCl and 1.76 ml (1.596 g, 13.86 mmol, 2.6 eq.) of NEM. The mixture was stirred at 0° C. to RT for 16 h. The reaction mixture was then diluted with 40 ml of DCM and extracted by shaking with 1 N HCl solution, saturated sodium hydrogencarbonate solution and saturated NaCl solution. The organic phase was dried over sodium sulfate and concentrated by evaporation under reduced pressure. The product was sufficiently clean for further reactions.

Yield: 1.5 g, 89% of theory.

Example 18

N-(1-cyanocyclopropyl)-(S)-2-amino-4,4-difluoropentanamide

To detach the Boc protecting group, the compound from example 17 (580 mg, 1.83 mmol) was admixed with 10 ml of 1:1 TFA/DCM and stirred at RT for 30 min. Subsequently, the mixture was concentrated by evaporation under reduced pressure and subjected to azeotropic distillation with dichloromethane and toluene, and solvent residues were removed under high vacuum. The product was present as the trifluoroacetate.

Yield: 340 mg.

Example 19

General Preparation Method: Reaction of an N-Carbonyl Chloride with C-Terminally Protected Amino Acid Units 1 mmol of the free amino acid which has been C-terminally protected or is present as the amide (for example the product from example 18 after it has been released by basic treatment) was dissolved in 10 ml of THF and cooled to 0° C. The acid chloride from example 10 (1 mmol dissolved in 5 ml of cold THF) was then added slowly in two portions over 60 min.

Subsequently, the mixture was stirred further overnight. The reaction mixture was added to 50 ml of dichloromethane, washed with water and saturated NaHCO₃ solution, dried over sodium sulfate and concentrated by a rotary evaporation. The resulting oily product was subsequently in each case purified directly by HPLC(RP-18, acetonitrile-water), and product fractions were freeze-dried. The yields in this process of urea formation were from about 10 to 50% of theory).

Example 20

Benzyl (S)-5-oxo-4-(2-oxo-3-phenylpropyl)oxazolidine-3-carboxylate

Analogously to example 13, benzyl (S)-5-oxo-4-(2-oxo-3-phenylpropyl)oxazolidine-3-carboxylate was prepared starting from benzyl (S)-4-chlorocarbonylmethyl-5-oxo-oxazolidine-3-carboxylate (5.00 g, 16.8 mmol) and 15 ml of a 20% benzylmagnesium chloride solution (20.2 mmol, 1.2 eq) in THF. The product was obtained as a yellow oil.
Yield: 5.0 g, 84% of theory.

Example 21

Benzyl (S)-4-(2,2-difluoro-3-phenylpropyl)-5-oxooxazolidine-3-carboxylate

Analogously to example 14, benzyl (S)-4-(2,2-difluoro-3-phenylpropyl)-5-oxo-oxazolidine-3-carboxylate was prepared starting from benzyl (S)-5-oxo-4-(2-oxo-3-phenylpropyl)oxazolidine-3-carboxylate (5.00 g, 14.2 mmol) and BAST (12.5 g, 56.60 mmol, 4 eq.). After chromatography on silica gel (dichloromethane/methanol), pure benzyl (S)-4-(2,2-difluoro-3-phenylpropyl)-5-oxooxazolidine-3-carboxylate was obtained in the form of a yellow oil.
Yield: 1.2 g, 23% of theory Example 22

(S)-2-Benzyloxycarbonylamino-4,4-difluoro-5-phenylpentanoic acid

Analogously to example 15, (S)-2-benzyloxycarbonylamino-4,4-difluoro-5-phenylpentanoic acid was prepared starting from benzyl (S)-4-(2,2-difluoro-3-phenylpropyl)-5-oxooxazolidine-3-carboxylate (1.2 g, 3.20 mmol). The product was obtained in the form of a yellow oil which was used directly for the subsequent reactions.
Yield: 1.02 g, 88% of theory.

Example 23

Methyl (S)-2-benzyloxycarbonylamino-4,4-difluoro-5-phenylpentanoate

Trimethylsilyl chloride (0.61 g, 5.61 mmol, 2 eq) was added dropwise to a solution of (S)-2-benzyloxycarbonylamino-4,4-difluoro-5-phenylpentanoic acid (1.02 g, 2.81 mmol) in 40 ml of methanol. After the addition had ended, the mixture was stirred at RT for 3 h. The solvent was removed under reduced pressure and the residue was used crude in the reaction which followed.
Yield: 1.0 g, 94% of theory.

Example 24

Methyl (S)-2-amino-4,4-difluoro-5-phenylpentanoate

In a three-neck flask, methyl (S)-2-benzyloxycarbonylamino-4,4-difluoro-5-phenyl-pentanoate (1.0 g, 2.65 mmol) was dissolved in 25 ml of methanol. After repeated evacuation and sparging with argon, 350 mg of Pd/C (10%) were added. After degassing and sparging with argon again, the argon atmosphere was replaced by hydrogen (balloon with H₂ gas). The mixture was stirred at RT for 3 h. Owing to incomplete conversion, a further 350 mg of catalyst were added and the mixture was hydrogenated at RT for a further 5 h. On completion of conversion, the reaction mixture was filtered. The mixture was washed with 20 ml of methanol and the filtrate was concentrated by evaporation under reduced pressure. A waxy residue was obtained which, as well as the desired product, also contained smaller amounts of the monodefluorinated and didefluorinated product. This residue was used without further purification for the further reaction.
Yield: 530 mg, 82% of theory.

Example 25

Methyl (S)-4,4-difluoro-2-isocyanato-5-phenylpentanoate

Under argon, methyl (S)-2-amino-4,4-difluoro-5-phenylpentanoate (400 mg, 1.64 mmol) was dissolved in 20 ml of dichloromethane. At RT, pyridine (520 mg, 4 eq.) was added dropwise and the resulting solution was stirred for 15 minutes. The mixture was then cooled to 0° C. and admixed with 20% phosgene solution in toluene (2.16 ml, 4.1 mmol, 2.5 eq.). The mixture was stirred at RT for 90 minutes and then the solvent was removed under reduced pressure. The mixture was codistilled with 10 ml of toluene twice more. The crude product thus obtained was used for the reactions which followed without further purification.
Yield: 425 mg, 96% of theory Example 26

Methyl (S)-2-[(8-azaspiro[4.5]decane-8-carbonyl)amino]-4,4-difluoro-5-phenylpentanoate Methyl (S)-4,4-difluoro-2-isocyanato-5-phenylpentanoate (425 mg, 1.58 mmol) were dissolved in 25 ml of dichloromethane. 8-Azaspiro[4.5]decane (220 mg, 1.58 mmol, 1 eq.) and DIPEA (269 µl, 204 mg, 1.58 mmol, 1 eq.) were added to this solution which was stirred at RT overnight. The solvent was removed under reduced pressure and the residue was purified by preparative HPLC (gradient: acetonitrile/water and addition of 0.05% TFA). The product-containing fractions were combined and freed from the solvent under reduced pressure.
Yield: 245 mg, 38% of theory.

Example 27

(S)-2-[(8-Azaspiro[4.5]decane-8-carbonyl)amino]-4,4-difluoro-5-phenyl-pentanoic acid Methyl (S)-2-[(8-azaspiro[4.5]decane-8-carbonyl)amino]-4,4-difluoro-5-phenylpentanoate (240 mg, 0.59 mmol) was dissolved in a mixture of 15 ml of THF and 5 ml of methanol. A solution of 42 mg of LiOH (1.76 mmol, 3 eq.) in 5 ml of water was added and the mixture was stirred at RT for 3 h. After the reaction had ended, the reaction mixture was acidified to pH=3 by adding a 2 M HCl solution. The organic solvent was removed under reduced pressure and the remaining aqueous phase was extracted with ethyl acetate. Subsequently, the organic phase was washed another three times with water and once with saturated NaCl solution, dried over MgSO₄ and freed from the solvent under reduced pressure. The product was obtained in the form of a yellow solid which was used in the reaction which followed without further purification.

Yield: 192 mg, 82% of theory.

Example 28

N—[(S)-1-(1-Cyanocyclopropylcarbamoyl)-3,3-difluoro-4-phenylbutyl]-8-azaspiro[4.5]decane-8-carboxamide DIPEA (331 µl, 252 mg, 1.95 mmol, 4 eq.), HATU (185 mg, 0.49 mmol, 1 eq.) and 1-aminocyclopropanecarbonitrile hydrochloride (58 mg, 0.49 mmol, 1 eq.) were added successively to a solution of the (S)-2-[(8-azaspiro[4.5]decane-8-carbonyl)amino]-4,4-difluoro-5-phenylpentanoic acid obtained as a crude product (192 mg, 0.49 mmol) in 10 ml of DMF. The reaction mixture was stirred at RT overnight and, the next day, concentrated under reduced pressure. The residue thus obtained was purified by preparative HPLC (gradient: acetonitrile/water and addition of 0.05% TFA). The title compound was obtained in the form of a colorless crystalline material.

Yield: 34 mg, 15% of theory.

$^1$H NMR: 8.83 (s, 1H); 7.48-7.15 (m, 5H); 6.62 (s, 1H); 4.39 (m, 1H); 3.30-3.15 (m, 6H); 2.39 (m, 1H); 2.22 (m, 1H); 1.65-1.05 (m, about 16H); MS (ESI⁺): 459.2

Example 29 tert-Butyl 9-cyclopropyl-3,9-diazaspiro[5.5]undecane-3-carboxylate tert-Butyl 3,9-diazaspiro[5.5]undecane-3-carboxylate (250 mg, 0.98 mmol) were dissolved in 10 ml of absolute methanol. 3 g of molecular sieves (3 Å, which had been dried beforehand under high vacuum) were added to this solution. Under argon, glacial acetic acid (0.55 ml, 10 eq.), [(1-ethoxycyclopropyl)oxy]trimethylsilane (0.69 ml, 3.5 eq.) and 4.4 ml of a 1 M NaCNBH₃ solution in THF (4.4 mmol, 4.5 eq.) were then added successively. After stirring at RT for 20 minutes, the mixture was heated to 60° C. and stirred at this temperature for about 15 h. The reaction mixture was filtered and the filtrate was concentrated under reduced pressure. The residue was taken up in dichloromethane, washed successively with 1 M NaOH solution and NaCl solution, and dried over MgSO₄. After the solvent had been removed under reduced pressure, the product was obtained as a colorless oil.

Yield: 318 mg (quant.)

Example 30

3-Cyclopropyl-3,9-diazaspiro[5.5]undecane

The tert-butyl 9-cyclopropyl-3,9-diazaspiro[5.5]undecane-3-carboxylate obtained as a crude product (318 mg, 0.98 mmol) was dissolved in 6 ml of dichloromethane and admixed with 1 ml of a 4 M HCl solution in dioxane (4 mmol, 4 eq.) with ice bath cooling. The mixture was stirred at RT for about 16 h. The solvent was evaporated under reduced pressure. The residue was taken up in 20 ml of water and lyophilized. Thus, 3-cyclopropyl-3,9-diazaspiro[5.5]undecane hydrochloride was obtained as a crude product in the form of a colorless amorphous material which was clean enough for further reactions.

Yield: 252 mg, quantitative.

The piperidine derivative thus obtained was converted to the end products, which are listed in table 1a and 1b, as in the above-described examples.

Example 31 tert-Butyl 9-butyl-3,9-diazaspiro[5.5]undecane-3-carboxylate tert-Butyl 3,9-diazaspiro[5.5]undecane-3-carboxylate (150 mg, 0.59 mmol) was dissolved in 10 ml of absolute dichloromethane and admixed with butyraldehyde (52 µl, 1 eq.). With ice bath cooling, 17 µl of glacial acetic acid (0.5 eq.) and sodium triacetoxyborohydride (137 mg, 1.1 eq.) were added. The mixture was stirred at RT for 16 h. Owing to incomplete reaction, butyraldehyde (52 µl, 1 eq.), glacial acetic acid (17 µl, 0.5 eq.) and sodium triacetoxyborohydride (137 mg, 1.1 eq.) were again added. After stirring at RT for a further 4 h, a little water was added and the reaction mixture was washed with saturated NH₄Cl solution. The organic phase was dried over MgSO₄ and freed from the solvent under reduced pressure. The product was obtained as a colorless oil.

Yield: 211 mg (quant.)

Example 32

3-Butyl-3,9-diazaspiro[5.5]undecane

The tert-butyl 9-butyl-3,9-diazaspiro[5.5]undecane-3-carboxylate obtained as a crude product (183 mg, 0.59 mmol) was dissolved in 4 ml of dichloromethane and admixed with 0.6 ml of a 4 M HCl solution in dioxane (2.4 mmol, 4 eq.) with ice bath cooling. The mixture was stirred at RT for about 16 h. The solvent was removed under reduced pressure. The residue was taken up in 20 ml of water and lyophilized. Thus, 3-butyl-3,9-diazaspiro[5.5]undecane hydrochloride was obtained as a crude product in the form of a colorless amorphous material which was clean enough for further reactions.

Yield: 176 mg, quantitative.

The piperidine derivative thus obtained was converted to the end products, which are listed in table 1a and 1b, as in the above-described examples.

Example 33

1,4-Dioxaspiro[4.5]decane-8-carboxylic acid 3.0 g (14 mmol) of the ethyl ester precursor, ethyl 1,4-dioxaspiro[4.5]decane-8-carboxylate, were dissolved in 5 ml of methanol and admixed at RT slowly with 28 ml (2 eq.) of 1 M LiOH solution. The mixture was stirred overnight; HPLC-MS indicated complete reaction. Methanol was distilled off under reduced pressure and the residue was acidified cautiously with 1 ml of HCl such that no acid excess was present. The mixture was extracted with ethyl acetate, and the ethyl acetate phase was dried over sodium sulfate and then concentrated by evaporation under reduced pressure. Yield: 2.25 g, 86% of theory.

Example 34 tert-Butyl [(S)-1-(1-cyanocyclopropylcarbamoyl)-3-methylbutyl]carbamate 5 g of Boc-(S)-Leu-OH (21.6 mmol), 3.3 g of 1-aminocyclopropanecarbonitrile hydrochloride (28.1 mmol, 1.3 eq.) and 3.8 g of HOBt (28.1 mmol, 1.3 eq.) were suspended in 60 ml of dichloromethane and admixed at 0° C. successively with 5.4 g of EDCl (28.1 mmol, 1.3 eq.) and 7.15 ml of NEM (6.5 g, 56.2 mmol, 2.6 eq.). The mixture was stirred at 0° C. to RT overnight, extracted by shaking under acidic (1 M HCl solution), basic (saturated NaHCO₃ solution) and neutral (saturated NaCl solution) conditions, and dried over sodium sulfate, and the solvent was distilled off under reduced pressure. The mixture was then chromatographed on silica gel in ethyl acetate/heptane. Yield: 3.62 g, 57% of theory.

¹H NMR: 8.82 (s, 1H); 6.92 (d, 1H); 3.86 (m, 1H); 1.55 (m, 1H); 1.47 (m, 2H); 1.36 (s, 9H); 1.09 (m, 2H); 0.86 (dd, 6H); MS (ESI⁺): 296.3.

Example 35

N—[(S)-1-(1-cyanocyclopropylcarbamoyl)-3-methylbutyl]-1,4-dioxaspiro[4.5]decane-8-carboxamide The product from example 34, tert-butyl [(S)-1-(1-cyanocyclopropylcarbamoyl)-3-methylbutyl]carbamate, (1.1 g, 3.72 mmol) was admixed with 20 ml of 1:1 TFA/dichloromethane and stirred at RT for 30 min. Subsequently, the mixture was concentrated by evaporation under reduced pressure and taken up again in dichloromethane and toluene, and solvent and TFA residues were removed under reduced pressure. The resulting N-terminally protected product was reacted further directly. 283 mg (1.5 mmol) thereof were admixed at 0° C. with 136 mg of HOAt (1 mmol, 0.67 eq.), 195 mg of 1,4-dioxaspiro[4.5]decane-8-carboxylic acid from example 33 (1 mmol, 0.67 eq.), 268 mg of EDCI (1.4 mmol, 0.93 eq.) and 0.32 ml of NEM (2.5 mmol) in 2.5 ml of THF and 0.25 ml of DMF, and the mixture was stirred at 0° C. to RT overnight. Subsequently, the solvent was distilled off under reduced pressure, and the residue was taken up in ethyl acetate and extracted by shaking with saturated sodium hydrogencarbonate solution and saturated NaCl solution. Drying over sodium sulfate and evaporating-off the solvent were followed by purification using RP-HPLC (gradient: acetonitrile/water and addition of 0.05% TFA). The product fractions were combined and freeze-dried. Yield: 25 mg (without mixed fractions), corresponds to 7% of theory. ¹H NMR: 8.81 (s, 1H); 7.84 (d, 1H); 4.20 (m, 1H); 3.83 (s, 4H); 2.22 (m, 1H); 1.75-0.8 (3 m, about 13H, 1.05 (m, 2H); 0.82 (dd, 6H); MS (ESI⁺): 364.2.

The examples listed in table 1a were prepared in a manner analogous to that described above. Table 1a shows the examples with accompanying characterization:

TABLE 1a

| Ex. | Molar mass (parent compound) | Structure | MS (ESI⁺) | ¹H NMR |
|---|---|---|---|---|
| 36 | 382.46 | 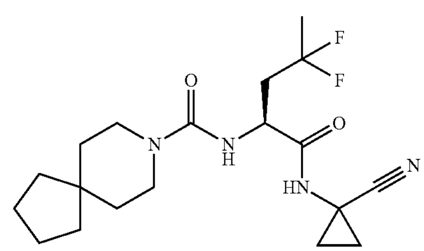 [SMILES: CC(F)(F)C[C@H](NC(=O)N1CCC2(CCCC2)CC1)C(=O)NC1(C#N)CC1] | 383.1 | 8.82 (s, 1H); 6.62 (d, 1H); 4.28 (m, 1H); 3.29 (m, 4H); 2.26 (m, 2H); 1.65-1.05 (mm, 19 H) |
| 37 | 386.4 | 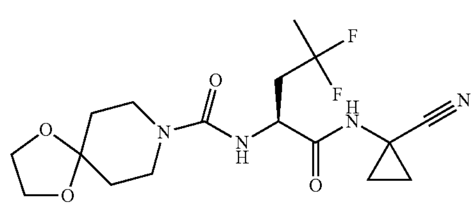 [SMILES: CC(F)(F)C[C@H](NC(=O)N1CCC2(CC1)OCCO2)C(=O)NC1(C#N)CC1] | 387.1 | 8.83 (s, 1); 6.80 (d, 1H); 4.30 (m, 1H); 3.6 (m, 1H); 3.4 (m, approx, 4 H); 2.25 (m, approx, 4H); 1.7-1.4 (mm, approx, 11H); 1.1 (m, 2H) |
| 38 | 396.48 | 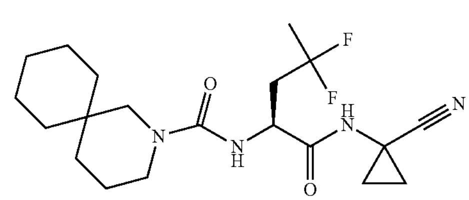 [SMILES: CC(F)(F)C[C@H](NC(=O)N1CCCC2(CCCCC2)C1)C(=O)NC1(C#N)CC1] | 397.1 | 8.81 (s, 1H); 6.6 (d, 1H); 4.3 (m, 1H); 3.3 (m, 2H); 3.15 (dd, 2H); 2.29 (m, 2H); 1.6-1.0 (mm, approx. 20H) |

TABLE 1a-continued

| Ex. | Molar mass (parent compound) | Structure | MS (ESI+) | 1H NMR |
|---|---|---|---|---|
| 39 | 410.51 | CHIRAL | 411.5 | 8.82 (s, 1H); 6.62 (d, 1H); 4.28 (m, 1H); 3.29 (m, 4H); 2.26 (m, 2H); 1.82 (m, 2H); 1.65-1.05 (mm, approx. 18H); 0.88 (t, 3H) |
| 40 | 424.54 | 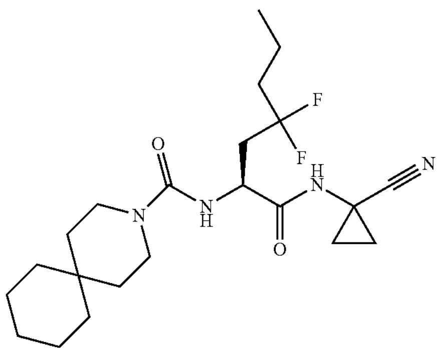 [SMILES: CCCC(F)(F)C[C@H](NC(=O)N1CCC2(CCCCC2)CC1)C(=O)NC1(C#N)CC1] | 425.6 | 8.82 (s, 1H); 6.62 (d, 1H); 4.28 (m, 1H); 3.29 (m, 4H); 2.26 (m, 2H); 1.60-1.05 (mm, approx. 20H); 0.88 (t, 3H) |
| 41 | 503.55 | 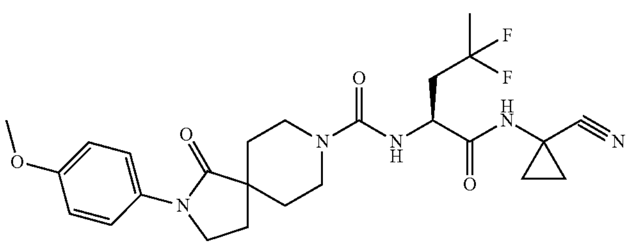 [SMILES: COc1ccc(N2CCC3(CCN(C(=O)N[C@@H](CC(C)(F)F)C(=O)NC4(C#N)CC4)CC3)C2=O)cc1] | 504.2 | 9 (s, 1H); 7.58 (d, 2H); 6.93 (d, 2H); 6.82 (d, 1H); 4.31 8m, 1H); 3.92 (m, 2H); 3.77 (m, 2H); 3.76 (s, 3H); 2.92 (m, 2H); 2.30 (m, 2H); 2.07 (m, 2H); 1.69-1.4 (2m, 9H); 1.1 (m, 2H) |
| 42 | 474.51 | 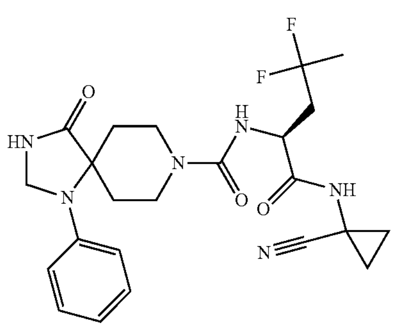 [SMILES: CC(F)(F)C[C@H](NC(=O)N1CCC2(CC1)C(=O)NCN2c1ccccc1)C(=O)NC1(C#N)CC1] | 475.3 | 8.94 (s, 1H); 8.88 (s, 1 H); 7.4 (t, 2H); 6.87 (d, 1H); 6.7 (m, 3H); 4.6 (s, 2H); 4.39 (m, 1H); 3.96 (m, 2H); 2.6-2.2 (m, br, approx, 6H); 1.6 (m, br, approx, 7H); 1.11 (m, 2H) |

TABLE 1a-continued

| Ex. | Molar mass (parent compound) | Structure | MS (ESI+) | 1H NMR |
|---|---|---|---|---|
| 43 | 397.43 | 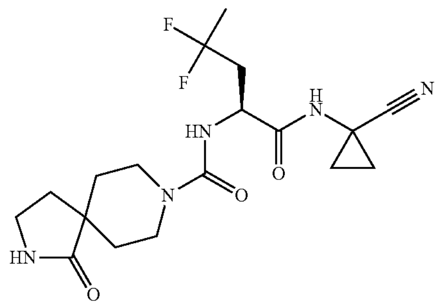 [SMILES: CC(F)(F)C[C@H](NC(=O)N1CCC2(CCNC2=O)CC1)C(=O)NC1(C#N)CC1] | 398.4 | 8.88 (s, 1H); 7.57 (s, 1H); 6.72 (d, 1H); 4.28 (m, 1H); 3.85 (m, 2H); 3.2 (t, 2H); 2.88 (m, 2H); 2.3 (m, 2H); 1.92 (m, 2H); 1.65-1.4 (m, br, 7H); 1.29 (m, 2H); 1,1 (m, 2H) |
| 44 | 411.46 | 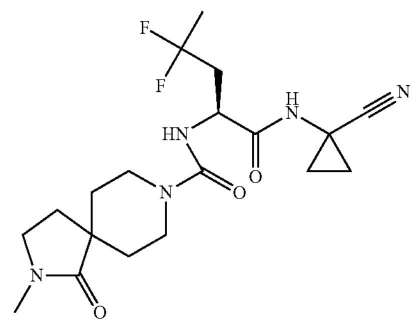 [SMILES: CN1CCC2(CCN(C(=O)N[C@@H](CC(C)(F)F)C(=O)NC3(C#N)CC3)CC2)C1=O] | 412.5 | 8.88 (s, 1H); 6.72 (d, 1H); 4.28 (m, 1H); 3.85 (m, 2H); 3.28 (t, 2H); 2.88 (m, 2H); 2.7 (s, 3H); 2.3 (m, 2H); 1.92 (m, 2H); 1.65-1.4 (m, br, 7H); 1.29 (m, 2H); 1.1 (m, 2H) |
| 45 | 427.5 | 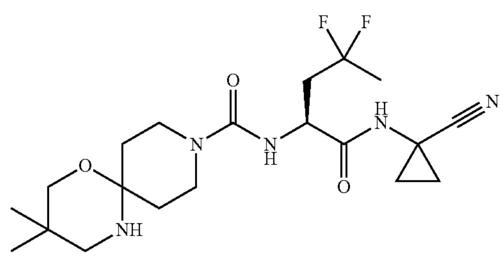 [SMILES: CC(F)(F)C[C@H](NC(=O)N1CCC2(CC1)NCC(C)(C)CO2)C(=O)NC1(C#N)CC1] | 429.5 | 8.85 (s, 1H); 6.75 (d, 1H); 4.29 (m, 1H); 3.6 (s, 1H, overl, water); 3.46 (s, 4H); 3.3 (m, 4H); 2.3 (m, 2H); 1.73-1.42 (3m, 9H); 1.1 (m, 2H); 0.88 (s, 6H) |
| 46 | 430.5 | 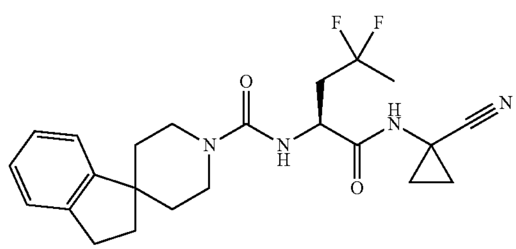 [SMILES: CC(F)(F)C[C@H](NC(=O)N1CCC2(CCc3ccccc32)CC1)C(=O)NC1(C#N)CC1] | 431.2 | 8.89 (s, 1H); 7.15 (m, 4H); 6.74 (d, 1H); 4.34 (m, 1H); 3.98 (dd, 2H); 2.9 (m, 4H); 2.3 (m, 2H); 2.0 (m, 2H); 1.65 (m, 5H); 1.45 (m, 4H); 1.1 (m, 2H) |
| 47 | 412.4 | 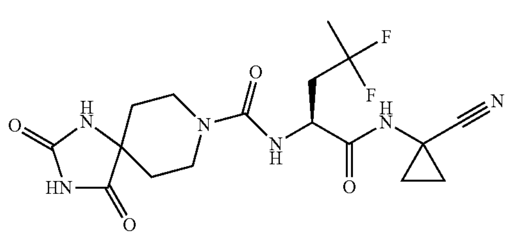 [SMILES: CC(F)(F)C[C@H](NC(=O)N1CCC2(CC1)NC(=O)NC2=O)C(=O)NC1(C#N)CC1] | 413.4 | 8.88 (s, 1H); 8.51 (s, 1H); 6.8 (d, 1H); 4.3 (m, 1H); 3.1 (m, 2H); 2.8-2.1 (m, br, approx. 6H); 1.6 (m, br, approx. 5H); 1.24; 1.11 (2m, 4H) |

TABLE 1a-continued

| Ex. | Molar mass (parent compound) | Structure | MS (ESI+) | ¹H NMR |
|---|---|---|---|---|
| 48 | 368.43 | 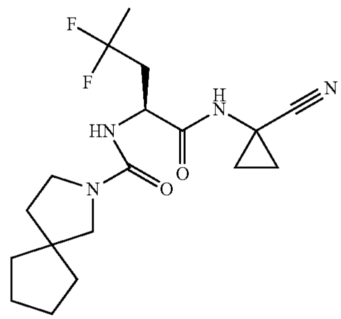 [SMILES: CC(F)(F)C[C@H](NC(=O)N1CCC2(CCCC2)C1)C(=O)NC1(C#N)CC1] | 369.3 | 8.88 (s, 1H); 6.24 (d, 1H); 4.3 (m, 1H); 3.3 (m, 2H); 3.1 (dd, 2H); 2.3 (m, 1H); 1.75-0.9 (mm, 15H); 1.1 (m, 2H) |
| 49 | 487.55 | 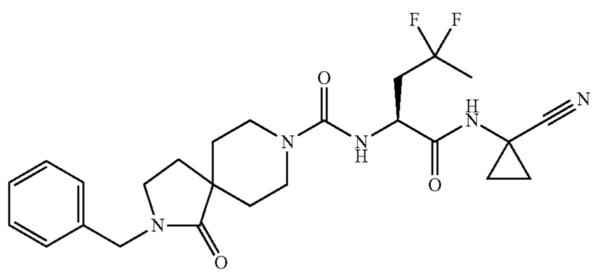 [SMILES: CC(F)(F)C[C@H](NC(=O)N1CCC2(CC1)CCN(Cc1ccccc1)C2=O)C(=O)NC1(C#N)CC1] | 488.5 | 8.88 (s, 1H); 7.4-7.15 (3m, 5H); 6.74 (d, 1H); 4.39 (s, 2H); 4.3 (m, 1H); 3.9 (dd, 2H); 3.18 (m, 2H); 2.9 (dt, 2H); 2.3 (m, 2H); 1.7-1.3 (3m, 6H); 1.1 (m, 1H) |
| 50 | 491.52 | 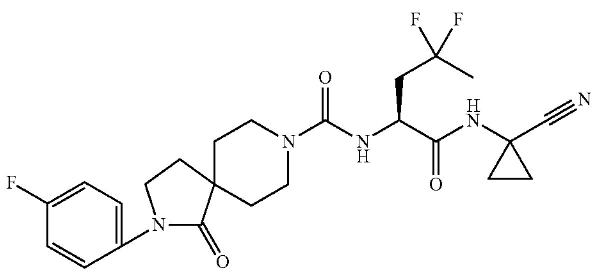 [SMILES: CC(F)(F)C[C@H](NC(=O)N1CCC2(CC1)CCN(c1ccc(F)cc1)C2=O)C(=O)NC1(C#N)CC1] | 492.5 | 8.89 (s, 1H); 7.68 (m, 2H); 7.20 (m, 2H); 6.78 (d, 1H); 4.31 8m, 1H); 3.92 (m, 2H); 3.77 (m, 2H); 2.92 (m, 2H); 2.30 (m, 2H); 2.07 (m, 2H); 1.7-1.4 (2m, 9H); 1.1 (m, 2H) |
| 51 | 400.43 | 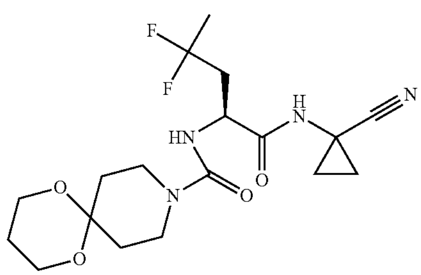 [SMILES: CC(F)(F)C[C@H](NC(=O)N1CCC2(CC1)OCCCO2)C(=O)NC1(C#N)CC1] | 401.3 | 8.82 (s, 1H); 6.72 (d, 1H); 4.28 (m, 1H); 3.83 (m, 4H); 3.3 (m, approx. 4H, water overlap); 2.28 (m, 2H); 1.75-1.4 (3m, approx. 11H); 1.1 (m, 2H) |
| 52 | 476.53 | 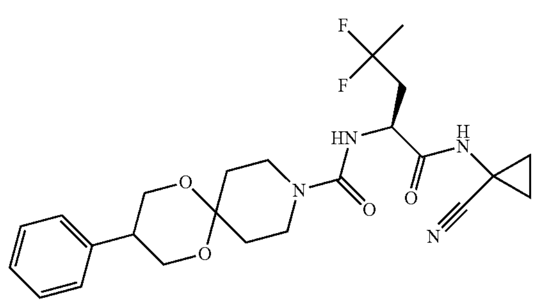 [SMILES: CC(F)(F)C[C@H](NC(=O)N1CCC2(CC1)OCC(c1ccccc1)CO2)C(=O)NC1(C#N)CC1] | 477.4 | 8.86 (s, 1H); 7.31 (s, 5H); 6.8 (d, 1H); 4.30 (m, 1H); 4.0 (m, 2H); 3.9 (m, 2H); 3.4 (m, approx. 5H, overlap water); 3.05 (m, 1H); 2.28 (m, 2H); 2.0 (m, 2H); 1.7-1.3 (2m, approx. 7H); 1.1 (m, 2H) |

TABLE 1a-continued

| Ex. | Molar mass (parent compound) | Structure | MS (ESI+) | 1H NMR |
|---|---|---|---|---|
| 53 | 372.51 | 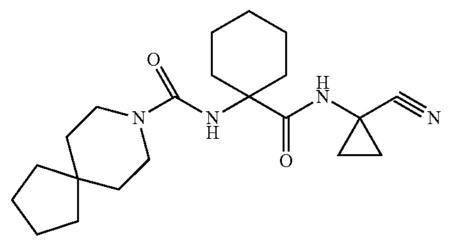 [SMILES: N#CC1(NC(=O)C2(NC(=O)N3CCC4(CCCC4)CC3)CCCCC2)CC1] | 373.2 | 8.26 (s, 1H); 5.83 (s, 1H); 3.26 (m, approx. 5H); 1.9-1.0 (mm, approx. 25 H) |
| 54 | 386.54 | 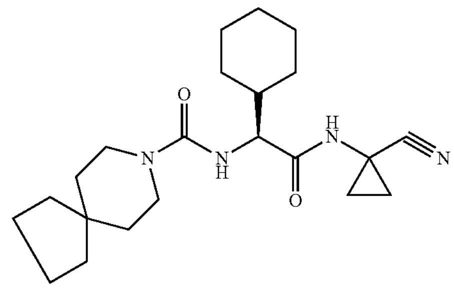 [SMILES: N#CC1(NC(=O)[C@@H](NC(=O)N2CCC3(CCCC3)CC2)C2CCCCC2)CC1] | 387.2 | 8.83 (s, 1H); 6.20 (m, 1H); 3.9, 3.8 (2t, 1H); 3.28 (m, 4H); 1.75-0.8 (mm, approx. 27H) |
| 55 | 453.29 | 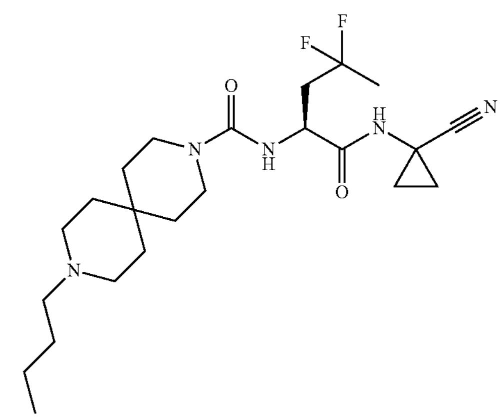 [SMILES: CCCCN1CCC2(CC1)CCN(C(=O)N[C@@H](CC(C)(F)F)C(=O)NC1(C#N)CC1)CC2] | 454.3 | 8.86 (s, 1H); 6.68 (d, 1H); 4.29 (m, 1H); 3.3 (m, 6H); 3.0 (m, 4H); 2.28 (m, 2H); 1.81 (m, 2H); 1.65-1.4 (m, 11H); 1.3 (m, 4H); 1.1 (m, 2H); 0.9 (t, 3H) |
| 56 | 437.26 | 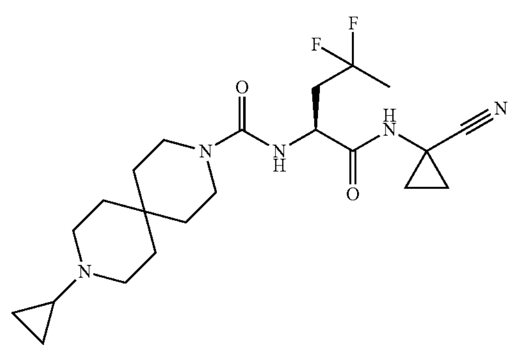 [SMILES: CC(F)(F)C[C@H](NC(=O)N1CCC2(CC1)CCN(C1CC1)CC2)C(=O)NC1(C#N)CC1] | 438.2 | 8.89 (s, 1H); 6.7 (d, 1H); 4.28 (m, 1H); 3.32 (m, approx. 8H, water overlap); 2.89 (m, 1H); 2.26 (m, 2H); 1.83 ("d", 2H); 1.66-1.37 (m, 2m, 9H); 1.28 (m, 2H); 1.1 (m, 2H); 0.85 (2m, 4H) |
| 57 | 303.41 | 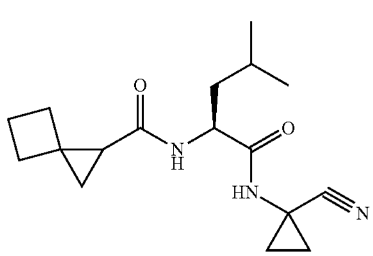 [SMILES: CC(C)C[C@H](NC(=O)C1CC12CCC2)C(=O)NC1(C#N)CC1] | 302.4 (ES−) | 8.89 (s, 1H); 8.1 (d, 1H); 4.18 (m, 1H); 2.0 (m, br, approx. 5H); 1.66-1.32 (m mm, approx. 6H); 1.07 (m, 2H); 0.94-0.74 (m, dd, approx. 10H) |

Further spirocyclic amines which have been used hereinafter for the preparation of further inventive examples were prepared as follows: the spirocyclic amines 7-cyclo-propyl-2,7-diazaspiro[3.5]-nonane, 7-propyl-2,7-diazaspiro[3.5]nonane, 2-cyclopropyl-2,8-diazaspiro[4.5]decane, 2-cyclopropyl-2,7-diazaspiro[3.5]nonane, 2-propyl-2,7-diazaspiro[3.5]nonane, 9-cyclopropyl-1-oxa-4,9-diazaspiro[5.5]undecane and 4-cyclo-propyl-1-oxa-4,9-diazaspiro[5.5]undecane were prepared according to the above-described examples 29-32 starting from the tert-butyloxycarbonyl-protected precursors which are commercially available.

2-Cyclopropylmethyl-2,8-diazaspiro[4.5]decan-3-one was obtained by alkylating tert-butyl 3-oxo-2,8-diazaspiro[4.5]decane-8-carboxylate (commercially available) with cyclopropylmethyl bromide and subsequent elimination of the tert-butyloxycarbonyl protecting group with TFA. 6-Azaspiro[2.5]octane can be prepared according to the literature (Bull. Soc Chim. France 10, 2572-81 (1964)) or else as described below by cyclopropanating tert-butyl 4-methylenepiperidine-1-carboxylate and then detaching the tert-butyloxycarbonyl protecting group.

Example 58

6-Azaspiro[2.5]octane

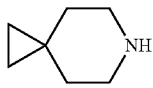

In a baked-out dry flask under protective gas (argon), a mixture of 9.90 g of zinc dust (151 mmol) and 1.50 g of CuCl (15.15 mmol) in 20 ml of abs. diethyl ether was stirred at 50° C. (bath temperature) for approx. 100 min. The mixture was cooled to 15° C. (bath temperature). 6.1 ml of diiodomethane (75.0 mmol), 7.8 ml of abs. dimethoxyethane and finally 4.27 g of tert-butyl 4-methylenepiperidine-1-carboxylate (21.7 mmol) were successively and rapidly added dropwise. The reaction mixture was heated gradually to 50° C. (bath temperature) and stirred at this temperature for approx. 20 h. After this time, owing to still incomplete conversion, another 20 ml of diethyl ether and 6.1 ml of diiodomethane were added with cooling. The reaction mixture was heated to 50° C. (bath temperature) for a further 8 h. Cooling was followed by dilution with THF and filtration through Celite. The filtrate was admixed with 4.3 g of p-toluenesulfonic acid and a few drops of water, and then concentrated under reduced pressure. The crude product thus obtained was dissolved in 100 ml of THF and admixed with 7.09 g of Boc anhydride (1.5 eq.) and 5.5 ml of DIPEA (1.5 eq.). The mixture was stirred at RT for 48 h and then concentrated under reduced pressure. The residue thus obtained was stirred with approx. 150 ml of diethyl ether. The mixture was filtered with suction and the filter residue was washed thoroughly with diethyl ether. The filtrate thus obtained was concentrated. What remained was an oil which was taken up in 200 ml of dichloromethane and was washed twice with sat. NaHCO$_3$ solution and once with dil. HCl solution (pH=5). The organic phase was dried over MgSO$_4$ and then concentrated under reduced pressure. In this way, 2.8 g of tert-butyl 6-azaspiro[2.5]octane-6-carboxylate were obtained as a light-colored oil. This oil was dissolved in 5 ml of dichloromethane and admixed with a mixture of 10 ml of TFA and 0.5 ml of water. After stirring at RT for 48 h, the reaction solution was concentrated under reduced pressure and codistilled with toluene three times more. In this way, 6-azaspiro[2.5]octane was obtained as a TFA salt in the form of a brown oil which was clean enough for further reactions.

Yield: 1.50 g (31% of theory) MS (ESI$^+$): 112.

The 6-azaspiro[2.5]octane thus obtained was converted to the inventive compounds which have been described in examples 61-63 and 68-70.

Example 59

Methyl (S)-2-amino-4,4-difluoropentanoate hydrochloride

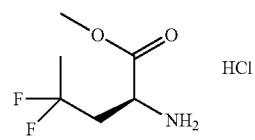

At approx. 5° C. (ice bath cooling), 8.2 ml of thionyl chloride (112.6 mmol; 1.5 eq.) were added dropwise to 100 ml of methanol (p.a.) under argon. The mixture was allowed to come to RT within 30 min and stirred for a further 30 min. 19.0 g of (S)-2-tert-butoxycarbonylamino-4,4-difluoropentanoic acid (75.0 mmol) were added in portions to this reaction mixture. The reaction mixture was stirred at RT for 2 h. Thereafter, the reaction mixture was warmed to 35° C. (internal temperature) and stirred at this temperature for another 3 h. Subsequently, the mixture was concentrated under reduced pressure, which afforded methyl (S)-2-amino-4,4-difluoropentanoate hydrochloride as a slightly brownish crystalline solid which was clean enough for further reactions. Yield: 13.5 g (89% of theory).

Example 60

Methyl (S)-4,4-difluoro-2-isocyanatopentanoate

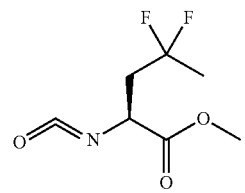

Under argon, 2.0 g of methyl (S)-2-amino-4,4-difluoropentanoate hydrochloride (9.8 mmol) were dissolved in 80 ml of dichloromethane, admixed with 3.2 ml of pyridine (4 eq.) and cooled to approx. 5° C. (ice bath). After 10 min, 6.7 ml (1.3 eq.) of a 20% phosgene solution in toluene were slowly added dropwise. The resulting suspension was stirred with ice bath cooling for 3 h and then concentrated under reduced pressure. The residue thus obtained was taken up in toluene and filtered. After the solvent had been removed under reduced pressure, methyl (S)-4,4-difluoro-2-isocyanatopentanoate was obtained as a brown oil which was used in the subsequent reaction without further purification. Yield: 1.1 g (58% of theory).

Example 61

Methyl (S)-2-[(6-azaspiro[2.5]octane-6-carbonyl)amino]-4,4-difluoropentanoate

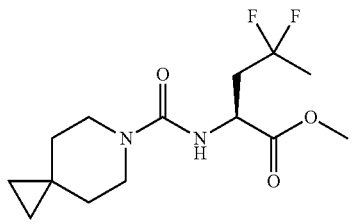 [SMILES: COC(=O)[C@H](CC(C)(F)F)NC(=O)N1CCC2(CC1)CC2]

A solution of 0.75 g of 6-azaspiro[2.5]octane trifluoroacetate (3.30 mmol, 1 eq.) and 0.75 ml of DIPEA (1.3 eq.) in 6 ml of dichloroethane was added under argon to a solution of 0.65 g of methyl (S)-4,4-difluoro-2-isocyanatopentanoate (3.36 mmol) in 4 ml of dichloroethane. The reaction mixture was stirred at RT overnight. The mixture was diluted with 10 ml of dichloromethane and washed with saturated NaHCO₃ solution. The organic phase was dried over MgSO₄ and then concentrated under reduced pressure. The residue thus obtained was purified by preparative HPLC (gradient: acetonitrile/water and addition of 0.05% TFA). The product-containing fractions were combined and freeze-dried.

Yield: 200 mg, 20% of theory MS (ESI⁺): 305.

Example 62

(S)-2-[(6-Azaspiro[2.5]octane-6-carbonyl)amino]-4,4-difluoropentanoic acid

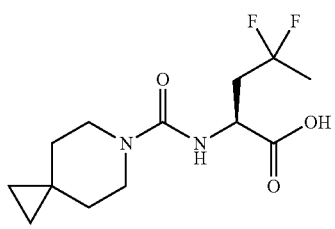 [SMILES: CC(F)(F)C[C@H](NC(=O)N1CCC2(CC1)CC2)C(=O)O]

365.0 mg of methyl (S)-2-[(6-azaspiro[2.5]octane-6-carbonyl)amino]-4,4-difluoropentanoate (1.2 mmol) were dissolved in a mixture of 10.8 ml of THF and 3.6 ml of methanol. 3.6 ml of an aqueous 1 M LiOH solution (3 eq.) were added to this solution. The mixture was stirred at 45° C. (bath temperature) for one hour and then 3.6 ml of 1 M HCl solution were added. The mixture was concentrated under reduced pressure and codistilled with DMF twice more. The (S)-2-[(6-azaspiro[2.5]octane-6-carbonyl)amino]-4,4-difluoropentanoic acid thus obtained was clean enough for the next reaction. Yield: 400 mg (quant.)

Example 63

N—[(S)-1-(1-cyanocyclopropylcarbamoyl)-3,3-difluorobutyl]-6-azaspiro[2.5]octane-6-carboxamide

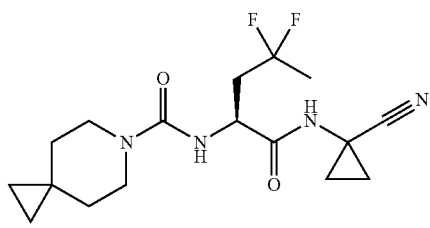 [SMILES: CC(F)(F)C[C@H](NC(=O)N1CCC2(CC1)CC2)C(=O)NC1(C#N)CC1]

142.3 mg of 1-aminocyclopropanecarbonitrile hydrochloride (1.2 mmol, 1.0 eq.), 163.3 mg of HOAt (1.0 eq.), 0.61 ml of DIPEA (3 eq.) and 456 mg of HATU (1.0 eq.) were added successively to a solution of 348.0 mg of (S)-2-[(6-azaspiro[2.5]octane-6-carbonyl)amino]-4,4-difluoropentanoic acid (1.2 mmol) in 5 ml of DMF. The reaction mixture was stirred at RT for 24 h and then concentrated under reduced pressure. The residue was taken up in 10 ml of dichloromethane, washed with a little sat. NaHCO₃ solution and then a little dilute HCl solution (pH=5), and dried over MgSO₄. The residue thus obtained was purified by preparative HPLC (gradient: acetonitrile/water and addition of 0.05% TFA). The product-containing fractions were combined and freeze-dried. In this way, N—[(S)-1-(1-cyanocyclopropylcarbamoyl)-3,3-difluorobutyl]-6-azaspiro[2.5]octane-6-carboxamide was obtained as a colorless amorphous solid.

Yield: 200 mg, 47% of theory. MS (ESI⁺): 355.1.

¹H NMR: 8.85 (s, 1H); 6.68 (d, 1H); 4.30 (m, 1H); 3.30-3.40 (m, 4H); 2.30 (m, 2H); 1.60 (t, 3H); 1.50 (m, 2H); 1.25 (m, 4H); 1.10 (m, 2H); 0.30 (s, 4H).

Example 64

Methyl (S)-2-benzyloxycarbonylamino-4-oxo-5-phenylpentanoate

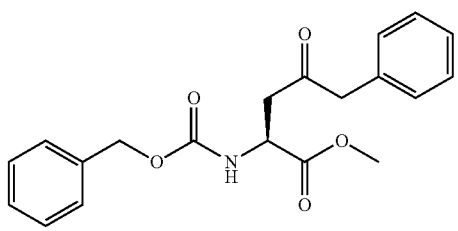 [SMILES: COC(=O)[C@H](CC(=O)Cc1ccccc1)NC(=O)OCc1ccccc1]

In a baked-out, argon-purged flask, 3.7 g of lithium bromide (2.4 eq.) and 4.38 g (1.2 eq) of CuBr-Me₂S were dissolved in 55 ml of abs. THF and stirred at RT for 20 min. The resulting yellow solution was cooled to −70° C. and admixed with 16.2 ml (1.2 eq.) of benzylmagnesium chloride solution (20% in THF). After a further 20 min at −70° C., a solution of 5.32 g of methyl (S)-2-benzyloxycarbonylamino-3-chlorocarbonylpropionate (example 1) (17.75 mmol) in 15 ml of THF was added. After 2 h, the mixture was heated slowly to −35° C. and 50 ml of a sat. NH₄Cl solution were added. The reaction mixture was diluted with 400 ml of dichloromethane and washed with 100 ml of a 2 M HCl solution. The aqueous phase was washed twice more with 50 ml of dichloromethane. The combined organic phases were washed successively with 2 M HCl solution, sat. NaHCO₃ solution and sat. NaCl solution, dried over MgSO₄ and concentrated under reduced pressure. Methyl (S)-2-benzyloxycarbonylamino-4-oxo-5-phenylpentanoate was obtained as a yellow oil which was used in the next stage without further purification.

Yield: 6.39 g (quant.)

Example 65

Methyl (S)-2-benzyloxycarbonylamino-4,4-difluoro-5-phenylpentanoate

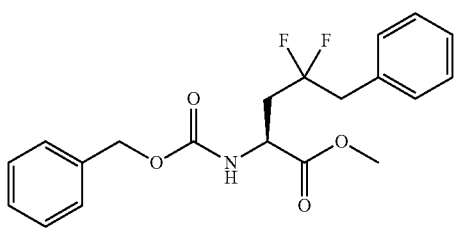 [SMILES: COC(=O)[C@H](CC(F)(F)Cc1ccccc1)NC(=O)OCc1ccccc1]

In a Teflon vessel, 6.3 g of methyl (S)-2-benzyloxycarbonylamino-4-oxo-5-phenylpentanoate (17.7 mmol) were dissolved in 10 ml of dichloromethane. Under argon, 5 g of BAST (1.28 eq.) were added. The reaction mixture was stirred at 40° C. (bath temperature) for 20 h. Another 5 g of BAST (1.28 eq.) were added and the mixture was stirred at 40° C. for a further 20 h. The reaction mixture was added dropwise to 500 ml of an ice-cooled NaHCO₃ solution and diluted with 200 ml of dichloromethane. The phases were separated and the aqueous phase was washed twice with 100 ml of dichloromethane. The combined organic phases were washed with a 1 M HCl solution and with sat. NaCl solution, dried over MgSO₄ and concentrated under reduced pressure. The residue (dark brown oil) was purified by flash chromatography on silica gel with a heptane/ethyl acetate mixture. Methyl (S)-2-benzyloxycarbonylamino-4,4-difluoro-5-phenylpentanoate was obtained as a yellow waxy substance.

Yield: 3.03 g (45% of theory).

Example 66

Methyl (S)-2-amino-4,4-difluoro-5-phenylpentanoate

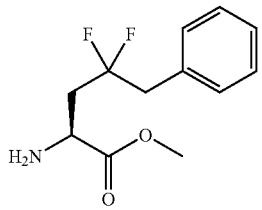 [SMILES: COC(=O)[C@@H](N)CC(F)(F)Cc1ccccc1]

3.0 g of methyl (S)-2-benzyloxycarbonylamino-4,4-difluoro-5-phenylpentanoate (8.0 mmol) were admixed with 8.0 ml (5 eq.) of a 30% HBr solution in glacial acetic acid with ice bath cooling and stirred for 3 h. 100 ml of diethyl ether were added and the resulting precipitate was filtered off with suction. The crude product thus obtained was purified by preparative HPLC (gradient: acetonitrile/water and addition of 0.05% TFA). The amorphous solid obtained after freeze-drying was taken up in dichloromethane and washed with sat. NaHCO₃ solution. The organic phase was dried over MgSO₄ and concentrated under reduced pressure. Thus, methyl (S)-2-amino-4,4-difluoro-5-phenyl-pentanoate was obtained as a yellow oil.

Yield: 817 mg (42% of theory)

Example 67

Methyl (S)-4,4-difluoro-2-isocyanato-5-phenylpentanoate

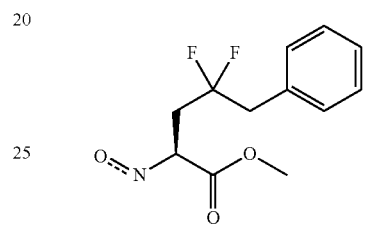

817 mg of methyl (S)-2-amino-4,4-difluoro-5-phenylpentanoate (3.36 mmol) were dissolved in 20 ml of dichloromethane, admixed with 1.08 ml of pyridine (4 eq.) and cooled to approx. 5° C. (ice bath). After 10 min, 2.3 ml (1.3 eq.) of a 20% phosgene solution in toluene were added dropwise. The resulting suspension was stirred with ice bath cooling for 4 h and then concentrated under reduced pressure. The residue thus obtained was taken up in toluene and filtered. After the solvent had been removed under reduced pressure, methyl (S)-4,4-difluoro-2-isocyanato-5-phenylpentanoate was obtained as an orange oil which was used without further purification in the subsequent reaction. Yield: 943 mg (quant.)

Example 68

Methyl (S)-2-[(6-azaspiro[2.5]octane-6-carbonyl)amino]-4,4-difluoro-5-phenylpentanoate

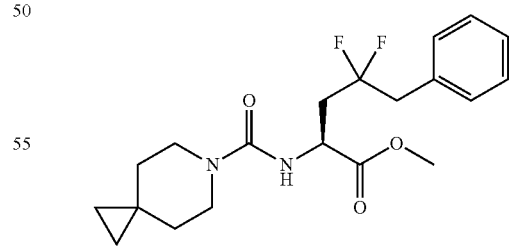

Methyl (S)-2-[(6-azaspiro[2.5]octane-6-carbonyl)amino]-4,4-difluoro-5-phenylpentanoate was prepared analogously to example 61, starting from 904 mg of methyl (S)-4,4-difluoro-2-isocyanato-5-phenylpentanoate (3.36 mmol) and 907 mg of 6-azaspiro[2.5]octane trifluoroacetate (1.2 eq.). Chromatographic separation by preparative HPLC (gradient: acetonitrile/water and addition of 0.05% TFA) gave methyl (S)-2-[(6-azaspiro[2.5]octane-6-carbonyl)amino]-4,4-difluoro-5-phenylpentanoate as a yellow oil. Yield: 234 mg (18% of theory)

Example 69

(S)-2-[(6-Azaspiro[2.5]octane-6-carbonyl)amino]-4,4-difluoro-5-phenylpentanoic acid

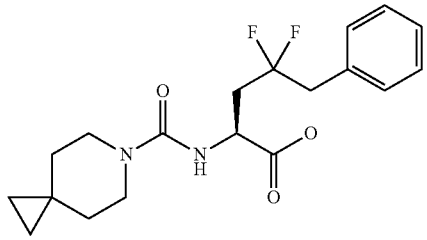 [SMILES: O=C(O)[C@H](CC(F)(F)Cc1ccccc1)NC(=O)N1CCC2(CC1)CC2]

(S)-2-[(6-Azaspiro[2.5]octane-6-carbonyl)amino]-4,4-difluoro-5-phenylpentanoic acid was prepared analogously to example 62, starting from 234 mg of methyl (S)-2-[(6-azaspiro[2.5]octane-6-carbonyl)amino]-4,4-difluoro-5-phenylpentanoate (0.62 mmol). Chromatographic separation by preparative HPLC (gradient: acetonitrile/water and addition of 0.05% TFA) gave (S)-2-[(6-azaspiro[2.5]octane-6-carbonyl)amino]-4,4-difluoro-5-phenylpentanoic acid as a colorless amorphous solid.
Yield: 41 mg (18% of theory).

Example 70

N—[(S)-1-(1-cyanocyclopropylcarbamoyl)-3,3-difluoro-4-phenylbutyl]-6-azaspiro[2.5]octane-6-carboxamide

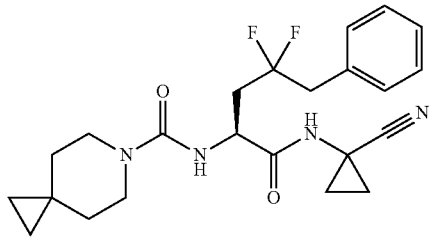 [SMILES: N#CC1(NC(=O)[C@H](CC(F)(F)Cc2ccccc2)NC(=O)N2CCC3(CC2)CC3)CC1]

13.3 mg of 1-aminocyclopropanecarbonitrile hydrochloride (1.0 eq.), 15.2 mg of HOAt (1.0 eq.), 57 μl of DIPEA (3 eq.) and 42.5 mg of HATU (1.0 eq.) were added successively to a solution of 41.0 mg of (S)-2-[(6-azaspiro[2.5]octane-6-carbonyl)amino]-4,4-difluoro-5-phenylpentanoic acid (0.11 mmol) in 5 ml of DMF. The reaction mixture was stirred at RT for 4 h and then concentrated under reduced pressure. The residue thus obtained was purified by preparative HPLC (gradient: acetonitrile/water and addition of 0.05% TFA). The product-containing fractions were combined and freeze-dried. In this way, N—[(S)-1-(1-cyanocyclopropylcarbamoyl)-3,3-difluoro-4-phenylbutyl]-6-azaspiro[2.5]octane-6-carboxamide was obtained as a colorless amorphous solid.
Yield: 30 mg, 62% of theory.
$^1$H NMR: 8.85 (s, 1H); 7.22-7.40 (m, 5H); 6.68 (d, 1H); 4.40 (m, 1H); 3.20-3.40 (m, 6H); 2.15-2.40 (m, 2H); 1.48 (d, 2H); 1.25 (t, 4H); 1.10 (d, 2H); 0.30 (s, 4H);
MS (ESI$^+$): 431.3.

Example 71

8-Azaspiro[4.5]decane-8-sulfonyl chloride

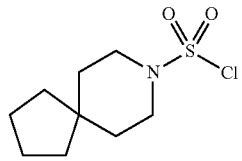 [SMILES: O=S(=O)(Cl)N1CCC2(CCCC2)CC1]

1.0 g of 8-azaspiro[4.5]decane (7.2 mmol) were dissolved in 25 ml of dichloromethane. After addition of 1.5 ml of triethylamine (1.5 eq.), the mixture was cooled to 0° C. At this temperature, a solution of 0.48 ml of chorosulfonic acid (7.2 mmol, 1 eq.) in 5 ml of dichloromethane and then 1.9 ml of pyridine (3.2 eq.) were added. The mixture was stirred at RT for 48 h. The reaction mixture was washed with a 1 M HCl solution and the aqueous phase was removed. Thereafter, the organic phase was shaken with an Na$_2$CO$_3$ solution. The aqueous phase thus obtained was then washed three times more with a little diethyl ether. The aqueous phase was concentrated under reduced pressure and codistilled three times more with 20 ml of toluene each time. The residue was taken up in water and lyophilized. The colorless residue thus obtained was treated three times with 10 ml each time of ethanol. The combined alcoholic phases were concentrated under reduced pressure and codistilled twice more with toluene. The residue thus obtained (1.58 g of 8-azaspiro[4.5]decane-8-sulfonic acid sodium salt) was suspended in 30 ml of toluene and admixed under argon with 1.65 g of phosphorus pentachloride (1.1 eq.) The reaction mixture thus obtained was stirred at 100° C. for 18 h. After cooling, the reaction mixture was filtered off from undissolved constituents and the filtrate was concentrated under reduced pressure. In this way, 8-azaspiro[4.5]decane-8-sulfonyl chloride was obtained as a colorless oil which was used in the next reaction without further purification.
Yield: 520 mg (30% of theory).

Example 72

Methyl (S)-2-(8-azaspiro[4.5]decane-8-sulfonylamino)-4,4-difluoro-pentanoate

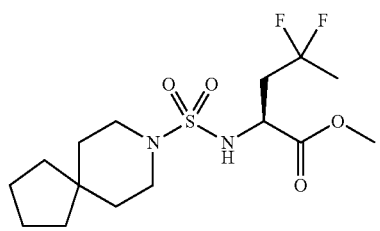 [SMILES: COC(=O)[C@H](CC(C)(F)F)NS(=O)(=O)N1CCC2(CCCC2)CC1]

In a reaction vessel, 100 mg of methyl (S)-2-amino-4,4-difluoropentanoate hydrochloride (0.49 mmol) were admixed with 320 mg of N,O-bis(trimethylsilyl)-acetamide (3.2 eq.) in 3 ml of acetonitrile. The reaction mixture was treated at 100° C. in a microwave for 30 min. 128 mg of 8-azaspiro[4.5]decane-8-sulfonyl chloride (1.1 eq.), dissolved in 2.5 ml of acetonitrile, were then added and the resulting reaction mixture was treated at 100° C. in a microwave for a further 2.5 h. The reaction mixture was concentrated under reduced pressure and the resulting residue was purified by preparative HPLC (gradient: acetonitrile/water and addition of 0.05% TFA). Methyl (S)-2-(8-azaspiro[4.5]decane-8-sulfonylamino)-4,4-difluoropentanoate was obtained as a colorless amorphous material.

Yield: 75 mg, (41% of theory) MS (ESI+): 369.

Example 73

(S)-2-(8-Azaspiro[4.5]decane-8-sulfonylamino)-4,4-difluoropentanoic acid

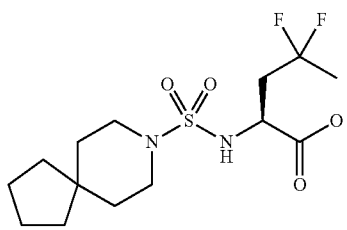 [SMILES: CC(F)(F)C[C@H](NS(=O)(=O)N1CCC2(CCCC2)CC1)C(=O)O]

(S)-2-(8-Azaspiro[4.5]decane-8-sulfonylamino)-4,4-difluoropentanoic acid was prepared analogously to example 62 starting from 50 mg of methyl (S)-2-(8-azaspiro[4.5]decane-8-sulfonylamino)-4,4-difluoropentanoate (0.14 mmol).

Yield: 30 mg (62% of theory)

Example 74

N-(1-Cyanocyclopropyl)-(S)-2-(8-azaspiro[4.5]decane-8-sulfonylamino)-4,4-difluoropentamide

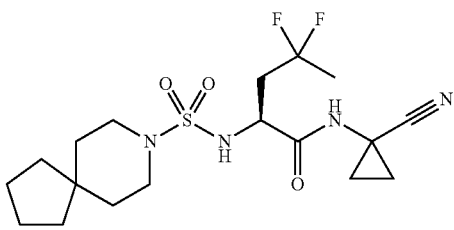 [SMILES: CC(F)(F)C[C@H](NS(=O)(=O)N1CCC2(CCCC2)CC1)C(=O)NC1(C#N)CC1]

12.0 mg of 1-aminocyclopropanecarbonitrile hydrochloride (1.2 eq.), 13.8 mg of HOAt (1.2 eq.), 33 μl of N-ethylmorpholine (3 eq.) and 19.5 mg of EDCI (1.2 eq.) were added successively to a solution of 30.0 mg of (S)-2-(8-azaspiro[4.5]decane-8-sulfonylamino)-4,4-difluoropentanoic acid (0.08 mmol) in 2 ml of THF and 1 ml of dichloromethane. The reaction mixture was stirred at RT for 4 h and then concentrated under reduced pressure. The residue thus obtained was purified by preparative HPLC (gradient: acetonitrile/water and addition of 0.05% TFA). The product-containing fractions were combined and freeze-dried. In this way, N-(1-cyanocyclopropyl)-(S)-2-(8-azaspiro[4.5]decane-8-sulfonylamino)-4,4-difluoropentamide was obtained as a colorless amorphous material.

Yield: 20 mg, 56% of theory.

$^1$H NMR: 9.1 (s, 1H); 7.85 (d, 1H); 3.85 (m, 1H); 3.00 (m, 4H); 2.15 (m, 2H); 1.65 (t, 3H); 1.55 (m, 4H); 1.50 (m, 2H); 1.40 (t, 4H); 1.37 (m, 4H); 1.10 (m, 2H);

MS (ESI+): 419.1.

Analogously to the examples described in detail above (examples 1-35 and 58-74), the following further compounds were prepared.

These further compounds are shown in table 1b) with accompanying characterization:

TABLE 1b

| Example | Molar mass (parent compound) | Structure | MS (ESI+) | $^1$H NMR |
|---|---|---|---|---|
| 75 | 325.36 | 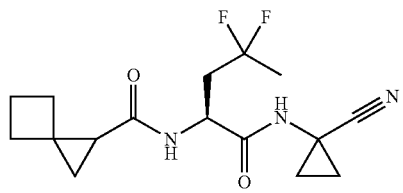 [SMILES: CC(F)(F)C[C@H](NC(=O)C1CC12CCC2)C(=O)NC1(C#N)CC1] | 326.2 | 9.03 (s, 1H); 8.35 (d, 1H); 4.49 (m, 1H); 1.85-2.40 (m, 9H); 1.62 (t, 3H); 1.50 (d, 2H); 1.10 (d, 2H); 0.75-0.95 (m, 2H) |
| 76 | 412.48 | 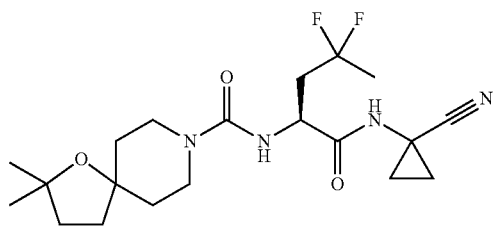 [SMILES: CC(F)(F)C[C@H](NC(=O)N1CCC2(CC1)CCC(C)(C)O2)C(=O)NC1(C#N)CC1] | 413.1 | 8.85 (s, 1H); 6.70 (d, 1H); 4.30 (m, 1H); 3.20-3.40 (m, 4H); 2.25 (m, 2H); 1.80 (m, 4H); 1.62 (t, 3H); 1.45 (m, 6H); 1.20 (s, 6H); 1.10 (m, 2H) |

TABLE 1b-continued

| Example | Molar mass (parent compound) | Structure | MS (ESI+) | 1H NMR |
|---|---|---|---|---|
| 77 | 382.46 | 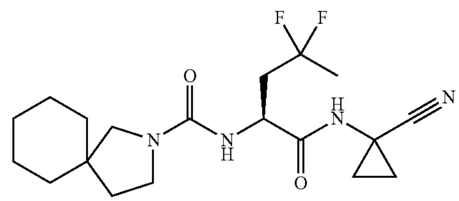 [SMILES: CC(F)(F)C[C@H](NC(=O)N1CCC2(CCCCC2)C1)C(=O)NC1(C#N)CC1] | 383.1 | 8.87 (s, 1H); 6.28 (d, 1H); 4.30 (m, 1H); 3.22-3.38 (m, 2H); 3.08 (m, 2H); 2.20-2.38 (m, 2H); 1.55-1.68 (m, 5H); 1.30-1.52 (m, 12 H); 1.10 (d, 2H) |
| 78 | 432.47 | 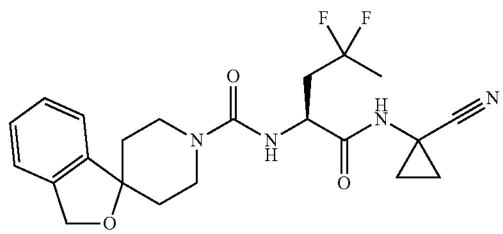 [SMILES: CC(F)(F)C[C@H](NC(=O)N1CCC2(CC1)OCc1ccccc12)C(=O)NC1(C#N)CC1] | 433.3 | 8.90 (s, 1H); 7.29 (m, 3H); 7.20 (m, 1H); 6.80 (d, 1H); 5.00 (s, 2H); 4.35 (m, 1H); 4.00 (m, 2H); 3.05 (m, 2H); 2.30 (m, 2H); 1.80 (m, 2H); 1.65 (t, 3H); 1.58 (m, 2H); 1.50 (d, 2H); 1.10 (d, 2H) |
| 79 | 430.50 | 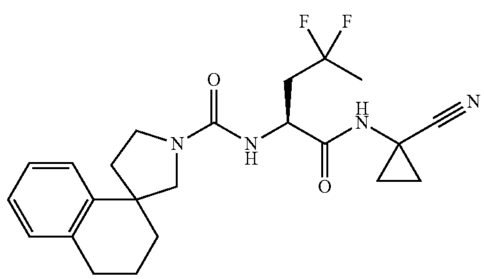 [SMILES: CC(F)(F)C[C@H](NC(=O)N1CCC2(CCCc3ccccc32)C1)C(=O)NC1(C#N)CC1] | 431.1 | 8.90 (s, 1H); 7.31 (m, 1H); 7.05-7.20 (m, 3H); 6.40 (d, 1H); 4.38 (m, 1H); 3.30-3.45 (m, 4H); 2.80 (t, 2H); 2.15-2.40 (m, 4H); 1.90 (m, 1H); 1.60-1.80 (m, 6H); 1.50 (d, 2H); 1.10 (d, 2H) |
| 80 | 384.43 | 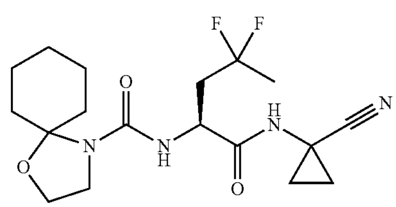 [SMILES: CC(F)(F)C[C@H](NC(=O)N1CCOC12CCCCC2)C(=O)NC1(C#N)CC1] | 385.3 | 8.85 (s,1 H); 6.35 (d, 1H); 4.30 (m, 1H); 3.90 (t, 2H); 3.50 (q, 2H); 3.30-3.40 (m, 2H); 2.20-2.40 (m, 4H); 1.38-1.65 (m, 11H); 1.10 (d, 2H) |
| 81 | 400.43 | 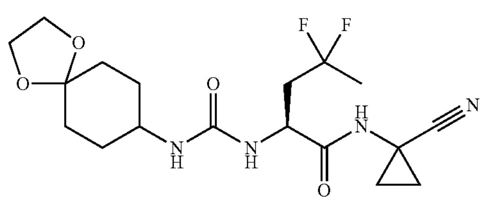 [SMILES: CC(F)(F)C[C@H](NC(=O)NC1CCC2(CC1)OCCO2)C(=O)NC1(C#N)CC1] | 401.2 | 9.05 (s, 1H); 6.69 (d, 1H); 6.60 (d, 1H); 4.32 (m, 1H), 3.86 (s, 4H); 3.48 (m, 1H); 2.05-2.32 (m, 2H); 1.72 (m, 2H); 1.58-1.68 (m, 5H); 1.45-1.55 (m, 4H); 1.38 (m, 2H); 1.10 (dd, 2H) |
| 82 | 444.53 | 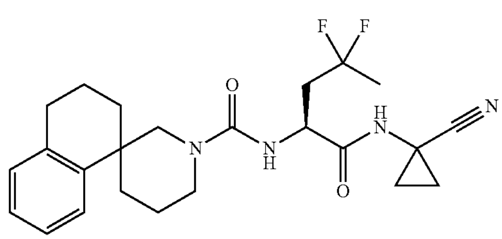 [SMILES: CC(F)(F)C[C@H](NC(=O)N1CCCC2(CCCc3ccccc32)C1)C(=O)NC1(C#N)CC1] | 445.4 | 8.81 (s, 1H); 7.50 (t, 1H); 7.05-7.29 (m, 3H); 6.60 (t, 1H); 4.35 (m, 1 H); 3.90-4.10 (m, 2H); 2.72-2.90 (m, 2H); 2.70 (s, 2H); 2.19-2.35 (m, 2H); 1.85-2.05 (m, 2H); 1.39-1.75 (m, 11H); 1.10 (d, 2H) |

TABLE 1b-continued
| Example | Molar mass (parent compound) | Structure | MS (ESI+) | 1H NMR |
|---|---|---|---|---|
| 83 | 409.48 | 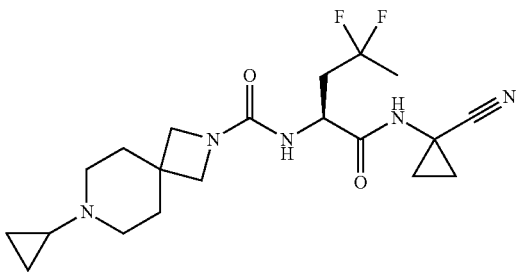 [SMILES: CC(F)(F)C[C@H](NC(=O)N1CC2(CCN(C3CC3)CC2)C1)C(=O)NC1(C#N)CC1] | 410.3 | Fumarate: 8.90 (s, 1H); 6.60 (s, 2H); 6.50 (d, 1H); 4.25 (m, 1H); 3.58 (d, 2H); 3.48 (d, 2H); 2.25-2.55 (m, 6H); 2.15 (m, 1H); 1.50-1.68 (m, 7 H); 1.45 (d, 2H); 1.10 (d, 2H); 0.40 (d, 2H); 0.28 (d, 2H) |
| 84 | 409.48 | 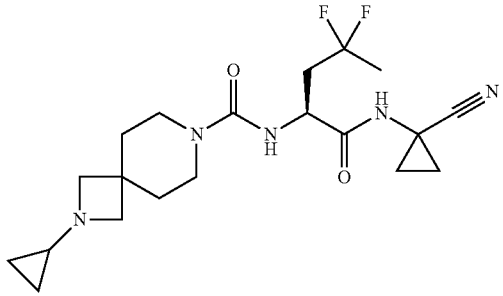 [SMILES: CC(F)(F)C[C@H](NC(=O)N1CCC2(CC1)CN(C1CC1)C2)C(=O)NC1(C#N)CC1] | 410.3 | Fumarate: 8.85 (s, 1H); 6.68 (d, 1H); 6.60 (s, 2H); 4.30 (m, 1H); 3.15-3.50 (m, 4H); 3.05 (s, 4H); 2.25 (m, 2H); 1.95 (m, 1H); 1.52-1.65 (m, 7H); 1.48 (m, 2H); 1.10 (m, 2H); 0.34 (d, 2H); 0.25 (d, 2H) |
| 85 | 411.50 | 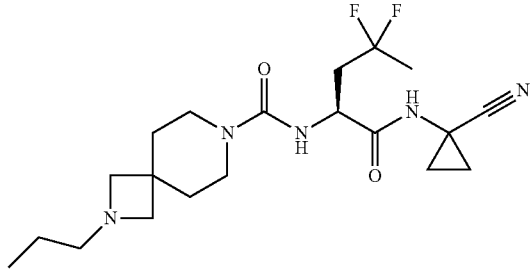 [SMILES: CCCN1CC2(CCN(C(=O)N[C@@H](CC(C)(F)F)C(=O)NC3(C#N)CC3)CC2)C1] | 412.4 | Fumarate: 8.90 (s, 1H); 6.72 (d, 1H), 6.50 (s, 2H); 4.28 (m, 1H); 3.10-3.50 (m, 8H); 2.65 (m, 2H); 2.25 (m, 2H); 1.53-1.65 (m, 7H); 1.45 (d, 2H); 1.38 (q, 2H); 1.10 (m, 2H); 0.87 (t, 3H) |
| 86 | 439.51 | 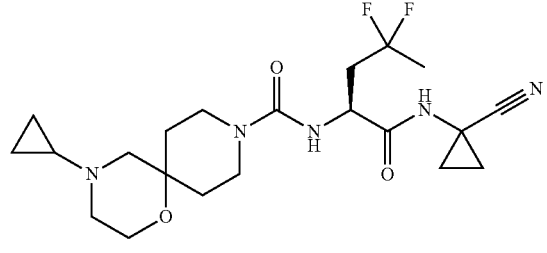 [SMILES: CC(F)(F)C[C@H](NC(=O)N1CCC2(CC1)CN(C1CC1)CCO2)C(=O)NC1(C#N)CC1] | 440.3 | TFA salt: 9.02 (s$_b$, 1H); 8.88 (s, 1H); 6.75 (d, 1H); 4.30 (m, 1H); 3.40-3.90 (m, 6H); 2.88-3.25 (m, 6H); 2.15-2.35 (m, 3H); 1.62 (t, 3H); 1.35-1.48 (m, 4H); 1.10 (d, 2H); 0.90-1.05 (m, 2H); 0.78 (m, 2H) |
| 87 | 439.51 | 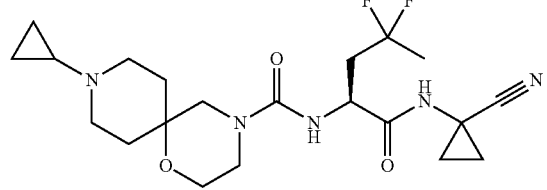 | 440.3 | TFA salt: 8.90 (s, 1H); 8.70 (s$_b$, 1H); 6.82 (d, 1H); 4.32 (m, 1H); 3.35-3.70 (m, 8H); 3.15-3.33 (m, 4H); 2.95 (m, 1H); 2.25 (m, 2H); 2.03 (t, 2H); 1.62 (t, 3H); 1.50 (d, 2H); 1.10 (d, 2H); 0.90 (d, 2H); 0.80 (d, 2H) |

TABLE 1b-continued
| Example | Molar mass (parent compound) | Structure | MS (ESI+) | ¹H NMR |
|---|---|---|---|---|
| 88 | 451.52 | 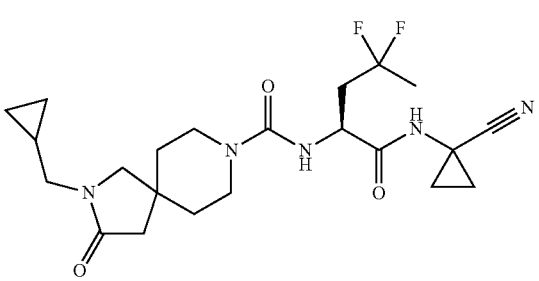 [SMILES: CC(F)(F)C[C@H](NC(=O)N1CCC2(CC1)CC(=O)N(CC1CC1)C2)C(=O)NC1(C#N)CC1] | 452.3 | 8.85 (s, 1H); 6.72 (d, 1 H); 4.30 (m, 1H); 3.40 (m, 4H); 3.25 (m, 4H); 3.05 (d, 2H); 2.25 (m, 2H); 2.15 (s, 2H); 1.62 (t, 3 H); 1.45 (m, 5H); 1.10 (m, 2H); 0.45 (d, 2H); 0.20 (d, 2H) |
| 89 | 444.53 | 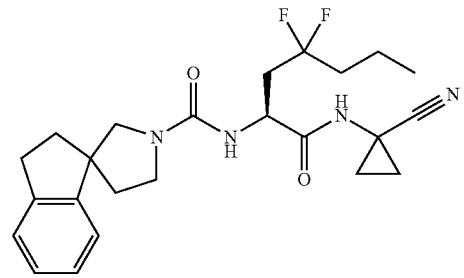 [SMILES: CCCC(F)(F)C[C@H](NC(=O)N1CCC2(CCc3ccccc32)C1)C(=O)NC1(C#N)CC1] | 445.1 | 8.45 (s, 1H); 7.10-7.28 (m, 4H); 5.90 (d, 1H); 4.38 (m, 1H); 3.30-3.60 (m, 4H); 2.90 (t, 2H); 2.15-2.40 (m, 2H); 1.75-2.10 (m, 6H); 1.38-1.52 (m, 4H); 1.15 (m, 2H); 0.90 (t, 3H) |
| 90 | 531.61 | 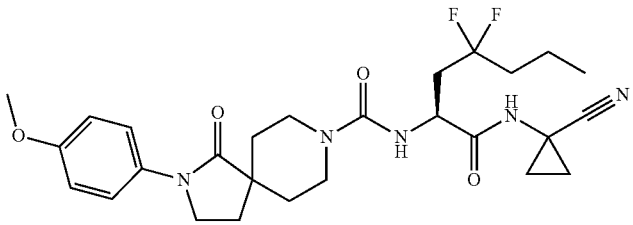 [SMILES: CCCC(F)(F)C[C@H](NC(=O)N1CCC2(CC1)CCN(c1ccc(OC)cc1)C2=O)C(=O)NC1(C#N)CC1] | 532.2 | 8.88 (s, 1H); 7.58 (d, 2H); 6.95 (d, 2H); 6.77 (d, 1H); 4.30 (m, 1H); 3.90 (m, 2H); 3.77 (m, 2H); 3.73 (s, 3H); 2.90 (m, 2H); 2.25 (m, 2H); 2.10 (t, 2H); 1.85 (m, 2H); 1.65 (q, 2H); 1.40-1.50 (m, 6H); 1.10 (m, 2H); 0.90 (t, 3H) |
| 91 | 517.62 | 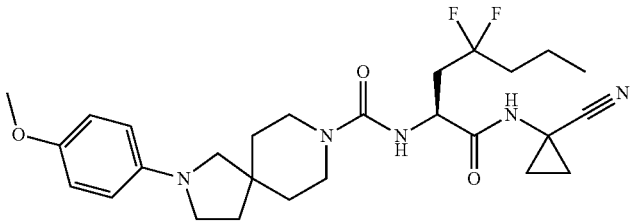 [SMILES: CCCC(F)(F)C[C@H](NC(=O)N1CCC2(CC1)CCN(c1ccc(OC)cc1)C2)C(=O)NC1(C#N)CC1] | 518.2 | 8.85 (s, 1H); 6.82 (d, 2H); 6.70 (d, 1 H); 6.55 (d, 2H), 4.30 (m, 1H); 3.68 (s, 3H); 3.25-3.55 (m, 6H); 3.10 (s, 2H); 2.25 (m, 2H); 1.80 (m, 4H); 1.35-1.55 (m, 8H), 1.10 (d, 2H); 0.90 (t, 3H) |
| 92 | 437.54 | 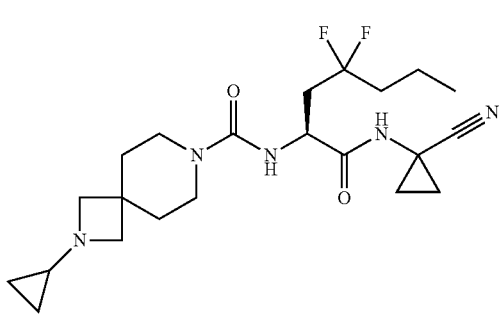 [SMILES: CCCC(F)(F)C[C@H](NC(=O)N1CCC2(CC1)CN(C1CC1)C2)C(=O)NC1(C#N)CC1] | 436.3 (ES⁻) | TFA salt: 9.80 (s$_b$, 1H); 8.90 (s, 1H); 6.75 (d, 1H); 4.30 (m, 1H); 3.97 (m, 2H); 3.90 (m, 2H); 3.15-3.30 (m, 4H); 3.10 (m, 1H); 2.15-2.30 (m, 2H); 1.75-1.86 (m, 2H); 1.70 (s, 4H); 1.45 (d, 2H); 1.40 (m, 2H); 1.10 (d, 2H); 0.89 (t, 3H); 0.80 (d, 4H) |

TABLE 1b-continued
| Example | Molar mass (parent compound) | Structure | MS (ESI⁺) | ¹H NMR |
|---|---|---|---|---|
| 93 | 451.56 | 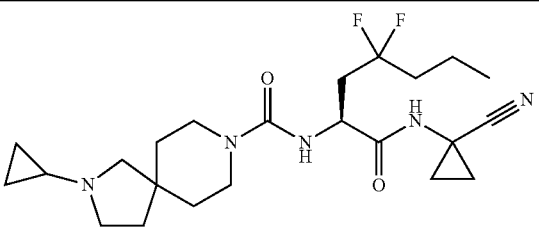 | 452.3 | TFA salt: 9.45 (s_b, 1H); 8.90 (s, 1H); 6.72 (d, 1H); 4.31 (m, 1H); 3.52-3.70 (m, 2H); 3.20-3.40 (m, 4H); 3.05 (m, 1H); 2.95 (m, 1H); 2.25 (m, 2H); 2.00 (m, 1H); 1.72-1.88 (m, 4H); 1.58 (m, 1H); 1.38-1.55 (m, 7H); 1.10 (d, 2H); 0.90 (m, 5H); 0.82 (d, 2H) |
| 94 | 465.59 | 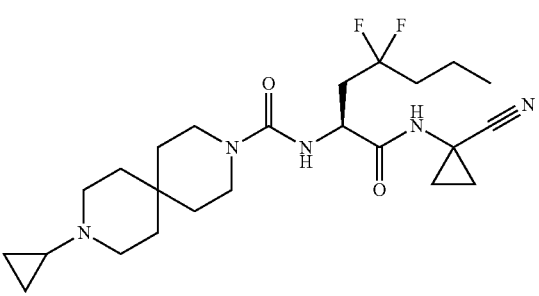 [SMILES: CCCC(F)(F)C[C@H](NC(=O)N1CCC2(CC1)CCN(C1CC1)CC2)C(=O)NC1(C#N)CC1] | 464.3 (ES⁻) | TFA salt: 8.89 (s, 1H); 8.52 (s_b, 1H); 6.70 (d, 1H); 4.30 (m, 1H); 3.20-3.40 (m, 8H); 2.90 (m, 1H); 2.20-2.30 (m, 2H); 1.78-1.88 (m, 4H); 1.57 (s_b, 2H); 1.35-1.49 (m, 6H); 1.29 (s_b, 2H); 1.10 (d, 2H); 0.90 (m, 5H); 0.82 (d, 2H) |
| 95 | 437.54 | 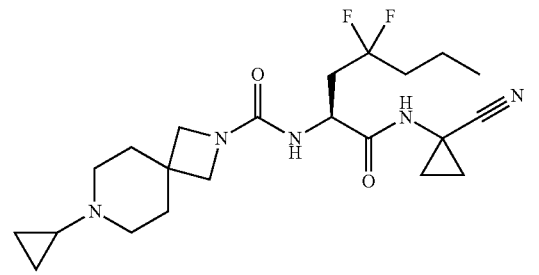 [SMILES: CCCC(F)(F)C[C@H](NC(=O)N1CC2(CCN(C3CC3)CC2)C1)C(=O)NC1(C#N)CC1] | 438.2 | TFA salt: 8.90 (s, 1H); 8.68 (s_b, 1H); 6.65 (d, 1H); 4.29 (m, 1H); 3.70 (d, 1H); 3.65 (dd, 2H); 3.55 (d, 1H); 3.30-3.45 (m, 2H); 3.12 (m, 2H); 2.87 (s_b, 1H); 2.12-2.40 (m, 2H); 2.05 (m, 2H); 1.73-1.89 (m, 4H); 1.50 (d, 2H); 1.40 (m, 2H); 1.10 (dd, 2H); 0.90 (m, 5H); 0.85 (d, 2H) |
| 96 | 439.55 | 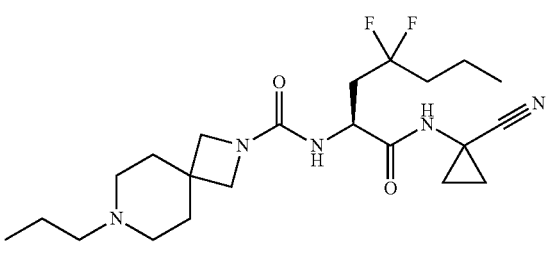 [SMILES: CCCN1CCC2(CC1)CN(C(=O)N[C@@H](CC(F)(F)CCC)C(=O)NC1(C#N)CC1)C2] | 438.3 (ES⁻) | TFA salt: 9.01 (s_b, 1H); 8.90 (s, 1H); 6.62 (d, 1H); 4.29 (m, 1H); 3.50-3.68 (m, 4H); 3.25-3.40 (m, 2H); 3.00 (m, 2H); 2.87 (q, 2H); 2.10-2.38 (m, 2H); 2.02 (m, 2H); 1.80 (m, 4H); 1.65 (m, 2H); 1.50 (d, 2H); 1.40 (m, 2H); 1.10 (d, 2H); 0.90 (t, 6H) |
| 97 | 513.64 | 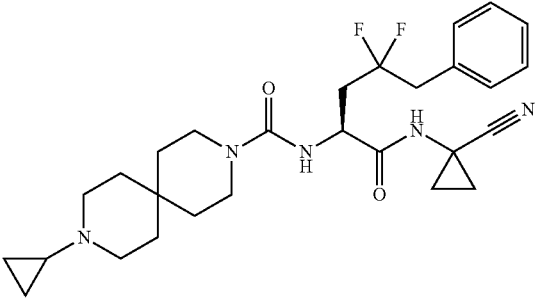 [SMILES: N#CC1(NC(=O)[C@H](CC(F)(F)Cc2ccccc2)NC(=O)N2CCC3(CC2)CCN(C2CC2)CC3)CC1] | 514.2 | TFA salt: 8.89 (s, 1H); 8.51 (s_b, 1H); 7.22-7.39 (m, 5H); 6.72 (d, 1H); 4.39 (m, 1H); 3.20-3.40 (m, 10H); 2.90 (m, 1H); 2.35 (m, 1H); 2.18 (m, 1H); 1.80-1.90 (m, 2H); 1.57 (s_b, 2H); 1.38-1.48 (m, 4H); 1.28 (t, 2H); 1.10 (dd, 2H); 0.90 (d, 2H); 0.80 (d, 2H) |

TABLE 1b-continued
| Example | Molar mass (parent compound) | Structure | MS (ESI+) | 1H NMR |
|---|---|---|---|---|
| 98 | 485.58 | 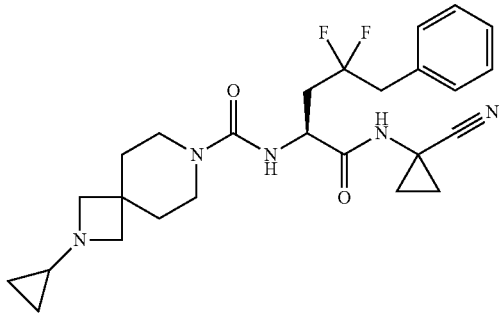 [SMILES: N#CC1(NC(=O)[C@H](CC(F)(F)Cc2ccccc2)NC(=O)N2CCC3(CC2)CN(C2CC2)C3)CC1] | 486.2 | TFA salt: 9.80 (s_b, 1H); 8.90 (s, 1H); 7.23-7.40 (m, 5H); 6.75 (d, 1H); 4.38 (m, 1 H); 3.95 (m, 2H); 3.89 (m, 2H); 3.15-3.42 (m, 6H); 3.09 (m, 1H); 2.38 (m, 1H); 2.20 (m, 1H); 1.59-1.69 (m, 4H); 1.50 (d, 2H); 1.10 (dd, 2H); 0.80 (d, 4H) |
| 99 | 487.60 | 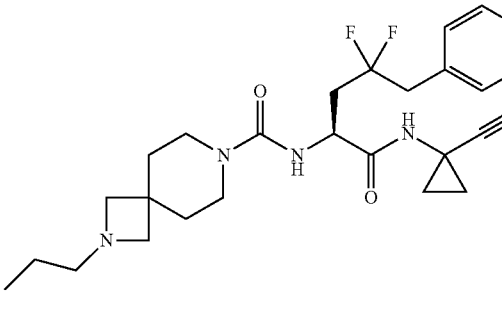 | 488.2 | TFA salt: 9.80 (s_b, 1H); 8.90 (s, 1H); 7.23-7.42 (m, 5H); 6.75 (d, 1H); 4.38 (m, 1 H); 3.92 (m, 2H); 3.82 (m, 2H); 3.15-3.40 (m, 6H); 3.11 (t, 2H); 2.35 (m, 1H); 2.15 (m, 1H); 1.60-1.75 (m, 4H); 1.39-1.46 (m, 4 H); 1.10 (dd, 2H); 0.90 (t, 3H) |
| 100 | 485.58 | 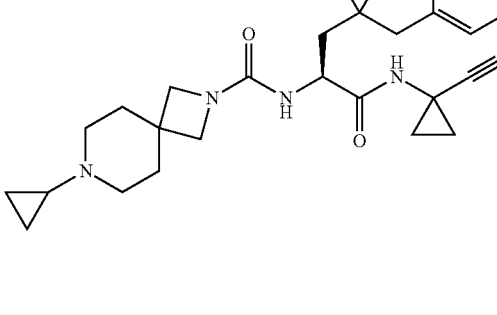 | 486.2 | TFA salt: 8.90 (s, 1H); 8.60 (d_b, 1H); 7.20-7.40 (m, 5H); 6.60 (d, 1H); 4.40 (m, 1H); 3.40-3.70 (m, 6H); 3.25 (t, 2H); 3.10 (q, 2H); 2.85 (m, 1H); 2.35 (m, 1H), 2.15 (m, 1H); 2.0 (m, 2H); 1.72 (t, 2H); 1.50 (d, 2H); 1.10 (dd, 2H); 0.90 (d, 2H); 0.80 (d, 2H) |
| 101 | 328.36 | 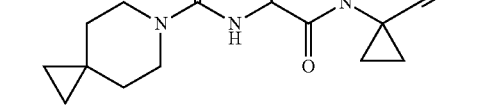 | 329.2 | 8.58 (t, 1H); 6.75 (d, 1H); 4.40 (m, 1H); 4.10 (d, 2 H); 3.30-3.40 (m, 4 H); 2.25 (m, 2H); 1.62 (t, 3H); 1.25 (m, 4H); 0.30 (s, 4 H) |

TABLE 1b-continued

| Example | Molar mass (parent compound) | Structure | MS (ESI+) | 1H NMR |
|---|---|---|---|---|
| 102 | 382.46 | 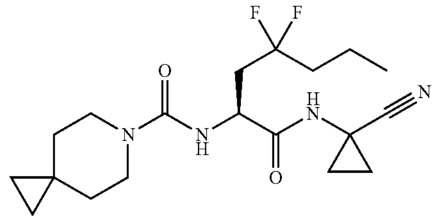 [SMILES: CCCC(F)(F)C[C@H](NC(=O)N1CCC2(CC1)CC2)C(=O)NC1(C#N)CC1] | 383.3 | 8.85 (s, 1H); 6.70 (d, 1H); 4.30 (m, 1H); 3.30-3.40 (m, 4H); 2.25 (m, 2H); 1.82 (m, 2H); 1.48 (d, 2H); 1.42 (m, 2H); 1.25 (m, 4H), 1.10 (m, 2H), 0.90 (t, 3H). 0.30 (s, 4 H) |
| 103 | 411.50 | 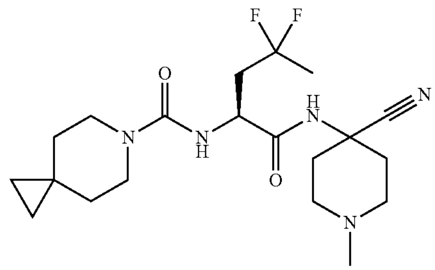 [SMILES: CN1CCC(C#N)(NC(=O)[C@H](CC(C)(F)F)NC(=O)N2CCC3(CC2)CC3)CC1] | 412.2 | 8.41 (s, 1H); 6.70 (d, 2H); 4.42 (m, 1H); 3.30-3.40 (m, 4H); 2.55 (m, 2H); 2.10-2.40 (m, 9H); 1.88 (m, 2H); 1.25 (m, 6H); 0.30 (s, 4H) |
| 104 | 439.55 | 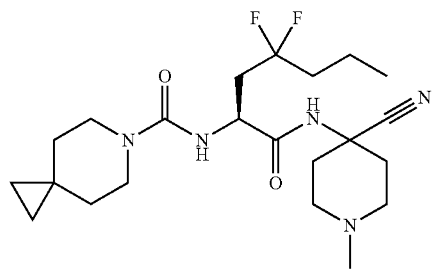 [SMILES: CCCC(F)(F)C[C@H](NC(=O)N1CCC2(CC1)CC2)C(=O)NC1(C#N)CCN(C)CC1] | 440.5 | 8.40 (s, 1H); 6.70 (d, 1H); 4.40 (q, 1H); 4.05 (m, 2H); 3.40 (m, 4H); 2.18-2.35 (m, 4H); 2.15 (s, 3H); 1.78-1.94 (m, 4H); 1.42 (m, 2H); 1.26 (t, 4H); 1.19 (m, 2H); 0.90 (t, 3H); 0.30 (s, 4H) |
| 105 | 368.43 | 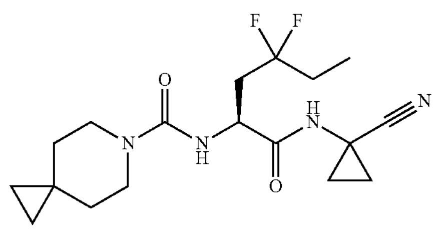 [SMILES: CCC(F)(F)C[C@H](NC(=O)N1CCC2(CC1)CC2)C(=O)NC1(C#N)CC1] | 369.4 | 8.82 (s, 1H); 6.68 (d, 1H); 4.30 (m, 1H); 3.29-3.40 (m, 4H); 2.30 (m, 2H); 1.88 (m, 2H); 1.48 (m, 2H); 1.25 (t, 4H); 1.10 (m, 2H); 0.90 (t, 3H); 0.30 (s, 4H) |

The examples which follow can be prepared in an analogous manner:

N—[(S)-1-(1-cyanocyclopropylcarbamoyl)-3,3-difluoro-5-methylhexyl]-6-azaspiro[2.5]octane-6-carboxamide N—[(S)-1-(1-cyanocyclopropylcarbamoyl)-4-cyclopropyl-3,3-difluorobutyl]-6-azaspiro[2.5]octane-6-carboxamide

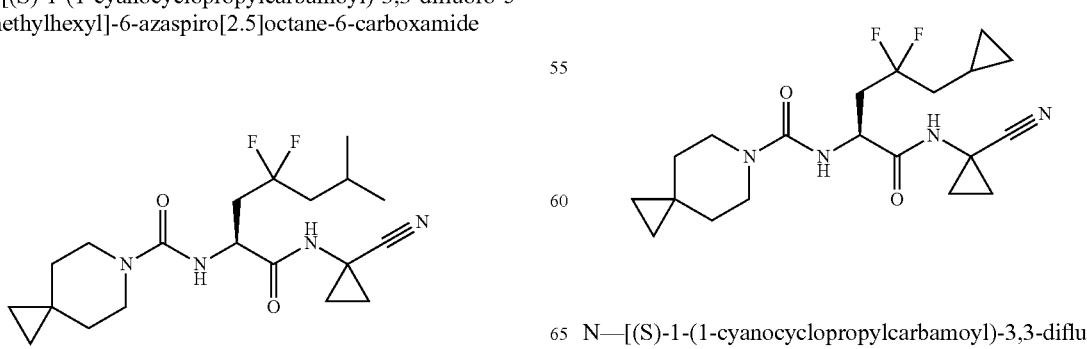

N—[(S)-1-(1-cyanocyclopropylcarbamoyl)-3,3-difluoro-4-(2-methoxyphenyl)butyl]-6-azaspiro[2.5]octane-6-carboxamide

89

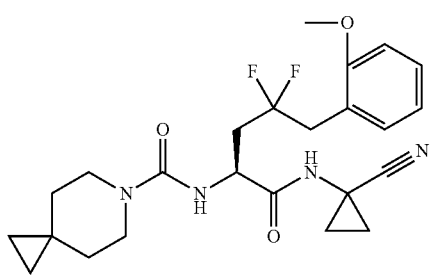 [SMILES: COc1ccccc1CC(F)(F)C[C@H](NC(=O)N1CCC2(CC1)CC2)C(=O)NC1(C#N)CC1]

N—[(S)-1-(1-cyanocyclopropylcarbamoyl)-3,3-difluoro-4-(2-trifluoromethoxyphenyl)-butyl]-6-azaspiro[2.5]octane-6-carboxamide

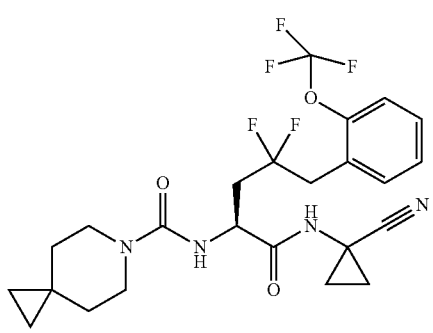 [SMILES: N#CC1(NC(=O)[C@H](CC(F)(F)Cc2ccccc2OC(F)(F)F)NC(=O)N2CCC3(CC2)CC3)CC1]

N—[(S)-1-(1-cyanocyclopropylcarbamoyl)-3,3-difluoro-4-(2-fluorophenyl)butyl]-6-azaspiro[2.5]octane-6-carboxamide

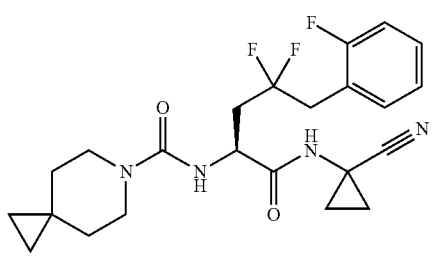 [SMILES: N#CC1(NC(=O)[C@H](CC(F)(F)Cc2ccccc2F)NC(=O)N2CCC3(CC2)CC3)CC1]

N—[(S)-1-(1-cyanocyclopropylcarbamoyl)-3,3-difluoro-4-(4-fluorophenyl)butyl]6-azaspiro[2.5]octane-6-carboxamide

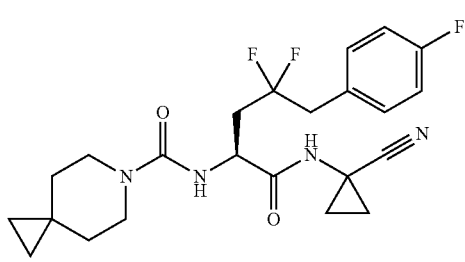 [SMILES: N#CC1(NC(=O)[C@H](CC(F)(F)Cc2ccc(F)cc2)NC(=O)N2CCC3(CC2)CC3)CC1]

90

N—[(S)-1-(1-cyanocyclopropylcarbamoyl)-3,3-difluoro-4-pyridin-2-ylbutyl]-6-aza-spiro[2.5]octane-6-carboxamide

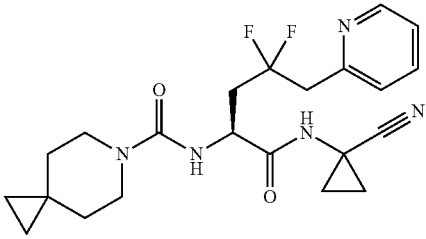 [SMILES: N#CC1(NC(=O)[C@H](CC(F)(F)Cc2ccccn2)NC(=O)N2CCC3(CC2)CC3)CC1]

N—[(S)-1-(1-cyanocyclopropylcarbamoyl)-3,3-difluoro-4-pyridin-3-ylbutyl]-6-aza-spiro[2.5]octane-6-carboxamide

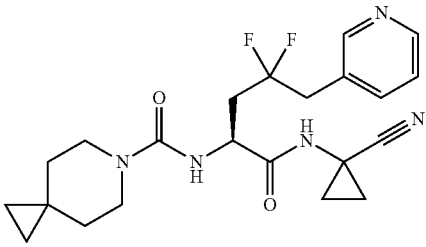 [SMILES: N#CC1(NC(=O)[C@H](CC(F)(F)Cc2cccnc2)NC(=O)N2CCC3(CC2)CC3)CC1]

N—[(S)-1-(1-cyanocyclopropylcarbamoyl)-3,3-difluoro-4-pyridin-4-ylbutyl]-6-aza-spiro[2.5]octane-6-carboxamide

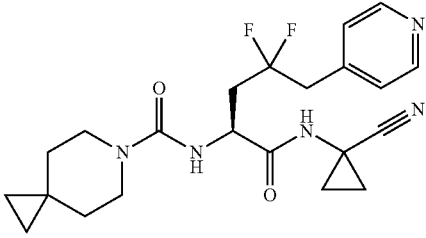 [SMILES: N#CC1(NC(=O)[C@H](CC(F)(F)Cc2ccncc2)NC(=O)N2CCC3(CC2)CC3)CC1]

N—[(S)-1-(cyanomethylcarbamoyl)-3,3-difluoro-4-phenyl-butyl]-6-azaspiro[2.5]octane-6-carboxamide

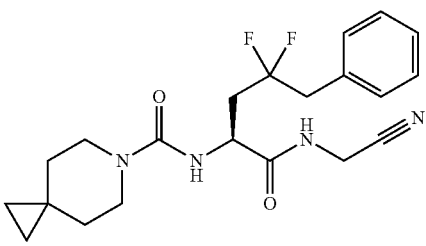 [SMILES: N#CCNC(=O)[C@H](CC(F)(F)Cc1ccccc1)NC(=O)N1CCC2(CC1)CC2]

N—[(S)-1-(cyanomethylcarbamoyl)-4-cyclopropyl-3,3-difluorobutyl]-6-aza-spiro[2.5]octane-6-carboxamide

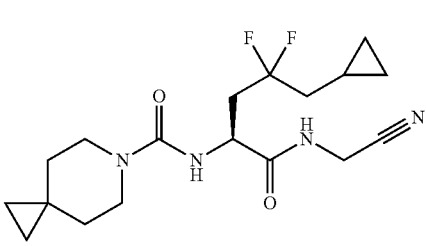 [SMILES: N#CCNC(=O)[C@H](CC(F)(F)CC1CC1)NC(=O)N1CCC2(CC1)CC2]

N—[(S)-1-(cyanomethylcarbamoyl)-3,3-difluoro-4-pyridin-3-ylbutyl]-6-aza-spiro[2.5]octane-6-carboxamide

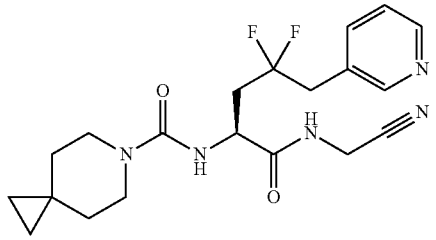 [SMILES: N#CCNC(=O)[C@H](CC(F)(F)Cc1cccnc1)NC(=O)N1CCC2(CC1)CC2]

N—[(S)-1-(cyanomethylcarbamoyl)-4-(2-difluoromethoxyphenyl)-3,3-difluorobutyl]-6-azaspiro[2.5]octane-6-carboxamide

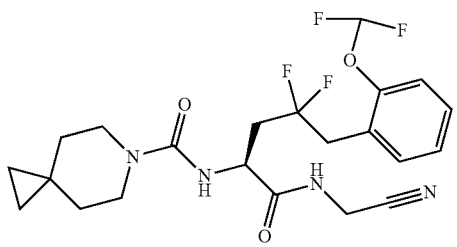 [SMILES: N#CCNC(=O)[C@H](CC(F)(F)Cc1ccccc1OC(F)F)NC(=O)N1CCC2(CC1)CC2]

N—[(S)-1-(1-cyanocyclopropylcarbamoyl)-3,3-difluorobutyl]-7-azaspiro[3.5]nonane-7-carboxamide

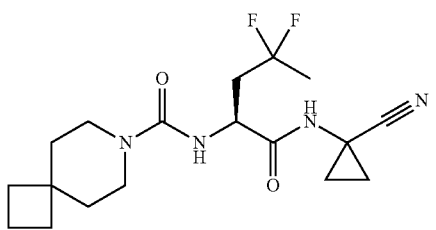 [SMILES: CC(F)(F)C[C@H](NC(=O)N1CCC2(CCC2)CC1)C(=O)NC1(C#N)CC1]

N—[(S)-1-(1-cyanocyclopropylcarbamoyl)-4-cyclopropyl-3,3-difluorobutyl]-7-aza-spiro[3.5]nonane-7-carboxamide

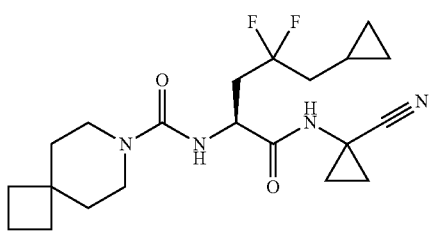 [SMILES: N#CC1(NC(=O)[C@H](CC(F)(F)CC2CC2)NC(=O)N2CCC3(CCC3)CC2)CC1]

N—[(S)-1-(1-cyanocyclopropylcarbamoyl)-3,3-difluoro-4-phenylbutyl]-7-aza-spiro[3.5]nonane-7-carboxamide

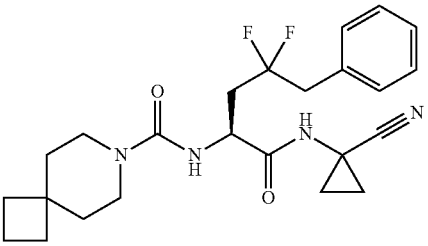 [SMILES: N#CC1(NC(=O)[C@H](CC(F)(F)Cc2ccccc2)NC(=O)N2CCC3(CCC3)CC2)CC1]

N—[(S)-1-(1-cyanocyclopropylcarbamoyl)-3,3-difluoro-4-pyridin-2-ylbutyl]-7-aza-spiro[3.5]nonane-7-carboxamide

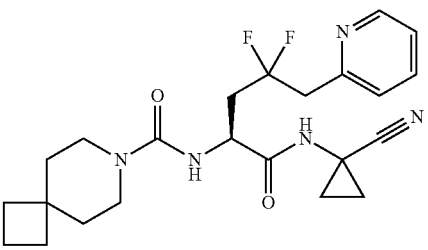 [SMILES: N#CC1(NC(=O)[C@H](CC(F)(F)Cc2ccccn2)NC(=O)N2CCC3(CCC3)CC2)CC1]

N—[(S)-1-(1-cyanocyclopropylcarbamoyl)-3,3-difluoro-4-pyridin-3-ylbutyl]-7-aza-spiro[3.5]nonane-7-carboxamide

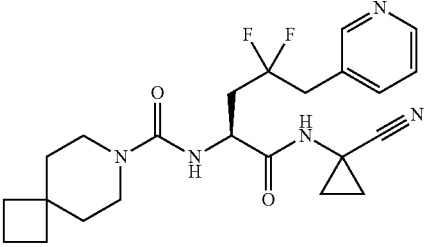 [SMILES: N#CC1(NC(=O)[C@H](CC(F)(F)Cc2cccnc2)NC(=O)N2CCC3(CCC3)CC2)CC1]

N—[(S)-1-(1-cyanocyclopropylcarbamoyl)-3,3-difluoro-4-pyridin-4-ylbutyl]-7-aza-spiro[3.5]nonane-7-carboxamide

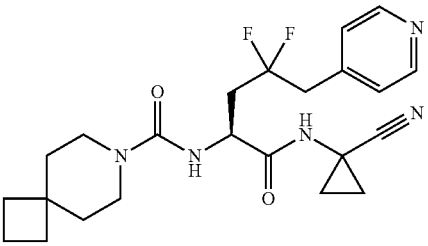

N—[(S)-1-(1-cyanocyclopropylcarbamoyl)-3,3-difluoro-4-(2-methoxyphenyl)butyl]-7-cyclopropyl-2,7-diazaspiro[3.5]nonane-2-carboxamide

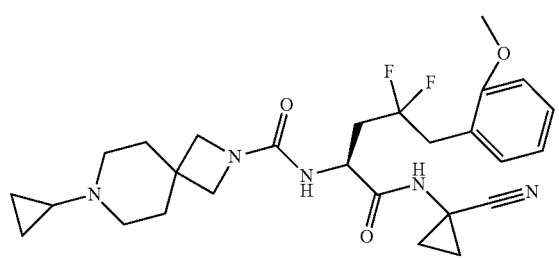 [SMILES: COc1ccccc1CC(F)(F)C[C@H](NC(=O)N1CC2(CCN(C3CC3)CC2)C1)C(=O)NC1(C#N)CC1]

N—[(S)-1-(1-cyanocyclopropylcarbamoyl)-3,3-difluoro-4-(2-fluorophenyl)butyl]-7-cyclopropyl-2,7-diazaspiro[3.5]nonane-2-carboxamide

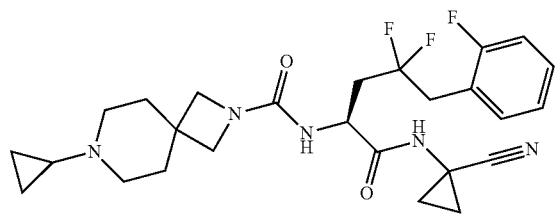 [SMILES: N#CC1(NC(=O)[C@H](CC(F)(F)Cc2ccccc2F)NC(=O)N2CC3(CCN(C4CC4)CC3)C2)CC1]

N—[(S)-1-(1-cyanocyclopropylcarbamoyl)-3,3-difluoro-4-(4-fluorophenyl)butyl]-7-cyclopropyl-2,7-diazaspiro[3.5]nonane-2-carboxamide

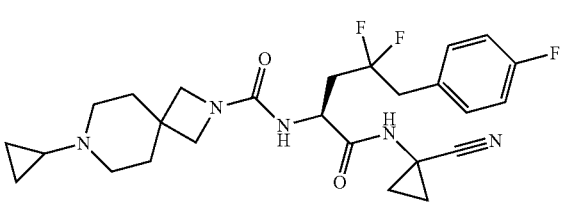 [SMILES: N#CC1(NC(=O)[C@H](CC(F)(F)Cc2ccc(F)cc2)NC(=O)N2CC3(CCN(C4CC4)CC3)C2)CC1]

N—[(S)-1-(1-cyanocyclopropylcarbamoyl)-3,3-difluoro-4-pyridin-2-ylbutyl]-7-cyclopropyl-2,7-diazaspiro[3.5]nonane-2-carboxamide

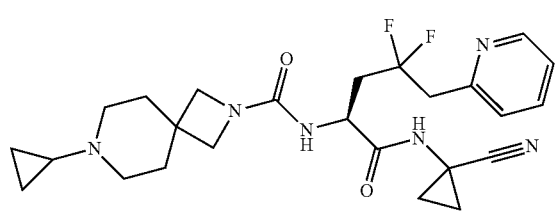 [SMILES: N#CC1(NC(=O)[C@H](CC(F)(F)Cc2ccccn2)NC(=O)N2CC3(CCN(C4CC4)CC3)C2)CC1]

N—[(S)-1-(1-cyanocyclopropylcarbamoyl)-3,3-difluoro-4-pyridin-3-ylbutyl]-7-cyclopropyl-2,7-diazaspiro[3.5]nonane-2-carboxamide

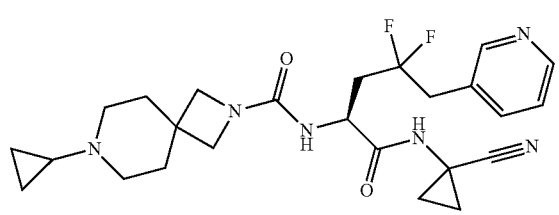 [SMILES: N#CC1(NC(=O)[C@H](CC(F)(F)Cc2cccnc2)NC(=O)N2CC3(CCN(C4CC4)CC3)C2)CC1]

N—[(S)-1-(1-cyanocyclopropylcarbamoyl)-3,3-difluoro-4-pyridin-4-ylbutyl]-7-cyclopropyl-2,7-diazaspiro[3.5]nonane-2-carboxamide

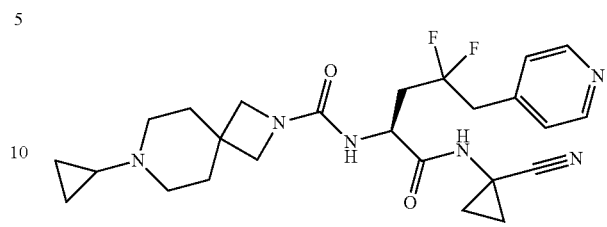

N—[(S)-1-(1-cyanocyclopropylcarbamoyl)-3,3-difluoro-5-methylhexyl]-7-cyclopropyl-2,7-diazaspiro[3.5]nonane-2-carboxamide

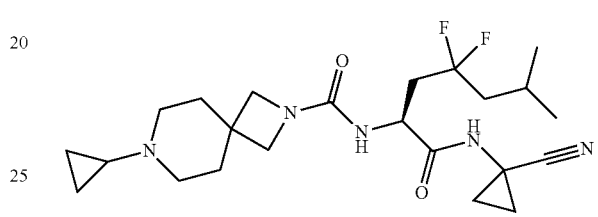

N—[(S)-1-(1-cyanocyclopropylcarbamoyl)-4-cyclopropyl-3,3-difluorobutyl]-7-cyclopropyl-2,7-diazaspiro[3.5]nonane-2-carboxamide

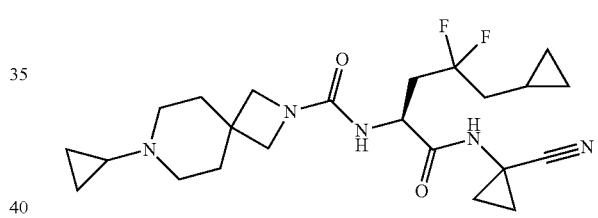

N—[(S)-1-(cyanomethylcarbamoyl)-3,3-difluoro-4-phenyl-butyl]-7-cyclopropyl-2,7-di-azaspiro[3.5]nonane-2-carboxamide

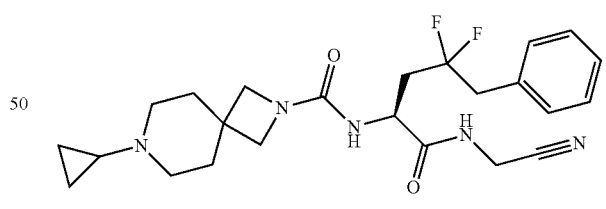

N—[(S)-1-(cyanomethylcarbamoyl)-3,3-difluoro-4-pyridin-3-ylbutyl]-7-cyclopropyl-2,7-diazaspiro[3.5]nonane-2-carboxamide

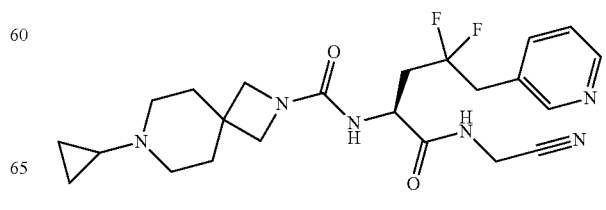

N—[(S)-1-(cyanomethylcarbamoyl)-4-cyclopropyl-3,3-difluorobutyl]-7-cyclopropyl-2,7-diazaspiro[3.5]nonane-2-carboxamide

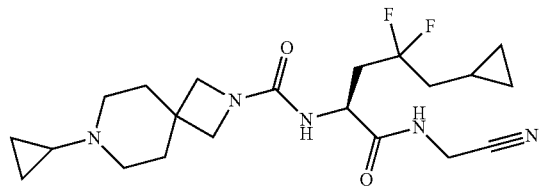 [SMILES: N#CCNC(=O)[C@H](CC(F)(F)CC1CC1)NC(=O)N1CC2(CCN(C3CC3)CC2)C1]

N—[(S)-1-(cyanomethylcarbamoyl)-3,3-difluoro-4-(2-fluorophenyl)butyl]-7-cyclopropyl-2,7-diazaspiro[3.5]nonane-2-carboxamide

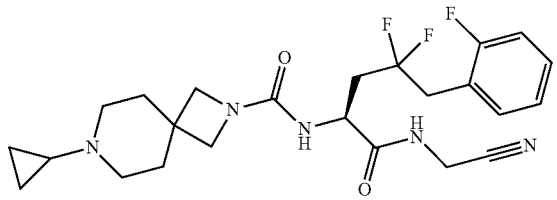 [SMILES: N#CCNC(=O)[C@H](CC(F)(F)Cc1ccccc1F)NC(=O)N1CC2(CCN(C3CC3)CC2)C1]

N—[(S)-1-(1-cyanocyclopropylcarbamoyl)-3,3-difluorobutyl]-1,1-difluoro-6-aza-spiro[2.5]octane-6-carboxamide

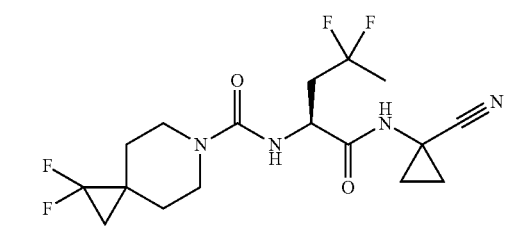 [SMILES: CC(F)(F)C[C@H](NC(=O)N1CCC2(CC1)CC2(F)F)C(=O)NC1(C#N)CC1]

N—[(S)-1-(1-cyanocyclopropylcarbamoyl)-3,3-difluoropentyl]-1,1-difluoro-6-aza-spiro[2.5]octane-6-carboxamide

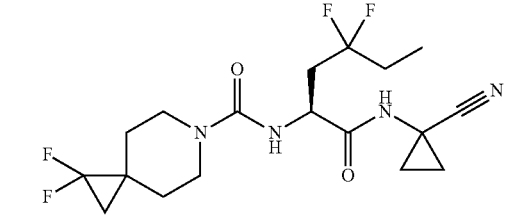 [SMILES: CCC(F)(F)C[C@H](NC(=O)N1CCC2(CC1)CC2(F)F)C(=O)NC1(C#N)CC1]

N—[(S)-1-(1-cyanocyclopropylcarbamoyl)-4-cyclopropyl-3,3-difluorobutyl]-1,1-difluoro-6-azaspiro[2.5]octane-6-carboxamide

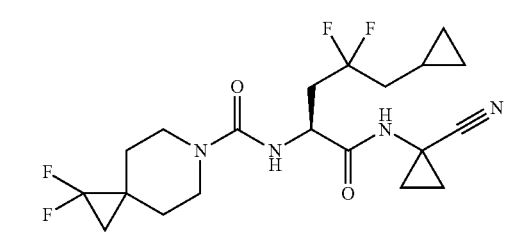 [SMILES: N#CC1(NC(=O)[C@H](CC(F)(F)CC2CC2)NC(=O)N2CCC3(CC2)CC3(F)F)CC1]

N—[(S)-1-(1-cyanocyclopropylcarbamoyl)-3,3-difluoro-4-pyridin-3-ylbutyl]-1,1-difluoro-6-azaspiro[2.5]octane-6-carboxamide

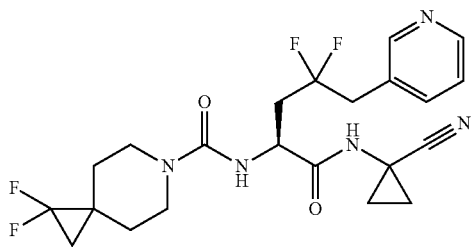 [SMILES: N#CC1(NC(=O)[C@H](CC(F)(F)Cc2cccnc2)NC(=O)N2CCC3(CC2)CC3(F)F)CC1]

N—[(S)-1-(1-cyanocyclopropylcarbamoyl)-4,4-difluoropentyl]-6-azaspiro[2.5]octane-6-carboxamide

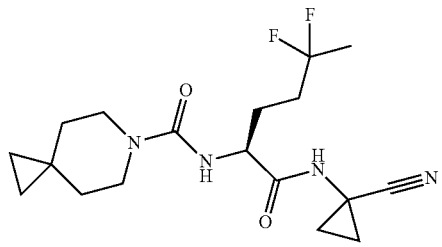 [SMILES: CC(F)(F)CC[C@H](NC(=O)N1CCC2(CC1)CC2)C(=O)NC1(C#N)CC1]

N—[(S)-1-(1-cyanocyclopropylcarbamoyl)-4,4-difluoro-4-phenylbutyl]-6-aza-spiro[2.5]octane-6-carboxamide

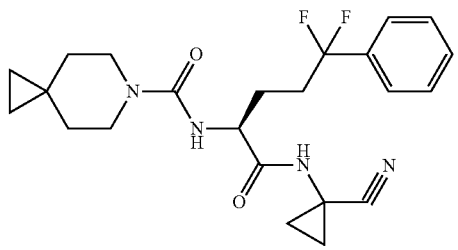

N—[(S)-1-(1-cyanocyclopropylcarbamoyl)-4,4-difluoro-4-pyridin-2-ylbutyl]-6-aza-spiro[2.5]octane-6-carboxamide

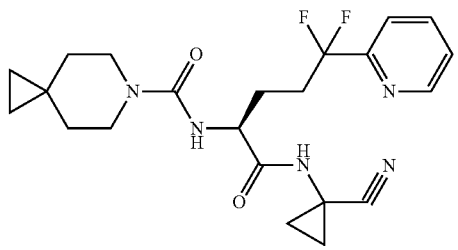

N—[(S)-1-(1-cyanocyclopropylcarbamoyl)-4,4-difluoro-4-pyridin-3-ylbutyl]-6-aza-spiro[2.5]octane-6-carbonsäure

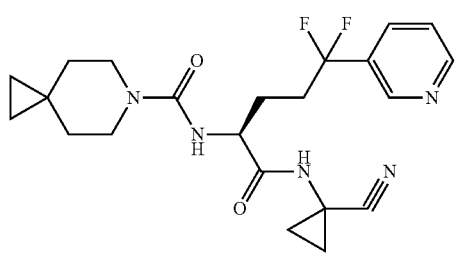 [SMILES: N#CC1(NC(=O)[C@H](CCC(F)(F)c2cccnc2)NC(=O)N2CCC3(CC2)CC3)CC1]

N—[(S)-1-(1-cyanocyclopropylcarbamoyl)-4,4-difluoro-4-pyridin-4-ylbutyl]-6-aza-spiro[2.5]octane-6-carboxamide

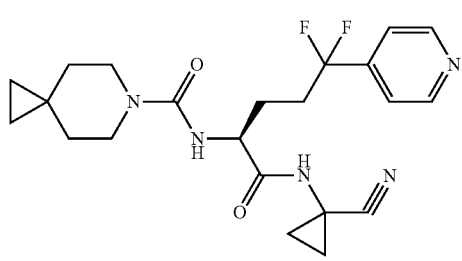 [SMILES: N#CC1(NC(=O)[C@H](CCC(F)(F)c2ccncc2)NC(=O)N2CCC3(CC2)CC3)CC1]

N—[(S)-1-(1-cyanocyclopropylcarbamoyl)-4-(2-difluoromethoxyphenyl)-4,4-difluoro-butyl]-6-azaspiro[2.5]octane-6-carboxamide

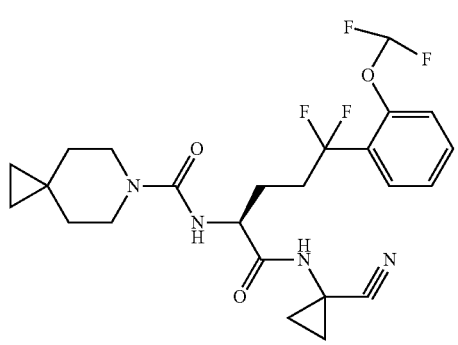 [SMILES: N#CC1(NC(=O)[C@H](CCC(F)(F)c2ccccc2OC(F)F)NC(=O)N2CCC3(CC2)CC3)CC1]

N—[(S)-1-(1-cyanocyclopropylcarbamoyl)-4,4-difluoro-4-(4-fluorophenyl)butyl]-6-aza-spiro[2.5]octane-6-carboxamide

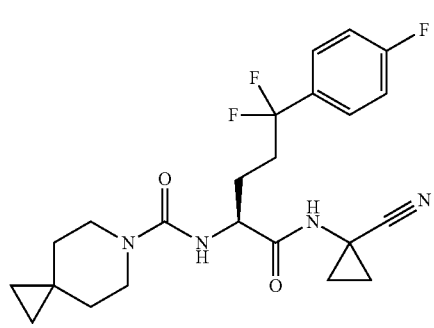 [SMILES: N#CC1(NC(=O)[C@H](CCC(F)(F)c2ccc(F)cc2)NC(=O)N2CCC3(CC2)CC3)CC1]

N—[(S)-1-(1-cyanocyclopropylcarbamoyl)-4,4-difluoro-4-(2-fluorophenyl)butyl]-6-aza-spiro[2.5]octane-6-carboxamide

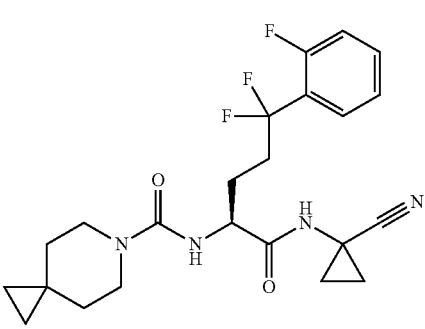 [SMILES: N#CC1(NC(=O)[C@H](CCC(F)(F)c2ccccc2F)NC(=O)N2CCC3(CC2)CC3)CC1]

N—[(S)-1-(4-cyano-1-methylpiperidin-4-ylcarbamoyl)-4,4-difluoro-4-phenylbutyl]-6-aza-spiro[2.5]octane-6-carboxamide

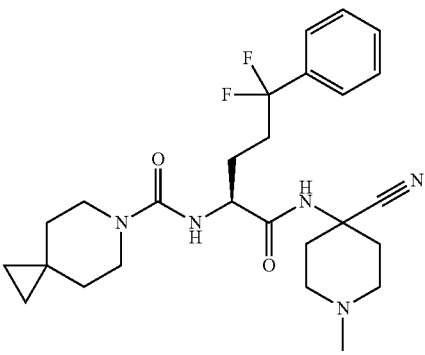 [SMILES: CN1CCC(C#N)(NC(=O)[C@H](CCC(F)(F)c2ccccc2)NC(=O)N2CCC3(CC2)CC3)CC1]

N—[(S)-1-(1-cyanocyclopropylcarbamoyl)-4,4-difluoro-4-phenylbutyl]-7-cyclopropyl-2,7-diazaspiro[3.5]nonane-2-carboxamide

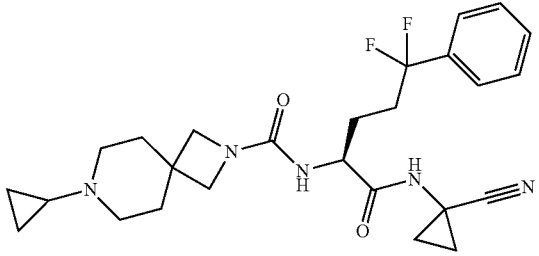 [SMILES: N#CC1(NC(=O)[C@H](CCC(F)(F)c2ccccc2)NC(=O)N2CC3(CCN(C4CC4)CC3)C2)CC1]

N—[(S)-1-(1-cyanocyclopropylcarbamoyl)-4,4-difluoro-4-(4-fluorophenyl)butyl]-7-cyclopropyl-2,7-diazaspiro[3.5]nonane-2-carboxamide

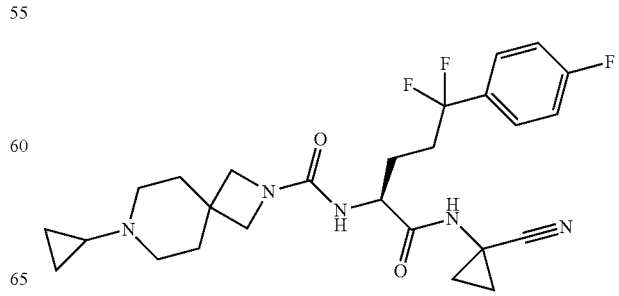

N—[(S)-1-(1-cyanocyclopropylcarbamoyl)-4,4-difluoro-4-(2-fluorophenyl)butyl]-7-cyclopropyl-2,7-diazaspiro[3.5]nonane-2-carboxamide

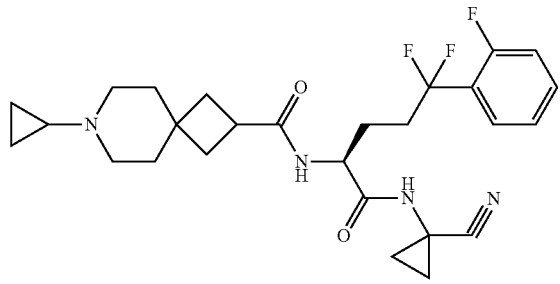 [SMILES: N#CC1(NC(=O)[C@H](CCC(F)(F)c2ccccc2F)NC(=O)C2CC3(CCN(C4CC4)CC3)C2)CC1]

N—[(S)-1-(1-cyanocyclopropylcarbamoyl)-4-(2-difluoromethoxyphenyl)-4,4-difluorobutyl]-7-cyclopropyl-2,7-diazaspiro[3.5]nonane-2-carboxamide

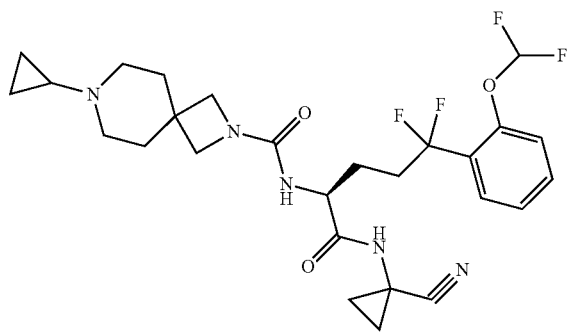 [SMILES: N#CC1(NC(=O)[C@H](CCC(F)(F)c2ccccc2OC(F)F)NC(=O)N2CC3(CCN(C4CC4)CC3)C2)CC1]

N—[(S)-1-(1-cyanocyclopropylcarbamoyl)-4,4-difluoro-4-pyridin-2-ylbutyl]-7-cyclopropyl-2,7-diazaspiro[3.5]nonane-2-carboxamide

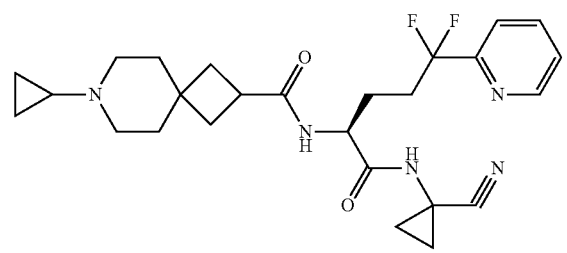 [SMILES: N#CC1(NC(=O)[C@H](CCC(F)(F)c2ccccn2)NC(=O)C2CC3(CCN(C4CC4)CC3)C2)CC1]

N—[(S)-1-(1-cyanocyclopropylcarbamoyl)-4,4-difluoro-4-pyridin-3-ylbutyl]-7-cyclopropyl-2,7-diazaspiro[3.5]nonane-2-carboxamide

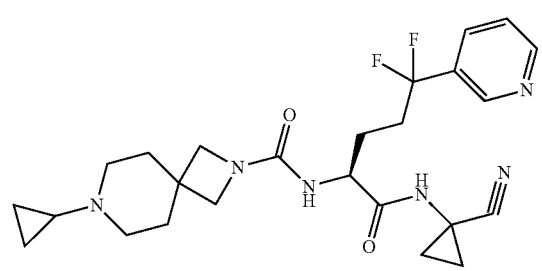 [SMILES: N#CC1(NC(=O)[C@H](CCC(F)(F)c2cccnc2)NC(=O)N2CC3(CCN(C4CC4)CC3)C2)CC1]

N—[(S)-1-(1-cyanocyclopropylcarbamoyl)-4,4-difluoro-4-pyridin-4-ylbutyl]-7-cyclopropyl-2,7-diazaspiro[3.5]nonane-2-carboxamide

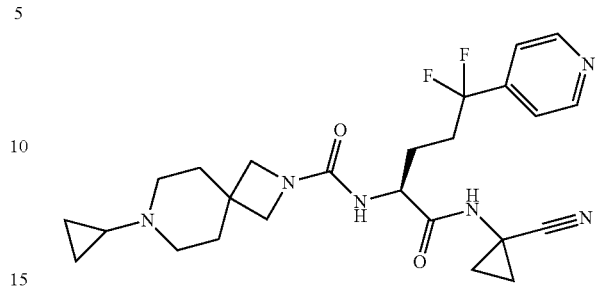

N—[(S)-1-(1-cyanocyclopropylcarbamoyl)-3,3-difluoro-4-phenylbutyl]-7-methyl-2,7-diazaspiro[3.5]nonane-2-carboxamide

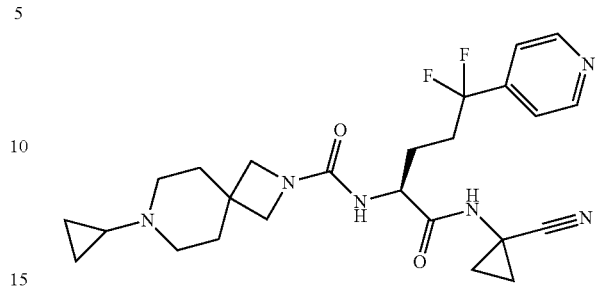

N—[(S)-1-(1-cyanocyclopropylcarbamoyl)-3,3-difluoro-4-phenylbutyl]-7-(2-methoxyethyl)-2,7-diazaspiro[3.5]nonane-2-carboxamide

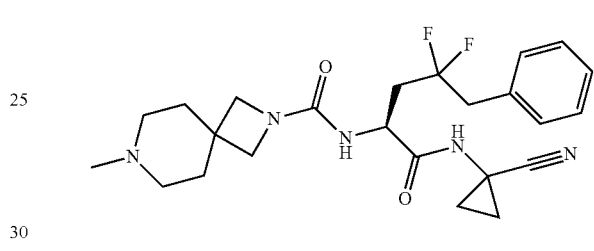

N—[(S)-1-(1-cyanocyclopropylcarbamoyl)-3,3-difluoro-4-phenylbutyl]-9-(2-methoxyethyl)-3,9-diazaspiro[5.5]undecane-3-carboxamide

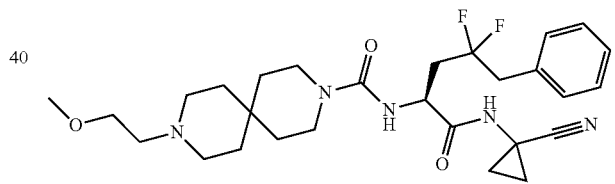

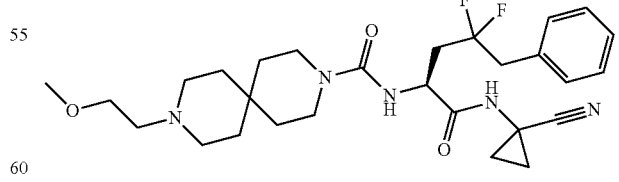

N—[(S)-1-(1-cyanocyclopropylcarbamoyl)-3,3-difluoro-4-phenylbutyl]-7-amino-5-aza-spiro[2.4]heptane-5-carboxamide

101

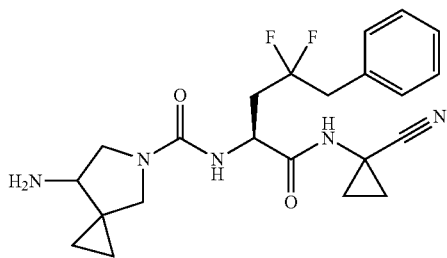 [SMILES: N#CC1(NC(=O)[C@H](CC(F)(F)Cc2ccccc2)NC(=O)N2CC(N)C3(CC3)C2)CC1]

N—[(S)-1-(1-cyanocyclopropylcarbamoyl)-3,3-difluoro-4-phenylbutyl]-7-dimethylamino-5-azaspiro[2.4]heptane-5-carboxamide

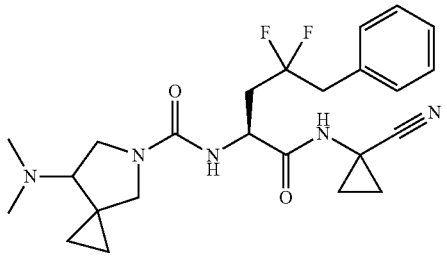 [SMILES: CN(C)C1CN(C(=O)N[C@@H](CC(F)(F)Cc2ccccc2)C(=O)NC2(C#N)CC2)CC12CC2]

N—[(S)-1-(1-cyanocyclopropylcarbamoyl)-3,3-difluorobutyl]-7-(cyclopropanecarbonyl-amino)-5-azaspiro[2.4]heptane-5-carboxamide

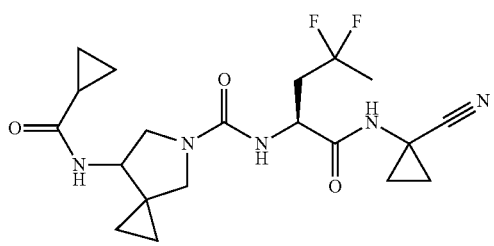 [SMILES: CC(F)(F)C[C@H](NC(=O)N1CC(NC(=O)C2CC2)C2(CC2)C1)C(=O)NC1(C#N)CC1]

N-6-[(S)-1-(1-cyanocyclopropylcarbamoyl)-3,3-difluorobutylcarbamoyl]-6-aza-spiro[2.5]octane-1-carboxylic acid

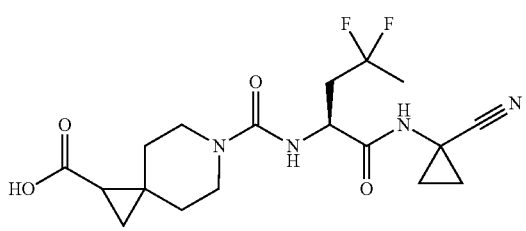 [SMILES: CC(F)(F)C[C@H](NC(=O)N1CCC2(CC1)CC2C(=O)O)C(=O)NC1(C#N)CC1]

102 ethyl 6-[(S)-1-(1-canocyclopropylcarbamoyl)-3,3-difluorobutylcarbamoyl]-6-azaspiro[2.5]octane-1-carboxylate

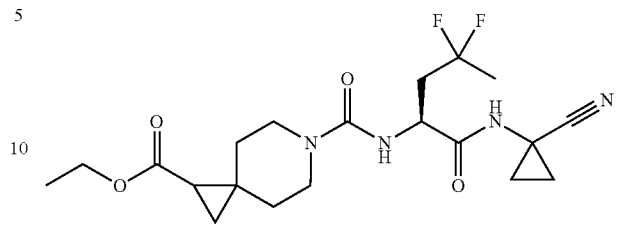

N—[S)-1-(1-cyanocyclopropylcarbamoyl)-3,3-difluorobutyl]-1-hydroxymethyl-6-aza-spiro[2.5]octane-6-carboxamide

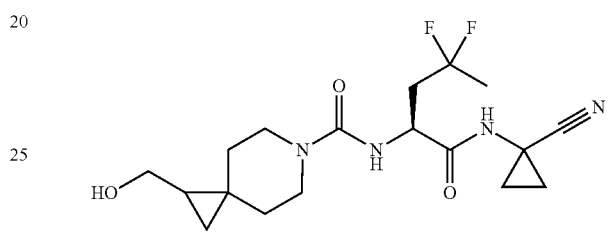

8-[(S)-1-(1-cyanocyclopropylcarbamoyl)-3,3-difluorobutylcarbamoyl]-1-oxa-2,8-diaza-spiro[4.5]dec-2-ene-3-carboxylic acid

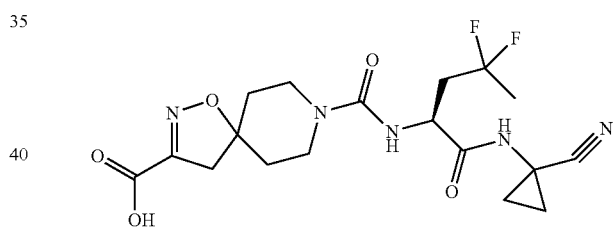

8-[(S)-1-(1-cyanocyclopropylcarbamoyl)-3,3-difluoro-4-phenylbutylcarbamoyl]-1-oxa-2,8-diazaspiro[4.5]dec-2-ene-3-carboxylic acid

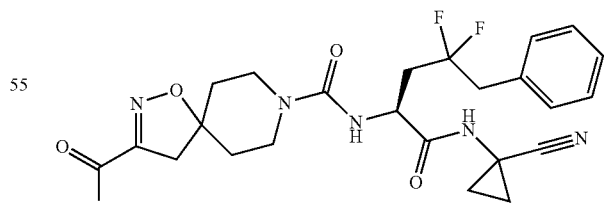

8-[(S)-1-(1-cyanocyclopropylcarbamoyl)-3,3-difluoropentylcarbamoyl]-1-oxa-2,8-diaza-spiro[4.5]dec-2-ene-3-carboxylic acid

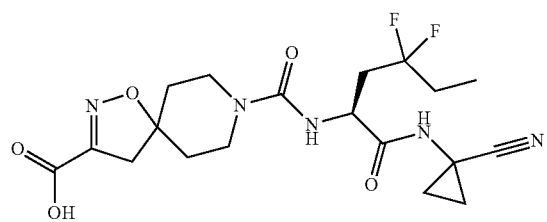 [SMILES: CCC(F)(F)C[C@H](NC(=O)N1CCC2(CC1)CC(C(=O)O)=NO2)C(=O)NC1(C#N)CC1]

7-[(S)-1-(1-cyanocyclopropylcarbamoyl)-3,3-difluoro-4-phenylbutylcarbamoyl]-1-oxa-2,7-diazaspiro[4.5]dec-2-ene-3-carboxylic acid

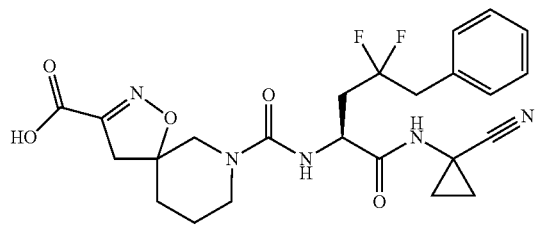 [SMILES: N#CC1(NC(=O)[C@H](CC(F)(F)Cc2ccccc2)NC(=O)N2CCCC3(CC(C(=O)O)=NO3)C2)CC1]

7-[(S)-1-(1-cyanocyclopropylcarbamoyl)-3,3-difluoro-4-phenylbutylcarbamoyl]-1-oxa-2,7-diazaspiro[4.4]non-2-ene-3-carboxylic acid

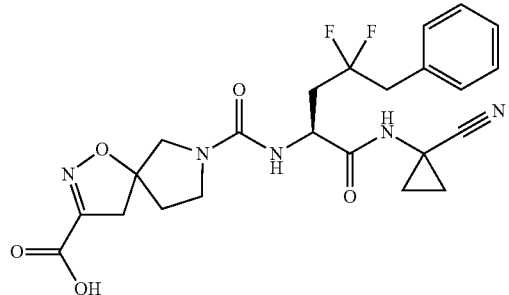 [SMILES: N#CC1(NC(=O)[C@H](CC(F)(F)Cc2ccccc2)NC(=O)N2CCC3(CC(C(=O)O)=NO3)C2)CC1]

{3-[(S)-1-(1-cyanocyclopropylcarbamoyl)-3,3-difluorobutylcarbamoyl]-3-aza-spiro[5.5]undec-9-yl}acetic acid

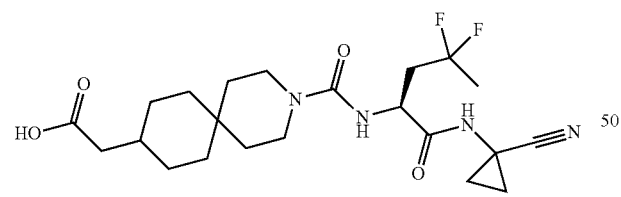

{3-[(S)-1-(1-cyanocyclopropylcarbamoyl)-3,3-difluoropentylcarbamoyl]-3-aza-spiro[5.5]undec-9-yl}acetic acid

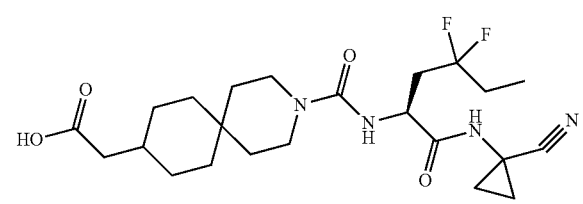 [SMILES: CCC(F)(F)C[C@H](NC(=O)N1CCC2(CCC(CC(=O)O)CC2)CC1)C(=O)NC1(C#N)CC1]

N—[(S)-1-(1-cyanocyclopropylcarbamoyl)-3,3-difluoropentyl]-1,3-dioxo-2,8-diazaspiro[4.5]decane-8-carboxamide

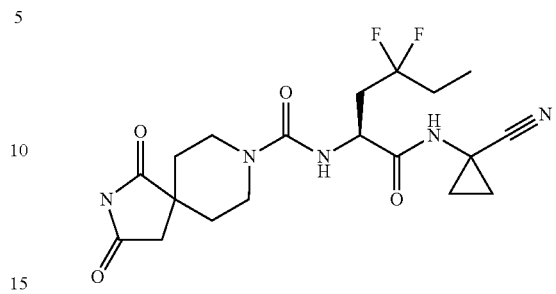

N—[(S)-1-(1-cyanocyclopropylcarbamoyl)-3,3-difluorobutyl]-1,3-dioxo-2,8-diaza-spiro[4.5]decane-8-carboxamide

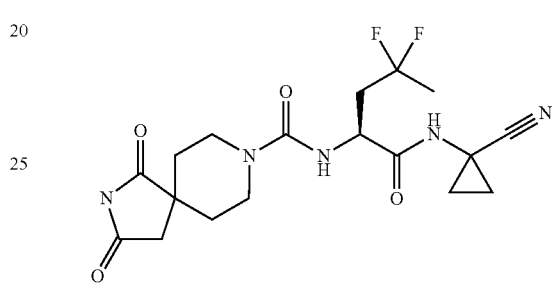

N—[(S)-1-(1-cyanocyclopropylcarbamoyl)-3,3-difluoro-4-phenylbutyl]-1,3-dioxo-2,8-diazaspiro[4.5]decane-8-carboxamide

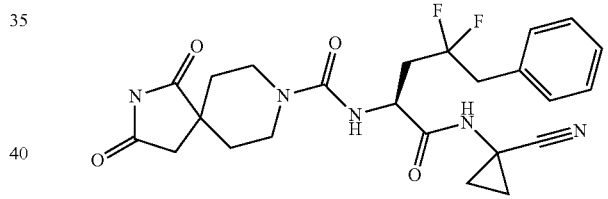

N—[(S)-1-(1-cyanocyclopropylcarbamoyl)-3,3-difluoro-5-methylhexyl]-5-aza-spiro[2.5]octane-5-carboxamide

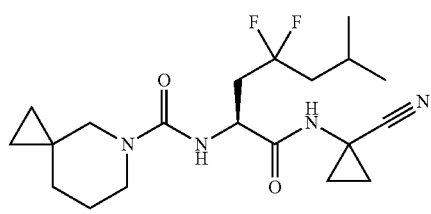 [SMILES: CC(C)CC(F)(F)C[C@H](NC(=O)N1CCCC2(CC2)C1)C(=O)NC1(C#N)CC1]

N—[(S)-1-(1-cyanocyclopropylcarbamoyl)-3,3-difluorobutyl]-5-azaspiro[2.5]octane-5-carboxamide

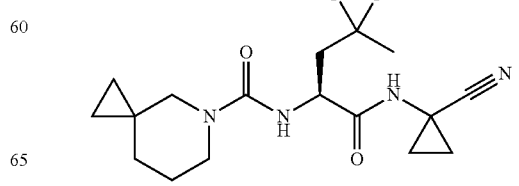

N—[(S)-1-(1-cyanocyclopropylcarbamoyl)-3,3-difluoro-4-phenylbutyl]-5-aza-spiro[2.5]octane-5-carboxamide

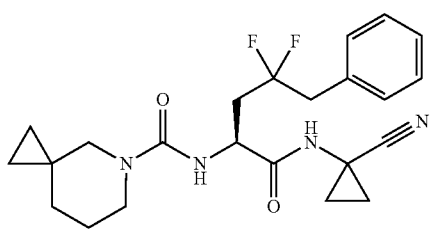 [SMILES: N#CC1(NC(=O)[C@H](CC(F)(F)Cc2ccccc2)NC(=O)N2CCCC3(CC3)C2)CC1]

N—[(S)-1-(cyanomethylcarbamoyl)-3,3-difluorobutyl]-5-azaspiro[2.5]octane-5-carboxamide

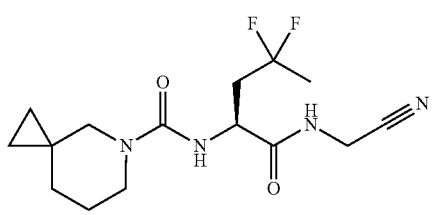 [SMILES: CC(F)(F)C[C@H](NC(=O)N1CCCC2(CC2)C1)C(=O)NCC#N]

N—[(S)-1-(cyanomethylcarbamoyl)-3,3-difluoro-4-phenylbutyl]-5-azaspiro[2.5]octane-5-carboxamide

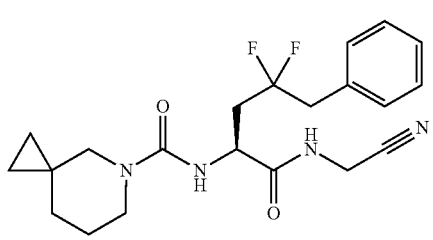 [SMILES: N#CCNC(=O)[C@H](CC(F)(F)Cc1ccccc1)NC(=O)N1CCCC2(CC2)C1]

N—[(S)-1-(1-cyanocyclopropylcarbamoyl)-3,3-difluoro-4-(4-fluorophenyl)-butyl]-5-azaspiro[2.5]octane-5-carboxamide

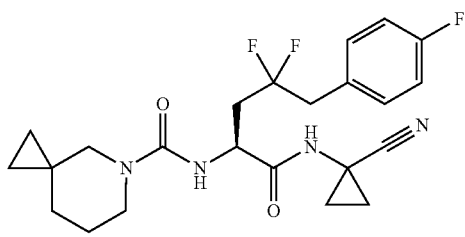 [SMILES: N#CC1(NC(=O)[C@H](CC(F)(F)Cc2ccc(F)cc2)NC(=O)N2CCCC3(CC3)C2)CC1]

N—[(S)-1-(1-cyanocyclopropylcarbamoyl)-3,3-difluorobutyl]-8-cyclopropyl-1-oxa-2,8-diazaspiro[4.5]dec-2-ene-3-carboxamide

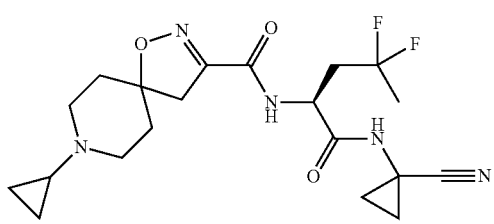 [SMILES: CC(F)(F)C[C@H](NC(=O)C1=NOC2(CCN(C3CC3)CC2)C1)C(=O)NC1(C#N)CC1]

N—[(S)-1-(1-cyanocyclopropylcarbamoyl)-3,3-difluorobutyl]-8-propyl-1-oxa-2,8-diaza-spiro[4.5]dec-2-en-3-carboxamide

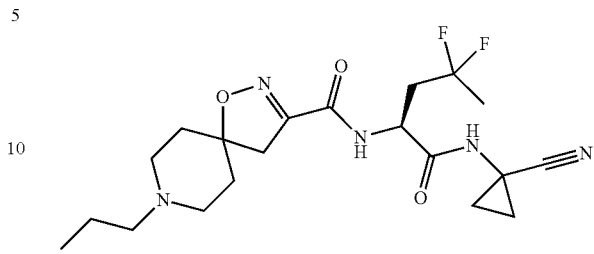

N—[(S)-1-(1-cyanocyclopropylcarbamoyl)-3,3-difluorobutyl]-7-cyclopropyl-1-oxa-2,7-diazaspiro[4.5]dec-2-ene-3-carboxamide

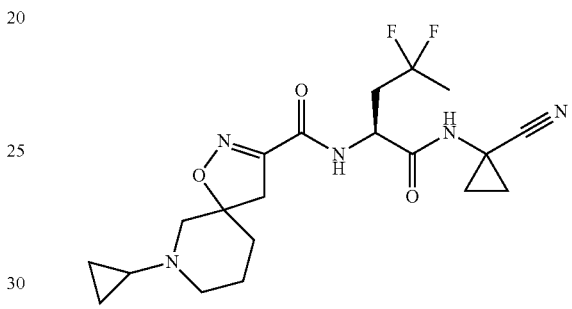

N—[(S)-1-(1-cyanocyclopropylcarbamoyl)-3,3-difluorobutyl]-7-propyl-1-oxa-2,7-diaza-spiro[4.5]dec-2-ene-3-carboxamide

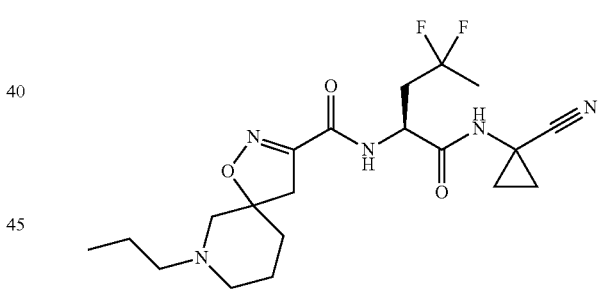

N—[(S)-1-(1-cyanocyclopropylcarbamoyl)-3,3-difluorobutyl]-7-cyclopropyl-1-oxa-2,7-diazaspiro[4.4]non-2-ene-3-carboxamide

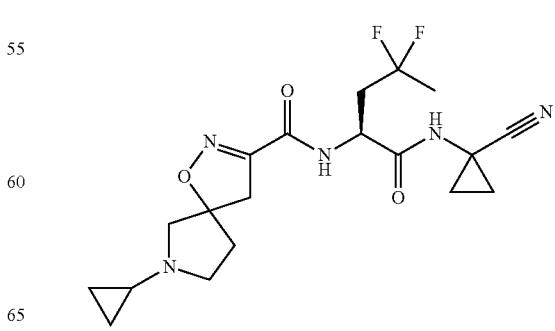

N—[(S)-1-(1-cyanocyclopropylcarbamoyl)-3,3-difluorobutyl]-7-methyl-1-oxa-2,7-diaza-spiro[4.4]non-2-ene-3-carboxamide

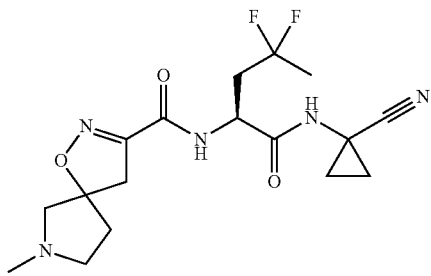 [SMILES: CN1CCC2(CC(C(=O)N[C@@H](CC(C)(F)F)C(=O)NC3(C#N)CC3)=NO2)C1]

N—[(S)-1-(1-cyanocyclopropylcarbamoyl)-3,3-difluoro-4-phenylbutyl]-7-methyl-1-oxa-2,7-diazaspiro[4.4]non-2-ene-3-carboxamide

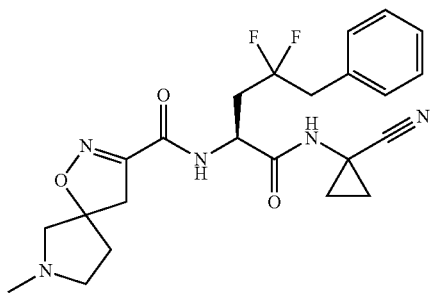 [SMILES: CN1CCC2(CC(C(=O)N[C@@H](CC(F)(F)Cc3ccccc3)C(=O)NC3(C#N)CC3)=NO2)C1]

Pharmacological Examples

Determination of the enzymatic activity of the catalytic domain of human Cathepsin B. This protein is obtained as an inactive enzyme from Sigma, Wiesbaden, Germany (catalog No. C8571). The enzyme is activated as follows:

25 µg of enzyme are diluted with acetate buffer to a concentration of 12.5 µg/ml. 1 part by volume of enzyme is admixed with 20 parts by volume of cysteine solution and diluted with the acetate/Hepes buffer to a concentration of 0.11 µg/ml and incubated at 37° C. for 5 minutes.

To measure the enzyme activity, 10 µl of enzyme solution are incubated with 10 µl of a 3% (v/v) aqueous dimethyl sulfoxide solution (reaction 1) for 10 minutes. To measure the enzyme inhibitor activity, 10 µl of enzyme solution are incubated with 10 µl of a 3% (v/v) aqueous dimethyl sulfoxide solution which contains the enzyme inhibitor (reaction 2).

Both in reaction 1 and in reaction 2, after addition of 10 µl of a 3% (v/v) aqueous dimethyl sulfoxide solution which contains 0.3 mmol/l of the substrate, the enzyme reaction is monitored by fluorescence spectroscopy (360 nm (excitation)/465 nm (emission)).

The enzyme activity is shown as fluorescence increase/minute.

The inhibitor action is calculated as the percentage inhibition by the following formula:

inhibition=100−[(fluorescence increase/minute in reaction 2)/(fluorescence increase/minute in reaction 1)×100].

The $IC_{50}$, which is the inhibitor concentration required for a 50% inhibition in the enzyme activity, is determined graphically by plotting the percentage inhibitions at different inhibitor concentrations.

The acetate buffer contains 0.1 mol/l of sodium acetate, 0.1 mol/l of sodium chloride and 0.001% Pluronic (Sigma, Deisenhofen, Germany) pH 4.5.

The cysteine solution contains 0.3 mol/l of cysteine in water. The acetate/Hepes buffer contains 0.15 mol/l of sodium acetate, 0.15 mol/l of Hepes, 0.3 mol/l of sodium chloride and 0.001% Pluronic (Sigma, Deisenhofen, Germany) pH 6.5.

The enzyme solution contains 0.11 µg/ml of the enzyme domain.

The substrate solution contains 0.3 mmol/l of the fluorogenic substrate 2-Arg-Arg-AMC (Bachem, Heidelberg, Germany).

Determination of the enzymatic activity of the catalytic domain of human Cathepsin K. This protein is obtained as an inactive enzyme from Sanofi-Aventis, Frankfurt, Germany. The enzyme is activated as follows:

1 part by volume of enzyme is admixed with 4 parts by volume of cysteine solution and diluted with the acetate/Hepes buffer to a concentration of 0.22 µg/ml.

To measure the enzyme activity, 10 µl of enzyme solution are incubated with 10 µl of a 3% (v/v) aqueous dimethyl sulfoxide solution (reaction 1) for 10 minutes. To measure the enzyme inhibitor activity, 10 µl of enzyme solution are incubated with 10 µl of a 3% (v/v) aqueous dimethyl sulfoxide solution which contains the enzyme inhibitor (reaction 2).

Both in reaction 1 and in reaction 2, after addition of 10 µl of a 3% (v/v) aqueous dimethyl sulfoxide solution which contains 0.3 mmol/l of the substrate, the enzyme reaction is monitored by fluorescence spectroscopy (360 nm (excitation)/465 nm (emission)).

The enzyme activity is shown as fluorescence increase/minute.

The inhibitor action is calculated as the percentage inhibition by the following formula:

% inhibition=100−[(fluorescence increase/minute in reaction 2)/(fluorescence increase/minute in reaction 1)×100].

The $IC_{50}$, which is the inhibitor concentration required for a 50% inhibition in the enzyme activity, is determined graphically by plotting the percentage inhibitions at different inhibitor concentrations.

The cysteine solution contains 0.3 mol/l of cysteine in water. The acetate/Hepes buffer contains 0.15 mol/l of sodium acetate, 0.15 mol/l of Hepes, 0.3 mol/l of sodium chloride and 0.001% Pluronic (Sigma, Deisenhofen, Germany) pH 6.5.

The enzyme solution contains 0.22 µg/ml of the enzyme domain.

The substrate solution contains 0.3 mmol/l of the fluorogenic substrate Boc-Ala-Gly-Pro-Arg-AMC (Bachem, Heidelberg, Germany).

Determination of the enzymatic activity of the catalytic domain of human Cathepsin S. This protein is obtained as an inactive enzyme from R&D Systems, Wiesbaden, Germany (catalog No. 1183-CY). The enzyme is activated as follows:

5 parts by volume of enzyme are incubated with 20 parts by volume of acetate buffer and 50 parts by volume of cysteine solution at 37° C. for 5 minutes. After the activation of the enzyme, it is diluted with the Tris/HCl buffer to a concentration of 0.65 µg/ml. To measure the enzyme activity, 10 µl of enzyme solution are incubated with 10 µl of a 3% (v/v) aqueous dimethyl sulfoxide solution (reaction 1) for 10 minutes. To measure the enzyme inhibitor activity, 10 µl of enzyme solution are incubated with 10 µl of a 3% (v/v) aqueous dimethyl sulfoxide solution which contains the enzyme inhibitor (reaction 2). Both in reaction 1 and in reaction 2, after addition of 10 µl of a 1.5% (v/v) aqueous dimethyl sulfoxide solution which contains 0.15 mmol/l of the substrate, the enzyme reaction is monitored by fluorescence spectroscopy (360 nm (excitation)/465 nm (emission)).

The enzyme activity is shown as fluorescence increase/minute.

The inhibitor action is calculated as the percentage inhibition by the following formula:

% inhibition=100−[(fluorescence increase/minute in reaction 2)/(fluorescence increase/minute in reaction 1)×100].

The $IC_{50}$, which is the inhibitor concentration required for a 50% inhibition in the enzyme activity, is determined graphically by plotting the percentage inhibitions at different inhibitor concentrations.

The acetate buffer contains 0.05 mol/l of sodium acetate, 0.1 mol/l of sodium chloride and 0.001% Pluronic (Sigma, Deisenhofen, Germany) pH 5.5.

The cysteine solution contains 0.3 mol/l of cysteine in water. The Tris/HCl buffer contains 0.1 mol/l of Tris/HCl, 0.04 mol/l of EDTA and 0.001% Pluronic pH=7.5. The enzyme solution contains 0.65 µg/ml of the enzyme domain.

The substrate solution contains 0.15 mmol/l of the fluorogenic substrate Z-Val-Val-Arg-AMC (Bachem, Heidelberg, Germany).

Corresponding Ki values are obtained by applying the Cheng-Prusoff equation:

$K_i = K_{i,app}/(1+[S]/K_M)$; where $K_{i,app}=IC_{50}$ ($K_{i,app}$ is the concentration of the competing substance which leads to 50% inhibition of the enzymatic activity at a substrate concentration [S])

Table 2 reports corresponding inhibition values in the form of Ki values for a few representative examples:

TABLE 2

| Example | Ki [nM] Cathepsin K | Ki [nM] Cathepsin B | Ki [nM] Cathepsin S |
|---|---|---|---|
| 9 | 1.8 | 46 | 3.2 |
| 35 | 31 | >7100 | 150 |
| 36 | 3 | 44 | 2 |
| 37 | 21 | 560 | 13 |
| 42 | 32 | 4500 | 11 |
| 45 | 21 | 1200 | 24 |
| 49 | 52 | 2200 | 16 |
| 53 | 4.5 | 1500 | 53 |
| 56 | 7.5 | 210 | 7.2 |
| 63 | 22 | 260 | 5 |
| 70 | 910 | 110 | 0.3 |
| 74 | 150 | >7100 | 16 |
| 76 | 47 | 930 | 22 |
| 77 | 20 | 220 | 7 |
| 78 | 38 | 530 | 19 |
| 79 | 16 | 620 | 9 |
| 80 | 36 | 3900 | 9 |
| 83 | 28 | 2300 | 8 |
| 88 | 15 | 310 | 9 |
| 91 | 43 | 140 | 2 |
| 94 | 24 | 84 | 2 |
| 97 | 400 | 100 | 1 |
| 102 | 33 | 62 | 0.5 |
| 103 | 84 | 99 | 27 |

Caco-2/TC7 permeability determinations for forecasting the absorption of the inventive compounds: (Caco-2/TC7 permeability test)

Caco-2/TC-7 cells from Sanofi are used. In addition, HTS Multiwell plates (24-well, non-coated, Becton Dickinson, surface area of the Becton Dickinson Filter 0.3 cm²) are used. The cell density on the filters was $2 \times 10^5/cm^2$, and $1.3 \times 10^4/cm^2$ on the T-75 flasks (Costar with vent-cap) for the cell line growth.

The incubation conditions are 37° C., 95% air humidity, 10% $CO_2$. The medium is changed three times per week (DMEM, Glutamax I, nonessential AA, penicillin/streptomycin, FBS 20%).

Permeability assay conditions: asymmetric conditions for the screening with apical buffer HBSS (with 10 mM HEPES and 0.5% BSA at pH 6.5) and basal buffer HBSS (with 10 µM HEPES and 5% BSA at pH 7.4). The permeability experiments were performed at 37° C. with agitation for 2 h. The samples were analyzed by LC-MS. The results were reported as the mean Papp value (single point, cm/sec) (permeability coefficient):

$$P = \frac{B_2}{[A_0] \times S \times t}$$

B2: basolateral amount of the compound to be analyzed after 2 h
[A₀]: apical concentration of the test solution
S: "insert area": 0.3 cm²
t: time: 2 h

What is claimed is:
1. A compound of the formula Ia,

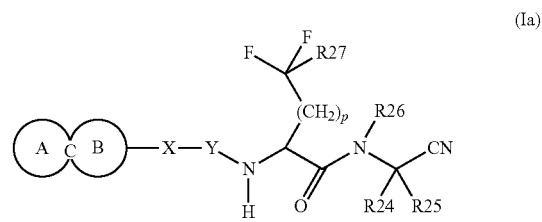

where
the

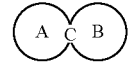

radical is a spiro compound,
in which the sub-rings

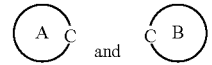

are in each case the same or different and are each independently
a) a saturated or partly saturated —($C_3$-$C_{11}$)-cycloalkyl, in which cycloalkyl is unbridged, bridged or fused and is unsubstituted or independently, according to the ring size, mono-, di-, tri, tetra- or pentasubstituted by R4, or
b) a saturated or partly saturated, three- to eleven-membered heterocycle which, according to the ring size, may contain one, two, three or four identical or different heteroatoms from the group of oxygen, nitrogen or sulfur, and in which the heterocycle is unbridged, bridged or fused and is unsubstituted or independently, according to the ring size, mono-, di-, tri-, tetra- or pentasubstituted by R4;
wherein the

radical is other than a 6-azaspiro[2.5]octane or 5-azaspiro[2.5]octane ring;

R4 is —NO$_2$, —CN, =O, =S, —OH, —CF$_3$, —SF$_5$, —(C$_0$-C$_3$)-alkylene-S—R10, —O—CF$_3$, —Si—(CH$_3$)$_3$, —(C$_0$-C$_5$)-alkylene-O—C(O)—R21, —(C$_0$-C$_5$)-alkylene-C(O)—O—R10, —(C$_0$-C$_3$)-alkylene-O—R10, —(C$_0$-C$_3$)-alkylene-N(R21)-R22, —(C$_0$-C$_3$)-alkylene-N(R10)-S(O$_2$)—R10, —(C$_0$-C$_5$)-alkylene-(C$_3$-C$_8$)-cycloalkyl-R23, —S—CF$_3$, —(C$_0$-C$_5$)-alkylene-(C$_1$-C$_3$)-fluoroalkyl, —(C$_0$-C$_5$)-alkylene-N(R10)-C(O)—R21, —(C$_0$-C$_3$)-alkylene-C(O)—N(R21)-R22, —(C$_0$-C$_4$)-alkyl where alkyl is unsubstituted or mono-, di- or trisubstituted independently by R9, —(C$_0$-C$_4$)-alkylene-aryl where aryl is selected from the group of phenyl, indanyl, indenyl, and naphthyl, where aryl is unsubstituted or mono-, di- or trisubstituted independently by R8, or —(C$_0$-C$_4$)-alkylene-Het where Het is selected from the group of azetidinyl, benzimidazolinyl, benzimidazolyl, benzofuranyl, benzothiophenyl, benzoxazolyl, benzthiazolyl, benzisoxazolyl, benzisothiazolyl, quinolinyl, dioxolyl, dioxanyl, furanyl, imidazolidinyl, imidazolinyl, imidazolyl, indolinyl, indolyl, 3H-indolyl, isoindolinyl, isoindolyl, isoquinolinyl, isothiazolidinyl, 2-isothiazolinyl, isothiazolyl, isoxazolyl, isoxazolidinyl, 2-isoxazolinyl, morpholinyl, octahydroisoquinolinyl, oxazolyl, oxazolidinyl, pyrimidinyl, piperazinyl, piperidinyl, pyranyl, pyrazinyl, pyrazolinyl, pyrazolyl, pyridazinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyridinyl, thiazolyl, thienyl, thienopyridinyl, thiomorpholinyl, and thiophenyl, and this Het radical is unsubstituted or independently mono-, di- or trisubstituted by R8;

R8 is halogen, carbamimidoyl, —NO$_2$, =O, —CF$_3$, —SF$_5$, —C(O)—O—R10, —CN, —C(O)—NH$_2$, —OH, —NH$_2$, —O—CF$_3$, —C(O)—N(R10)-R20, —N(R10)-R20, —(C$_3$-C$_8$)-cycloalkyl, —O—(C$_1$-C$_8$)-alkyl, —O—(C$_0$-C$_4$)-alkylene-(C$_3$-C$_6$)-cycloalkyl, —(C$_1$-C$_8$)-alkyl, or —(C$_0$-C$_4$)-alkylene-(C$_3$-C$_8$)-cycloalkyl, where the alkyl radicals mentioned are each unsubstituted or mono-, di- or trisubstituted independently by halogen, NH$_2$, —OH, —O—CH$_3$, —SO$_2$—CH$_3$ or —SO$_2$—CF$_3$;

R9 is halogen, —NO$_2$, —CN, =O, —OH, —CF$_3$, —C(O)—O—R10, —C(O)—N(R21)-R22, —N(R21)-R22, —(C$_3$-C$_8$)-cycloalkyl, —(C$_0$-C$_3$)-alkylene-O—R10, —Si—(CH$_3$)$_3$, —N(R10)-S(O)$_u$—R10 where u is the integer 1 or 2, —S—R10, —SO$_r$—R10 where r is the integer 1 or 2, —S(O)$_v$—N(R10)-R20 where v is the integer 1 or 2, —C(O)—R10, —(C$_1$-C$_8$)-alkyl, —(C$_1$-C$_8$)-alkoxy, phenyl, phenyloxy-, —(C$_1$-C$_3$)-fluoroalkyl, —O—R19, —NH—C(O)—NH—R10, —(C$_0$-C$_4$)-alkyl-C(O)—O—C(R11,R19)-O—C(O)—R12, —NH—C(O)—NH—R21, —N(R21)-C(O)—R22, —(C$_0$-C$_4$)-alkyl-C(O)—O—C(R11,R19)-O—C(O)—O—R12, —NH—C(O)—O—R10, —O—CF$_3$ or Het where Het is as defined above and is unsubstituted or mono-, di- or trisubstituted independently by R8;

R10 and R20 are the same or different and are each independently a hydrogen atom, —(C$_1$-C$_6$)-alkyl, —(C$_0$-C$_4$)-alkyl-OH, —(C$_1$-C$_3$)-fluoroalkyl, —(C$_0$-C$_4$)-alkyl-O—(C$_1$-C$_4$)-alkyl, —(C$_0$-C$_5$)-alkyl-(C$_3$-C$_8$)-cycloalkyl, —(C$_0$-C$_2$)-alkylene-aryl where aryl is as defined above and is unsubstituted or mono-, di- or trisubstituted independently by —(C$_1$-C$_6$)-alkyl, —O—(C$_1$-C$_6$)-alkyl, halogen or —(C$_3$-C$_8$)-cycloalkyl, or —(C$_0$-C$_2$)-alkylene-Het where Het is as defined above and is unsubstituted or mono-, di- or trisubstituted independently by —(C$_1$-C$_6$)-alkyl, —O—(C$_1$-C$_6$)-alkyl, halogen or —(C$_3$-C$_8$)-cycloalkyl;

R11 and R19 are the same or different and are each independently a hydrogen atom or —(C$_1$-C$_6$)-alkyl;

R12 is —(C$_1$-C$_6$)-alkyl, —(C$_1$-C$_6$)-alkyl-OH, —(C$_1$-C$_6$)-alkyl-O—(C$_1$-C$_6$)-alkyl, —(C$_3$-C$_8$)-cycloalkyl, —(C$_1$-C$_6$)-alkyl-O—(C$_1$-C$_8$)-alkyl-(C$_3$-C$_8$)-cycloalkyl, or —(C$_1$-C$_6$)-alkyl-(C$_3$-C$_8$)-cycloalkyl, where the cycloalkyl radical is unsubstituted or mono-, di- or trisubstituted independently by —OH, —O—(C$_1$-C$_4$)-alkyl or R10;

R21 and R22 are the same or different and are each independently a hydrogen atom, —(C$_1$-C$_6$)-alkyl where alkyl is unsubstituted or mono-, di- or trisubstituted independently by R8, —(C$_0$-C$_6$)-alkylene-(C$_3$-C$_8$)-cycloalkyl, —SO$_t$—R10 where t is the integer 1 or 2, —(C$_1$-C$_3$)-fluoroalkyl, —O—R12, —(C$_0$-C$_6$)-alkylene-aryl where aryl is as defined above and alkylene and aryl are each unsubstituted or mono-, di- or trisubstituted independently by R8 or —(C$_0$-C$_6$)-alkylene-Het where Het is as defined above and alkylene and Het are each unsubstituted or mono-, di- or trisubstituted independently by R8;

R21 and R22, together with the nitrogen atom to which they are bonded, form a four- to eight-membered monocyclic heterocyclic ring which, as well as the nitrogen atom, additionally, according to the ring size, may contain one or two identical or different heteroatoms selected from the group of oxygen, nitrogen and sulfur and in which the heterocycle is unsubstituted or mono-, di- or trisubstituted independently by R8;

R23 is a hydrogen atom, —OH or —O—(C$_1$-C$_4$)-alkyl;

X is a covalent bond, —N(R7)- or —O—, where

R7 is a hydrogen atom, —(C$_0$-C$_4$)-alkylene-(C$_3$-C$_6$)-cycloalkyl or —(C$_1$-C$_4$)-alkyl;

Y is —C(O)—, —C(S)— or —S(O$_2$)—;

p is the integer 1 or 2;

R27 is a hydrogen atom, —(C$_1$-C$_6$)-alkyl, halogen, —(C$_0$-C$_4$)-alkylene-(C$_3$-C$_6$)-cycloalkyl, —(C$_0$-C$_4$)-alkylene-Het where Het is as defined above and is unsubstituted or substituted by halogen, —(C$_1$-C$_6$)-alkyl, —O—(C$_1$-C$_3$)-fluoroalkyl or —O—(C$_1$-C$_6$)-alkyl, or —(C$_0$-C$_2$)-alkylene-phenyl where phenyl is unsubstituted or substituted by halogen, —(C$_1$-C$_6$)-alkyl, —O—(C$_1$-C$_3$)-fluoroalkyl or —O—(C$_1$-C$_6$)-alkyl;

R26 is a hydrogen atom, —(C$_1$-C$_4$)-alkyl or —(C$_0$-C$_4$)-alkylene-(C$_3$-C$_6$)-cycloalkyl;

R24 and R25 are the same or different and are each independently a hydrogen atom, —(C$_1$-C$_6$)-alkyl, —(C$_1$-C$_3$)-fluoroalkyl, —(C$_0$-C$_4$)-alkylene-(C$_3$-C$_6$)-cycloalkyl, —(C$_0$-C$_4$)-alkylene-aryl where aryl is as defined above and is unsubstituted or mono-, di- or trisubstituted independently by R8, or —(C$_0$-C$_4$)-alkylene-Het where Het is as defined above and is unsubstituted or mono-, di- or trisubstituted independently by R8; or R24 and R25, together with the carbon atom to which they are bonded, form a three- to six-membered cycloalkyl ring which is unsubstituted or mono-, di- or trisubstituted independently by R10 or fluorine; or R24 and R25, together with the carbon atom to which they are bonded, form a three- to six-membered heterocycloalkyl radical which is unsubstituted or mono-, di- or trisubstituted independently by R10 or fluorine;

or a physiologically tolerated salt thereof.

2. The compound of claim 1 wherein the sub-ring

is selected from the following group:

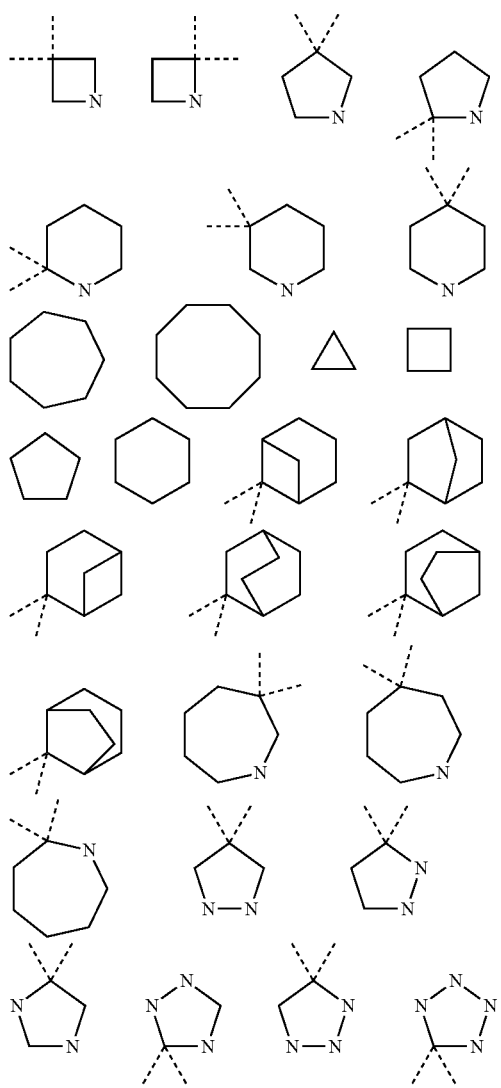

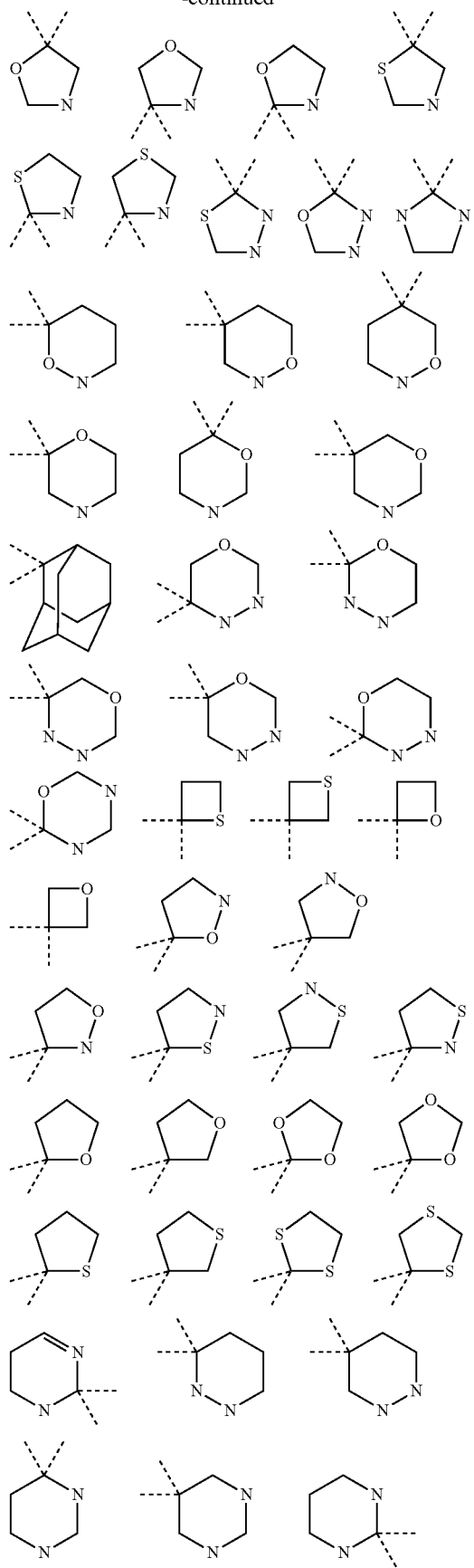

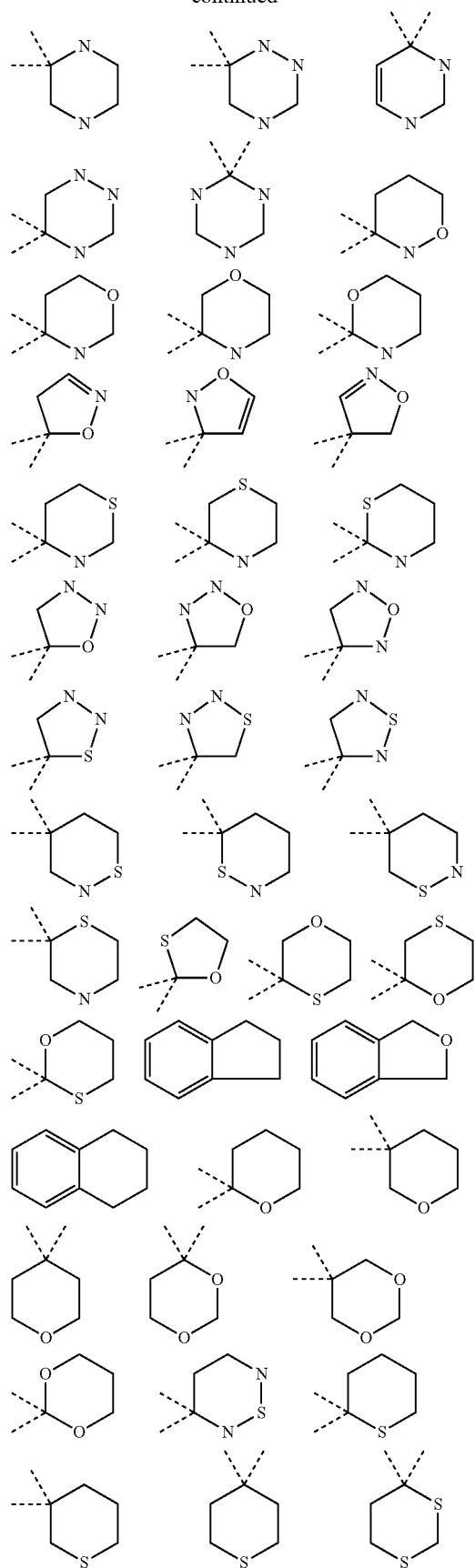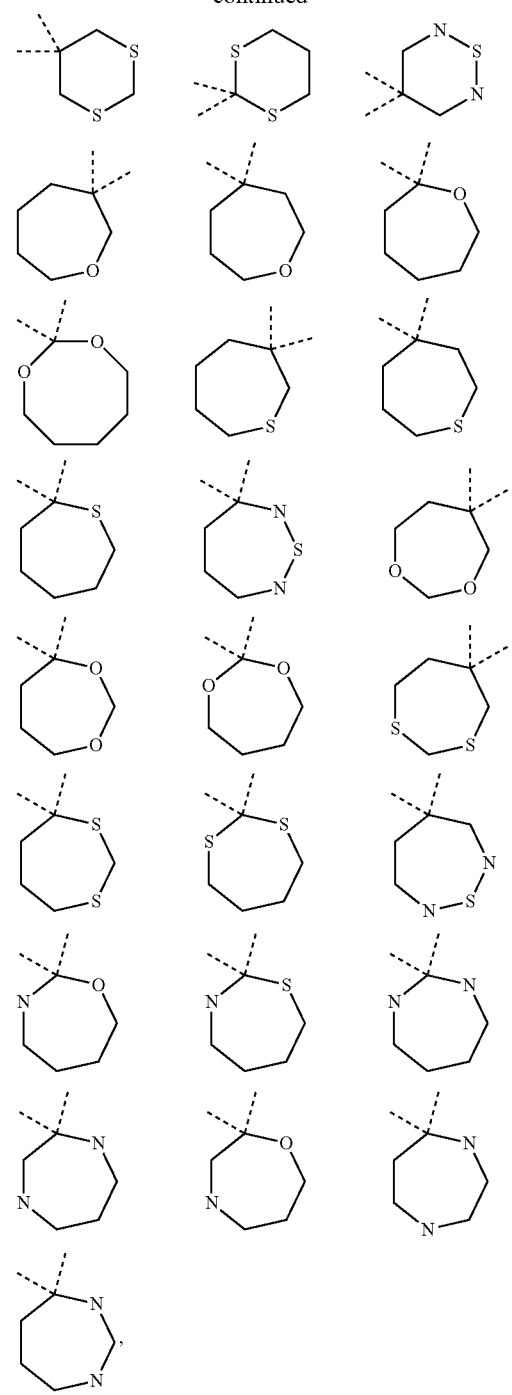
where the dotted lines indicate the particular point of attachment to the second sub-ring, single bonds in the structures listed may be replaced partly by double bonds, or further ring systems may be fused on; and
in which the sub-ring

is selected from the following group:

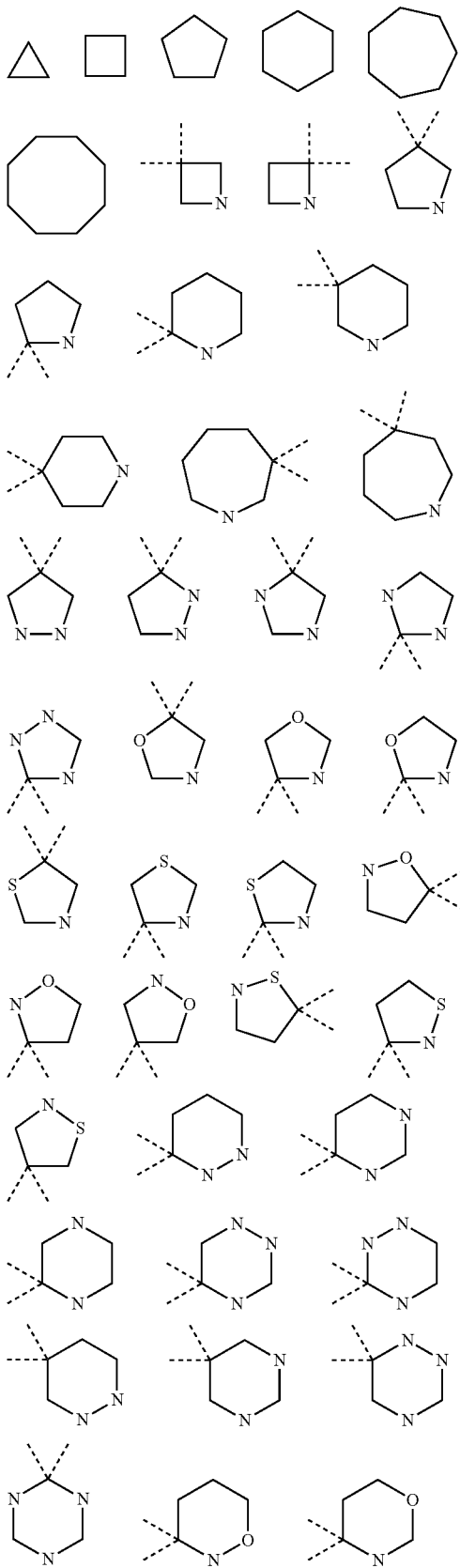

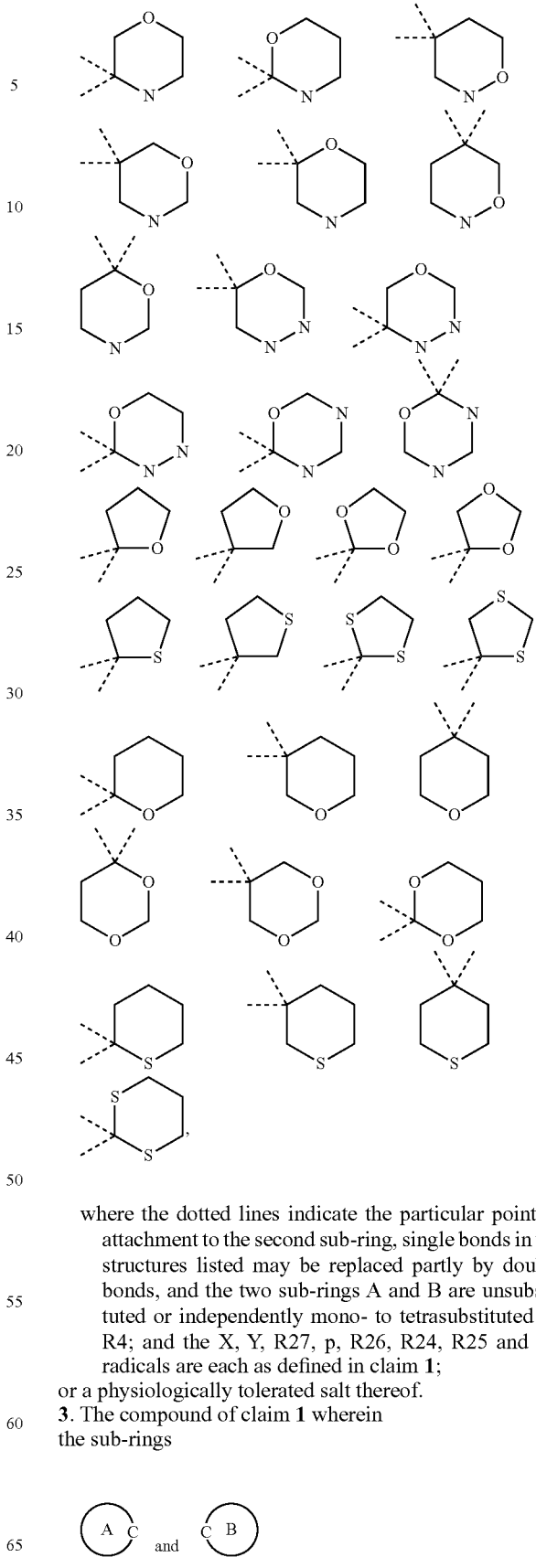

where the dotted lines indicate the particular point of attachment to the second sub-ring, single bonds in the structures listed may be replaced partly by double bonds, and the two sub-rings A and B are unsubstituted or independently mono- to tetrasubstituted by R4; and the X, Y, R27, p, R26, R24, R25 and R4 radicals are each as defined in claim 1;

or a physiologically tolerated salt thereof.

3. The compound of claim 1 wherein the sub-rings

 and are in each case selected from cyclopropane, cyclobutane, cyclopentane, cyclohexane, cycloheptane, cyclooctane, bicyclo[4.2.0]octane, octahydroindene, decalin, decahydrobenzocycloheptene, dodecahydroheptalene, bicyclo[3.1.1]heptane, bicyclo[2.2.1]heptane, bicyclo[3.3.0]octane, bicyclo[2.2.2]octane, spiro[2.5]octane, spiro[3.4]octane, azepane, azepine, azetidine, aziridine, azirine, azocane, benzimidazoline, 2,3-dihydrobenzo[b]thiophene, 1,3-dihydrobenzo[c]thiophene, 2,3-dihydrobenzofuran, 2,3-dihydrobenzooxazole, 2,3-dihydrobenzothiazole, 1,3-dihydroisobenzofuran, 4,5-dihydroisothiazole, 2,3-dihydroisoxazole, 2,5-dihydroisoxazole, 4,5-dihydroisoxazole, 5,6-dihydro-4H-[1,2]oxazine, benzo[1,3]dioxole, 1,4-diazepane, 1,2-diazepine, 1,3-diazepine, 1,4-diazepine, diaziridine, diazirine, 1,4-diazocane, dioxane, 1,3-dioxane, dioxazine, [1,3]dioxepane, 1,4-diozocane, dioxole, dioxolane, 1,3-dioxolane, 1,3-dioxolene, [1,3]dithiane, [1,3]dithiolane, hexahydropyridazine, hexahydropyrimidine, imidazoline, imidazolidine, indane, indoline, isoindoline, isothiazolidine, isothiazoline, isoxazoline, isoxazolidine, 2-isoxazoline, morpholine, [1,3,4]oxadiazinane, [1,3,5]oxadiazinane, [1,2,3]oxadiazolidine, [1,3,4]oxadiazolidine, 1,2-oxathiepane, 1,2-oxathiolane, [1,3]oxathiolane, 1,4-oxazepane, 1,2-oxazine, 1,3-oxazine, 1,4-oxazine, oxazinane, 1,3-oxazinane, oxazocane, oxaziridine, oxazolidine, oxepane, oxetane, oxirane, oxocane, piperazine, piperidine, pyran, pyrazoline, pyrazolidine, pyrrolidine, pyrrolidinone, pyrroline, tetrahydroquinoline, tetrahydrofuran, tetrahydroisoquinoline, 1,2,3,4-tetrahydronaphthalene, tetrahydropyran, tetrahydropyridine, 1,2,3,4-tetrahydro-pyrimidine, 1,2,5,6-tetrahydropyrimidine, tetrahydrothiophene, tetrazine, thiadiazine, [1,2,6]thiadiazinane, [1,3,4]thiadiazolidine, 1,2-thiazine, 1,3-thiazine, 1,4-thiazine, [1,2]thiazinane, [1,3]thiazinane, thiazolidine, thiazoline, thiepane, thietane, thiomorpholine, thiopyran, 1,2,3-triazine, 1,2,4-triazine, 1,3,5-triazine, [1,2,4]triazinane and [1,2,4]triazolidine;

and in which the two sub-rings are each unsubstituted or independently, according to the ring size, mono-, di-, tri-, tetra- or pentasubstituted by R4, and the radicals X, Y, R27, p, R26, R24, R25 and R4 are each as defined in claim 1;

or a physiologically tolerated salt thereof.

4. The compound of claim 1 wherein
the sub-rings

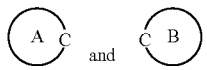

are each independently selected from the group consisting of azetidine, cyclopropyl, cyclobutyl, cyclopentyl, cyclohexyl, 1,3-dihydroisobenzofuran, 2,3-dihydroisoxazole, 2,5-dihydroisoxazole, 4,5-dihydroisoxazole, 1,3-dioxane, dioxolane, 1,3-dioxolane, imidazolidine, indane, morpholine, 1,3-oxazinane, oxazolidine, piperazine, piperidine, pyrrolidine, tetrahydrofuran, and 1,2,3,4-tetrahydronaphthalene;

and in which the two sub-rings are each unsubstituted or independently, according to the ring size, mono-, di- or trisubstituted by R4;

R4 is =O, =S, —(C$_0$-C$_3$)-alkylene-C(O)—O—R10, —(C$_0$-C$_3$)-alkylene-N(R21)-R22, —(C$_0$-C$_3$)-alkylene-NH—C(O)—R21, —(C$_0$-C$_4$)-alkylene-(C$_3$-C$_6$)-cycloalkyl-R23, —(C$_0$-C$_3$)-alkylene-O—R10, —(C$_0$-C$_4$)-alkylene-phenyl, where phenyl is unsubstituted or mono-, di- or trisubstituted independently by R8, or —(C$_0$-C$_4$)-alkyl where alkyl is unsubstituted or mono-, di- or trisubstituted independently by R9;

R8 is fluorine, chlorine, bromine, —O—(C$_1$-C$_3$)-fluoroalkyl or —O—(C$_1$-C$_4$)-alkyl;

R9 is halogen, —NO$_2$, —CN, =O, —OH, —CF$_3$, —C(O)—O—R10, —C(O)—N(R21)-R22, —N(R21)-R22, —(C$_3$-C$_8$)-cycloalkyl, —(C$_0$-C$_3$)-alkylene-O—R10, —Si—(CH$_3$)$_3$, —N(R10)-S(O)$_u$—R10 where u is the integer 1 or 2, —S—R10, —SO$_r$—R10 where r is the integer 1 or 2, —S(O)$_v$—N(R10)-R20 where v is the integer 1 or 2, —C(O)—R10, —(C$_1$-C$_8$)-alkyl, —(C$_1$-C$_8$)-alkoxy, phenyl, phenyloxy-, —(C$_1$-C$_3$)-fluoroalkyl, —O—R19, —NH—C(O)—NH—R10, —(C$_0$-C$_4$)-alkyl-C(O)—O—C(R11,R19)-O—C(O)—R12, —NH—C(O)—NH—R21, —N(R21)-C(O)—R22, —(C$_0$-C$_4$)-alkyl-C(O)—O—C(R11,R19)-O—C(O)—O—R12, —NH—C(O)—O—R10 or —O—CF$_3$;

R10 and R20 are the same or different and are each independently a hydrogen atom or —(C$_1$-C$_6$)-alkyl;

R11 and R19 are the same or different and are each independently a hydrogen atom or —(C$_1$-C$_6$)-alkyl;

R12 is —(C$_1$-C$_6$)-alkyl, —(C$_1$-C$_6$)-alkyl-OH, —(C$_1$-C$_6$)-alkyl-O—(C$_1$-C$_6$)-alkyl, —(C$_3$-C$_8$)-cycloalkyl, —(C$_1$-C$_6$)-alkyl-O—(C$_1$-C$_8$)-alkyl-(C$_3$-C$_8$)-cycloalkyl, —(C$_1$-C$_6$)-alkyl-(C$_3$-C$_8$)-cycloalkyl, where the cycloalkyl radical is unsubstituted or mono-, di- or trisubstituted independently by —OH, —O—(C$_1$-C$_4$)-alkyl or R10;

R21 and R22 are the same or different and are each independently a hydrogen atom, —(C$_1$-C$_6$)-alkyl, —O—R12, —(C$_0$-C$_6$)-alkylene-(C$_3$-C$_8$)-cycloalkyl, —SO$_t$—R10 where t is the integer 1 or 2, or —(C$_1$-C$_3$)-fluoroalkyl;

R23 is a hydrogen atom, —OH or —O—(C$_1$-C$_4$)-alkyl;

X is a covalent bond or —N(R7)- where
R7 is a hydrogen atom or —(C$_1$-C$_4$)-alkyl;

Y is —C(O)— or —S(O$_2$)—;

p is the integer 1 or 2;

R26 is a hydrogen atom;

R27 is a hydrogen atom, —(C$_0$-C$_4$)-alkylene-(C$_3$-C$_6$)-cycloalkyl, —(C$_1$-C$_6$)-alkyl, —(C$_0$-C$_2$)-alkylene-phenyl where phenyl is unsubstituted or substituted by halogen, —(C$_1$-C$_6$)-alkyl, —O—(C$_1$-C$_3$)-fluoroalkyl or —O—(C$_1$-C$_6$)-alkyl, or —(C$_0$-C$_2$)-alkylene-pyridyl;

R24 and R25 are the same or different and are each independently a hydrogen atom, —(C$_1$-C$_4$)-alkyl or —(C$_0$-C$_4$)-alkylene-(C$_3$-C$_6$)-cycloalkyl, or R24 and R25, together with the carbon atom to which they are bonded, form a cycloalkyl ring which is selected from the group of cyclopropyl, cyclobutyl, cyclopentyl and cyclohexyl, and is unsubstituted or mono-, di- or trisubstituted independently by R10 or fluorine, or R24 and R25, together with the carbon atom to which they are bonded, form a three- to six-membered heterocycloalkyl radical selected from the group of aziridine, azetidine, diazetidine, diaziridine, hexohydropyridazine, hexohydropyrimidine, imidazolidine, morpholine, oxadiazinane, oxadiazolidine, oxathianane, oxathiolane, oxazetidine, oxazolidine, oxetane, oxirane, piperazine, piperidine, pyrazolidine, pyrrolidine, tetrahydrofuran, tetrahydropyran, tetrahydrothiophene, tetrahydrothiopyran, tetrazinane, thiadiazolidine, thiazetidine, thiaziridine, thiazolidine, thietane, thiirane, thiomorpholine, triazetidine, triazinane or triazolidine, which is unsubstituted or mono-, di- or trisubstituted independently by R10 or fluorine;
or a physiologically tolerated salt thereof.

5. The compound of claim 1 wherein the sub-ring

is selected from the group of azetidine, cyclopropyl, cyclobutyl, cyclopentyl, cyclohexyl, 1,3-dihydroisobenzofuran, 1,3-dioxane, 1,3-dioxolane, imidazolidine, indane, morpholine, 1,3-oxazinane, piperazine, piperidine, pyrrolidine, tetrahydrofuran, and 1,2,3,4-tetrahydronaphthalene;

the sub-ring

is selected from the group of azetidine, cyclopropyl, cyclopentyl, cyclohexyl, morpholine, oxazolidine, piperidine and pyrrolidine, and in which the two sub-rings are unsubstituted or independently, according to the ring size, mono-, di- or tri-substituted by R4 where R4 is —O—($C_1$-$C_4$)-alkyl, =O, —($C_0$-$C_4$)-alkylene-($C_3$-$C_6$)-cycloalkyl, —($C_1$-$C_4$)-alkyl or —($C_0$-$C_4$)-alkylene-phenyl where phenyl is unsubstituted or substituted by F, Cl, Br or —O—($C_1$-$C_4$)-alkyl;

X is a covalent bond or —NH—;
Y is —C(O)— or —S($O_2$)—;
p is the integer 1;
R27 is a hydrogen atom, —($C_1$-$C_6$)-alkyl, 4-F-benzyl or benzyl;
R26 is a hydrogen atom;
R24 and R25 are the same or different and are each independently a hydrogen atom, methyl or ethyl, or
R24 and R25, together with the carbon atom to which they are bonded, form a cyclopropyl or cyclobutyl radical, or
R24 and R25, together with the carbon atom to which they are bonded, form a piperidine ring which is unsubstituted or substituted by —($C_1$-$C_4$)-alkyl;
or a physiologically tolerated salt thereof.

6. The compound of claim 1 selected from the group consisting of:
N—[(S)-1-(1-cyanocyclopropylcarbamoyl)-3,3-difluorobutyl]-3-azaspiro[5.5]undecane-3-carboxamide;
N—[(S)-1-(1-cyanocyclopropylcarbamoyl)-3,3-difluorobutyl]-8-azaspiro[4.5]decane-8-carboxamide;
N—[(S)-1-(1-cyanocyclopropylcarbamoyl)-3,3-difluorobutyl]-1,4-dioxa-8-azaspiro[4.5]decane-8-carboxamide;
N—[(S)-1-(1-cyanocyclopropylcarbamoyl)-3,3-difluorobutyl]-2-azaspiro[5.5]undecane-2-carboxamide;
N—[(S)-1-(1-cyanocyclopropylcarbamoyl)-3,3-difluorohexyl]-8-aza-spiro[4.5]decane-8-carboxamide;
N—[(S)-1-(1-cyanocyclopropylcarbamoyl)-3,3-difluorohexyl]-3-azaspiro[5.5]undecane-3-carboxamide;
N—[(S)-1-(1-cyanocyclopropylcarbamoyl)-3,3-difluorobutyl]-2-(4-methoxyphenyl)-1-oxo-2,8-diazaspiro[4.5]decane-8-carboxamide;
N—[(S)-1-(1-cyanocyclopropylcarbamoyl)-3,3-difluorobutyl]-4-oxo-1-phenyl-1,3,8-triazaspiro[4.5]decane-8-carboxamide;
N—[(S)-1-(1-cyanocyclopropylcarbamoyl)-3,3-difluorobutyl]-1,5-dioxa-9-aza-spiro[5.5]undecane-9-carboxamide;
N—[(S)-1-(1-cyanocyclopropylcarbamoyl)-3,3-difluorobutyl]-1-oxo-2,8-diazaspiro[4.5]decane-8-carboxamide;
N—[(S)-1-(1-cyanocyclopropylcarbamoyl)-3,3-difluorobutyl]-2-methyl-1-oxo-2,8-diazaspiro[4.5]decane-8-carboxamide;
N—[(S)-1-(1-cyanocyclopropylcarbamoyl)-3,3-difluorobutyl]-3,3-dimethyl-1-oxa-5,9-diazaspiro[5.5]undecane-9-carboxamide;
N—[(S)-1-(1-cyanocyclopropylcarbamoyl)-3,3-difluoro-4-phenylbutyl]-8-azaspiro[4.5]decane-8-carboxamide;
N—[(S)-1-(1-cyanocyclopropylcarbamoyl)-3,3-difluorobutyl]-2,4-dioxo-1,3,8-triazaspiro[4.5]decane-8-carboxamide;
N—[(S)-1-(1-cyanocyclopropylcarbamoyl)-3,3-difluorobutyl]-2-aza-spiro[4.4]nonane-2-carboxamide;
N—[(S)-1-(1-cyanocyclopropylcarbamoyl)-3,3-difluorobutyl]-2-benzyl-1-oxo-2,8-diazaspiro[4.5]decane-8-carboxamide;
N—[(S)-1-(1-cyanocyclopropylcarbamoyl)-3,3-difluorobutyl]-2-(4-fluoro phenyl)-1-oxo-2,8-diazaspiro[4.5]decane-8-carboxamide;
N—[(S)-1-(1-cyanocyclopropylcarbamoyl)-3,3-difluorobutyl]-3-phenyl-1,5-dioxa-9-azaspiro[5.5]undecane-9-carboxamide;
N—[(S)-1-(1-cyanocyclopropylcarbamoyl)-3,3-difluorobutyl]-9-butyl-3,9-diazaspiro[5.5]undecane-3-carboxamide;
N—[(S)-1-(1-cyanocyclopropylcarbamoyl)-3,3-difluorobutyl]-9-cyclopropyl-3,9-diazaspiro[5.5]undecane-3-carboxamide;
N—[(S)-1-(1-cyanocyclopropylcarbamoyl)-3,3-difluorobutyl]spiro[2.3]hexane-1-carboxamide;
N—[(S)-1-(1-cyanocyclopropylcarbamoyl)-3,3-difluorobutyl]-2,2-dimethyl-1-oxa-8-azaspiro[4.5]decane-8-carboxamide;
N—[(S)-1-cyanocyclopropylcarbamoyl)-3,3-difluorobutyl]-2-azaspiro[4.5]decane-2-carboxamide;

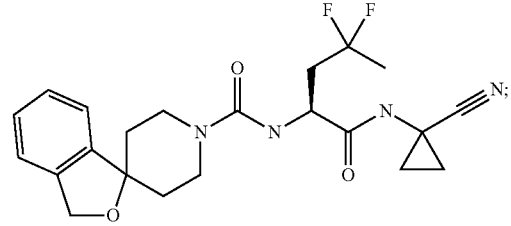

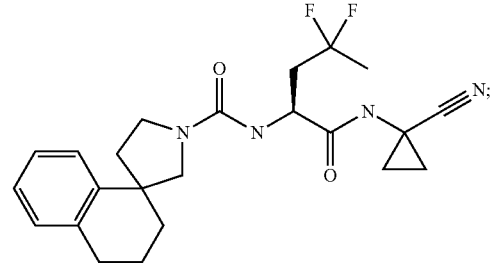

N—[(S)-1-(1-cyanocyclopropyl-carbamoyl)-3,3-difluorobutyl]-1-oxa-4-azaspiro[4.5]decane-4-carboxamide;
N-(1-cyanocyclopropyl)-(S)-2-[3-(1,4-dioxaspiro[4.5]dec-8-yl)-ureido]-4,4-difluoropentoxide;

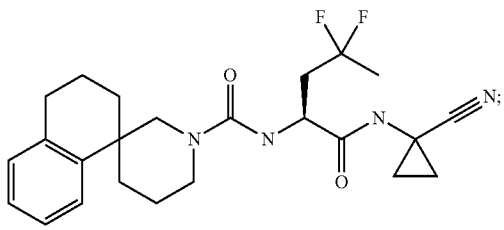

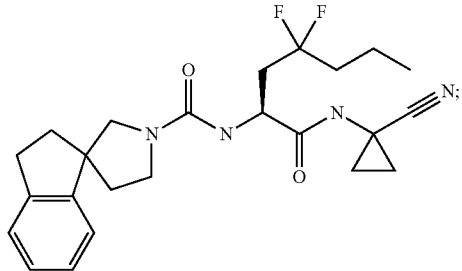

N—[(S)-1-(1-cyanocyclopropylcarbamoyl)-3,3-difluorobutyl]-7-cyclopropyl-2,7-diazaspiro[3.5]nonane-2-carboxamide;
N—[(S)-1-(1-cyanocyclopropylcarbamoyl)-3,3-difluorobutyl]-2-cyclopropyl-2,7-diazaspiro[3.5]nonane-7-carboxamide;
N—[(S)-1-(1-cyanocyclopropylcarbamoyl)-3,3-difluorobutyl]-2-propyl-2,7-diazaspiro[3.5]nonane-7-carboxamide;
N-(1-cyanocyclopropyl)-(S)-2-(8-azaspiro[4.5]decane-8-sulfonylamino)-4,4-difluoropentanamide;
N—[(S)-1-(1-cyanocyclopropylcarbamoyl)-3,3-difluorobutyl]-4-cyclopropyl-1-oxa-4,9-diazaspiro[5.5]undecane-9-carboxamide;
N—[(S)-1-(1-cyanocyclopropylcarbamoyl)-3,3-difluorobutyl]-9-cyclopropyl-1-oxa-4,9-diazaspiro[5.5]undecane-4-carboxamide;
N—[(S)-1-(1-cyanocyclopropylcarbamoyl)-3,3-difluorobutyl]-2-cyclopropylmethyl-3-oxo-2,8-diazaspiro[4.5]decane-8-carboxamide;
N—[(S)-1-(1-cyanocyclopropylcarbamoyl)-3,3-difluorohexyl]-2-(4-methoxyphenyl)-1-oxo-2,8-diazaspiro[4.5]decane-8-carboxamide;
N—[(S)-1-(1-cyanocyclopropylcarbamoyl)-3,3-difluorohexyl]-2-(4-methoxyphenyl)-2,8-diazaspiro[4.5]decane-8-carboxamide;
N—[(S)-1-(1-cyanocyclo-propylcarbamoyl)-3,3-difluorohexyl]-2-cyclopropyl-2,7-diazaspiro[3.5]nonane-7-carboxamide;
N—[(S)-1-(1-cyanocyclopropylcarbamoyl)-3,3-difluorohexyl]-2-cyclopropyl-2,8-diazaspiro[4.5]decane-8-carboxamide;
N—[(S)-1-(1-cyanocyclo-propylcarbamoyl)-3,3-difluorohexyl]-9-cyclopropyl-3,9-diazaspiro[5.5]undecane-3-carboxamide;
N—[(S)-1-(1-cyanocyclopropylcarbamoyl)-3,3-difluorohexyl]-7-cyclopropyl-2,7-diazaspiro[3.5]nonane-2-carboxamide;
N—[(S)-1-(1-cyanocyclopropyl-carbamoyl)-3,3-difluorohexyl]-7-propyl-2,7-diazaspiro[3.5]nonane-2-carboxamide;
N—[(S)-1-(1-cyanocyclopropylcarbamoyl)-3,3-difluoro-4-phenylbutyl]-9-cyclopropyl-3,9-diazaspiro[5.5]undecane-3-carboxamide;
N—[(S)-1-(1-cyanocyclopropylcarbamoyl)-3,3-difluoro-4-phenylbutyl]-2-cyclo-propyl-2,7-diazaspiro[3.5]nonane-7-carboxamide;
N—[(S)-1-(1-cyanocyclopropylcarbamoyl)-3,3-difluoro-4-phenylbutyl]-2-propyl-2,7-diazaspiro[3.5]nonane-7-carboxamide; and
N—[(S)-1-(1-cyanocyclopropylcarbamoyl)-3,3-difluoro-4-phenylbutyl]-7-cyclopropyl-2,7-diazaspiro[3.5]nonane-2-carboxamide;
or a physiologically tolerated salt thereof.

7. A process for preparing the compound of claim 1 or an N-oxide thereof, which comprises
a) reacting a compound of the formula II

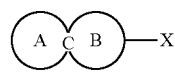

(II)

with a compound of the formula IIIa or IIIb or IIIc:

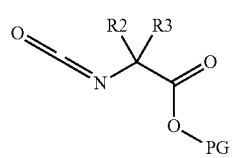

(IIIa)

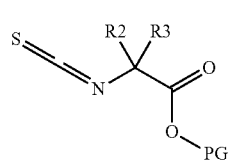

(IIIb)

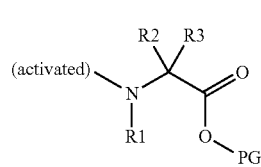

(IIIc)

where R1 is hydrogen, R2 is hydrogen, R3 is $(CH_2)_p F_2 R27$, PG is an ester protecting group and "activated" means that the amine is present in an activated form, to give a compound of the formula IVa or IVb

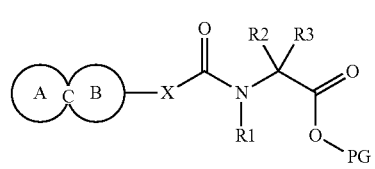

(IVa)

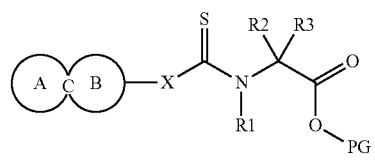

(IVb)

and reacting the resulting compound of the formula IVa or IVb, after converting the ester to the carboxylic acid, with Z to give the compound of the formula Ia, wherein A is —N(R26)-(C(R24)(R25))-CN, or b) reacting a compound of the formula Va or Vb

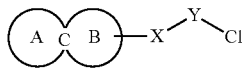
(Va)

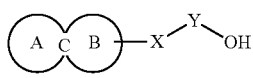
(Vb)

with a compound of the formula VI where R1, R2 and R3 are each as defined above and PG is an ester protecting group

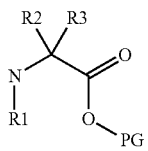
(VI)

to give a compound of the formula IVa or IVb, and reacting the resulting compound of the formula IVa or IVb, after converting the ester protecting group to the carboxylic acid, with Z to give the compound of the formula Ia, or c) reacting a compound of the formula VIIIa or VIIb

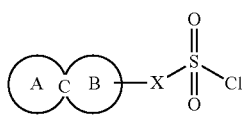
(VIIa)

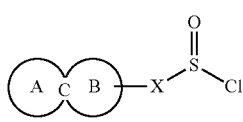
(VIIb)

with a compound of the formula VI

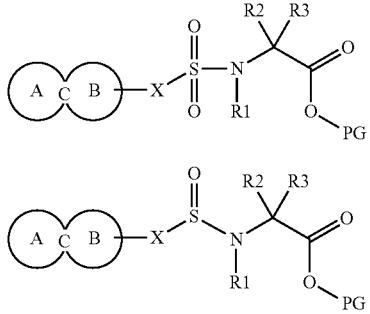
(VIIIa)

(VIIIb)

to give a compound of the formula VIIIa or VIIIb and reacting the resulting compound of the formula VIIIa or VIIIb, after converting the ester to the corresponding carboxylic acid, with Z to give the compound of the formula Ia, or d) reacting a compound of the formula IX

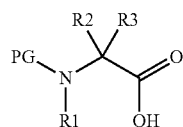
(IX)

with an amine Z where Z is as defined above to give a compound of the formula X

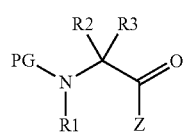
(X)

and then converting the compound X thus obtained by a protecting group elimination to give a compound of the formula XI:

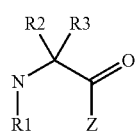
(XI)

and then reacting this compound XI with a compound Va or Vb, as detailed under b), to give the compound of the formula Ia, or e) separating a compound of the formula Ia prepared by processes a), b), c) or d), or a suitable precursor of the formula Ia which, owing to its chemical structure, occurs in enantiomeric or diastereomeric forms, into the pure enantiomers or diastereomers by salt formation with enantiomerically pure salts or bases, chromatography on chiral stationary phases or derivatization by means of chiral enantiomerically pure compounds, separating the diastereomers thus obtained, and eliminating the chiral auxiliary groups, or f) either isolating the compound of the formula Ia prepared by processes a), b), c) or d) in free form or releasing it from physiologically incompatible salts or, in the case of the presence or acidic or basic groups, converting it to physiologically acceptable salts, or g) converting the compound of the formula Ia prepared by processes a), b), c) or d), or a suitable precursor of the formula Ia which, owing to its chemical structure, is capable of forming an N-oxide to an N-oxide or, in the case of the presence of an N-oxide, converting it to the free amine or the salt of an amine.

8. A pharmaceutical composition comprising a therapeutically effective amount of the compound of claim 1 or a physiologically tolerated salt thereof and a pharmaceutically acceptable carrier.

9. A method of treating a disease, condition or disorder selected from bone loss and osteoarthritis; said method comprising administering to a patient in need thereof a therapeutically effective amount of a compound of formula Ia:

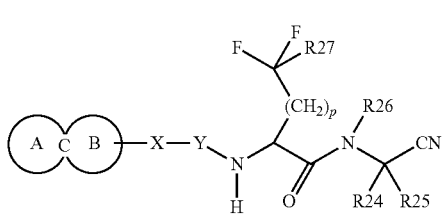

(Ia)

where
the

radical is a spiro compound,
in which the sub-rings

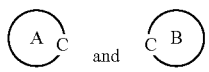

are in each case the same or different and are each independently a) a saturated or partly saturated —($C_3$-$C_{11}$)-cycloalkyl, in which cycloalkyl is unbridged, bridged or fused and is unsubstituted or independently, according to the ring size, mono-, di-, tri, tetra- or pentasubstituted by R4, or b) a saturated or partly saturated, three- to eleven-membered heterocycle which, according to the ring size, may contain one, two, three or four identical or different heteroatoms from the group of oxygen, nitrogen or sulfur, and in which the heterocycle is unbridged, bridged or fused and is unsubstituted or independently, according to the ring size, mono-, di-, tri-, tetra- or pentasubstituted by R4;

R4 is —$NO_2$, —CN, =O, =S, —OH, —$CF_3$, —$SF_5$, —($C_0$-$C_3$)-alkylene-S—R10, —O—$CF_3$, —Si—$(CH_3)_3$, —($C_0$-$C_5$)-alkylene-O—C(O)—R21, —($C_0$-$C_5$)-alkylene-C(O)—O—R10, —($C_0$-$C_3$)-alkylene-O—R10, —($C_0$-$C_3$)-alkylene-N(R21)-R22, —($C_0$-$C_3$)-alkylene-N(R10)-S($O_2$)—R10, —($C_0$-$C_5$)-alkylene-($C_3$-$C_8$)-cycloalkyl-R23, —S—$CF_3$, —($C_0$-$C_5$)-alkylene-($C_1$-$C_3$)-fluoroalkyl, —($C_0$-$C_5$)-alkylene-N(R10)-C(O)—R21, —($C_0$-$C_3$)-alkylene-C(O)—N(R21)-R22, —($C_0$-$C_4$)-alkyl where alkyl is unsubstituted or mono-, di- or trisubstituted independently by R9, —($C_0$-$C_4$)-alkylene-aryl where aryl is selected from the group of phenyl, indanyl, indenyl, and naphthyl, where aryl is unsubstituted or mono-, di- or trisubstituted independently by R8, or —($C_0$-$C_4$)-alkylene-Het where Het is selected from the group of azetidinyl, benzimidazolinyl, benzimidazolyl, benzofuranyl, benzothiophenyl, benzoxazolyl, benzthiazolyl, benzisoxazolyl, benzisothiazolyl, quinolinyl, dioxolyl, dioxanyl, furanyl, imidazolidinyl, imidazolinyl, imidazolyl, indolinyl, indolyl, 3H-indolyl, isoindolinyl, isoindolyl, isoquinolinyl, isothiazolidinyl, 2-isothiazolinyl, isothiazolyl, isoxazolyl, isoxazolidinyl, 2-isoxazolinyl, morpholinyl, octahydroisoquinolinyl, oxazolyl, oxazolidinyl, pyrimidinyl, piperazinyl, piperidinyl, pyranyl, pyrazinyl, pyrazolinyl, pyrazolyl, pyridazinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyridinyl, thiazolyl, thienyl, thienopyridinyl, thiomorpholinyl, and thiophenyl, and this Het radical is unsubstituted or independently mono-, di- or trisubstituted by R8;

R8 is halogen, carbamimidoyl, —$NO_2$, =O, —$CF_3$, —$SF_5$, —C(O)—O—R10, —CN, —C(O)—$NH_2$, —OH, —$NH_2$, —O—$CF_3$, —C(O)—N(R10)-R20, —N(R10)-R20, —($C_3$-$C_8$)-cycloalkyl, —O—($C_1$-$C_8$)-alkyl, —O—($C_0$-$C_4$)-alkylene-($C_3$-$C_6$)-cycloalkyl, —($C_1$-$C_8$)-alkyl, or —($C_0$-$C_4$)-alkylene-($C_3$-$C_8$)-cycloalkyl, where the alkyl radicals mentioned are each unsubstituted or mono-, di- or trisubstituted independently by halogen, $NH_2$, —OH, —O—$CH_3$, —$SO_2$—$CH_3$ or —$SO_2$—$CF_3$;

R9 is halogen, —$NO_2$, —CN, =O, —OH, —$CF_3$, —C(O)—O—R10, —C(O)—N(R21)-R22, —N(R21)-R22, —($C_3$-$C_8$)-cycloalkyl, —($C_0$-$C_3$)-alkylene-O—R10, —Si—$(CH_3)_3$, —N(R10)-S(O)$_u$—R10 where u is the integer 1 or 2, —S—R10, —$SO_r$—R10 where r is the integer 1 or 2, —S(O)$_v$—N(R10)-R20 where v is the integer 1 or 2, —C(O)—R10, —($C_1$-$C_8$)-alkyl, —($C_1$-$C_8$)-alkoxy, phenyl, phenyloxy-, —($C_1$-$C_3$)-fluoroalkyl, —O—R19, —NH—C(O)—NH—R10, —($C_0$-$C_4$)-alkyl-C(O)—O—C(R11,R19)-O—C(O)—R12, —NH—C(O)—NH—R21, —N(R21)-C(O)—R22, —($C_0$-$C_4$)-alkyl-C(O)—O—C(R11,R19)-O—C(O)—O—R12, —NH—C(O)—O—R10, —O—$CF_3$ or Het where Het is as defined above and is unsubstituted or mono-, di- or trisubstituted independently by R8;

R10 and R20 are the same or different and are each independently a hydrogen atom, —($C_1$-$C_6$)-alkyl, —($C_0$-$C_4$)-alkyl-OH, —($C_1$-$C_3$)-fluoroalkyl, —($C_0$-$C_4$)-alkyl-O—($C_1$-$C_4$)-alkyl, —($C_0$-$C_5$)-alkyl-($C_3$-$C_8$)-cycloalkyl, —($C_0$-$C_2$)-alkylene-aryl where aryl is as defined above and is unsubstituted or mono-, di- or trisubstituted independently by —($C_1$-$C_6$)-alkyl, —O—($C_1$-$C_6$)-alkyl, halogen or —($C_3$-$C_8$)-cycloalkyl, or —($C_0$-$C_2$)-alkylene-Het where Het is as defined above and is unsubstituted or mono-, di- or trisubstituted independently by —($C_1$-$C_6$)-alkyl, —O—($C_1$-$C_6$)-alkyl, halogen or —($C_3$-$C_8$)-cycloalkyl;

R11 and R19 are the same or different and are each independently a hydrogen atom or —($C_1$-$C_6$)-alkyl;

R12 is —($C_1$-$C_6$)-alkyl, —($C_1$-$C_6$)-alkyl-OH, —($C_1$-$C_6$)-alkyl-O—($C_1$-$C_6$)-alkyl, —($C_3$-$C_8$)-cycloalkyl, —($C_1$-$C_6$)-alkyl-O—($C_1$-$C_8$)-alkyl-($C_3$-$C_8$)-cycloalkyl, or —($C_1$-$C_6$)-alkyl-($C_3$-$C_8$)-cycloalkyl, where the cycloalkyl radical is unsubstituted or mono-, di- or trisubstituted independently by —OH, —O—($C_1$-$C_4$)-alkyl or R10;

R21 and R22 are the same or different and are each independently a hydrogen atom, —($C_1$-$C_6$)-alkyl where alkyl is unsubstituted or mono-, di- or trisubstituted independently by R8, —($C_0$-$C_6$)-alkylene-($C_3$-$C_8$)-cycloalkyl, —$SO_t$—R10 where t is the integer 1 or 2, —($C_1$-$C_3$)-fluoroalkyl, —O—R12, —($C_0$-$C_6$)-alkylene-aryl where aryl is as defined above and alkylene and aryl are each unsubstituted or mono-, di- or trisubstituted independently by R8 or —($C_0$-$C_6$)-alkylene-Het where Het is as defined above and alkylene and Het are each unsubstituted or mono-, di- or trisubstituted independently by R8;

R21 and R22, together with the nitrogen atom to which they are bonded, form a four- to eight-membered monocyclic heterocyclic ring which, as well as the nitrogen atom, additionally, according to the ring size, may contain one or two identical or different heteroatoms selected from the group of oxygen, nitrogen and sulfur and in which the heterocycle is unsubstituted or mono-, di- or trisubstituted independently by R8;

R23 is a hydrogen atom, —OH or —O—($C_1$-$C_4$)-alkyl;

X is a covalent bond, —N(R7)- or —O—, where

R7 is a hydrogen atom, —($C_0$-$C_4$)-alkylene-($C_3$-$C_6$)-cycloalkyl or —($C_1$-$C_4$)-alkyl;

Y is —C(O)—, —C(S)— or —S($O_2$)—;

p is the integer 1 or 2;

R27 is a hydrogen atom, —($C_1$-$C_6$)-alkyl, halogen, —($C_0$-$C_4$)-alkylene-($C_3$-$C_6$)-cycloalkyl, —($C_0$-$C_4$)-alkylene-Het where Het is as defined above and is unsubstituted or substituted by halogen, —($C_1$-$C_6$)-alkyl, —O—($C_1$-$C_3$)-fluoroalkyl or —O—($C_1$-$C_6$)-alkyl, or —($C_0$-$C_2$)-alkylene-phenyl where phenyl is unsubstituted or substituted by halogen, —($C_1$-$C_6$)-alkyl, —O—($C_1$-$C_3$)-fluoroalkyl or —O—($C_1$-$C_6$)-alkyl;

R26 is a hydrogen atom, —($C_1$-$C_4$)-alkyl or —($C_0$-$C_4$)-alkylene-($C_3$-$C_6$)-cycloalkyl;

R24 and R25 are the same or different and are each independently a hydrogen atom, —($C_1$-$C_6$)-alkyl, —($C_1$-$C_3$)-fluoroalkyl, —($C_0$-$C_4$)-alkylene-($C_3$-$C_6$)-cycloalkyl, —($C_0$-$C_4$)-alkylene-aryl where aryl is as defined above and is unsubstituted or mono-, di- or trisubstituted independently by R8, or —($C_0$-$C_4$)-alkylene-Het where Het is as defined above and is unsubstituted or mono-, di- or trisubstituted independently by R8; or R24 and R25, together with the carbon atom to which they are bonded, form a three- to six-membered cycloalkyl ring which is unsubstituted or mono-, di- or trisubstituted independently by R10 or fluorine; or R24 and R25, together with the carbon atom to which they are bonded, form a three- to six-membered heterocycloalkyl radical which is unsubstituted or mono-, di- or trisubstituted independently by R10 or fluorine;

or a physiologically tolerated salt thereof.

10. The method of claim 9, wherein for the compound of formula Ia:
the sub-rings

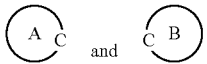

are each independently selected from the group of azetidine, cyclopropyl, cyclobutyl, cyclopentyl, cyclohexyl, 1,3-dihydroisobenzofuran, 2,3-dihydroisoxazole, 2,5-dihydroisoxazole, 4,5-dihydroisoxazole, 1,3-dioxane, dioxolane, 1,3-dioxolane, imidazolidine, indane, morpholine, 1,3-oxazinane, oxazolidine, piperazine, piperidine, pyrrolidine, tetrahydrofuran, and 1,2,3,4-tetrahydronaphthalene, and in which the two sub-rings are each unsubstituted or independently, according to the ring size, mono-, di- or trisubstituted by R4;

R4 is =O, =S, —($C_0$-$C_3$)-alkylene-C(O)—O—R10, —($C_0$-$C_3$)-alkylene-N(R21)-R22, —($C_0$-$C_3$)-alkylene-NH—C(O)—R21, —($C_0$-$C_4$)-alkylene-($C_3$-$C_6$)-cycloalkyl-R23, —($C_0$-$C_3$)-alkylene-O—R10, —($C_0$-$C_4$)-alkylene-phenyl, where phenyl is unsubstituted or mono-, di- or trisubstituted independently by R8, or —($C_0$-$C_4$)-alkyl where alkyl is unsubstituted or mono-, di- or trisubstituted independently by R9;

R8 is fluorine, chlorine, bromine, —O—($C_1$-$C_3$)-fluoroalkyl or —O—($C_1$-$C_4$)-alkyl, R9 is halogen, —$NO_2$, —CN, =O, —OH, —$CF_3$, —C(O)—O—R10, —C(O)—N(R21)-R22, —N(R21)-R22, —($C_3$-$C_8$)-cycloalkyl, —($C_0$-$C_3$)-alkylene-O—R10, —Si—($CH_3$)$_3$, —N(R10)-S(O)$_u$—R10 where u is the integer 1 or 2, or —S—R10; —$SO_r$—R10 where r is the integer 1 or 2, —S(O)$_v$—N(R10)-R20 where v is the integer 1 or 2, —C(O)—R10, —($C_1$-$C_8$)-alkyl, —($C_1$-$C_8$)-alkoxy, phenyl, phenyloxy-, —($C_1$-$C_3$)-fluoroalkyl, —O—R19, —NH—C(O)—NH—R10, —($C_0$-$C_4$)-alkyl-C(O)—O—C(R11,R19)-O—C(O)—R12, —NH—C(O)—NH—R21, —N(R21)-C(O)—R22, —($C_0$-$C_4$)-alkyl-C(O)—O—C(R11,R19)-O—C(O)—O—R12, —NH—C(O)—O—R10 or —O—$CF_3$;

R10 and R20 are the same or different and are each independently a hydrogen atom or —($C_1$-$C_6$)-alkyl;

R11 and R19 are the same or different and are each independently a hydrogen atom or —($C_1$-$C_6$)-alkyl;

R12 is —($C_1$-$C_6$)-alkyl, —($C_1$-$C_6$)-alkyl-OH, —($C_1$-$C_6$)-alkyl-O—($C_1$-$C_6$)-alkyl, —($C_3$-$C_8$)-cycloalkyl, —($C_1$-$C_6$)-alkyl-O—($C_1$-$C_8$)-alkyl-($C_3$-$C_8$)-cycloalkyl, —($C_1$-$C_6$)-alkyl-($C_3$-$C_8$)-cycloalkyl, where the cycloalkyl radical is unsubstituted or mono-, di- or trisubstituted independently by —OH, —O—($C_1$-$C_4$)-alkyl or R10;

R21 and R22 are the same or different and are each independently a hydrogen atom, —($C_1$-$C_6$)-alkyl, —O—R12, —($C_0$-$C_6$)-alkylene-($C_3$-$C_8$)-cycloalkyl, —$SO_t$—R10 where t is the integer 1 or 2, or —($C_1$-$C_3$)-fluoroalkyl;

R23 is a hydrogen atom, —OH or —O—($C_1$-$C_4$)-alkyl;

X is a covalent bond or —N(R7)- where

R7 is a hydrogen atom or —($C_1$-$C_4$)-alkyl;

Y is —C(O)— or —S($O_2$)—;

p is the integer 1 or 2;

R26 is a hydrogen atom;

R27 is a hydrogen atom, —($C_0$-$C_4$)-alkylene-($C_3$-$C_6$)-cycloalkyl, —($C_1$-$C_6$)-alkyl, —($C_0$-$C_2$)-alkylene-phenyl where phenyl is unsubstituted or substituted by halogen, —($C_1$-$C_6$)-alkyl, —O—($C_1$-$C_3$)-fluoroalkyl or —O—($C_1$-$C_6$)-alkyl, or —($C_0$-$C_2$)-alkylene-pyridyl;

R24 and R25 are the same or different and are each independently a hydrogen atom, —($C_1$-$C_4$)-alkyl or —($C_0$-$C_4$)-alkylene-($C_3$-$C_6$)-cycloalkyl, or R24 and R25, together with the carbon atom to which they are bonded, form a cycloalkyl ring which is selected from the group of cyclopropyl, cyclobutyl, cyclopentyl and cyclohexyl, and is unsubstituted or mono-, di- or trisubstituted independently by R10 or fluorine, or R24 and R25, together with the carbon atom to which they are bonded, form a three- to six-membered heterocycloalkyl radical selected from the group of aziridine, azetidine, diazetidine, diaziridine, hexohydropyridazine, hexohydropyrimidine, imidazolidine, morpholine, oxadiazinane, oxadiazolidine, oxathianane, oxathiolane, oxazetidine, oxazolidine, oxetane, oxirane, piperazine, piperidine, pyrazolidine, pyrrolidine, tetrahydrofuran, tetrahydropyran, tetrahydrothiophene, tetrahydrothiopyran, tetrazinane, thiadiazolidine, thiazetidine, thiaziridine, thiazolidine, thietane, thiirane, thiomorpholine, triazetidine, triazinane or triazolidine, which is unsubstituted or mono-, di- or trisubstituted independently by R10 or fluorine;

or a physiologically tolerated salt thereof.

11. The method of claim 9, wherein for the compound of formula Ia:
the sub-ring

is selected from the group of azetidine, cyclopropyl, cyclobutyl, cyclopentyl, cyclohexyl, 1,3-dihydroisobenzofuran, 1,3-dioxane, 1,3-dioxolane, imidazolidine, indane, morpholine, 1,3-oxazinane, piperazine, piperidine, pyrrolidine, tetrahydrofuran, and 1,2,3,4-tetrahydronaphthalene;
the sub-ring

is selected from the group of azetidine, cyclopropyl, cyclopentyl, cyclohexyl, morpholine, oxazolidine, piperidine and pyrrolidine, and in which the two sub-rings are unsubstituted or independently, according to the ring size, mono-, di- or tri-substituted by R4, where
R4 is —O—($C_1$-$C_4$)-alkyl, =O, —($C_0$-$C_4$)-alkylene-($C_3$-$C_6$)-cycloalkyl, —($C_1$-$C_4$)-alkyl or —($C_0$-$C_4$)-alkylene-phenyl where phenyl is unsubstituted or substituted by F, Cl, Br or —O—($C_1$-$C_4$)-alkyl;
X is a covalent bond or —NH—;
Y is —C(O)— or —S($O_2$)—;
p is the integer 1;
R27 is a hydrogen atom, —($C_1$-$C_6$)-alkyl, 4-F-benzyl or benzyl;
R26 is a hydrogen atom;
R24 and R25 are the same or different and are each independently a hydrogen atom, methyl or ethyl; or
R24 and R25, together with the carbon atom to which they are bonded, form a cyclopropyl or cyclobutyl radical; or
R24 and R25, together with the carbon atom to which they are bonded, form a piperidine ring which is unsubstituted or substituted by —($C_1$-$C_4$)-alkyl;
or a physiologically tolerated salt thereof.
12. The method of claim 9, wherein the compound is selected from the group consisting of:
N—[(S)-1-(1-cyanocyclopropylcarbamoyl)-3,3-difluorobutyl]-3-azaspiro[5.5]undecane-3-carboxamide;
N—[(S)-1-(1-cyanocyclopropylcarbamoyl)-3,3-difluorobutyl]-8-azaspiro[4.5]decane-8-carboxamide;
N—[(S)-1-(1-cyanocyclopropylcarbamoyl)-3,3-difluorobutyl]-1,4-dioxa-8-azaspiro[4.5]decane-8-carboxamide;
N—[(S)-1-(1-cyanocyclopropylcarbamoyl)-3,3-difluorobutyl]-2-azaspiro[5.5]undecane-2-carboxamide;
N—[(S)-1-(1-cyanocyclopropylcarbamoyl)-3,3-difluorohexyl]-8-aza-spiro[4.5]decane-8-carboxamide;
N—[(S)-1-(1-cyanocyclopropylcarbamoyl)-3,3-difluorohexyl]-3-azaspiro[5.5]undecane-3-carboxamide;
N—[(S)-1-(1-cyanocyclopropylcarbamoyl)-3,3-difluorobutyl]-2-(4-methoxyphenyl)-1-oxo-2,8-diazaspiro[4.5]decane-8-carboxamide;
N—[(S)-1-(1-cyanocyclopropylcarbamoyl)-3,3-difluorobutyl]-4-oxo-1-phenyl-1,3,8-triazaspiro[4.5]decane-8-carboxamide;
N—[(S)-1-(1-cyanocyclopropylcarbamoyl)-3,3-difluorobutyl]-1,5-dioxa-9-aza-spiro[5.5]undecane-9-carboxamide;
N—[(S)-1-(1-cyanocyclopropylcarbamoyl)-3,3-difluorobutyl]-1-oxo-2,8-diazaspiro[4.5]decane-8-carboxamide;
N—[(S)-1-(1-cyanocyclopropylcarbamoyl)-3,3-difluorobutyl]-2-methyl-1-oxo-2,8-diazaspiro[4.5]decane-8-carboxamide;
N—[(S)-1-(1-cyanocyclopropylcarbamoyl)-3,3-difluorobutyl]-3,3-dimethyl-1-oxa-5,9-diazaspiro[5.5]undecane-9-carboxamide;
N—[(S)-1-(1-cyanocyclopropylcarbamoyl)-3,3-difluoro-4-phenylbutyl]-8-azaspiro[4.5]decane-8-carboxamide;
N—[(S)-1-(1-cyanocyclopropylcarbamoyl)-3,3-difluorobutyl]-2,4-dioxo-1,3,8-triazaspiro[4.5]decane-8-carboxamide;
N—[(S)-1-(1-cyanocyclopropylcarbamoyl)-3,3-difluorobutyl]-2-aza-spiro[4.4]nonane-2-carboxamide;
N—[(S)-1-(1-cyanocyclopropylcarbamoyl)-3,3-difluorobutyl]-2-benzyl-1-oxo-2,8-diazaspiro[4.5]decane-8-carboxamide;
N—[(S)-1-(1-cyanocyclopropylcarbamoyl)-3,3-difluorobutyl]-2-(4-fluoro phenyl)-1-oxo-2,8-diazaspiro[4.5]decane-8-carboxamide;
N—[(S)-1-(1-cyanocyclopropylcarbamoyl)-3,3-difluorobutyl]-3-phenyl-1,5-dioxa-9-azaspiro[5.5]undecane-9-carboxamide;
N—[(S)-1-(1-cyanocyclopropylcarbamoyl)-3,3-difluorobutyl]-9-butyl-3,9-diazaspiro[5.5]undecane-3-carboxamide;
N—[(S)-1-(1-cyanocyclopropylcarbamoyl)-3,3-difluorobutyl]-9-cyclopropyl-3,9-diazaspiro[5.5]undecane-3-carboxamide;
N—[(S)-1-(1-cyanocyclopropylcarbamoyl)-3,3-difluorobutyl]spiro[2.3]hexane-1-carboxamide;
N—[(S)-1-(1-cyanocyclopropylcarbamoyl)-3,3-difluorobutyl]-2,2-dimethyl-1-oxa-8-azaspiro[4.5]decane-8-carboxamide;
N—[(S)-1-cyanocyclopropylcarbamoyl)-3,3-difluorobutyl]-2-azaspiro[4.5]decane-2-carboxamide;

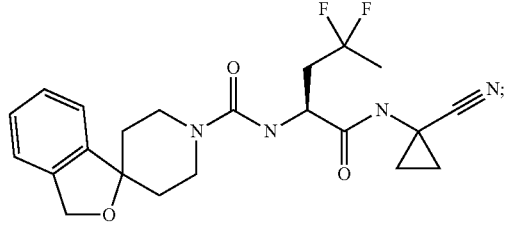

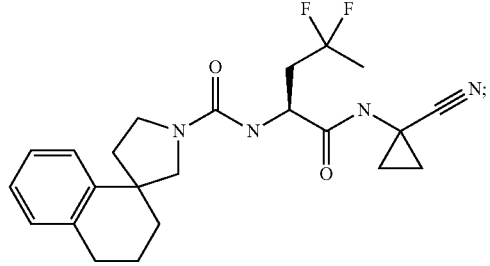

N—[(S)-1-(1-cyanocyclopropyl-carbamoyl)-3,3-difluorobutyl]-1-oxa-4-azaspiro[4.5]decane-4-carboxamide;
N-(1-cyanocyclopropyl)-(S)-2-[3-(1,4-dioxaspiro[4.5]dec-8-yl)-ureido]-4,4-difluoropentoxide;

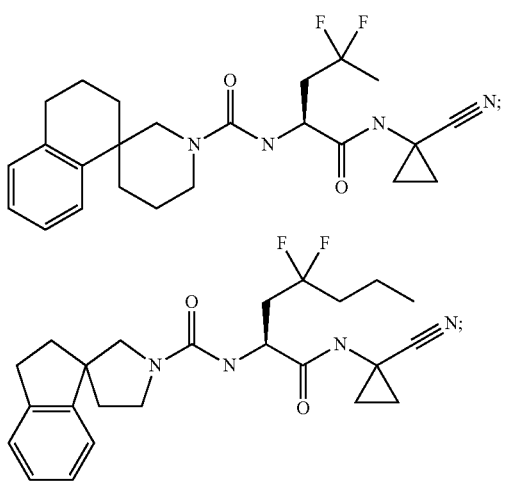

N—[(S)-1-(1-cyanocyclopropylcarbamoyl)-3,3-difluo-robutyl]-7-cyclopropyl-2,7-diazaspiro[3.5]nonane-2-carboxamide;
N—[(S)-1-(1-cyanocyclopropylcarbamoyl)-3,3-difluorobutyl]-2-cyclopropyl-2,7-diazaspiro[3.5]nonane-7-carboxamide;
N—[(S)-1-(1-cyanocyclopropylcarbamoyl)-3,3-difluo-robutyl]-2-propyl-2,7-diazaspiro[3.5]nonane-7-carboxamide;
N-(1-cyanocyclopropyl)-(S)-2-(8-azaspiro[4.5]decane-8-sulfonylamino)-4,4-difluoropentanamide;
N—[(S)-1-(1-cyanocyclopropylcarbamoyl)-3,3-difluo-robutyl]-4-cyclopropyl-1-oxa-4,9-diazaspiro[5.5]unde-cane-9-carboxamide;
N—[(S)-1-(1-cyanocyclopropylcarbamoyl)-3,3-difluo-robutyl]-9-cyclopropyl-1-oxa-4,9-diazaspiro[5.5]unde-cane-4-carboxamide;
N—[(S)-1-(1-cyanocyclopropylcarbamoyl)-3,3-difluo-robutyl]-2-cyclopropylmethyl-3-oxo-2,8-diazaspiro[4.5]decane-8-carboxamide;
N—[(S)-1-(1-cyanocyclopropylcarbamoyl)-3,3-difluoro hexyl]-2-(4-methoxyphenyl)-1-oxo-2,8-diazaspiro[4.5]decane-8-carboxamide;
N—[(S)-1-(1-cyanocyclopropylcarbamoyl)-3,3-difluoro-hexyl]-2-(4-methoxyphenyl)-2,8-diazaspiro[4.5]decane-8-carboxamide;
N—[(S)-1-(1-cyanocyclo-propylcarbamoyl)-3,3-difluo-rohexyl]-2-cyclopropyl-2,7-diazaspiro[3.5]nonane-7-carboxamide;
N—[(S)-1-(1-cyanocyclopropylcarbamoyl)-3,3-difluoro-hexyl]-2-cyclopropyl-2,8-diazaspiro[4.5]decane-8-carboxamide;
N—[(S)-1-(1-cyanocyclo-propylcarbamoyl)-3,3-difluo-rohexyl]-9-cyclopropyl-3,9-diazaspiro[5.5]undecane-3-carboxamide;
N—[(S)-1-(1-cyanocyclopropylcarbamoyl)-3,3-difluoro-hexyl]-7-cyclopropyl-2,7-diazaspiro[3.5]nonane-2-carboxamide;
N—[(S)-1-(1-cyanocyclopropyl-carbamoyl)-3,3-difluo-rohexyl]-7-propyl-2,7-diazaspiro[3.5]nonane-2-carboxamide;
N—[(S)-1-(1-cyanocyclopropylcarbamoyl)-3,3-difluoro-4-phenylbutyl]-9-cyclopropyl-3,9-diazaspiro[5.5]un-decane-3-carboxamide;
N—[(S)-1-(1-cyanocyclopropylcarbamoyl)-3,3-difluoro-4-phenylbutyl]-2-cyclo-propyl-2,7-diazaspiro[3.5]nonane-7-carboxamide;
N—[(S)-1-(1-cyanocyclopropylcarbamoyl)-3,3-difluoro-4-phenylbutyl]-2-propyl-2,7-diazaspiro[3.5]nonane-7-carboxamide; and
N—[(S)-1-(1-cyanocyclopropylcarbamoyl)-3,3-difluoro-4-phenylbutyl]-7-cyclopropyl-2,7-diazaspiro[3.5]nonane-2-carboxamide;
or a physiologically tolerated salt thereof.

13. The method of claim 9, wherein the compound is selected from the group consisting of:
N—[(S)-1-(1-cyanocyclopropylcarbamoyl)-3,3-difluo-robutyl]-6-azaspiro[2.5]octane-6-carboxamide;
N—[(S)-1-(cyanomethylcarbamoyl)-3,3-difluoro-butyl]-6-azaspiro[2.5]octane-6-carboxamide;
N—[(S)-1-(1-cyanocyclopropylcarbamoyl)-3,3-difluoro-hexyl]-6-azaspiro[2.5]octane-6-carboxamide;
N—[(S)-1-(4-cyano-1-methylpiperidin-4-ylcarbamoyl)-3,3-difluorobutyl]-6-azaspiro[2.5]octane-6-carboxamide;
N—[(S)-1-(4-cyano-1-methylpiperidin-4-ylcarbamoyl)-3,3-difluorohexyl]-6-azaspiro[2.5]octane-6-carboxamide; and
N—[(S)-1-(1-cyanocyclopropylcarbamoyl)-3,3-difluoro-pentyl]- or N—[(S)-1-(1-cyanocyclopropylcarbamoyl)-3,3-difluoro-4-phenylbutyl]-6-azaspiro[2.5]octane-6-carboxamide;
or a physiologically tolerated salt thereof.

14. The method of claim 9, wherein the condition or disorder is osteoarthritis.

15. The method of claim 9, wherein the condition or disorder is bone loss.

* * * * *